US011969398B2

(12) United States Patent
Pathak

(10) Patent No.: US 11,969,398 B2
(45) Date of Patent: *Apr. 30, 2024

(54) METHODS, COMPOSITIONS, AND DEVICES FOR MAKING SUSTAINED BIODEGRADABLE IMPLANTS IN TISSUE

(71) Applicant: Pathak Holdings LLC, Phoenix, AZ (US)

(72) Inventor: Chandrashekhar P. Pathak, Phoenix, AZ (US)

(73) Assignee: PATHAK HOLDINGS LLC, Phoenix, AZ (US)

( * ) Notice: Subject to any disclaimer, the term of this patent is extended or adjusted under 35 U.S.C. 154(b) by 427 days.

This patent is subject to a terminal disclaimer.

(21) Appl. No.: 17/324,738

(22) Filed: May 19, 2021

(65) Prior Publication Data
US 2021/0275472 A1    Sep. 9, 2021

Related U.S. Application Data

(60) Continuation of application No. 16/818,944, filed on Mar. 13, 2020, now Pat. No. 11,045,433, which is a (Continued)

(51) Int. Cl.
*A61K 31/155* (2006.01)
*A61K 9/00* (2006.01)
(Continued)

(52) U.S. Cl.
CPC ......... *A61K 31/155* (2013.01); *A61K 9/0014* (2013.01); *A61K 9/0021* (2013.01);
(Continued)

(58) Field of Classification Search
CPC .. A61K 31/155; A61K 9/0014; A61K 9/0024; A61K 9/1647
See application file for complete search history.

(56) References Cited

U.S. PATENT DOCUMENTS

| 4,935,008 A | 6/1990 | Lewis et al. |
| 5,410,016 A | 4/1995 | Hubbell et al. |
| (Continued) | | |

FOREIGN PATENT DOCUMENTS

| JP | 2000/024014 A | 1/2000 |
| JP | 2001/046497 A | 2/2001 |
| (Continued) | | |

OTHER PUBLICATIONS

Y. Lu et al.; "Microparticles Produced by the Hydrogel Template Method for Sustained Drug Delivery"; Int. J Pharm.; vol. 461(0), p. 258-269 (2014).
(Continued)

*Primary Examiner* — Carlos A Azpuru
(74) *Attorney, Agent, or Firm* — MASCHOFF BRENNAN

(57) ABSTRACT

This invention discloses methods and composition to form biodegradable polymer implant arrays in the live tissue. Artificial cavities are created in the live tissue by using laser ablation, oscillating needle, microneedle array and other methods. The cavities are then filled with biodegradable polymer solution. The solvent in the polymer solution is dissipated in the tissue to form a biodegradable polymer implant in artificial cavities. The cavities and implants formed are arranged to form of an array of implants. The biodegradable polymer in the cavity can also be loaded with drug to form biodegradable drug delivery array in the live tissue.

21 Claims, 29 Drawing Sheets

Related U.S. Application Data continuation of application No. 16/156,949, filed on Oct. 10, 2018, now Pat. No. 10,624,865, which is a continuation-in-part of application No. 15/704,792, filed on Sep. 14, 2017, now Pat. No. 10,123,980, which is a continuation of application No. 15/099,456, filed on Apr. 14, 2016, now Pat. No. 9,789,073, which is a continuation-in-part of application No. 14/736,007, filed on Jun. 10, 2015, now Pat. No. 9,345,777, which is a division of application No. 14/209,827, filed on Mar. 13, 2014, now Pat. No. 9,072,678, said application No. 16/156,949 is a continuation-in-part of application No. PCT/US2017/042798, filed on Jul. 19, 2017.

(60) Provisional application No. 61/786,215, filed on Mar. 14, 2013, provisional application No. 62/515,504, filed on Jun. 5, 2017, provisional application No. 62/466,291, filed on Mar. 2, 2017, provisional application No. 62/378,662, filed on Aug. 23, 2016, provisional application No. 62/363,839, filed on Jul. 19, 2016, provisional application No. 61/946,825, filed on Mar. 2, 2014, provisional application No. 61/934,795, filed on Feb. 2, 2014, provisional application No. 61/820,449, filed on May 7, 2013.

(51) Int. Cl.

| | | |
|---|---|---|
| *A61K 9/06* | (2006.01) | |
| *A61K 9/16* | (2006.01) | |
| *A61K 9/50* | (2006.01) | |
| *A61K 31/337* | (2006.01) | |
| *A61K 31/37* | (2006.01) | |
| *A61K 31/496* | (2006.01) | |
| *A61K 31/573* | (2006.01) | |
| *A61K 31/7036* | (2006.01) | |
| *A61K 31/727* | (2006.01) | |
| *A61K 41/00* | (2020.01) | |
| *A61K 47/02* | (2006.01) | |
| *A61K 47/32* | (2006.01) | |
| *A61K 47/34* | (2017.01) | |
| *A61L 27/22* | (2006.01) | |
| *A61L 27/38* | (2006.01) | |
| *A61L 27/50* | (2006.01) | |
| *A61M 5/32* | (2006.01) | |
| *A61M 37/00* | (2006.01) | |
| *A61L 27/54* | (2006.01) | |
| *A61M 5/30* | (2006.01) | |

(52) U.S. Cl.
CPC .......... *A61K 9/0024* (2013.01); *A61K 9/0048* (2013.01); *A61K 9/0051* (2013.01); *A61K 9/06* (2013.01); *A61K 9/1641* (2013.01); *A61K 9/1647* (2013.01); *A61K 9/1658* (2013.01); *A61K 9/5031* (2013.01); *A61K 9/5052* (2013.01); *A61K 31/337* (2013.01); *A61K 31/37* (2013.01); *A61K 31/496* (2013.01); *A61K 31/573* (2013.01); *A61K 31/7036* (2013.01); *A61K 31/727* (2013.01); *A61K 41/0028* (2013.01); *A61K 47/02* (2013.01); *A61K 47/32* (2013.01); *A61K 47/34* (2013.01); *A61L 27/225* (2013.01); *A61L 27/3804* (2013.01); *A61L 27/50* (2013.01); *A61M 5/3298* (2013.01); *A61M 37/0015* (2013.01); *A61M 37/0076* (2013.01); *A61L 27/54* (2013.01); *A61L 2300/442* (2013.01); *A61L 2400/06* (2013.01); *A61M 5/3015* (2013.01); *A61M 2037/0023* (2013.01); *A61M 2037/003* (2013.01); *A61M 2037/0046* (2013.01); *A61M 2037/0053* (2013.01); *A61M 2205/36* (2013.01); *A61M 2205/3606* (2013.01); *A61M 2205/3633* (2013.01); *A61M 2205/3653* (2013.01); *A61M 2207/00* (2013.01); *C12Y 304/21068* (2013.01); *C12Y 304/24069* (2013.01)

(56) References Cited

U.S. PATENT DOCUMENTS

| | | | |
|---|---|---|---|
| 5,411,554 | A | 5/1995 | Scopelianos et al. |
| 5,529,914 | A | 6/1996 | Hubbell et al. |
| 5,567,435 | A | 10/1996 | Hubbell et al. |
| 5,626,863 | A | 5/1997 | Hubbell et al. |
| 5,631,015 | A | 5/1997 | Bezwada et al. |
| 5,801,033 | A | 9/1998 | Hubbell et al. |
| 5,990,194 | A | 11/1999 | Dunn et al. |
| 6,004,573 | A | 12/1999 | Rathi et al. |
| 6,107,102 | A | 8/2000 | Ferrari |
| 6,323,278 | B2 | 1/2001 | Rhee et al. |
| 6,306,922 | B1 | 10/2001 | Hubbell et al. |
| 6,352,667 | B1 | 3/2002 | English |
| 6,534,591 | B2 | 3/2003 | Rhee et al. |
| 6,566,406 | B1 | 5/2003 | Pathak et al. |
| 6,599,627 | B2 | 7/2003 | Yeo et al. |
| 6,887,974 | B2 | 5/2005 | Pathak |
| 7,009,034 | B2 | 3/2006 | Pathak |
| 7,592,418 | B2 | 9/2009 | Pathak et al. |
| 7,790,141 | B2 | 9/2010 | Pathak et al. |
| 7,919,112 | B2 | 4/2011 | Pathak et al. |
| 8,067,031 | B2 | 11/2011 | Daniloff et al. |
| 8,557,535 | B2 | 10/2013 | Pathak |
| 8,821,945 | B2 | 9/2014 | Imran et al. |
| 9,072,678 | B2 | 7/2015 | Pathak |
| 9,345,777 | B2 * | 5/2016 | Pathak ................ A61K 9/0021 |
| 9,789,073 | B2 | 10/2017 | Pathak |
| 10,123,980 | B2 * | 11/2018 | Pathak ................ A61K 31/496 |
| 10,543,182 | B2 | 1/2020 | Pathak |
| 10,624,865 | B2 | 4/2020 | Pathak |
| 2001/0047153 | A1 | 11/2001 | Trocki et al. |
| 2005/0054969 | A1 | 3/2005 | Hoff et al. |
| 2005/0222565 | A1 | 10/2005 | Manstein et al. |
| 2006/0275310 | A1 | 12/2006 | Dwarakanath et al. |
| 2007/0055179 | A1 | 3/2007 | Deem et al. |
| 2008/0015522 | A1 | 1/2008 | Yeshurun et al. |
| 2009/0082721 | A1 | 3/2009 | Utley et al. |
| 2010/0049178 | A1 | 2/2010 | Deem et al. |
| 2012/0177612 | A1 | 7/2012 | Shyu et al. |
| 2014/0147510 | A1 | 5/2014 | Lahann et al. |
| 2014/0256617 | A1 | 9/2014 | Overstreet et al. |
| 2020/0230081 | A1 | 7/2020 | Pathak |

FOREIGN PATENT DOCUMENTS

| | | | |
|---|---|---|---|
| WO | 2008/066657 | A2 | 6/2008 |
| WO | 2010/065957 | A2 | 6/2010 |
| WO | 2011/089435 | A2 | 7/2011 |
| WO | 2014/160387 | A2 | 10/2014 |
| WO | 2018/017674 | A1 | 1/2018 |

OTHER PUBLICATIONS

M. Rizwan et al.; "pH Sensitive Hydrogels in Drug Delivery: Brief History, Properties, Swelling, and Release Mechanism, Material Selection and Applications"; Polymers, vol. 9, p. 137 (2017).

E. C. Opara et al.; "Microencapsulation of Pancreatic Islets for Use in a Bioartificial Pancreas"; Methods Mol Biol., vol. 1001, p. 261-266 (2013).

S.C. Byalekere et al.; "Evaluation of Microneedling Fractional Radiofrequency Device for Treatment of Acne Scars"; .1 Cutan. Aesthet Surg.; vol. 7(2), p. 93-97 (2014).

(56) References Cited

OTHER PUBLICATIONS

Bauman et al.; "An injectable drug delivery platform for sustained combination therapy"; Journal of Controlled Release, vol. 138(3); pp. 205-213 (May 9, 2009); 9 pages.

Hickerson et al.; "Gene Silencing in Skin After Deposition of Self-Delivery siRNA With a Motorized Microneedle Array Device"; Molecular Therapy-Nucleic Acids (2013) v2, e129; doi:10.1038/mtna.2013.56; 7 pages.

International Search Report and Written Opinion issued in App No. PCT/US2014/026467 dated Sep. 26, 2014; 19 pages.

B. Bediz et al.; "Dissolvable Microneedle Arrays for Intradermal Delivery of Biologics: Fabrication and Application"; Pharm Res.; vol. 31(1), p. 117-135 (2014).

B.M. Torrisi et al.; "Pocketed microneedles for rapid delivery of a liquid-state botulinum toxin A formulation into human skin"; J Control Release.; vol. 165(2), 146-152 (2013).

Xianhua et al.; "Research Progress in Magnesium Alloys as Functional Materials"; Rare Metal Materials and Engineering; vol. 45(9), p. 2269-2274 (2016).
X. Gu et al.; "Biodegradable, elastomeric coatings with controlled anti-proliferative agent release for magnesium-based cardiovascular stents"; Colloids and Surfaces B: Bio-interfaces; vol. 144, p. 170-179 (2016).
International Search Report and Written Opinion issued in app No. PCT/US2017/042798 dated Sep. 27, 2017; 11 pages.
E. Larraneta et al.; "Microneedle arrays as transdermal and intradermal drug delivery systems: Materials science, manufacture and commercial development"; Materials Science and Engineering R; vol. 104, p. 1-32 (2016).
J.Brandrup et al.; Polymer Handbook:; John Wiley & Sons (1999).
G. Orive et al.; Application of cell encapsulation for Controlled Delivery of Biological Therapeutics: Advanced Drug Delivery Reviews; 2014; 12 pages.
D.D. Perrin et al.; "Purification of Laboratory Chemicals"; Pergamon Press, Oxford (1980); 544 pages.
J. Seitz et al.; "Recent Advances in Biodegradable Metals for Medical Sutures: A Critical Review"; Adv. Healthcare Mater.; vol. 4, p. 1915-1936 (2015).
A.B. Nair et al.; "Alteration of the diffusional barrier property of the nail leads to greater terbinafine drug loading and permeation"; International Journal of Pharmaceutics, vol. 375, p. 22-27 (2009).
E. HH. Taudorf et al.; "Fractional Ablative Erbium YAG Laser: Histological Characterization of Relationships Between Laser Settings and Micropore Dimensions"; Lasers in Surgery and Medicine; vol. 46, pp. 281-289 (2014).
L. Y. Yeo et al.; "Microfluidic Devices for Bio-applications"; Small, vol. 7(1), p. 12-48 (2011).
R. G. Willaert et al.; "Microfluidic Bioreactors for Cellular Microarrays"; Fermentation, vol. 1, p. 38-78 (2015).
T.-M. Tuan-Mahmood et al.; "Microneedles for intradermal and transdermal delivery"; European Journal of Pharmaceutical Sciences; vol. 50, p. 623-637(2013).
M.R. Prausnitz et al., "Microneedles for transdermal drug delivery"; Advanced Drug Delivery Reviews; vol. 56, p. 581-587 (2004).

* cited by examiner

Panel 6B-1

Panel 6B-2

Panel 6B-3-1  Panel 6B-3-2

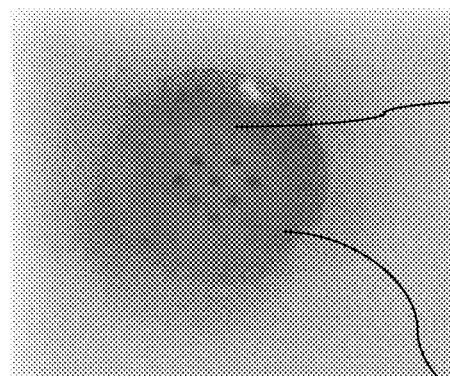
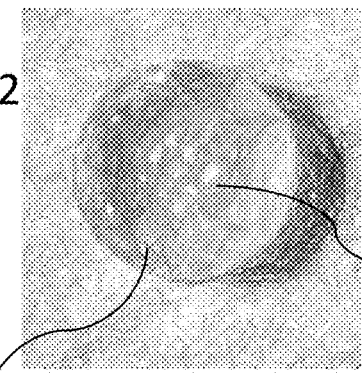
Figure 8A  Figure 8B
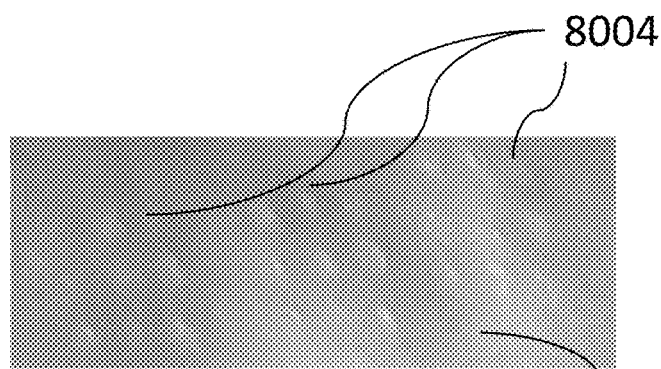
Figure 8C
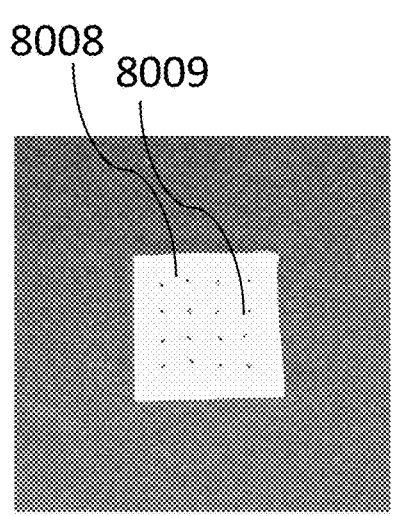
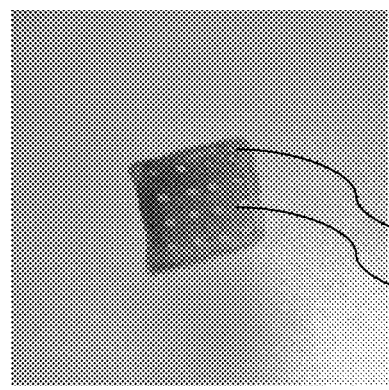
Figure 8D  Figure 8E

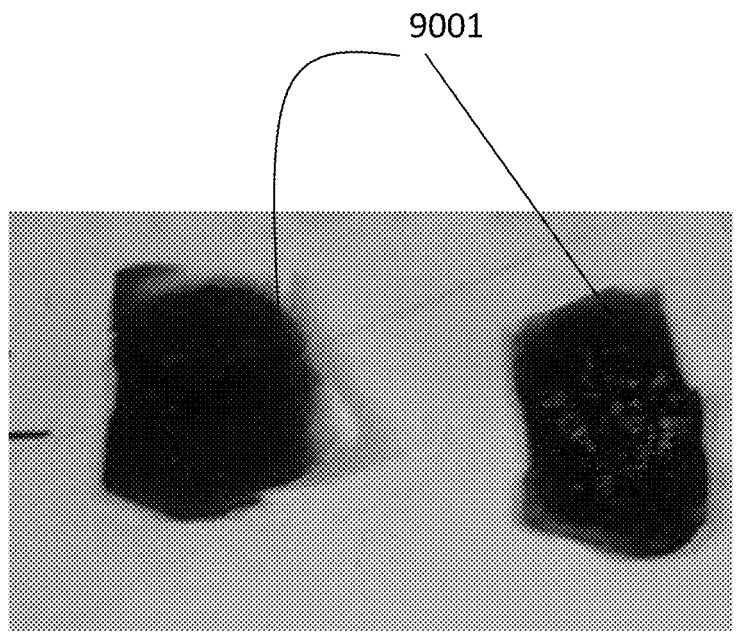
Figure 9A
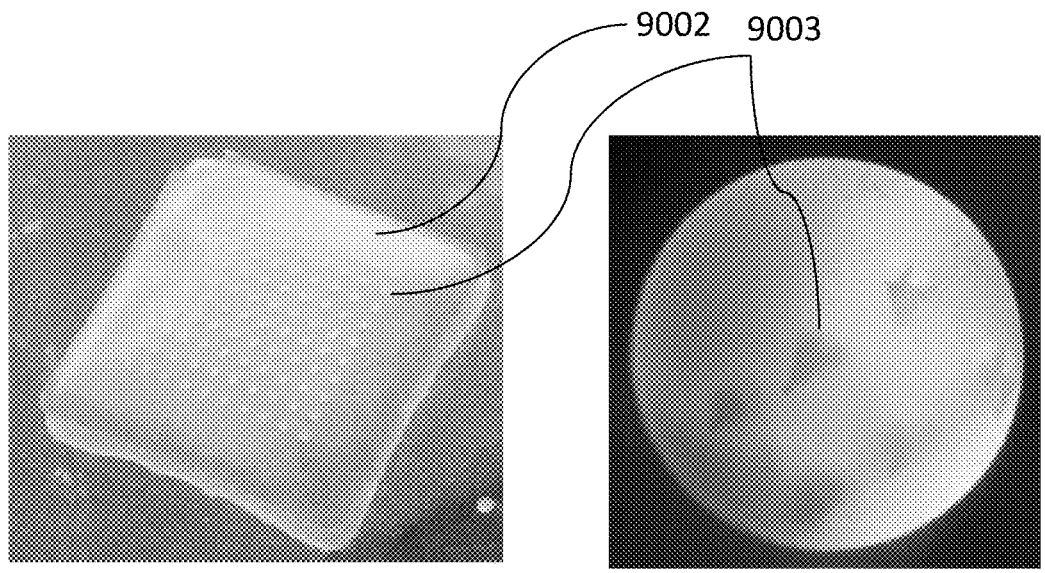
Figure 9B1        Figure 9B2

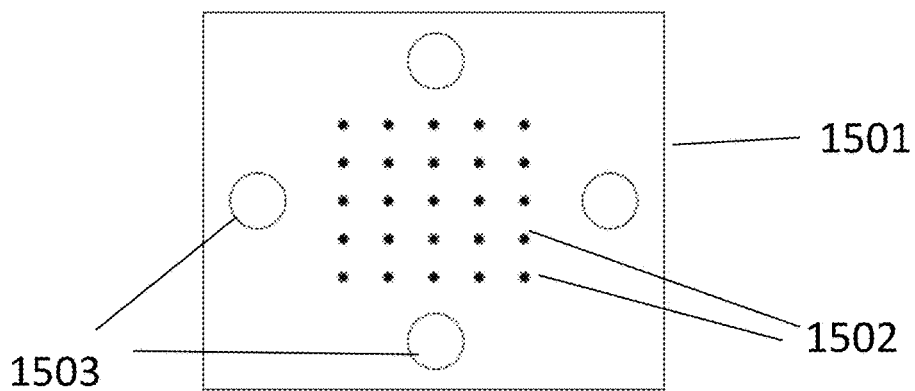
Figure 15A
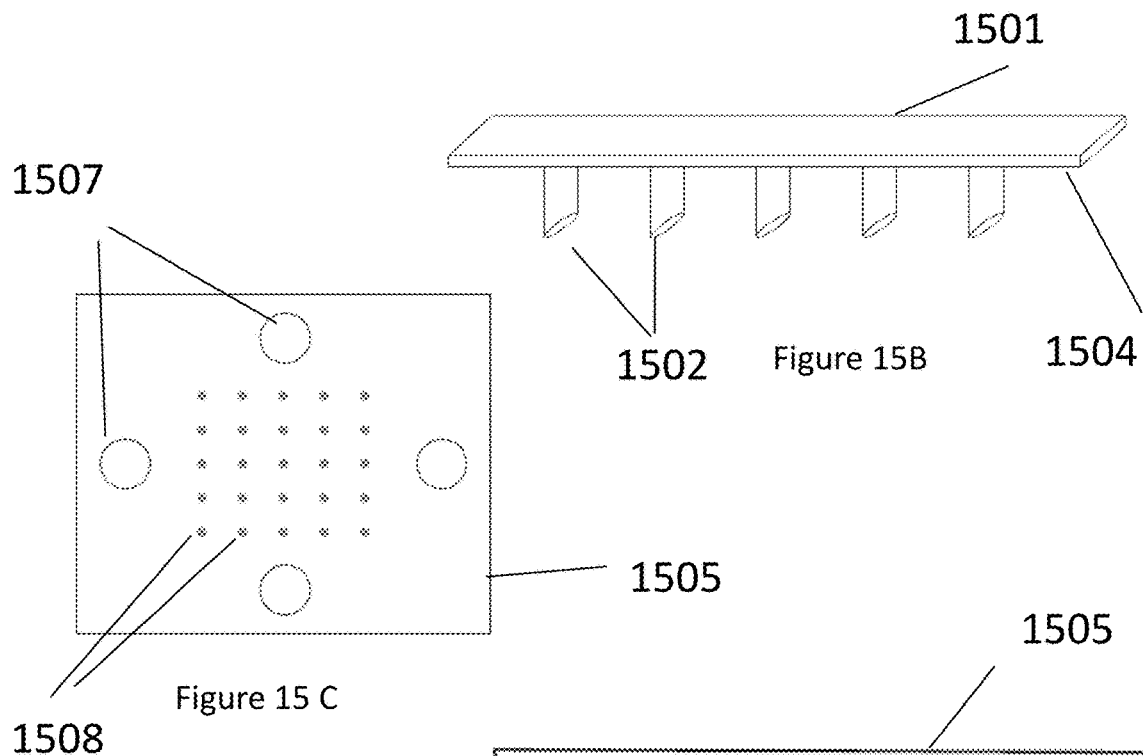
Figure 15B
Figure 15 C
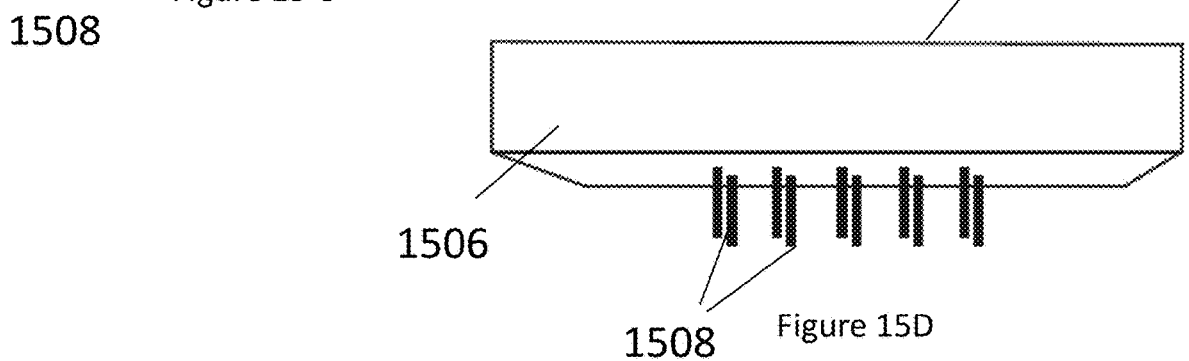
Figure 15D

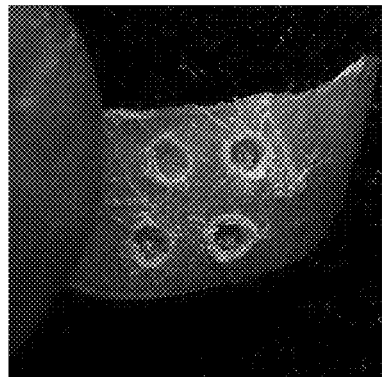
Figure 16A                Figure 16B
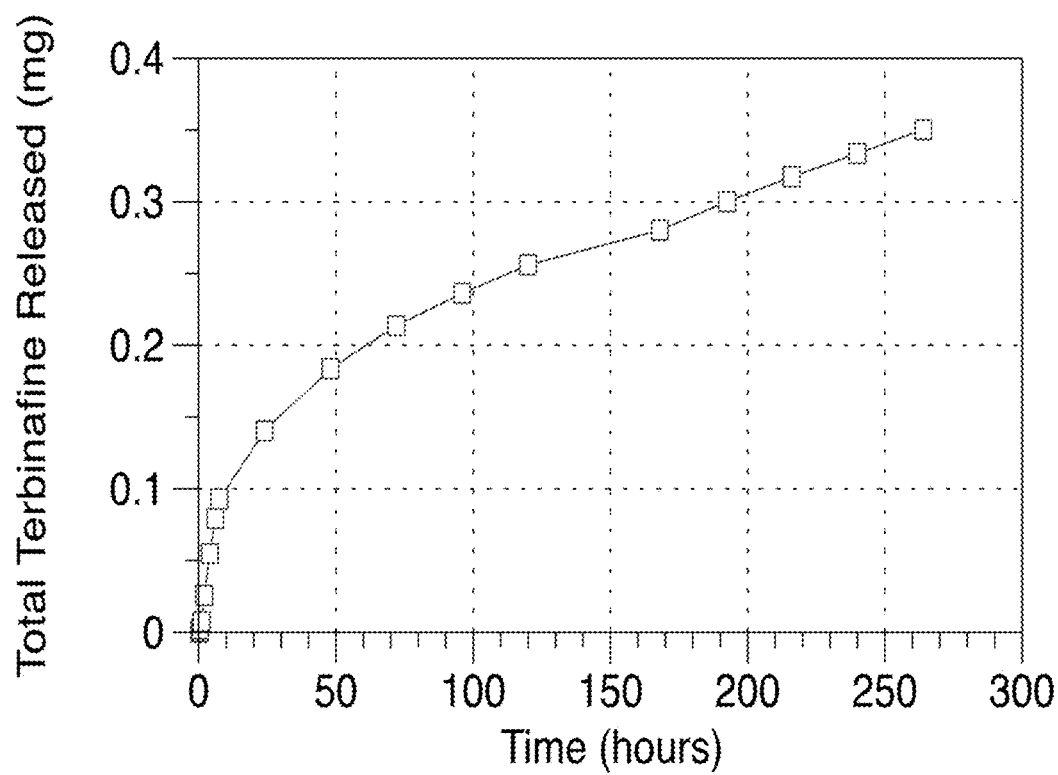
Figure 16C

1901

1902

A

B

C

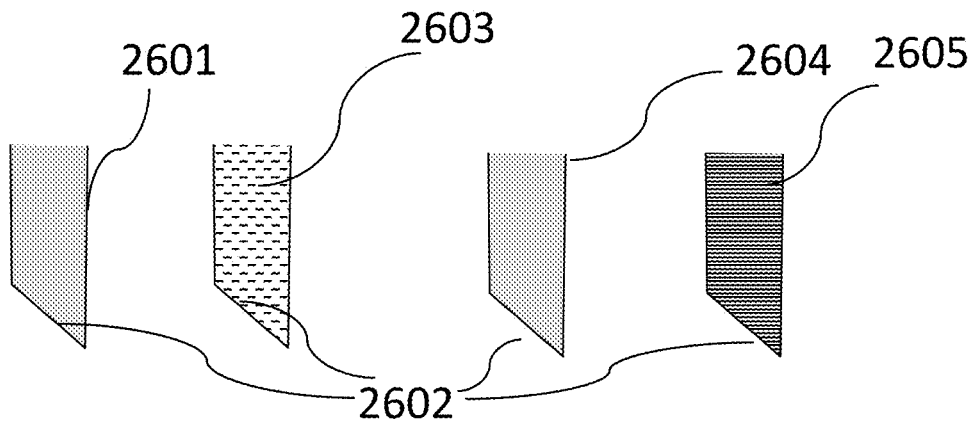
Figure 26A
Figure 26B
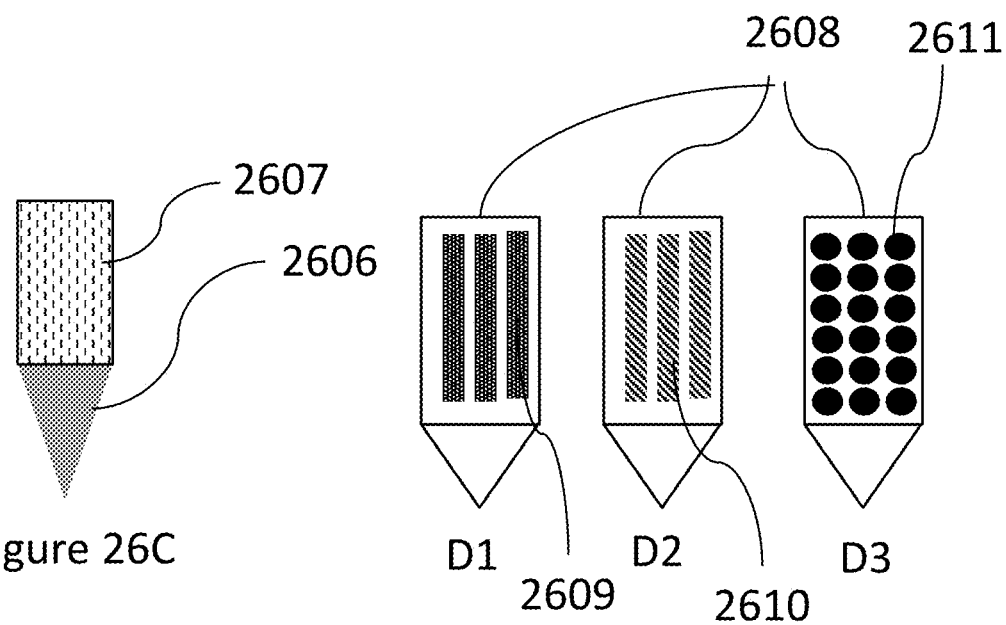
Figure 26C
Figure 26D
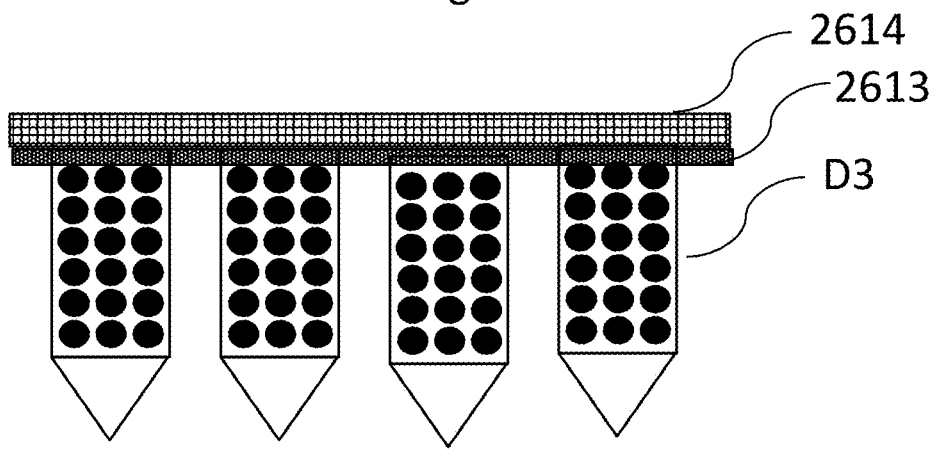
Figure 26E

METHODS, COMPOSITIONS, AND DEVICES FOR MAKING SUSTAINED BIODEGRADABLE IMPLANTS IN TISSUE

CROSS-REFERENCE TO RELATED APPLICATIONS

This application is a continuation of U.S. application Ser. No. 16/818,944 filed Mar. 13, 2020, which is a continuation of U.S. application Ser. No. 16/156,949 filed Oct. 10, 2018, which is a continuation-in-part of International Application PCT/US2017/042798 filed Jul. 19, 2017, which claims priority to: U.S. Provisional Patent Application No. 62/515,504 filed Jun. 5, 2017; U.S. Provisional Patent Application No. 62/466,291 filed Mar. 2, 2017; U.S. Provisional Patent Application No. 62/378,662 filed on Aug. 23, 2016; and U.S. Provisional Patent Application No. 62/363,839 filed on Jul. 19, 2016, each of these applications being herein incorporated by specific reference in their entirety for all purposes.

U.S. application Ser. No. 16/156,949 filed Oct. 10, 2018 is also a continuation-in-part of U.S. patent application Ser. No. 15/704,792 filed Sep. 14, 2017 now U.S. Pat. No. 10,123,980, which is a continuation of U.S. patent application Ser. No. 15/099,456 filed Apr. 14, 2016 now U.S. Pat. No. 9,789,073, which is a continuation-in-part of U.S. patent application Ser. No. 14/736,007 filed Jun. 10, 2015 now U.S. Pat. No. 9,345,777, which is a divisional of U.S. patent application Ser. No. 14/209,827 filed Mar. 13, 2014 now U.S. Pat. No. 9,072,678, which claims priority to each of U.S. Provisional Patent Application No. 61/946,825 filed Mar. 2, 2014; U.S. Provisional Patent Application No. 61/934,795 filed Feb. 2, 2014; U.S. Provisional Patent Application No. 61/820,449 filed May 7, 2013; and U.S. Provisional Patent Application No. 61/786,215 filed Mar. 14, 2013, each of these applications being herein incorporated by specific reference in their entirety for all purposes.

FIELD OF THE INVENTION

This invention generally relates to compositions, methods and devices for drug/live cell delivery as well as their applications. More particularly, the invention relates to compositions, methods and devices for local, and/or systemic sustained drug and live cell delivery, wherein such compositions comprise of drug/live cell microarrays that are made externally or made in situ and delivered in a sustained manner. The drug microarrays may be made from biostable or biodegradable polymer and may also include a colored or fluorescent additive to aid in visualization during the drug delivery. The present invention also relates to methods and devices for preparation and delivery of such compositions. The invention aims to achieve precise control over the drug dose in an implanted microarray to achieve systemic or local therapeutic effect.

BACKGROUND OF THE INVENTION

Prior Art

Sustained Drug Delivery Using Microneedle Array

Drug delivery using microneedle array is rapidly emerging as a new area in the pharmaceutical field. Please refer to recent reviews and references therein by T.-M. Tuan-Mahmood et al. (European Journal of Pharmaceutical Sciences, volume 50, Page 623-637, 2013) and M. R. Parasiteet et al. (Advanced Drug Delivery Reviews, volume 56, page 581-587, 2004 and E. Larraneta et al., Materials Science and Engineering R, Volume 104 Page 1-32, 2016). Microneedle array based systems generally consist of micron size microprojections or microneedles supported on one side with a supporting base or a base patch. The needles typically range in size from 25 microns to 2000 microns and are usually arranged in an array format. The drug is either coated onto or encapsulated in the microneedle array. The array along with its backing materials is pushed on the skin surface where the microneedles penetrate the epidermis and/or dermis tissue and/or muscular tissue. The needles deposit the drug inside the skin tissue where it is made available for local or systemic therapeutic effect. Microneedle array can be made using biodegradable or biostable materials. If made using biostable materials, the drug is generally coated on the array surface or the microarray is used to perforate the skin and the perforations are used to transport the drug solution across the skin barrier. The biodegradable array is left inside the skin tissue after insertion. In either case, the microneedle array must have sharp edges to enable smooth insertion inside the tissue with minimum pressure or force. The sharp edge limits the use of hard/solid materials in making array and soft materials generally cannot be used. The arrays are usually made externally in a pharmaceutical manufacturing environment and subsequently made available for clinical use. There is a strong need for alternative methods and compositions to make microneedle array for local and systemic drug delivery with superior performance and quality.

Treatment of Anemia

Iron deficiency or anemia associated with lack of iron in the blood is one of the most important health issues in the world today, especially, in the third world countries. Iron deficiency affects cognitive development of children from infancy through to adolescence and is believed to be associated with increased morbidity rates. Iron deficiency is generally managed through oral supplements and this is not considered to be very reliable method to manage anemia. Oral therapy not only has lower bioavailability of iron but also has side effects such as constipation. It also has compliance issue because patients may not complete the prescribed oral dose regimen. Severe iron deficiency can be managed via intravenous route but it requires careful monitoring in hospital settings. Clearly there is a need for better methods and compositions that can be useful in managing iron deficiency.

Treatment of Onychomycosis

Onychomycosis or infection of the nail is generally caused by a fungus. The infected nail becomes thick or may become discolored, yellow or green. The infected nail also becomes brittle and flakes off losing its normal shape. The infected nail has a gross look and may adversely affect the cosmetic appearance visually. The oral treatment of antifungal drugs can cause potential side effects to many people (A. B. Nair et al., International Journal of Pharmaceutics, volume 375, page 22-27, 2013). The local application of antifungal drug in the infected nail has penetration issues in the nail body. The drug cannot reach the nail plate which is in a deep part of the nail anatomy where infection generally resides. There is hence a need for newer compositions and methods to manage nail infections.

Surgical Pain Management

Several millions of surgeries are conducted throughout the world every year. Each surgical intervention is generally associated with a surgical pain which is sometimes managed by use of opioids and its derivatives. The use of opioids has side effects such as severe constipation and a potential risk of addiction.

Microimplant Array Containing Live Mammalian Cells

Microneedle arrays are known to deliver vaccines and drug solutions. Prior art is silent on use of this technology for delivery of therapeutic mammalian live cells, especially encapsulated cells. This is probably due to difficulty in making live mammalian cell containing arrays under the conditions which can be tolerated by cells. Hydrogels which are typically used for cells encapsulation are soft (in hydrated format) and array needles made from soft materials do not have sufficient hardness and strength (in hydrated form) to serve as a material for an array needle. In dry form, hydrogels like hyaluronic acid have sufficient strength to be useful as an array material, however mammalian cells cannot survive in the dehydrated dry form. This is especially true for islet cells which are known to control glucose level by secreting insulin on demand. Clearly there is a strong need for compositions, methods and devices which can enable delivery of mammalian cells in the microimplant array format for therapeutic use.

Devices for Implantation of Microimplants in Array Format

Microarray based implants have attracted lot of attention due to their utility in sustained drug delivery and pain free delivery. The use of biodegradable or dissolvable microarray for sustained drug delivery is also known. Microarray based implants known in the prior art must have a sharp edge for easy tissue penetration at distal end and a backing material at proximal end for pushing the implants. The sharp edge and other mechanical properties are generally considered as an essential property for microneedle implantation and it also limits the use of certain softer materials for to be useful as implantable arrays. For example, many hydrogels such as hydrogels used in soft contact lens application in fully hydrated form are soft and mechanically weak and therefore may not have sufficient strength to be implanted in the microneedle array format. Hydrogel materials like hyaluronic acid are generally used in dry format where they have sufficient strength and hardness to penetrate the tissue. It will hence be useful to provide devices and methods for implantation wherein soft materials like hydrogel materials can be implanted in hydrated format without the use of a sharp edge.

Devices and Compositions for Delivery of Drugs, Vaccines or Botulinum Toxin in a Solid State Many injectable drugs like vaccines, protein drugs are sold as solids which are dissolved in saline or other liquids to form an injectable solution. The solution is transferred into a syringe in a sterile manner and then injected subcutaneously/intramuscularly. The injection volume determines the amount of drug injected which needs to be carefully calculated and administered by a trained medical professional staff. The entire procedure requires many steps such as trained medical professional, preparation of solution under sterile condition, filling the solution in a syringe under sterile conditions and injecting a desired volume in the tissue. It will be beneficial to develop compositions and methods that will reduce/eliminate the number of steps involved in injecting a solution and human errors associated with such delivery. The use of one or more sterile needles and syringe and their proper and safe disposal creates additional financial and regulatory cost to the end user. Botox® is a trade name for Botulinum toxin. Botox is neurotoxic protein produced by the bacterium *Clostridium* and is sold to treat variety of medical conditions. Botox is sold as a sterile lyophilized powder which is reconstituted with sterile saline. Each vial contains 50 to 100 units of drug and physician generally dilutes it prior to use with 1-3 ml saline solution. The solution is injected using a fine needle syringe at treatment area and the solution has a recommended shelf life of 48 hours. If a given treatment procedure requires only 10-20 units of the drug, there is a potential to waste rest of the drug solution unless the same solution is used on a different patient within its required shelf life stability. The entire process involves many steps and each step may be prone to human error. Steps like a measuring a sterile saline volume, adding a sterile liquid in vial, filling the syringe with drug solution and the like are handled by trained human personnel. Each human step is prone to error like measurement error, sterility compromise etc. It will be a valuable contribution to the art if some or majority steps in delivering the Botulinum toxin is reduced or eliminated completely. It will be also valuable contribution to the art if the wastage due to limited shelf life of Botulinum toxin solution is reduced and eliminated completely. Removable metal microneedle arrays with liquid delivery of Botox solution has been explored in the past (B. M. Tones et al., J Control Release. volume 165(2), 146-152 (2013)).

Biodegradable Metal Based Drug Delivery Arrays

Biodegradable metal based devices have long history of human use (C Xianhua et al. and X. Gu et al. and cited reference therein, cited herein for reference only). Metal offers remarkable combination of toughness and hardness which is unmatched by other types of materials. However biodegradable metals such as magnesium based alloys generally cannot be used for sustained drug delivery applications. It will be valuable contribution to the art wherein biodegradable metal based microneedle arrays have been designed and used for sustained drug delivery applications. This invention discloses biodegradable devices, designs and compositions based on biodegradable metal.

BRIEF SUMMARY OF THE INVENTION

The present invention addresses the need for compositions, methods and devices for local and systemic sustained drug/cell delivery. Such compositions are made in situ in the body tissue in the form of microimplants incorporating one or more of a drug/cells, a biodegradable or biostable polymer and/or a visualization agent. The present invention is also directed towards methods for synthesizing such drug bearing microimplants in situ by using devices incorporating retrievable microneedle devices. Also provided are devices/apparatus and methods that enable to implant drug/cell containing arrays. The arrays can be prefabricated and then loaded in the inventive devices for therapeutic use.

Accordingly, there is a need for such compositions, methods and devices as summarized herein in some detail.

Therefore, a general aspect of the present invention is to provide methods for sustained drug delivery which are effective at local or systemic level and thereby more efficient and cause minimal side effects.

A further aspect of the present invention is to provide methods for in-situ formation of drug/live cell bearing microimplants in the skin tissue such that larger surface area is available for sustained drug delivery.

Yet another aspect of the present invention is to provide methods for creation of artificial cavities in the skin tissue such that drug bearing microimplants can be disposed within artificial cavities for sustained drug delivery.

A more specific aspect of the present invention is to provide devices capable of delivering compositions in microarray form in the skin tissue in a customized manner and do not require an external manufacturing set up and reduce the associated costs of manufacturing in a factory environment.

Another aspect of the present invention is to provide microarray based compositions that are dissolvable and biodegradable and have therapeutic use.

A further aspect of the present invention is to provide methods and devices capable of creating a plurality of microimplants comprising of drug bearing compositions within the skin tissue, formed in-situ at predetermined location and having a predefined shape and surface area.

Yet another aspect of the present invention is to provide method for treating nail infection. This invention provides methods and compositions to manage such nail infections.

A further aspect of the present invention is to provide methods and compositions for delivery of drugs like Botox in solid state. This invention bypasses the solution making steps and injects the compositions in solid state without forming solution eliminating the use of sterile syringe and needles.

A further aspect of the present invention is to provide a method for treating anemia.

A still further aspect of the present invention is to provide compositions for local anesthetic effect that can be used for surgical pain management. In this invention, compositions and methods for treatment of surgical pain are described. In particular, the inventive compositions and methods deliver bupivacaine based compositions for surgical pain management.

Still another aspect of the present invention is to provide method for efficient insulin delivery.

A further aspect of the present invention is to provide a method for therapeutic cell therapy.

Another aspect of this invention is to form a microimplant array in the live tissue or prosthesis tissue for cell or sustained drug delivery wherein the implanted microimplant does not need a sharp edge. This invention provides devices and methods of implantation wherein microimplant array can be formed from softer materials for sustained drug delivery compositions or with live cells and without the need of sharp edge.

Yet another aspect of the present invention is to provide devices, methods and composition for delivery of Botox and other protein drugs/vaccines in a painless, safe, and hygienic manner in the solid state form, thereby improving the treatment efficacy as well as eliminating problems associated with safe disposal of medical wastes, human effort, error and inaccuracy.

A further aspect of the present invention is to provide additional enhancements and improvements in the process of vaccine delivery methods, including encoding useful information while imparting the vaccines.

One embodiment of the present invention provides a method for creating a drug delivery composition inside the human or animal body wherein the method comprises: creating artificial porosity inside the human body or skin tissue; partially or completely filling the cavity with an injectable composition comprising biodegradable or biostable microparticles suspended in a biocompatible fluid carrier. The preferred compositions comprise visualization agent.

One embodiment of the present invention provides a method for creating a drug delivery composition inside the human or animal body wherein the method comprises: creating artificial porosity inside the human body or skin tissue; partially or completely filling the cavity with an injectable composition comprising liquid carrier and bioactive compound. The injectable composition stays substantially in liquid state for therapeutic effect or until biodegradation process is initiated.

One embodiment of the present invention provides a method for creating a drug delivery composition inside the human or animal body wherein the method comprises: creating an artificial porosity inside the human body or skin tissue; partially or completely filling the cavity with injectable composition comprising biostable or biodegradable melted polymer (melting point 60 degree C. or less) and drug; cooling the composition inside the cavity to body temperature to form a solid or semisolid implant in the cavity.

One embodiment of the present invention provides a method for creating a drug delivery composition inside the human or animal body wherein the method comprises: creating an artificial porosity inside the human body or skin tissue; partially or completely filling the cavity with injectable composition comprising biostable or biodegradable polymer dissolved in a water miscible biocompatible solvent and drug; dispersing the solvent in the surrounding tissue and precipitating polymer in the cavity and entrapping the drug.

One embodiment of the present invention provides a method for creating a drug delivery composition inside the human or animal body wherein the methods comprises: creating an artificial porosity inside the human body or skin tissue; partially or completely filling the cavity with injectable composition comprising crosslinkable polymer precursors and drug/cells; crosslinking the precursors to form crosslinked composition and entrapping the drug/cells; releasing the drug locally from the crosslinked composition for systemic or local therapeutic effect. Preferred crosslinked composition is biodegradable.

One embodiment of the present invention provides a method for creating a drug delivery composition inside the human or animal body wherein the method comprises: creating an artificial porosity inside the human body or skin tissue; partially or completely filling the cavity with injectable composition comprising water insoluble drug solution in a water miscible organic solvent; dispersing the solvent and precipitating the drug crystals/solids inside the cavity. The precipitated drug solids/crystals release the drug by slow dissolution or biodegradation process.

One embodiment of the present invention provides a method for creating a drug delivery composition inside the human or animal body wherein the method comprises: creating an artificial porosity inside the human body or skin tissue; completely or partially filling the porosity with injectable thermoreversible or pH sensitive gelling compositions in fluid state and drug; gelling the composition using thermoreversible property or gelation due to change in pH and entrapping the drug in the gel; releasing the drug locally from the gelled thermoreversible composition for systemic or local therapeutic effect. Preferred thermoreversible composition is biodegradable.

Another embodiment of this invention provides a method for treating nail infection, wherein the method comprises: creating an artificial porosity inside the nail body; filling the porosity with an injectable composition comprising an antifungal or antimicrobial compound. Optionally applying a nail polish or other cosmetic device/coating over the implanted nail surface to improve cosmetic appearance.

Another embodiment of this invention provides a method for treating iron deficiency. The method involves following steps: a) provide an injectable composition comprising iron complex or ferric pyrophosphate dissolved or suspended in a biocompatible liquid; b) injecting the composition using oscillating needle or a microneedle array under the skin; c) dissociating the complex in skin tissue to release the iron. In this invention, iron deficiency is managed by delivery of iron based compositions through the skin using oscillating needle or microneedle array based iron bearing compositions. Iron based microimplants array can be made in situ or may be prefabricated and implanted as described in this invention.

One embodiment of the present invention provides a method for delivering sustained release of bupivacaine composition for local anesthetic effect. The method involves following steps: a) provide an injectable composition comprising bupivacaine dissolved or suspended in a biodegradable polymer dissolved in a water miscible biocompatible solvent; b) injecting the composition using oscillating needle or a microneedle array under the skin; c) dispersing the solvent in the skin tissue and precipitating the polymer under skin and entrapping the bupivacaine; d) releasing the bupivacaine in a sustained manner in the tissue.

Another embodiment of this invention discloses a device wherein the device has inner and outer parts. The device is inserted in the body with inner part inside the outer part; the inner and outer part are separated to create a cavity inside the device. The cavity is then filled with an injectable composition which conforms to the shape of the cavity and then converted into solid or gel state in situ in the cavity. The inner and outer portions of the device are withdrawn leaving behind the formed implant.

Another embodiment of this invention discloses an "array in array" device to form a microimplant array in the body. One of the arrays (outer array) has hollow needles whose cavities may be filled with an injectable composition or a preformed implant with drug or live cells. The other array (inner array) has needles in the same format as outer array that can be easily inserted inside the hollow cavities of the outer array. The needles in the inner array can mechanically, magnetically or via gas pressure push or hold the microimplant in the outer array. The outer array and inner array are removed from the body leaving behind the preformed microimplants or in situ formed microimplants in the body.

Another embodiment of this invention discloses an "array in array" device to form microimplant array in the body. One of the arrays has hollow needles whose cavities may be filled with an injectable composition or preformed implant with drug or live cells. The other array has needles that can be easily inserted inside the hollow needles of the array and can push in situ formed microimplant or preformed microimplant inside the body.

One embodiment of the present invention provides a method for creating a microimplant array comprising live cells inside the human or animal body wherein the method comprises: providing a hollow microneedle array; filling the cavities of hollow microneedle array with hydrogels comprising live cells; inserting the array containing cells inside the body; pushing/expelling hydrogels with cells out of the hollow cavity into the body; removing the hollow array from the body leaving behind the cell based hydrogel array inside the body. The hydrogel used in the array may be biodegradable or biostable. In this invention, compositions, methods and devices are disclosed which enable implant of live cells in an array format. Cells like islet cells implanted in an array format, preferably under the skin, survive and produce insulin on demand. The array like format creates a controlled isolated environment for each cell or group of cells where each cell in the array can get nutrients from the surrounding tissue and provide needed therapeutic compounds such as insulin on demand. If desired, cells may be immuno isolated by using microencapsulation techniques known in the prior art before implantation in the array format. Cells may also be encapsulated during the implantation in an array format.

This invention provides methods, devices and compositions to create mammalian cell based array in live tissue.

One embodiment of this invention provides a dissolvable microimplant array based compositions comprising iron salts.

One embodiment of this invention provides a biodegradable microimplant array based compositions comprising cells for therapeutic use. The preferred compositions comprise biodegradable hydrogels with live mammalian cells implanted in the skin or body in an array format.

One embodiment of this invention provides a biodegradable microimplant array based compositions comprising crosslinked polyethylene glycol based synthetic biodegradable crosslinked gels. The crosslinked gels are made by free radical polymerization of biodegradable macromonomers. The crosslinked gels also can be made by condensation polymerization by reaction of polyethylene glycol comprising precursors. The PEG based precursors with nucleophilic and electrophilic reactive groups having at least five total reactive groups are reacted to produce crosslinked gels.

One embodiment of this invention provides a biodegradable hydrogel based microimplant array compositions that are reinforced using biodegradable microparticles/microspheres or inorganic or organic water soluble biocompatible salts like sodium chloride.

One embodiment of this invention provides biodegradable microarray based compositions comprising polyethylene glycol based degradable polymers such as polyethylene glycol-polylactone block copolymers, PEG-polytrimethylene carbonate block copolymers.

Another embodiment of this invention discloses an apparatus for making microimplant array in the tissue. The apparatus has specialized needles which can be inserted in the body at desired depth and a cavity is then created inside the needle while in the tissue. The cavity can be filled with the injectable composition which may form in situ implant in the needle. After implant is formed, the needle can be pulled from the tissue leaving behind the implant.

Another embodiment of this invention discloses a device for making biodegradable microimplant array in the tissue. The device has specialized biodegradable metal microneedles which are coated or infused with biodegradable drug delivery composition and has a flexible backing that enables insertion of arrays in the skin tissue. This invention discloses biodegradable devices, designs and compositions based on biodegradable metal. The inventive devices are biodegradable metal based microneedle implantable arrays for sustained drug or live cell delivery.

One embodiment of this invention provides biodegradable microarray based compositions comprising Botulinum toxin wherein each array needle comprises a bulking agent and total Botulinum toxin concentration in each array needle ranges from 0.01 units to 5 units. In this invention, the use of making Botulinum toxin solution prior to delivery is completely eliminated and the drug is delivered in the treatment area in the solid-state microimplant form where it dissolves in situ in the tissue and provides therapeutic action. The preferred compositions are fluorescent/colored microimplants which deliver the Botulinum toxin as a solid microimplant.

One embodiment of this invention provides injectable compositions for sustained drug delivery comprising biodegradable polymer solution in water miscible organic solvent and biodegradable inorganic salt/s polymeric/hydrogel microparticles as filler materials. Preferably polymeric materials are crosslinked.

According to one embodiment of the present invention, an "array in array" (AIA) device comprises: a base array, a plunger array, and optionally a spacer lock. The base array further comprises a base array plate, having a top surface and a bottom surface, and a plurality of hollow microneedles provided in an array format provided on the bottom surface of the base array plate. Optionally, a plurality of guiding posts may be provided on the bottom top surface of the base array plate. The plunger array further comprises a plunger array plate, having a top surface and a bottom surface, and a plurality of solid microneedles provided in an array format on the bottom surface of the plunger array plate. Optionally, a plurality of guiding holes may be provided on the plunger array plate. The base array and the plunger array are vertically aligned and dimensionally characterized, such that the plurality of solid microneedles of the plunger array is smoothly inserted in the plurality of the hollow microneedles of the base array.

The foregoing discussion summarizes some of the more pertinent objects of the present invention. These objects should be construed to be merely illustrative of some of the more prominent features and applications of the invention. Applying or modifying the disclosed invention in a different manner can attain many other beneficial results or modifying the invention as will be described. Accordingly, referring to the following drawings may have a complete understanding of the invention.

BRIEF DESCRIPTION OF THE DRAWINGS

The above-mentioned and other features and advantages of this present disclosure, and the manner of attaining them, will become more apparent and the present disclosure will be better understood by reference to the following description of embodiments of the present disclosure taken in conjunction with the accompanying drawings, wherein:

FIGS. 8A, 8B, 8C, 8D and 8E shows representative images of cavities formed in tissue or gelatin gel and then filled with injectable compositions like biodegradable polymers with drug and/or visualization agent.

FIG. 9A shows a representative photographic image of iron containing implant formed inside the tissue using methods described in this invention.

FIG. 9B1 depicts a photographic image of 10×10 microimplant array made from sodium hyaluronate and iron pyrophosphate.

FIG. 9B2 shows a microscopic image of a sharp tip of one of the needles of array shown in FIG. 9B 1.

FIGS. 15A-15F show illustrative images of microneedle "array in array" working device for in situ casting of microimplant or in situ insertion prefabricated microimplants made in accordance with one embodiment of the present invention.

FIGS. 16A, 16B and 16C show creation of artificial cavities in an array format in parts of a human nail, and the release profile of the antifungal drug from the biodegradable array made in accordance with one embodiment of the present invention.

FIG. 19A shows image of 4 by 4 microimplant array made in sheep skin, where the array is an exemplary synthetic biodegradable crosslinked hydrogel (white colored, opaque) containing magnesium carbonate encapsulated microparticles as a visualization agent. FIG. 19B shows image of 10 by 10 microimplant array made in sheep skin, where the array is an exemplary liquid carrier vitamin E acetate containing tea stained magnesium carbonate (red colored) added as a visualization agent, and the array is liquid at ambient/body temperature.

FIG. 21A shows steps involved in making the implant with filler.

FIG. 22A shows a microneedle array containing 20 microneedles used to create 20 micro cavities per insertion in the tissue. FIG. 22B shows 33MP hollow microneedle array with 3 by 3 hollow microneedles attached to a syringe containing injectable composition (PDLG 5002 biodegradable polymer solution in DMSO with methylene blue as a visualization agent). FIG. 22C shows a 3 by 3 array of fluorescent biodegradable cylindrical rods (100 microns diameter and 1000 microns height prepared by slicing 100 micron diameter fluorescent thread) and inserted in the tissue to form microimplant array. FIG. 22D shows image of 4 by 4 microimplant array made in sheep skin, where the array is an exemplary synthetic biodegradable thermosensitive polymer hydrogel containing rifampin encapsulated microspheres (red colored) for sustained drug delivery as well as visualization agent.

FIG. 26A to 26E show partial schematic representation of various configurations of degradable metal based, preferably magnesium alloy based, microneedles arrays that can be useful in sustained drug delivery applications.

Figure 1A:
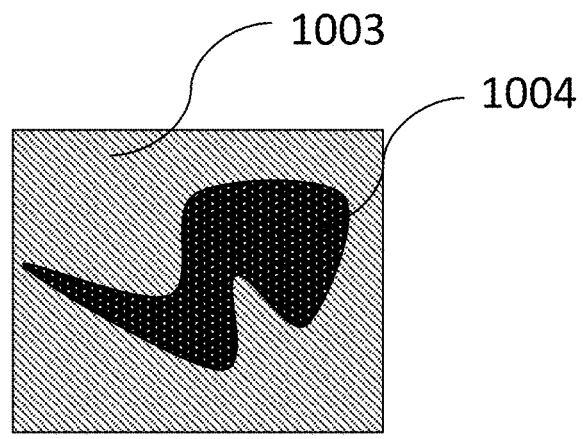
FIGS. 1A, 1B and 1C are partial schematic representative diagrams illustrating the comparison of an array formed by a conventional injectable in situ gelation drug delivery system as known in prior art (FIGS. 1A and 1B) and microimplant array comprising drugs/cells formed by methods disclosed in this invention (FIG. 1C).

The figures are not necessarily drawn to scale unless specifically indicated.

DETAILED DESCRIPTION OF THE INVENTION

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting. Exemplary embodiments of the present invention are directed towards compositions, methods and devices for facilitating local and sustained drug/cell delivery.

It is advantageous to define several terms, phrases and acronyms before describing the invention in detail. It should be appreciated that the following terms are used throughout this application. Where the definition of terms departs from the commonly used meaning of the term, applicant intends to utilize the definitions provided below, unless specifically indicated. The following definitions are provided to illustrate the terminology used in the present invention. Unless defined otherwise, all technical and scientific terms used herein have the same meaning as is commonly understood by one who is skilled in the art. All scientific literature and patent citations in this invention are incorporated herein for reference use only.

"Crosslinked material" is meant to denote the formation of intermolecular or intramolecular covalent bonds in the macromolecule or polymer. The crosslinked material may be in a highly hydrated state.

A "crosslinking agent" is defined as a compound capable of forming crosslinked material. For example, glutaraldehyde is generally known in the art as crosslinking agent for the tissue or with albumin or with collagen.

"In situ" is meant to denote at a local site, especially within or in contact with living organisms, tissue, skin, organs, or the body.

"Bioprosthesis" is defined to include any prosthesis, which is derived in whole or in part from animal or other organic tissue including cultured tissue and which is suitable for human or animal implantation.

The term "tissue/s" incorporates live human or explanted animal tissue for bioprosthesis used. Generally human organ tissue surface is used in most cases. The term tissue includes but is not limited to skin tissue, nails, bones, internal organ tissue surfaces such as beating heart tissue surface, arterial tissue surface accessed via catheter based MIS surgical techniques, abdominal tissue surface, peritoneal cavity surface, internal organ surfaces such as liver, large and small intestine surface, lung surface and the like. The preferred tissue surface is a skin tissue surface, membrane like tissue surface like pericardium tissue, bladder tissue and the like and the most preferred tissue is epidermal, dermal tissue or muscular tissue of the human body. The term 'tissue' also includes bioprosthesis tissue surface such as heart valve bioprosthesis, tissue based hernia patch, tissue based surgical patch, animal tissue based wound dressings and the like.

"Bioactive" refers to one or all of the activities of a compound that show pharmacological or biological activity in human or animal body. Such biological activity is preferred to have a therapeutic effect. Substances or compounds that are bioactive are referred to as "drugs" or "bioactive compounds." The bioactive compounds that can be used include, but are not limited to, antiviral agents; antiinfectives such as, by way of example, and not limitation, antibiotics; antiviral agents, antifungal agents, antibacterial agents, antipruritics; anticancer agents, antipsychotics; cholesterol- or lipid-reducing agents; cell cycle inhibitors; antiparkinsonism drugs; HMG-CoA inhibitors; antirestenosis agents; anti-inflammatory agents; antiasthmatic agents; anthelmintic; immunosuppressives; muscle relaxants; antidiuretic agents; vasodilators; nitric oxide; nitric oxide-releasing compounds; beta-blockers; hormones; antidepressants; decongestants; calcium channel blockers; growth factors such as, by way of example, and not limitation, bone growth factors or bone morphogenic proteins; wound healing agents; analgesics and analgesic combinations; local anesthetic agents; antihistamines; sedatives; angiogenesis-promoting agents; angiogenesis-inhibiting agents; tranquilizers and the like; cellular elements, which can be used for therapeutic use, include, but are not limited to mammalian cells including stem cells; cellular components or fragments, enzymes, DNA, RNA, and genes may also be included as bioactive components or drugs. Extensive list of bioactive compounds or drugs that may be used can be found in U.S. Pat. No. 8,067,031 cited herein for reference only.

The terms "Biodegradable" "Bioerodible" and "Bioabsorbable" have the same meaning unless specified. The terms are meant to denote a material or substance, that will degrade in a biological environment such as human body by either a biologically assisted mechanism, such as an enzyme catalyzed reaction or by a chemical mechanism which can occur in a biological medium, such as hydrolysis or by a dissolution mechanism in which the substance dissolves and is removed safely without any degradation.

"Biostable" is meant to denote a high chemical stability of a compound in an aqueous environment, which is similar to the environment found in the human body such as phosphate buffered saline (pH 7.2).

The term "biodegradable polymers" may include polymers or macromolecules which degrade/dissolve safely in the biological environment such as in human body. The term applies to polymers that are hydrophobic or hydrophilic. The term is applicable to polymers that are crosslinked or non-crosslinked. The crosslinking may be done via condensation polymerization or via free radical polymerization or via ionic bonding. The biodegradable polymers may be random or block or graft copolymers. The biodegradable polymers may be linear, graft, dendramer or branched. The hydrophobic biodegradable polymers include, but are not limited to, polymers, dendramers, copolymers or oligomers of glycolide, dl-lactide, d-lactide, l-lactide, caprolactone, dioxanone and trimethylene carbonate; degradable polyurethanes; degradable polyurethanes made by block copolymers of degradable polylactone such as polycaprolactone and polycarbonate such as poly(hexamethylene carbonate); tyrosine-derived polycarbonates, tyrosine-derived polyacrylates; polyamides; polyesters; polypeptides; polyhydroxyacids; polylactic acid; polyglycolic acid; polyanhydrides; and polylactones. Biodegradable polymers also include polyhydroxyalkanoates, which are polyesters produced by microorganisms including and not limited to poly(3-hydroxybutyrate), 3-hydroxyvalerate, 4-hydroxybutarate, 3-hydroxyhexanoate, 3-hydroxyoctanoate.

The term applies to hydrophilic polymers, which include, but are not limited to, polyethylene glycol-polyhydroxy acid or polyethylene glycol-polylactone copolymers (PEG-PL copolymers); polyvinyl alcohol-co-polylactone copolymers; and derivatives of cellulose; collagen or modified collagen derivatives; gelatin; albumin or crosslinked albumin; fibrinogen; keratin; starch; hyaluronic acid and dextran.

The term "biostable polymers" include but are not limited to aliphatic and aromatic polyurethanes; polycarbonate polyurethane; polyether polyurethane; silicone polyurethane block copolymers; silicone rubbers; polydimethylsiloxane copolymers; polytetrafluoroethylene and other fluorinated polymers; expanded polytetrafluoroethylene; polyethylene; polyesters, polyethylene terephthalate, polyimides, polypropylene; polyamide; polyamide block copolymers and the like. The polymers must be biocompatible and suitable for implantation in the human or animal body.

"Sustained release" or "controlled drug delivery" or "long term release" or "deliveries" are phrases used interchangeably herein, to mean longer than the expected delivery of a bioactive compound from the inventive composition. Typically, delivery will be at least for one hour or more, two to six hours or more, and may extend to one day, few days, weeks, months to few years. The long term release can be achieved by any of a number of known or yet to be discovered or unknown mechanisms.

A "hydrogel" as used herein, refers to a semisolid composition constituting a substantial amount of water, and in which polymers, macromolecules or non-polymeric materials or mixtures thereof are dissolved or dispersed. The polymers may be physically or chemically crosslinked or not crosslinked.

Polyethylene glycol (PEG) or polyethylene oxide (PEO) refers to the same polymer, which is made by polymerization of ethylene oxide.

Polypropylene glycol (PPG) or polypropylene oxide (PPO) refers to the same polymer, which is made by polymerization of propylene oxide.

Polymeric nomenclature used in this patent application such as poly (ethylene glycol) or polyethylene glycol or polyethyleneglycol refer to the same polymer, unless otherwise stated clearly. This is also true for all others polymers referred in this patent application.

The term "micron" means a length of $1/1000000$ of a meter.

The term "micro-implant/s" "microimplant/s" has same meaning. Microimplants are small size implants with an implant volume of 0.05 ml or less.

The term "microimplant array" is defined as group of, two but preferably three or more microimplants arranged or implanted in symmetrical or non-symmetrical fashion. A simple symmetric microimplant array may have rows and columns. The microimplants in the array are in close proximity with each other, such as having a separate distance of range of 10 microns to 5 mm.

The term "macromonomer" or "macromer" refers to oligomeric or polymeric materials capable of undergoing free radical polymerization.

The term "hydrophobic" is defined as a property of materials or polymers or macromolecules having a low degree of water absorption or attraction.

The terms "coloring compositions" include any coloring composition or chemical that is suitable for human or animal implantation and are preferably approved by FDA for use in implantable medical devices. The compounds include but are not limited to: Methylene blue; Eosin Y; Fluorescein sodium; Chromium-cobalt-aluminum oxide; Ferric ammonium citrate; Pyrogallol; Logwood extract; 1,4-Bis[(2-hydroxy-ethyl)amino]-9,10-anthracenedione bis(2-propenoic) ester copolymers(3; 1,4-Bis [(2-methylphenyl)amino]-9,10-anthracenedione; 1,4-Bis[4-(2-methacryloxyethyl) phenylamino] anthraquinone copolymers; Carbazole violet; Chlorophyllin-copper complex, oil soluble; Chromium-cobalt-aluminum oxide; Chromium oxide greens; C.I. Vat Orange 1; 2-[[2,5-Diethoxy-4-[(4-methylphenyl)thiol] phenyl]azo]-1,3,5-benzenetriol; 16,23-Dihydrodinaphtho [2,3-a:2',3'-i] naphth [2',3':6,7] indolo [2,3-c] carbazole-5,10,15,17,22,24-hexone; N,N'-(9,10-Dihydro-9,10-dioxo-1,5-anthracenediyl) bis benzamide; 7,16-Dichloro-6,15-dihydro-5,9,14,18-anthrazinetetrone; 16,17-Dimethoxydinaphtho (1,2,3-cd:3',2',1'-lm) perylene-5,10-dione; Poly(hydroxyethyl methacrylate)-dye copolymers: one or more of Reactive Black 5; Reactive Blue 21; Reactive Orange 78; Reactive Yellow 15; Reactive Blue No. 19; Reactive Blue No. 4; C.I. Reactive Red 11; C.I. Reactive Yellow 86; C.I. Reactive Blue 163; C.I. Reactive Red 180; 4-[(2,4-dimethylphenyl)azo]-2,4-dihydro-5-methyl-2-phenyl-3H-pyrazol-3-one; 6-Ethoxy-2-(6-ethoxy-3-oxobenzo[b] thien-2(3H)-ylidene) benzo[b]thiophen-3(2H)-one; Phthalocyanine green; Iron oxides; Titanium dioxide; Vinyl alcohol/methyl methacrylate-dye reaction products; one or more of: (1) C.I. Reactive Red 180; C.I. Reactive Black 5; C.I. Reactive Orange 78; C.I. Reactive Yellow 15; C.I. Reactive Blue No. 19; C.I. Reactive Blue 21; Mica-based pearlescent pigments; Disodium 1-amino-4-[[4-[(2-bromo-1-oxoallyl)amino]-2-sulphonatophenyl]amino]-9,10-dihydro-9,10-dioxoanthracene-2-sulphonate (Reactive Blue 69); D&C Blue No. 9; D&C Green No. 5; [Phthalocyaninato(2-)] copper; FD&C Blue No. 2; D&C Blue No. 6; D&C Green No. 6; D&C Red No.

17; D&C Violet No. 2; D&C Yellow No. 10; and the like. Preferred colored compositions are biodegradable.

The term "minimally invasive surgery" or (MIS) is used herein includes, but is not limited to, surgical techniques such as, by way of example, and not limitation, laparoscopy, thoracoscopy, arthroscopy, intraluminal endoscopy, endovascular techniques, catheter-based cardiac techniques (such as, by way of example, and not limitation, balloon angioplasty), and interventional radiology.

The term "hydrophilic" is defined as a property of materials or polymers or macromolecules having a strong affinity for water.

"Polylactic acid" or "poly(lactic acid)" or "poly(lactide)" or PLA is term used for a polymer which is made from lactide or lactic acid. Similarly, PGA is a term used for polyglycolic acid or polyglycolate. Some synthetic biodegradable polyesters polymers are generally referred to as polylactones or polyhydroxyacids. The terms "PLGA" and "PDLG" refer the same polymer and is a copolymer of PLA and PGA.

The term "oscillating" used in this patent application refers to and from motion of a needle along its transversal axis and preferably perpendicular to the tissue.

The term "polymerizable" denotes the characteristic of molecules that have the capacity to form additional covalent bonds resulting in monomer and/or monomers interlinking to oligomer or polymer formation, for example, molecules contain carbon-carbon double bonds of acrylate-type molecules. Such polymerization is characteristically initiated by free-radical formation, for example, resulting from photon absorption of certain dyes and chemical compounds to ultimately produce free radicals. The term polymerizable is also applicable to compounds, which can undergo condensation polymerization and form a linear or crosslinked polymer.

The term "water soluble" generally refers to solubility of a compound in water wherein the compound has a solubility of greater than 5 g/100 g, preferably greater than 1 g/100 g in water or buffered water solutions.

The term "water insoluble" generally refers to solubility of a compound in water wherein the compound has a solubility of less than 5 g/100 g, preferably less than 1 g/100 g in water or buffered water solutions.

The term "imaging agent(s)" or "visualization agent(s)" includes any medical imaging agent that helps to visualize the human body/tissue using naked human eye or using machine assisted viewing. The term generally applies to but not limited to: coloring compositions that induce color to medical devices and drug delivery compositions (as defined above), radio-opaque contrast agents that help to visualize organs/tissues using x-ray imaging techniques, NMR contrast agents that assist in MRI imaging techniques and the like.

The term "cavity" is defined as an empty space or void in an otherwise in the live tissue or bioprosthesis tissue. The cavity may be filled with injectable compositions, biological fluids, air or gas. Also, the "cavity" that is within a medium, such as live or prosthetic tissue, or other medium may be a "formed cavity" that is formed into the medium so that the "cavity" remains in the medium after formation. The medium may also be a gel, hydrogel, or other medium that can retain a "formed cavity" by the processes described herein. Once the "cavity" is formed, the medium becomes a "cavity-containing medium."

The term "porosity" is defined as the presence of pores, voids, cavities, grooves, pockets and indentations within a tissue. The phrases "creation of artificial cavities" and "creation of artificial porosities" have been used synonymously in this application and mean the same.

The term "cell/s" are defined as mammalian cells that can be grown as primary cultures as well as established mammalian cell lines, including transformed cells. Stem cells which can be converted into any type cells when provided with proper biological or chemical stimulus are most preferred.

The cells include but are not limited to human foreskin fibroblasts, pancreatic islet cells, dopamine secreting ventral mesencephalon cells, adrenal medulla cells, beta cell insula's, lymphoblastic leukemia cells, T-cells, Chinese hamster ovary cells, mouse 3T3, fibroblasts and neuroballistic cells and the like. Mammalian cells obtained from various organs such as brain, kidney, heart, liver, skin, pancreas, intestine, lung, muscle, artery, immune cells and the like. Additionally, therapeutic enzyme systems, therapeutic bacteria, therapeutic virus, therapeutic genes, hormones, and retroviruses for gene therapy may be referred as cells.

The term "unibody" is defined as a solid mass which when pushed at one end from the device, is pushed out at the other end without breaking or substantially changing its shape. An example of unibody is solid PLGA or HDPE plastic cylinder when pushed out from one end of the device, comes out at the other end as a cylinder. A loose dry powder filled inside the device is not considered as unibody implant as some of the powder particle may stay in the device. However, the same particles may be encased or encapsulated in a hydrogel or other material and can then form a unibody implant which may be pushed out from the device into the body as a unibody implant. The same particles may be partially or completely fused or sintered to form a unibody. The same particles may be bound using an adhesive or other binders to act as a unibody implant. The term "biodegradable unibody forming matrix" is defined as any biodegradable compound including biodegradable polymers and non-polymers such as sugars that has capability to from a unibody microimplant. In some instances a "unibody" may contain cracks, fissures, separations, or imperfections, but when formed as described herein may be considered to be a "unibiody."

The present invention is now described with reference to the drawings.

Figure 1B:
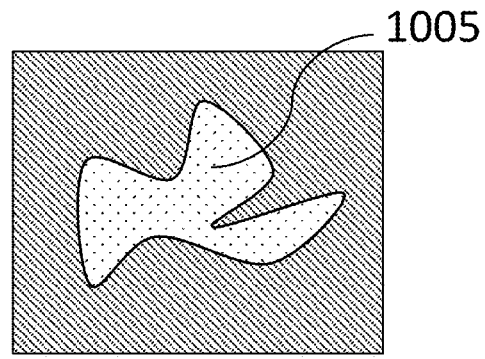
Figure 1C:
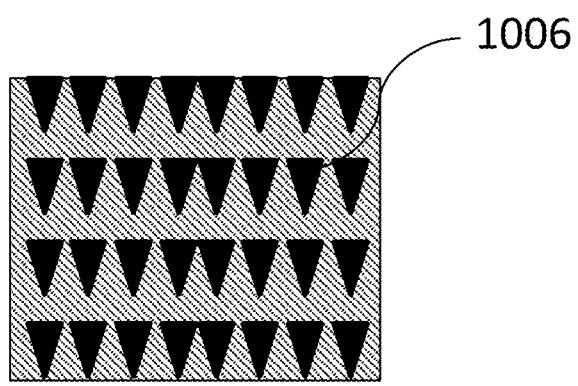

FIGS. 1A, 1B and IC show partial and schematic representation of in situ generated drug delivery implant made using conventional syringe based method and array based methods described in this invention. FIG. 1A shows an injectable composition that is injected as a crosslinkable precursor fluid/liquid from a conventional syringe using intramuscular injection into muscular tissue (1003). The precursor liquid forms a gel or polymer in situ inside the intramuscular tissue as a single solid implant having an irregular shape. The formed implant may have drug or cells entrapped in the implant. As depicted in FIGS. 1A, 1B, the implant (1004 or 1005) is created without creating any artificial cavity prior to injection. FIG. 1B shows an injectable composition comprising biodegradable microspheres with drugs (1005) and FIG. 1A shows encapsulated microspheres with cells (1004) injected into muscular tissue (1003). Some of the microspheres/cells in the 1004 or 1005 implants, typically the middle portions of 1004 or 1005, are in contact with itself and not with the surrounding tissue. This can potentially affect the in vivo drug release profile. This isolation of the implant from the muscular tissue can prohibit cells to get required nutrients from the tissue thereby potentially reducing cell viability. Microimplant array with drugs or cells (1006) formed using methods, compositions and apparatus described in this invention is shown in FIG. 1C. The microimplant array shows well defined shape and several microimplants are formed, hence providing large surface area. Due to uniform separation of microimplants, each microimplant is surrounded by a tissue enabling better drug diffusion and also helps access nutrients for the cells from the tissue.

Figure 2:
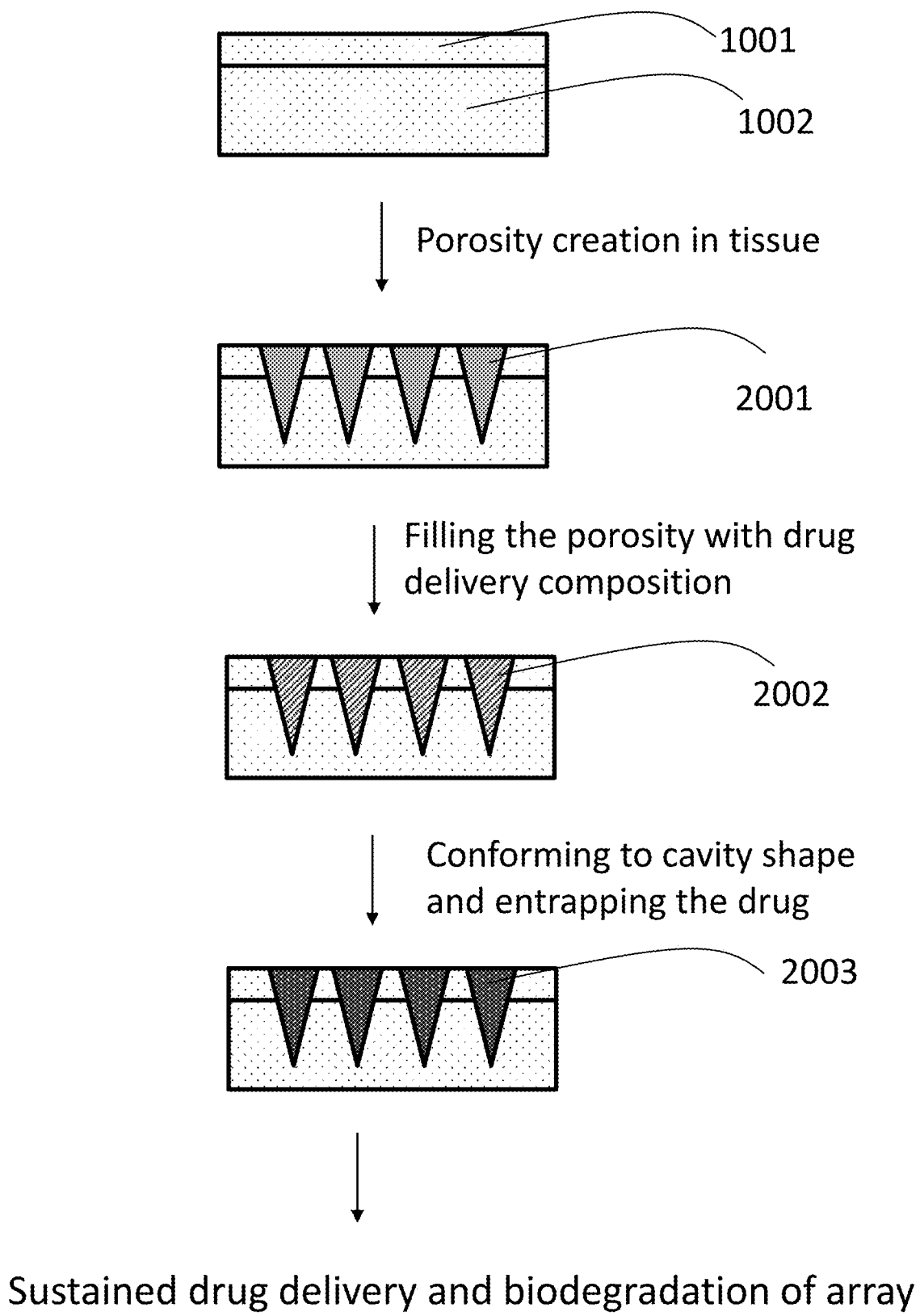
FIG. 2 is a partial schematic representative diagram illustrating a method for forming drug delivery implants in the tissue wherein the artificial cavities are formed first and then are filled with the injectable drug delivery compositions.

A partial and schematic representation of making in situ generated drug delivery array for sustained drug delivery is shown in FIG. 2. A partial schematic of skin tissue is represented by epidermis (1001) and dermis (1002) layers. Artificial porosity is generated in the epidermis and/or dermis layer by many methods known in the art or described in this invention. Artificially created cavities in the skin tissue are schematically shown as conical shaped cavities (2001), as an illustrative example. The cavities (2001) are then filled with fluid injectable drug delivery composition/s comprising drug/s or bioactive compound/s or live cells (2002). Optionally the fluid composition is converted into solid or semisolid or hydrogel (2003) by physical and/or chemical means and entrapping the drug/cells in the in situ formed solid or gel. The drug is released from the solid or gel in the surrounding tissue by diffusion and/or biodegradation or combinations thereof processes. Live cells in the array can also perform therapeutic function.

Figure 3:
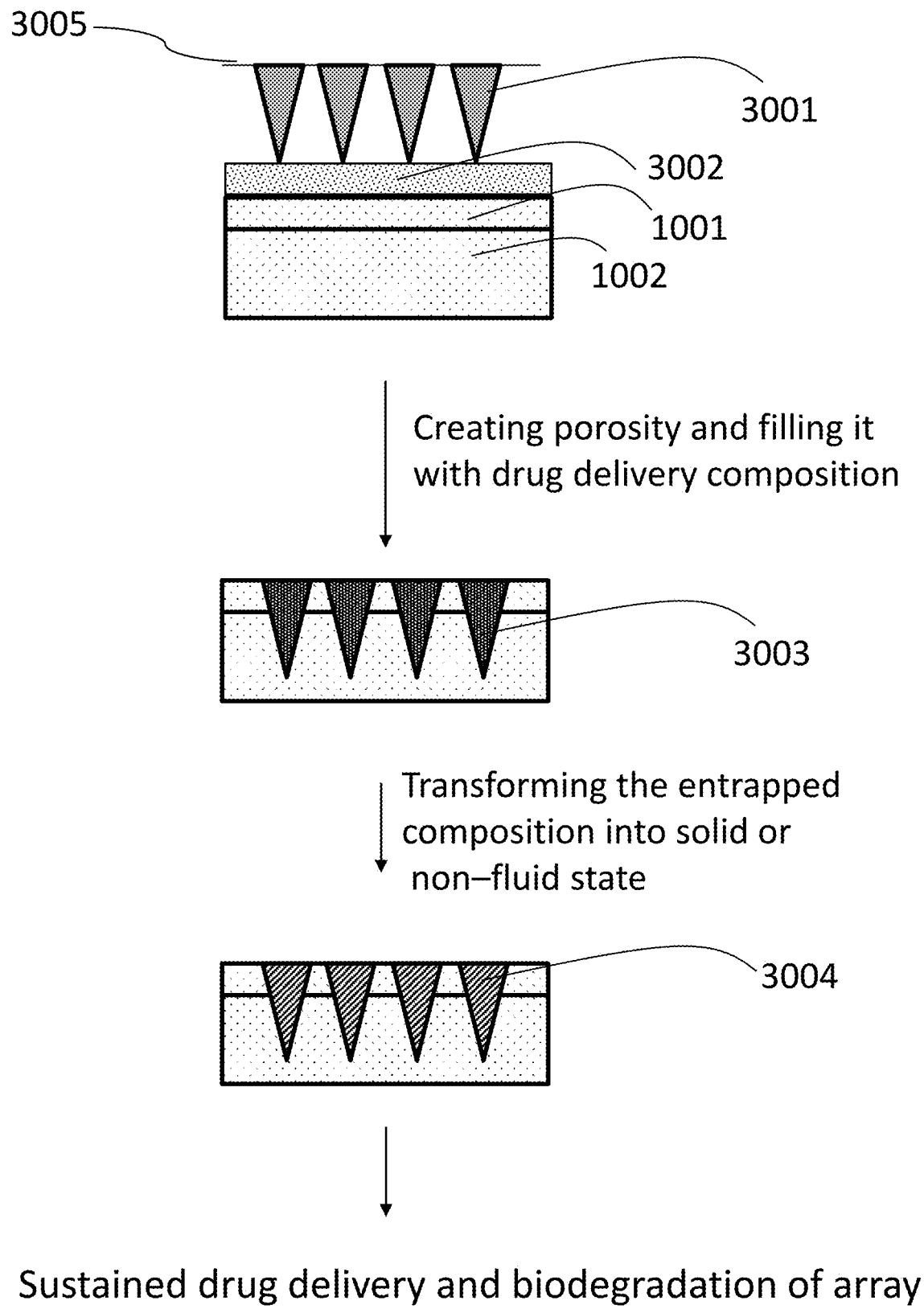
FIG. 3 is a partial schematic representative diagram illustrating a method for forming drug delivery implants in the tissue wherein a layer of injectable composition is first applied on the tissue followed by inserting a cavity making device such as microneedle array or oscillating needle through the liquid layer to form cavity and filling the cavity with drug delivery compositions.

A partial and schematic representation of making in situ generated drug delivery array for sustained drug delivery is shown in FIG. 3. Skin tissue (1001) is first covered with a fluid drug delivery composition such as 10 percent PLGA and coumarin solution (3002) in DMSO (coumarin is added as model drug, ten percent relative to PLGA plus drug weight). A metal, polymer or ceramic microarray comprising of needles with sharp edges (3001) and backing material (3005) is placed on the skin tissue covered with the polymer solution (3002) and is pressed against the epidermis (1001) and dermis (1002) layers to perforate the skin. During the perforation step, the needles of the microarray create artificial cavities and also carry the drug delivery composition in the cavities (3003). The microarray needles may be withdrawn or are dissolved away in the skin/body creating an artificial porosity which is then filled by the drug delivery composition. Optionally the fluid composition is converted into solid or semisolid or hydrogel (3004) by physical and/or chemical means and entrapping the drug in the in situ formed solid/gel matrix. The drug is released from the solid 3004 in the surrounding tissue by diffusion and/or biodegradation or combinations thereof processes.

Figure 4:
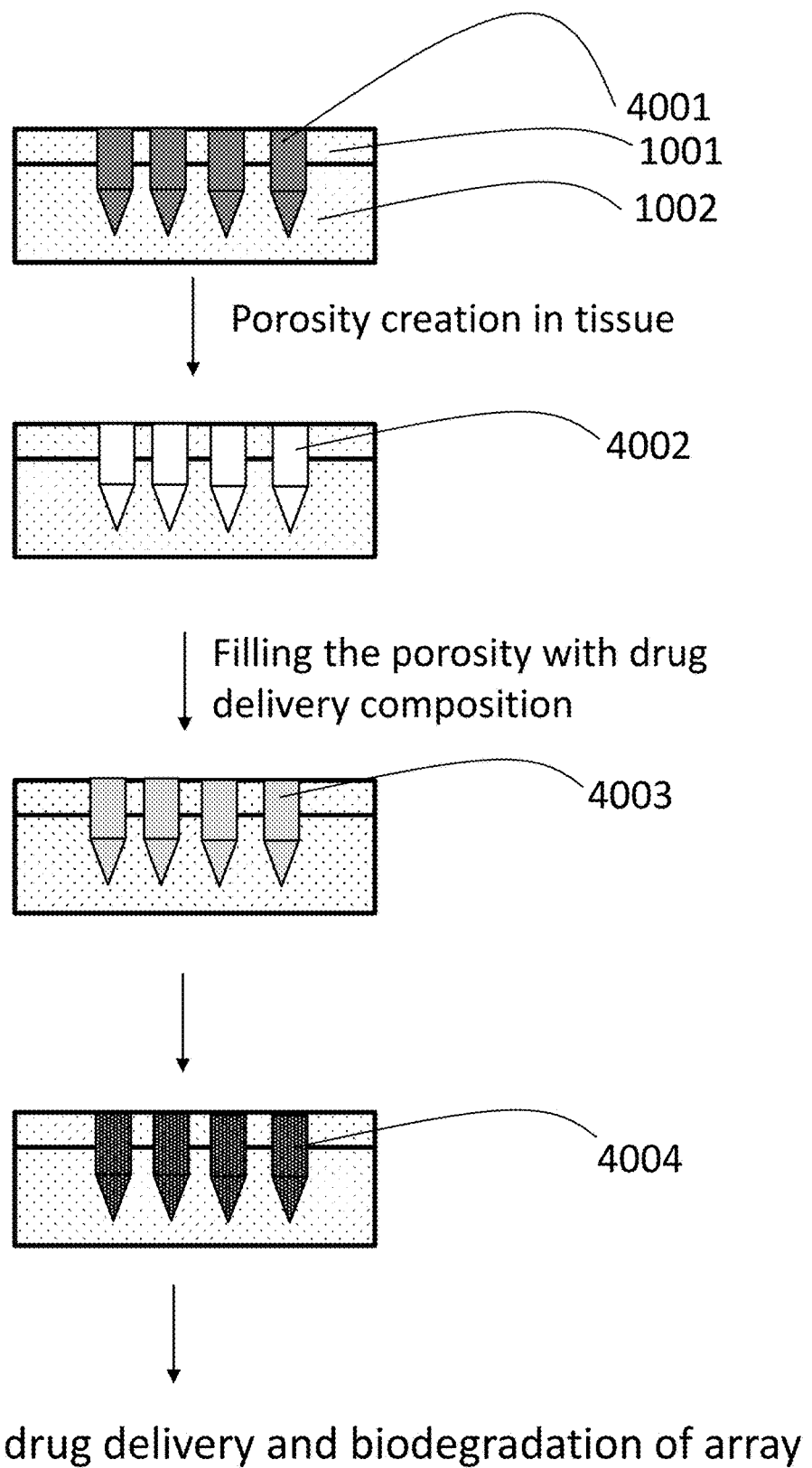
FIG. 4 is a partial schematic representative diagram illustrating a method for forming drug delivery implants in the tissue wherein the artificial cavities are formed first using dissolvable microneedle array which are then filled with injectable drug delivery compositions.

A partial and schematic representation of making in situ generated drug delivery array for sustained drug delivery is shown in FIG. 4. A partial schematic of skin tissue is represented by epidermis (1001) and dermis (1002) layers. Artificial porosity is generated in the epidermis and/or dermis layer by using dissolvable microneedle array (4001). The array (4001) is made using hyaluronic acid or dextran and the like. The dissolvable array (4001) is pushed in the tissue and needle materials are allowed to dissolve in the body or tissue. The cavities created by the dissolution of needles (4002) are then filled with fluid injectable drug delivery composition/s comprising drug/s or bioactive compound/s or live cells (4003). Optionally the fluid composition is converted into solid or semisolid or hydrogel (4004) by physical and/or chemical means and entrapping the drug/cells in the in situ formed solid or gel. The drug is released from the solid or gel in the surrounding tissue by diffusion and/or biodegradation or combinations thereof processes.

Figure 5:
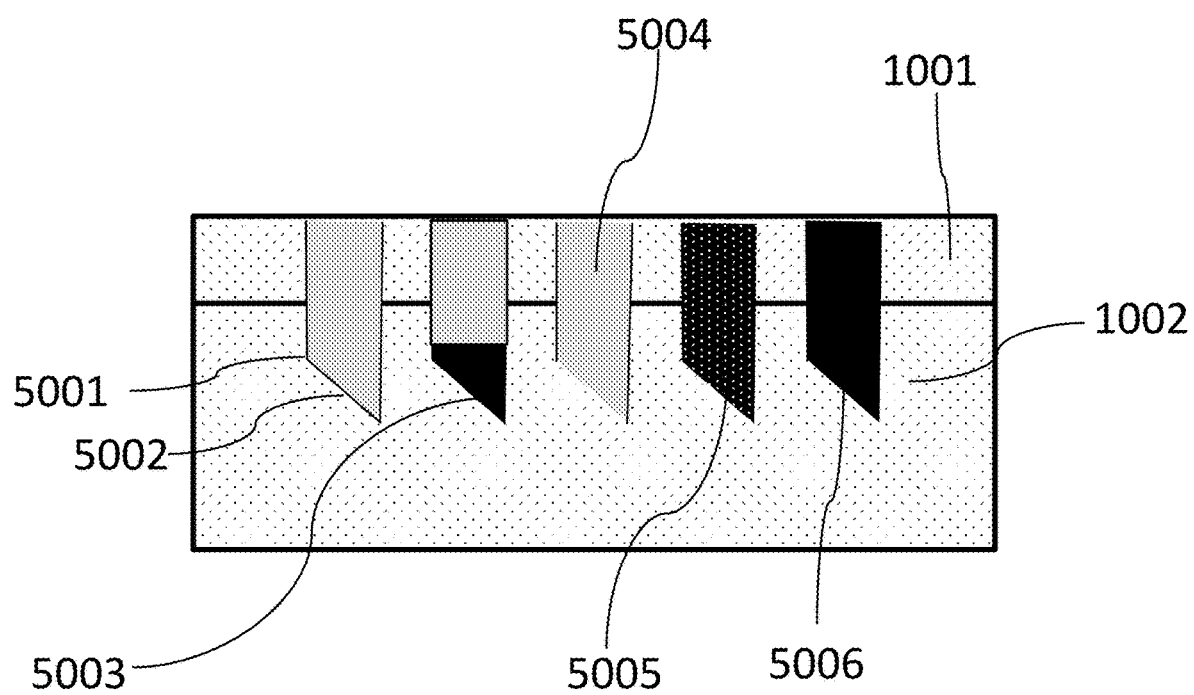
FIG. 5 shows a partial schematic representation of the epidermis layer and dermis layers along with hollow coated needle such that the coating on needle prevents the insertion of tissue inside the cavity during insertion.

FIG. 5 shows a partial schematic representation of a method of creation of cavities using microarray of coated hollow needles and filling the cavities with an injectable composition. The coating or plugging prevents tissue coring during the use of hollow microneedle based array. 5001 depicts a hollow microneedle of an array such as 33MP array. The tip of needle (5001) is coated with water dissolvable coating/plug or removable coating (5002). The needle tip also can be plugged with a water dissolvable or removable plug (5003). The coated needle is inserted in the skin tissue (1001 and 1002). The coating or the plug prevents insertion of tissue and other material in the inserted area of the needle and maintains the hollow space (5004) or cavity inside the needle. The needle is inserted in the tissue and is then filled with an injectable composition such as fibrin sealant, DuraSeal sealant or biodegradable polymer solution in water miscible biocompatible solvent (5005) with drugs and/or cells. The water in the tissue or components in the injectable material dissolve the coating 5002 or plug 5003 which enables removal of the needle from the tissue without obstruction from the coating/plug material. The injectable composition may undergo physical or chemical changes forming solid implant 5006 in the tissue. The needle may be removed after the solid implant is formed.

Figure 6A:
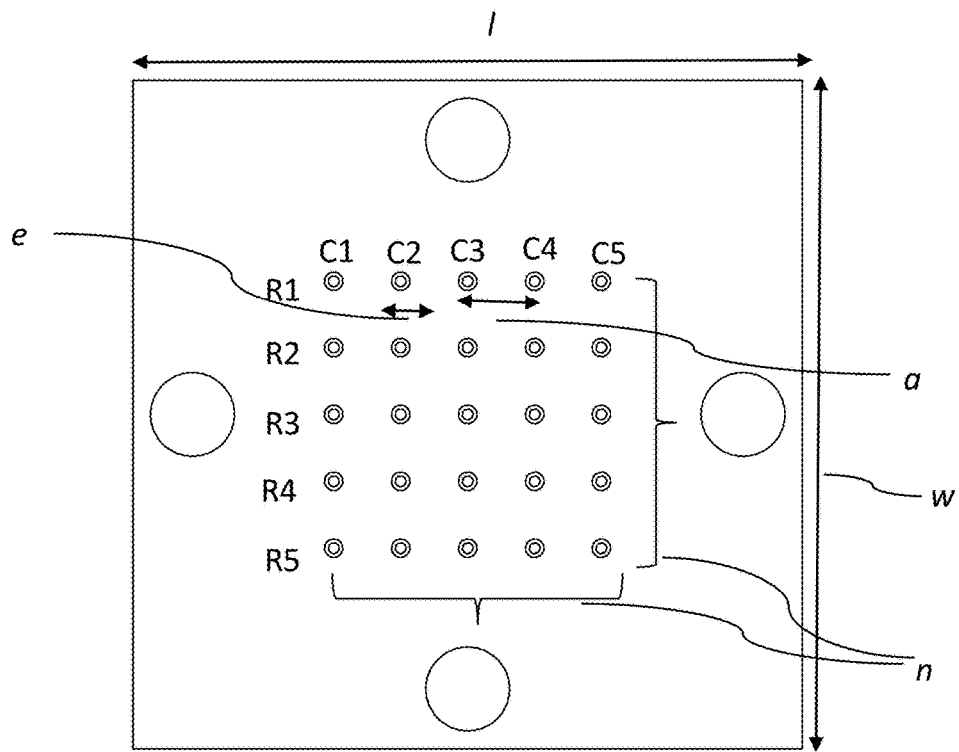
FIGS. 6A, 6B, 6C and 6D show a partial schematic representation of an "array in array" apparatus for creating microimplant array with drugs or live cells.
Figure 6A:
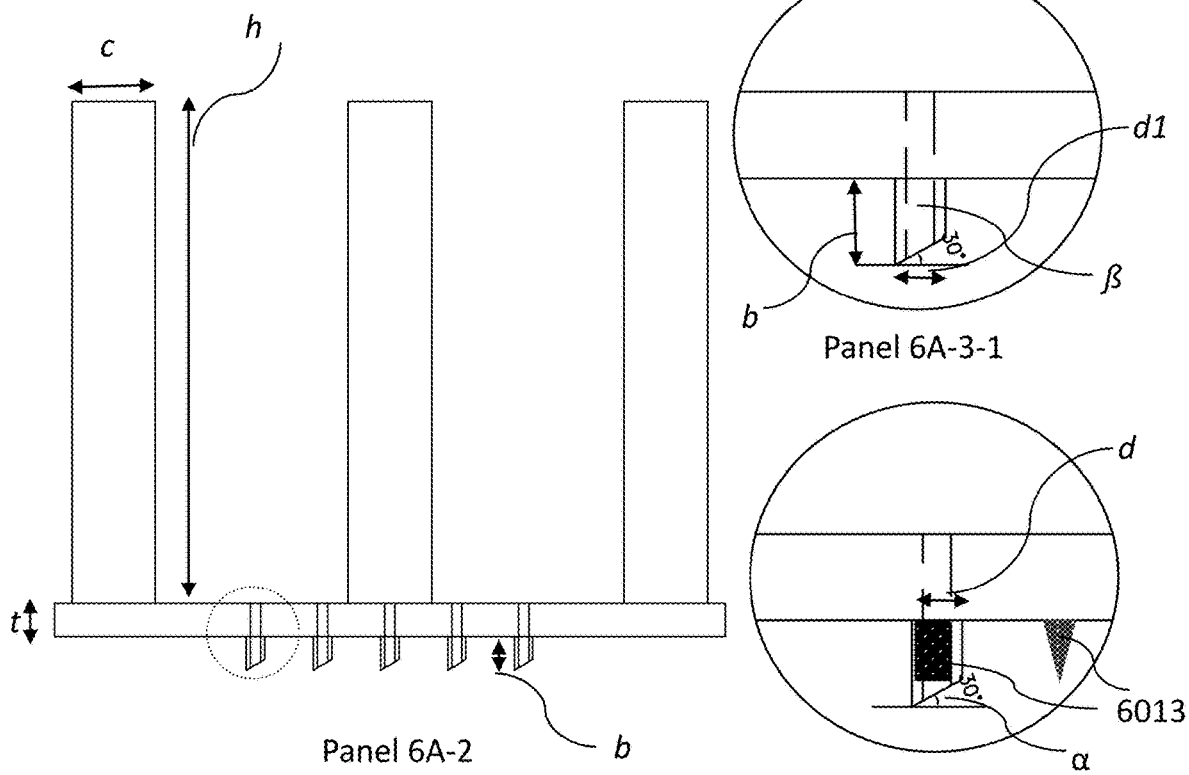
Figure 6B:
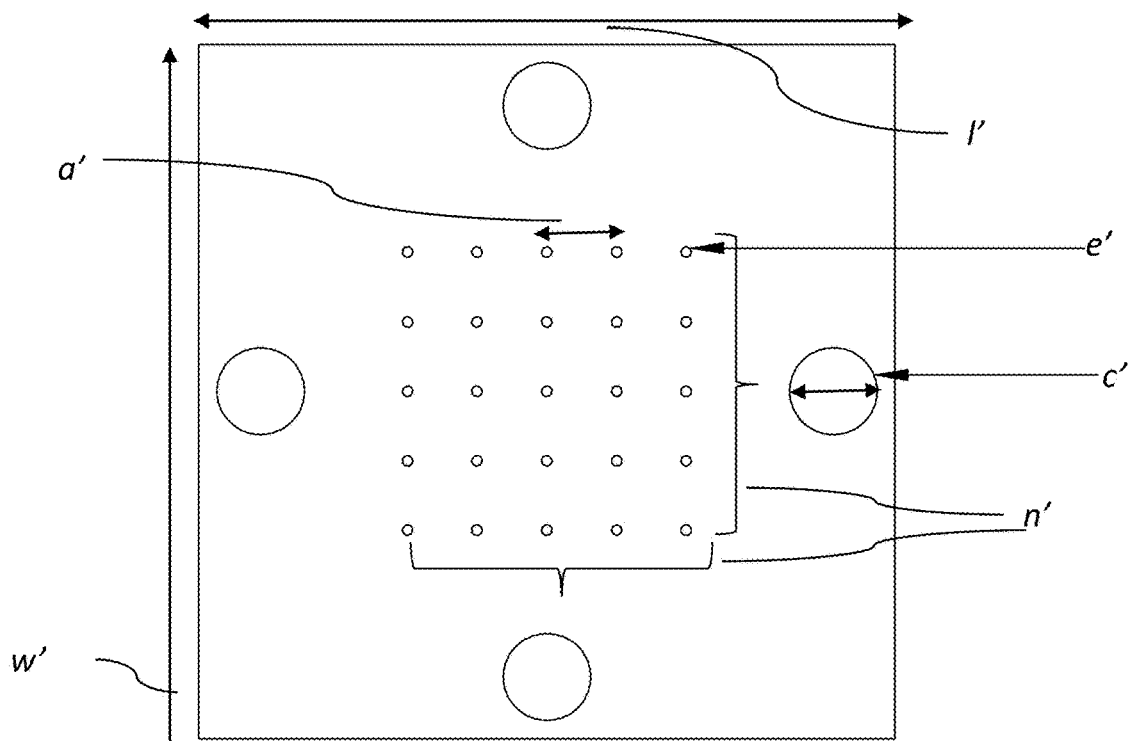
Figure 6B:
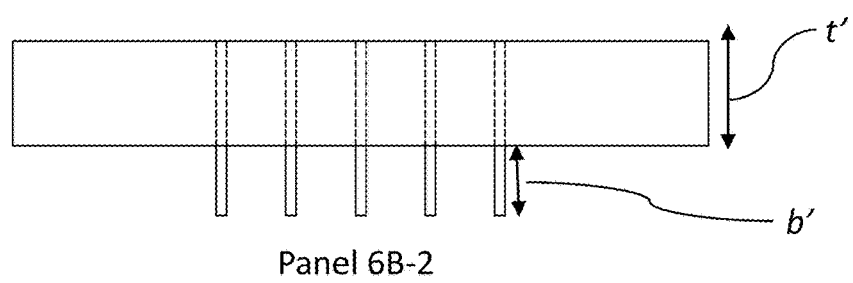
Figure 6B:
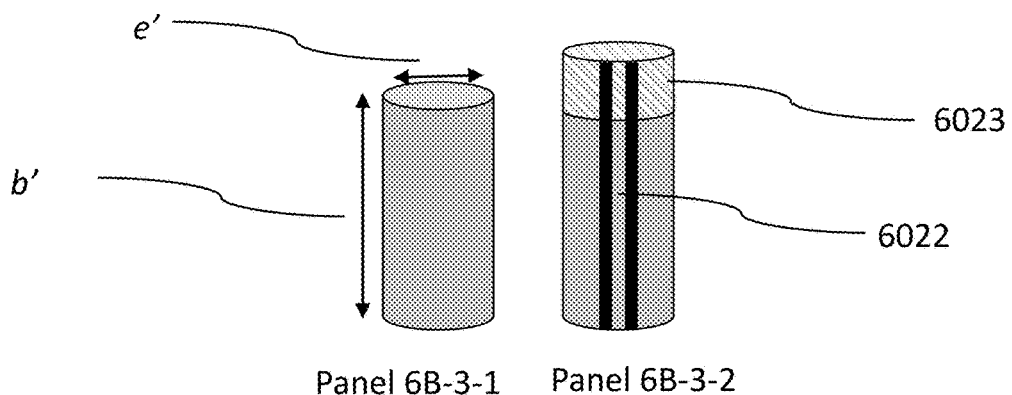
Figure 6C:
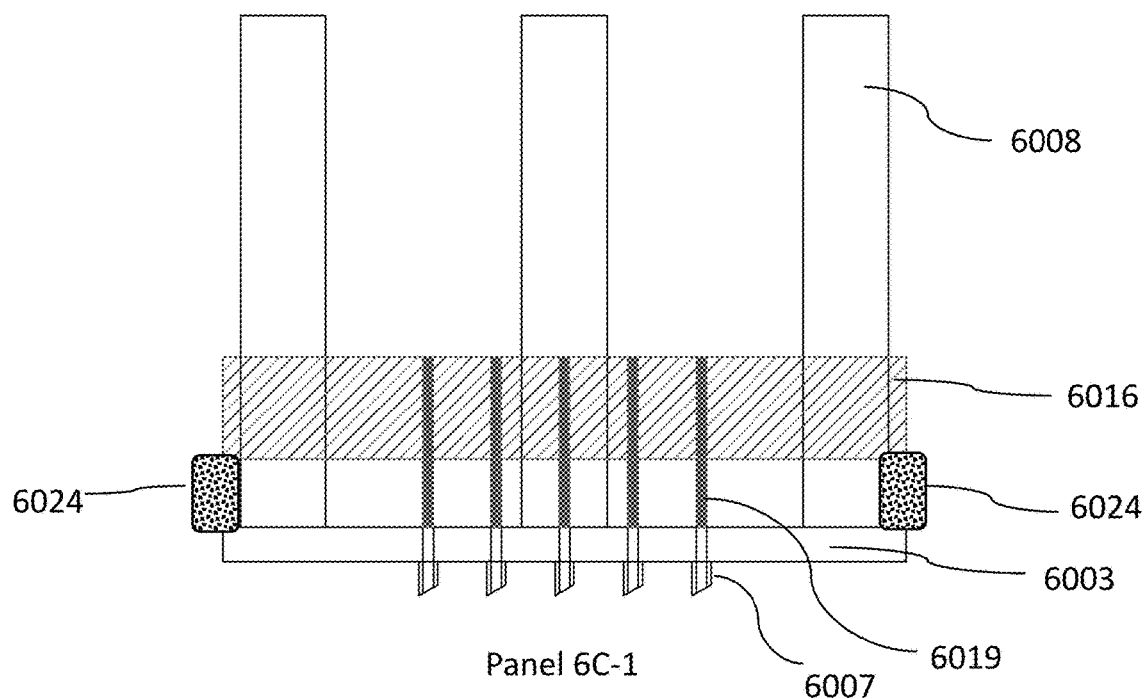
Figure 6C:
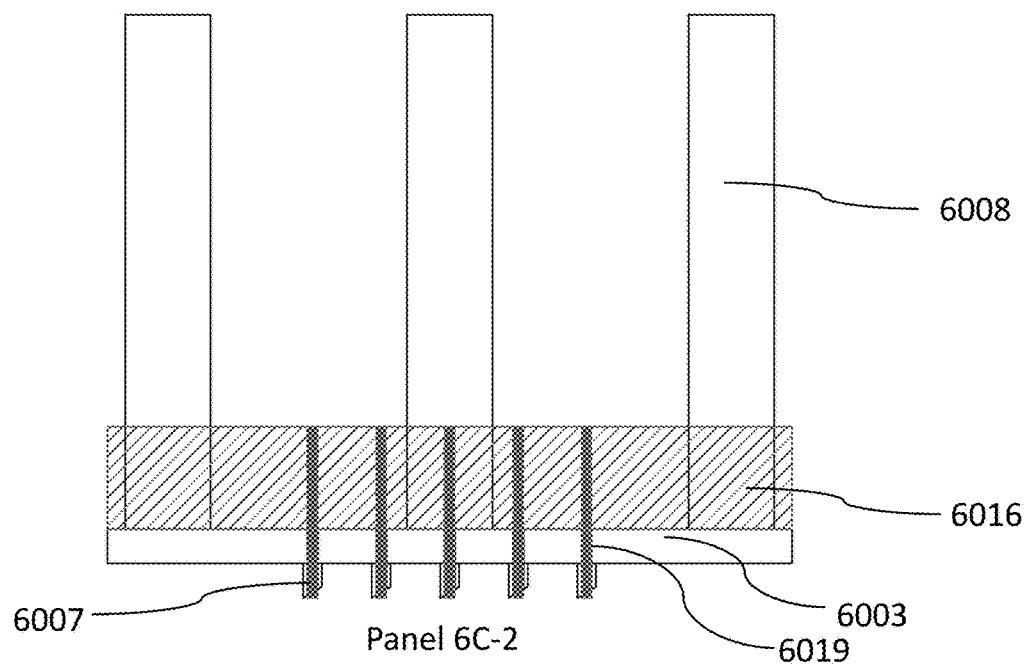
Figure 6D:
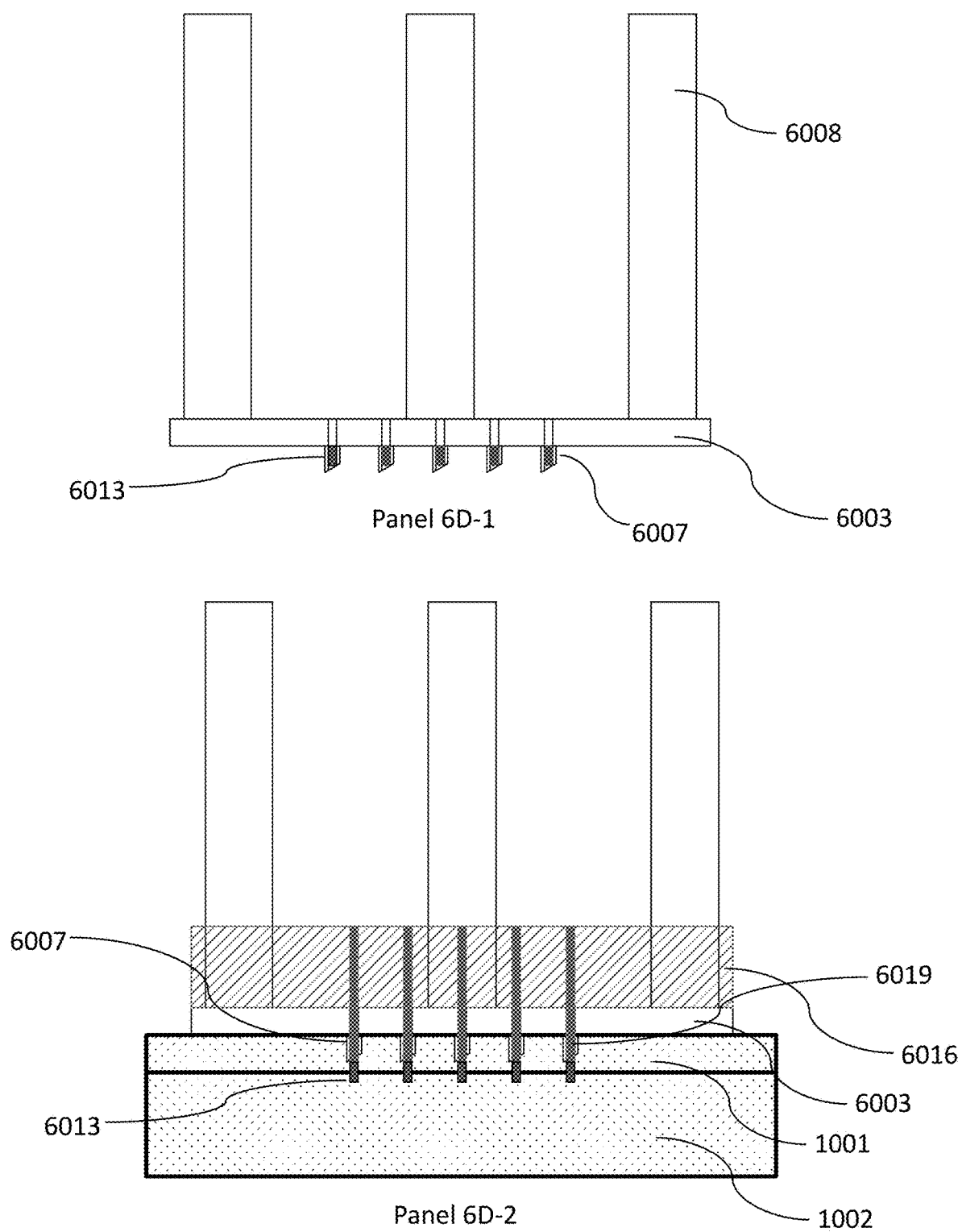

FIGS. 6A and 6B show partial schematic representation of "array in array" apparatus useful for forming microimplant array in the skin or tissue. FIG. 6A comprises of Panels 6A-1, 6A-2, 6A-3-1 and 6A-3-2. FIG. 6B comprises of Panels 6B-1, 6B-2, 6B-3-1 and 6B-3-2.

The apparatus has two parts namely a bottom "base array" and a top "plunger array", both schematically shown in FIG. 6A and FIG. 6B respectively. The base array has a base plate with a sharp hollow microneedle array protruding perpendicularly from one of the surfaces of the base plate. The base array may also contain the microneedle array, and may be referred to as the microneedle array. The top plunger array also has a base plate, designated as plunger plate, with solid needles (e.g., sharp or unsharp, which may be shafts, plungers, plunger shafts, or other) protruding perpendicular to the plunger plate. The arrangement, length/size and shape of the plunger and base array needles is identical except that the plunger array needle fits smoothly inside the hollow cavity of the base array needle and can move freely inside the cavity up and down. This is achieved since the diameter of the plunger array needles is lesser than the diameter of the base array needles. Panel 6C-1 shows the plunger array on top of the base array, with centers of both corresponding needles coaxially aligned such that the plunger array is disposed within but not completely inserted in the base array. The spacer lock prevents the plunger array from being inserted completely. Panel 6C-2 shows the plunger array on top of the base array inserted via guiding posts completely after removal of the spacer lock. Plunger array needles occupy space in the base array cavity. Panel 6D-1 shows base array cavities filled with preformed or in situ generated microimplants with drug and/or cells and is ready for implantation. Panel 6D-2 shows insertion of both the arrays in the skin tissue and the base array cavities are occupied by plunger array needles and the implants in the base array cavities are pushed into skin tissue. Both the arrays are subsequently removed leaving behind the implant array with drug/cells in the skin tissue.

Panel 6A-1 shows a schematic top view of the base array with hollow microneedles and optional four guide posts for ease of insertion and alignment of needles of base and plunger arrays respectively. The base array base plate has length l, width w and thickness t. It also shows number of needles (n) in an array format (5 by 5 hollow microneedles, 25 total needles, n equals to 25) in the base array base plate with average needle cavity diameter d. The proximal end of the hollow needle has opening on plate surface with average needle internal diameter d. The average needle diameter at the distal end is d1. The five needle rows are identified as R1, R2, R3, R4 and R5 and five columns are identified as C1, C2, C3, C4 and C5. Each needle in the array is identified by the respective column and row number. The first needle is identified as R1C1 and middle needle is identified R3C3 and other needles are identified in a similar manner. The distance between each needle is denoted by a and hollow needles protruding from the base plate surface with fixed length is shown as b. Optionally the base plate has four guiding posts with diameter c and height h which enables smooth insertion of the plunger array in the base array. The guiding post also helps to hold/grab the base array during its use and tissue insertion. Panel 6A-2 shows the base array with side view wherein hollow needles protrude from the base plate at 90 degree angle. Panel 6A-2 shows base plate having thickness t and hollow needle length b and external average diameter of needle e and internal average diameter is d. Panel 6A-3-1 shows an expanded view of one of the hollow needles where the needle has a sharp edge and cut at (a) degree angle (30 degree in this illustrative case) for ease of insertion in the tissue and average internal cavity diameter at distal end is dl. The cavity volume/space in the needle is shown as ß. The Panel 6A-3-2 depicts an alternate embodiment wherein the hollow needle volume/space ß is partially or completely occupied by a microimplant 6013 (6013 comprises drug and/or live cells and the shape of the implant is cylindrical or conical with sharp needle edge). Preferably 6013 is a unibody implant.

Panel 6B-1 shows a schematic top view of the plunger array with solid microneedles and optional four guide holes for ease of insertion and alignment of needles from base and plunger array. The holes in the plunger array and guide posts on the base array are at the same corresponding location on respective base plates. The center of guide posts on the base array matches with the center of guide holes on plunger array. The plunger array has a plunger plate with length l', width w' and thickness t'. It also shows an exemplary number of needles (n') in an array format (5 by 5 hollow microneedles in array format, 25 total needles, n' equals to 25). Each needle in the array is identified by its row and column number. The distance between each needle is a' and length of the needle protruding from the plunger plate is b'. Optionally the base plate has guiding holes with diameter c' which are slightly larger than guiding post diameter of base array (c) which enables smooth insertion of the plunger array in the base array. Panel 6B-2 shows plunger array in Panel 6B-1 with side view wherein solid plunger array needles are protruding from the base plate at 90 degree angle. Panel 6B-2 shows the plunger plate having thickness t' and needle length b' and external average diameter of the needle e'. Panel 6B-3-1 shows expanded view of one of the solid plunger array needles where needle has smooth cylindrical non-cutting shape designed for pushing the 6013 implant with length b' and diameter e'. The Panel 6B-3-2 depicts an alternate embodiment wherein the plunger array needle has passage/hollow tube (6022) in the needle and base plate for transfer of injectable composition in the base array needle cavity. The injectable composition is transferred via an injection port (6023) attached to base plate of plunger array via passage 6022 into base array needle cavity. If desired, a syringe with injectable composition may be connected via port 6023 to fill the base array cavity via 6022 passage. The composition is pushed from the syringe in the cavity. Panel 6C-1 shows schematic side view of plunger array positioned on top of base array, but not inserted. 6003 denotes the base plate of the base array. 6016 denotes the plunger plate of the plunger array. 6019 denotes the solid microneedles protruding from the plunger plate. 6007 denotes the hollow microneedles protruding from the base plate. 6008 denotes the guiding posts. The guidepost bars of base array are inside the holes of plunger array. This ensures alignment of center of base array needles with center of plunger array needles. This alignment is important to insert all plunger array needles entering in base array needles at the same time. The insertion of plunger array needles in the base array hollow cavity needle is prevented by a spacer lock 6024. As shown in Panel 6C-2, spacer lock is removed and the plunger array needles are pushed inside the hollow cavities of base array. The plunger array plate is on top of base array plate. Panel 6D-1 shows schematic side view of base array similar to Panel 6A-2 except the hollow cavities are occupied by prefabricated or insitu generated microimplants (6013) with cells/drugs in the array cavities. Panel 6D-2 shows schematic side view of base array and plunger array wherein the plunger array has pushed the implant from (Panel 6D-1, 6013) out of base array cavity into the skin tissue (1001 and 1002). The implants 6013 in the form of an array are left in place for therapeutic effect after withdrawal of both the arrays from the tissue.

Figure 7:
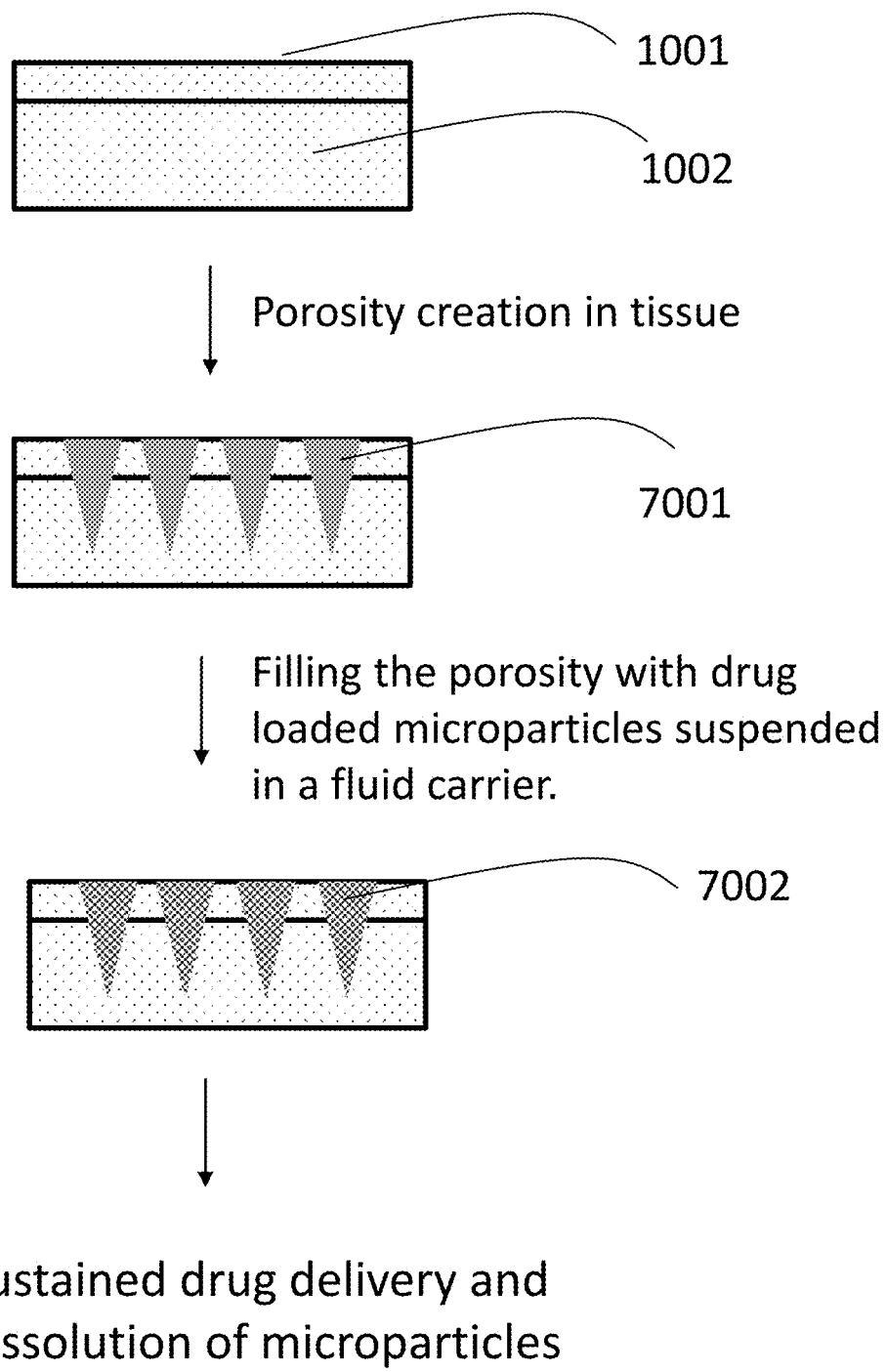
FIG. 7 is a partial schematic representative diagram illustrating a method for forming drug delivery implants in the tissue wherein the artificial cavities are formed first which are then filled with injectable drug delivery compositions comprising drug encapsulated microparticles.

A partial and schematic representation of an in situ generated drug delivery array comprising drug encapsulated microparticles is shown in FIG. 7. A partial schematic of skin tissue is represented by epidermis (1001) and dermis (1002) layers. Artificial porosity is created in the epidermis and/or dermis layer as conical shaped cavities is schematically shown as 7001. The cavities (7001) are filled with fluid injectable drug delivery compositions comprising microparticles encapsulated/coated with drugs (7002), preferably the composition or microparticles is colored or fluorescent. The drug is released from the microparticles in the cavities and in the surrounding tissue in a sustained manner. FIGS. 8A, 8B, 8C, 8D and 8E show representative images of cavities formed in the tissue and gelatin gel and then filled with polymers with drug and/or visualization agent. A microimplant array is formed in the model tissue like material (gelatin gel, 8001) and sheep skin tissue (8005) or pericardial tissue (8008). A 3 by 3 array (33MP) is used to create porosity in transparent gelatin gel (8001) which is then filled with PLGA polymer containing methylene blue as a colorant and/or drug. The precipitated PLGA polymer and its blue color in 3 by 3 microimplant array form (8002) is shown in FIG. 8A. FIG. 8B shows gelatin gel with 3×3 microimplant array made from PLGA polymer solution and coumarin as fluorescent dye using 33MP array. The PLGA implant array formed in situ which is fluorescent under blue light (8003) is shown in FIG. 8B. A PLGA polymer with coumarin microimplant array were formed by direct injection in the sheep dermal tissue (8005) using 33MP array at 3 separate locations is shown in FIG. 8C. The formed microimplants arrays are fluorescent under blue light (8004). FIG. 8D shows microcavities (8009) created in pericardial tissue (8008) before infusion of injectable composition. FIG. 8E shows sheep skin tissue (8005) infused with 4×4 array (8007). The array 8007 is made by infusing PLGA polymer solution containing magnesium carbonate stained with eosin. The array 8007 is pictured under blue light wherein eosin in the microimplant array formed is fluorescent.

FIG. 9A shows a representative image of an iron containing implant 9001 formed in situ inside the tissue using methods described in this invention. FIG. 9B1 depicts the image of 10×10 array (9002) made from hyaluronic acid salt and iron pyrophosphate formed by casting in silicone rubber mold and FIG. 9B2 shows microscope image of one of the needles of array (9003) shown in FIG. 9B1. The FIG. 9B2 shows sharp needle tip of one of the needles of array 9003.

Figure 10:
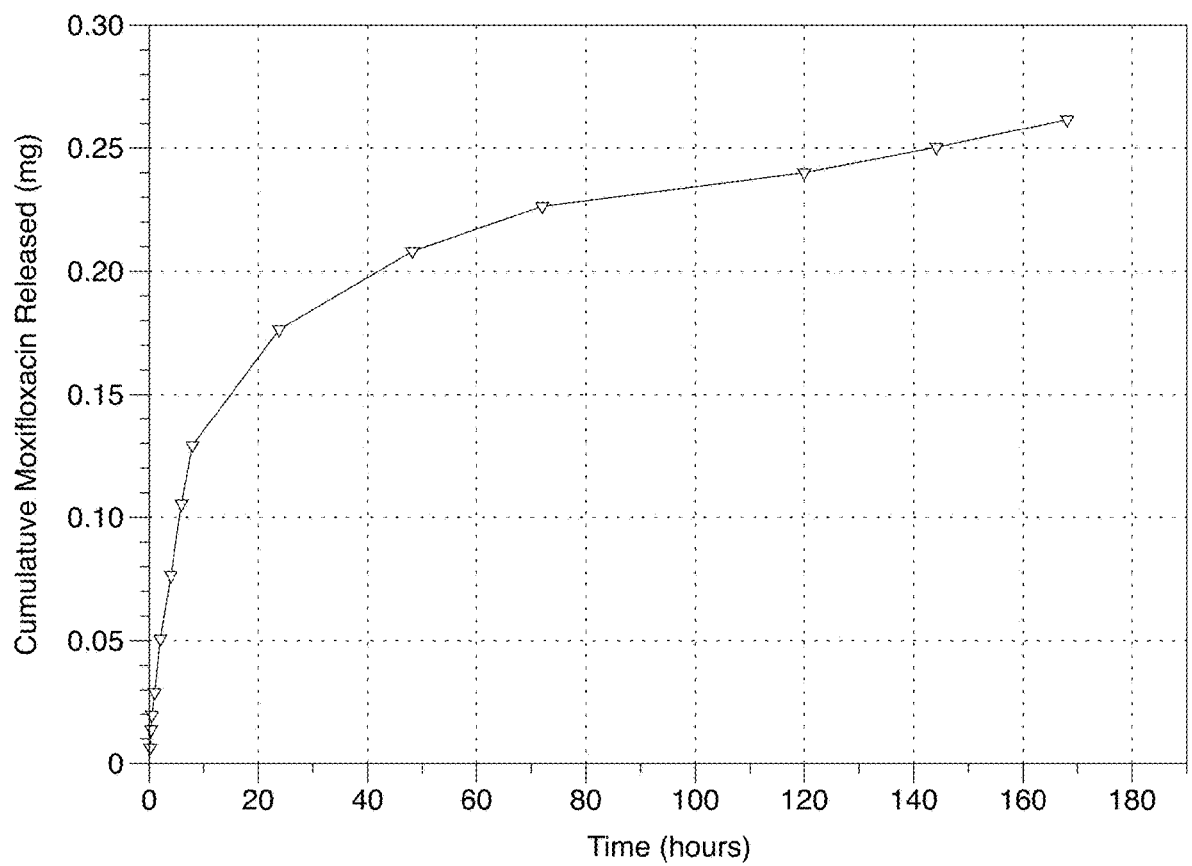
FIG. 10 shows a drug release profile of moxifloxacin from microimplants array formed in the tissue in an embodiment of the present invention.

FIG. 10 shows cumulative moxifloxacin base release profile from the 2 cm by 2 cm sheep tissue prepared according to Example 14B described subsequently in this application. The porosity was first created using a metal microneedle array in the tissue and the cavities created were then filled with biodegradable polymer (PLGA) solution in NMP comprising methylene blue as colorant and moxifloxacin base as a drug.

Figure 11:
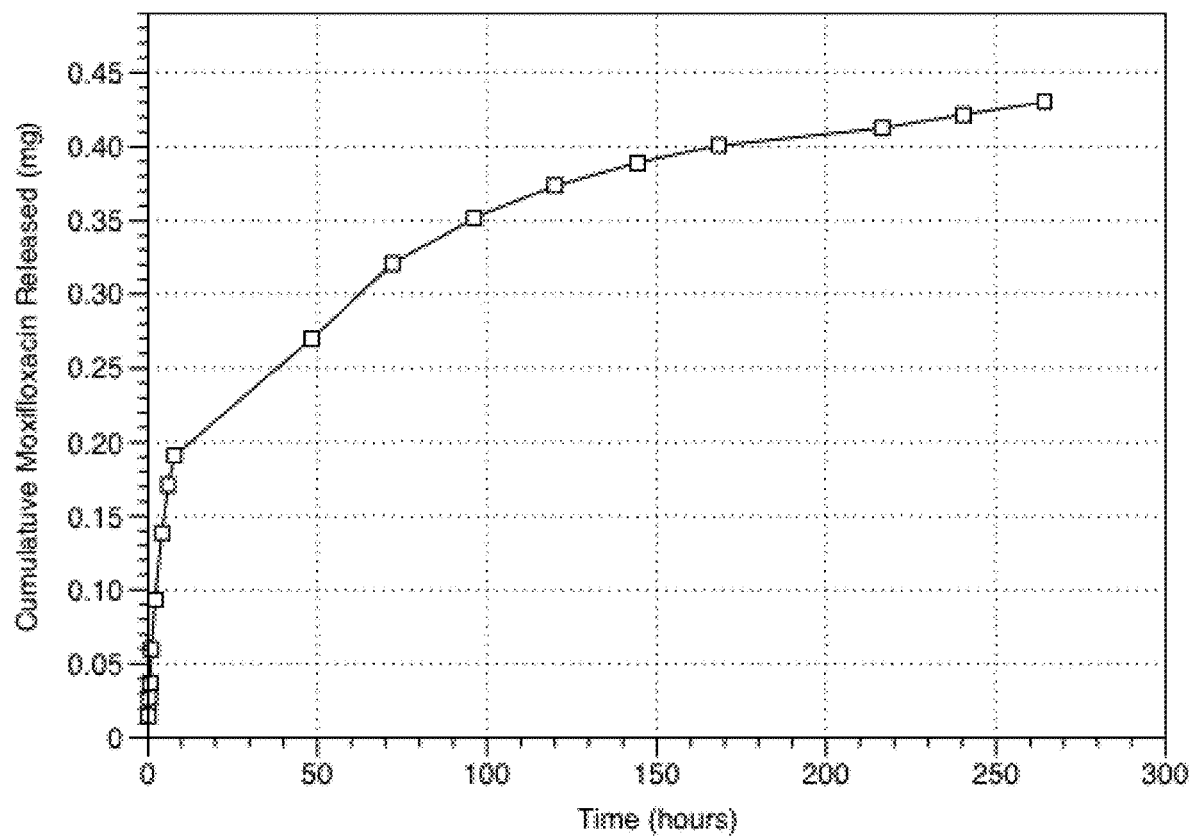
FIG. 11 shows a drug release profile of moxifloxacin from microimplants array formed in the tissue in an alternate embodiment of the present invention.

FIG. 11 shows cumulative moxifloxacin base release profile from the 2 cm by 2 cm sheep tissue prepared according to Example 14C described subsequently in this application. The implant array was prepared by applying a metal microneedle array through a layer of biodegradable polymer (PLGA) solution in NMP comprising methylene blue as colorant and moxifloxacin base as drug.

Figure 12:
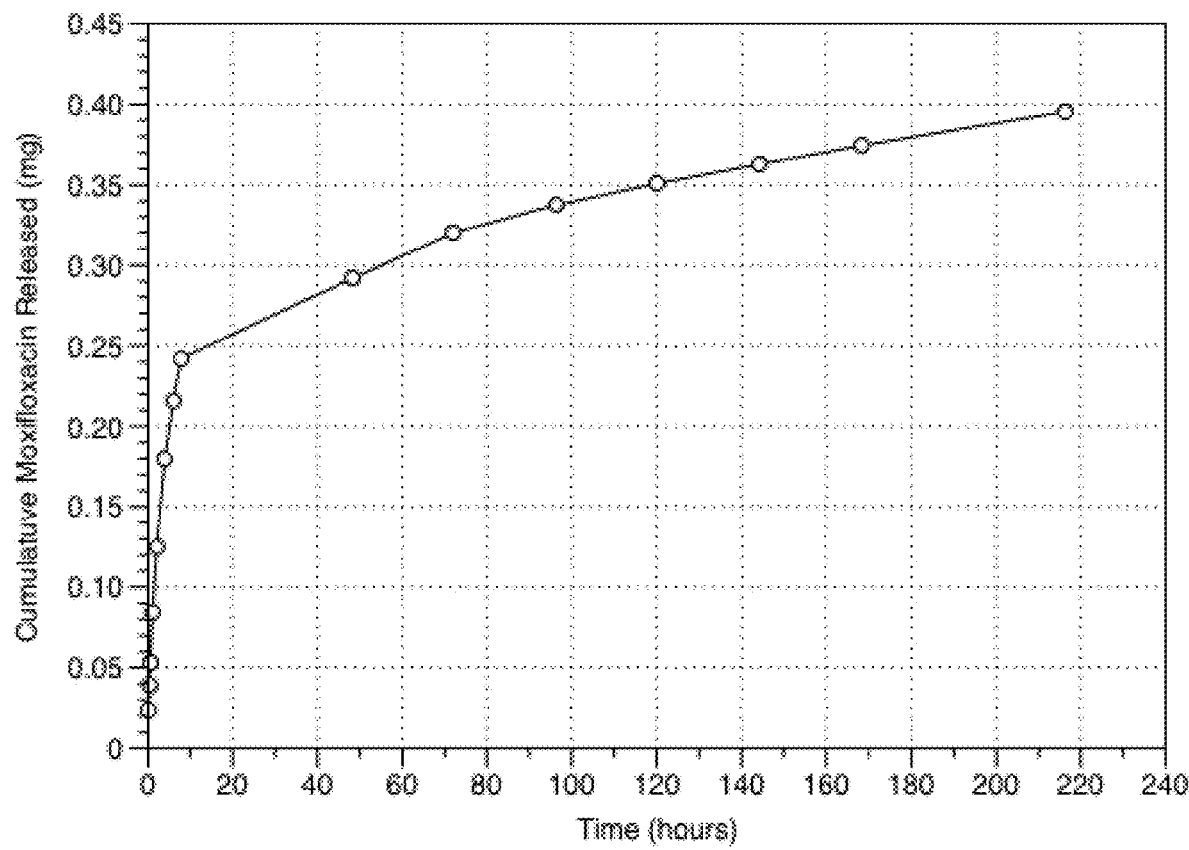
FIG. 12 shows a drug release profile of moxifloxacin from microimplants array formed in the tissue in another alternate embodiment of the present invention.

FIG. 12 shows cumulative moxifloxacin base release profile from the 2 cm by 2 cm sheep tissue prepared according to Example 14A described subsequently in this application. The implant array was prepared by direct injection of biodegradable polymer (PLGA) solution in NMP comprising methylene blue as colorant and moxifloxacin as drug. The injection was made using hollow microneedle array device (33MP).

Figure 13:
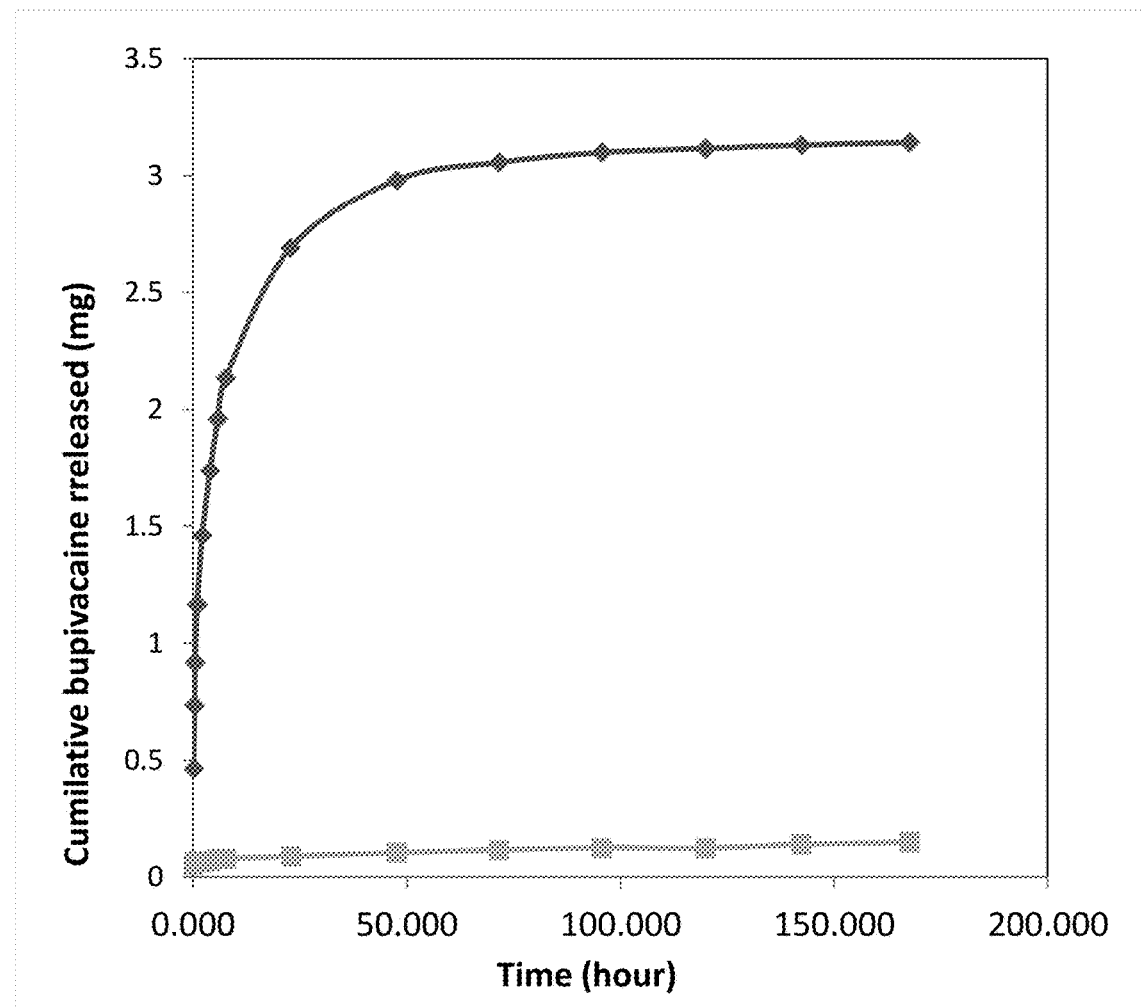
FIG. 13 shows a drug release profile of bupivacaine from microimplants array formed in the tissue using an oscillating needle device.

FIG. 13 shows a drug release profile of bupivacaine base from microimplants array formed in the tissue using oscillating needle. The artificial cavities are formed through the polymer solution on the tissue surface by the use of oscillating needle and not a microneedle array. The polymer solution was driven by the oscillating needle in the bovine pericardium precipitates in the cavities which encapsulates the drug and releases it in a sustained manner. The lower curve (solid squares) is for the control sample which is infused without drug. As expected the bupivacaine was released in a sustained manner from the in situ formed implant. The control sample did not show bupivacaine release, as expected.

Figure 14:
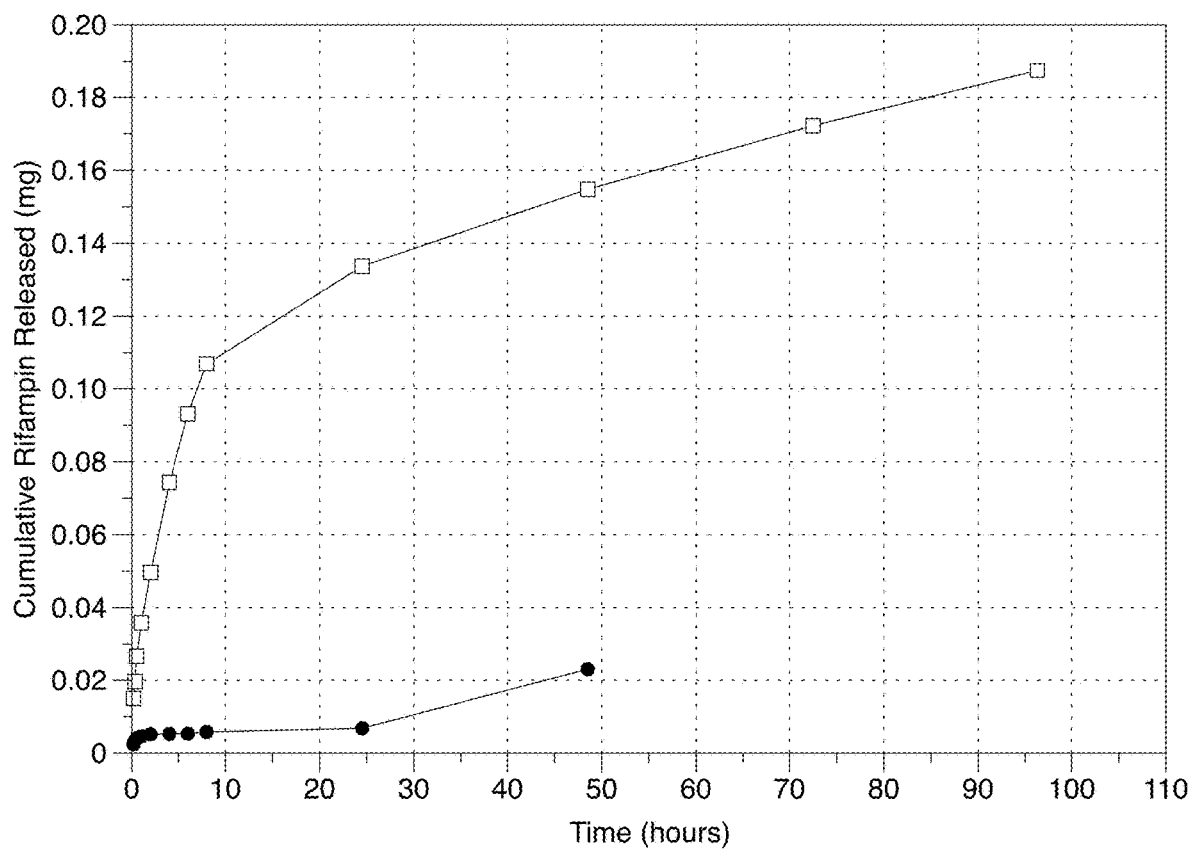
FIG. 14 shows a drug release profile of rifampin encapsulated microspheres from microimplants array formed in the tissue using a microneedle array in accordance with one embodiment of the present invention.

FIG. 14 shows a drug release profile of rifampin encapsulated microspheres from microimplants array formed in the tissue using a microneedle array. The artificial cavities are formed through the rifampin microspheres suspension in glycerol on the sheep skin tissue surface by the microneedle array. The array needles are pressed on the tissue through the suspension. As the needle penetrates the tissue and form a cavity, the suspension is carried along with it. The glycerol is dissipated in the tissue leaving behind microspheres in the artificial cavities. Microspheres without rifampin were also incorporated in the tissue and used as a control. Rifampin release profile from the tissue and from the control lower curve (solid circles) is shown. As expected the rifampin microspheres showed a sustained release of rifampin in the tissue and control microspheres did not show rifampin release (solid circles, bottom curve). The trace amount of drug in one data point in control sample is believed to be due to contamination or of unknown origin.

FIG. 15 shows an illustrative "array in array" apparatus as described in FIGS. 6A and 6B. FIG. 15A shows a base array 1501 with top view showing 5 by 5 hollow microneedle array created in stainless steel metal plate. Base array plate length and breadth is 20 mm and thickness is 1 mm. Outside diameter (OD) of the hollow microneedles 1502 is 0.55 mm while internal diameter (ID) of cylindrical cavity is 0.31 mm. The proximal end of the needle has opening on the base plate with ID 0.31 (same as needle ID, d) and the other end of the needle (distal end) has a sharp edge and ID of 0.31 (d1=0.31). The base array plate has 4 guiding posts 1503 with diameter 2.48 mm. Distance between each needle is 2 mm. FIG. 15B shows the side view of same base array 1501 showing base metal thickness and hollow sharp microneedles (at distal end) protruding out of the base plate 1504 surface. Total length of hollow needle is 2 mm of which 1 mm is inside the base plate and 1 mm is protruding out of base plate. The outer needle edge is cut at 30 degree angle for ease of insertion. FIG. 15C shows plunger array 1505 with top view showing 5 by 5 microneedle array with solid plunger needles 1508 (also may be referred to as shafts, plungers, plunger shaft, which may be blunt tipped, but may also be sharp) created in stainless steel metal. Length and breadth is 20 mm and thickness is 3 mm. Outside diameter (OD) of the solid microneedles is 0.3 mm which is smaller than the base array cavity ID (0.31 mm). The plunger array plate 1506 has 4 guiding holes 1507 w z 1000ith diameter 2.51 mm which is slightly larger than guiding posts diameter (2.48). Distance between each needle is 2 mm. FIG. 15D shows the side view of the plunger array 1505 showing base metal thickness and solid needles protruding out of the bottom surface of the plunger array plate 1506. FIG. 15E shows the plunger array 1505 placed on top of the base array 1501 (not inserted but aligned and ready for insertion) wherein each center of each needle of top array is aligned with center of base array needle. The holes of plunger array are aligned with guiding posts of the base array. FIG. 15F depicts the position when plunger array needles are completely inserted in cavities of base array needles.

Figure 15E:
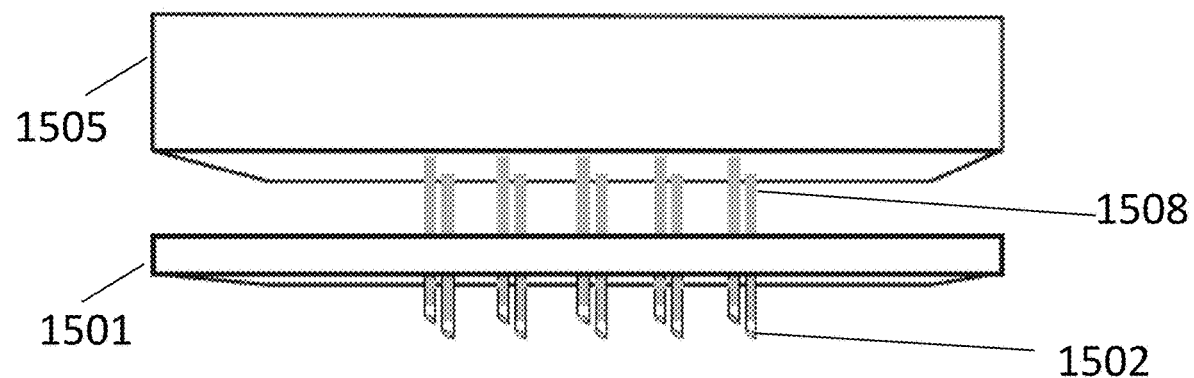
Figure 15F:
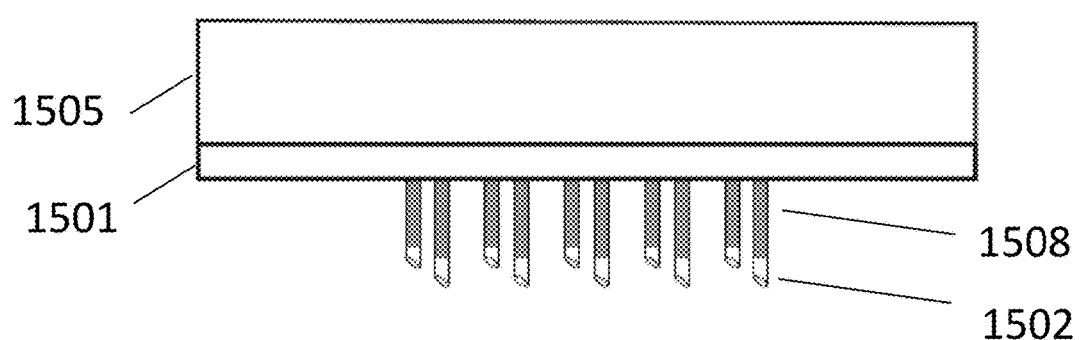
Figure 15G:
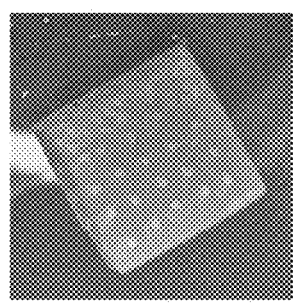
FIGS. 15G-15H show images of the array formed from the devices of FIGS. 15A-15F.
Figure 15H:
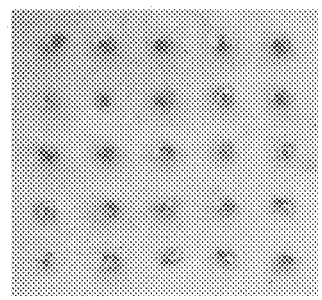

FIG. 15G shows PLGA based cylindrical implant with coumarin as model drug and fluorescent agent is formed in situ inside hollow cavities of base array first and then pushed inside gelatin gel using plunger array as shown in FIGS. 15E and 15F. The green fluorescence of PLGA polymer microimplant array (5×5 array) formed is clearly visible under blue light due to coumarin fluorescence. FIG. 15H shows catgut suture based cylindrical microimplants with fluorescent coating is created first. The preformed implants are then placed in hollow cavities of base array and then inserted in the sheep skin tissue using plunger array as described above. The inserted microimplants show green fluorescent coating on the outer edge of the implant under blue light. The apparatus used in making arrays (FIGS. 15G and 15H) is one of the several porotypes made and used to make implanted microarrays.

FIG. 16A shows a photographic image of part of human nail with artificially created four cavities (average diameter around 700 microns). FIG. 16B shows FIG. 16A cavities filled with PLGA based biodegradable composition with D and C violet as a colorant. FIG. 16C shows in vitro terbinafine hydrochloride (an exemplary antifungal drug suitable for treatment of fungal nail infection) release profile from PLGA based experimental composition from the implanted microarray.

Figure 17:
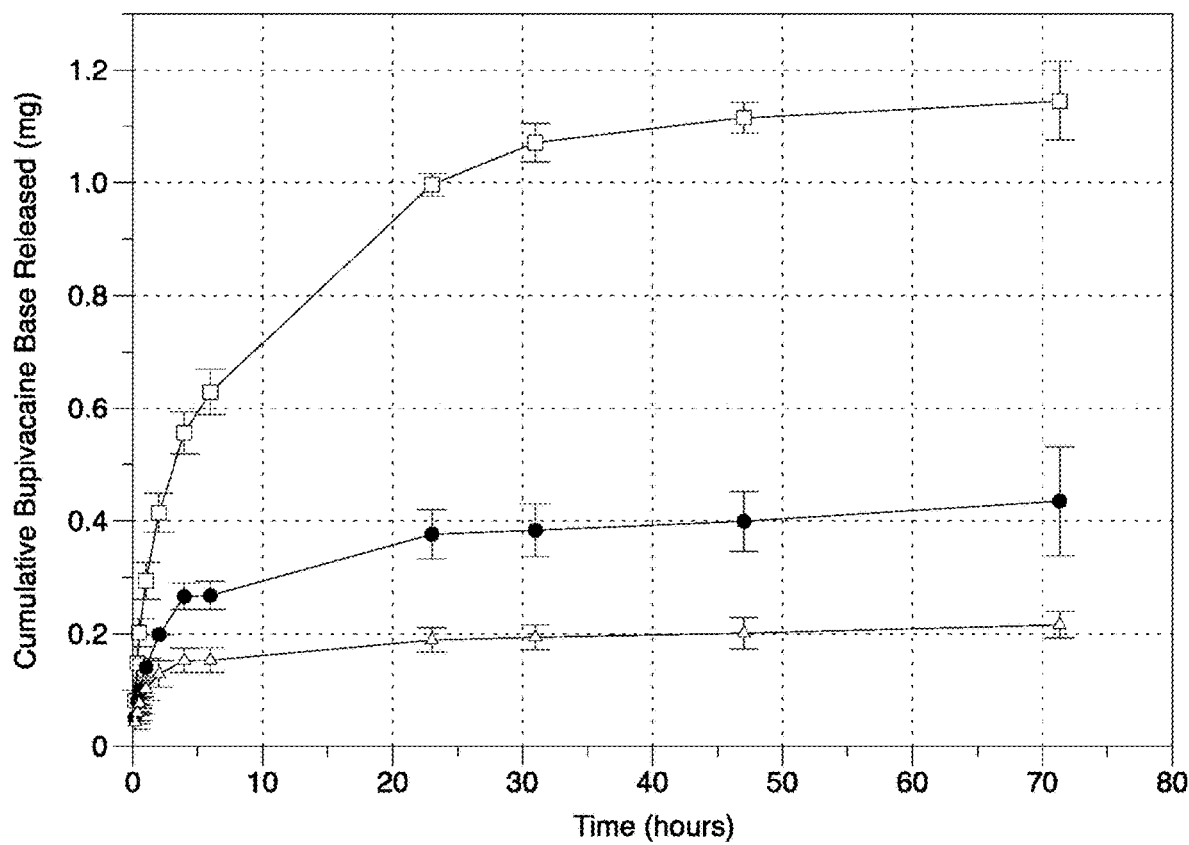
FIG. 17 shows bupivacaine base release profile of PLGA coated biodegradable tissue or tissue based suture threads.

FIG. 17 shows bupivacaine base release profile of coated threads. Submucosa twisted threads were coated with PLGA polymer and bupivacaine base. Bupivacaine base release from the control (no drug, polymer only, triangles), 20 percent coating (solid circles) and 50 percent coating (rectangles) is shown in FIG. 17. As expected, the control sample did not show any significant release of bupivacaine. The threads coated with 20 and 50 percent drug solution provides sustained release of bupivacaine up to 72 hours. The coated fibers or cylindrical threads can be cut/sectioned to form bupivacaine based coated microcylinders of suitable length, which can be used as preformed microimplants to make an implanted microarray using AIA device as described in this invention.

Figure 18:
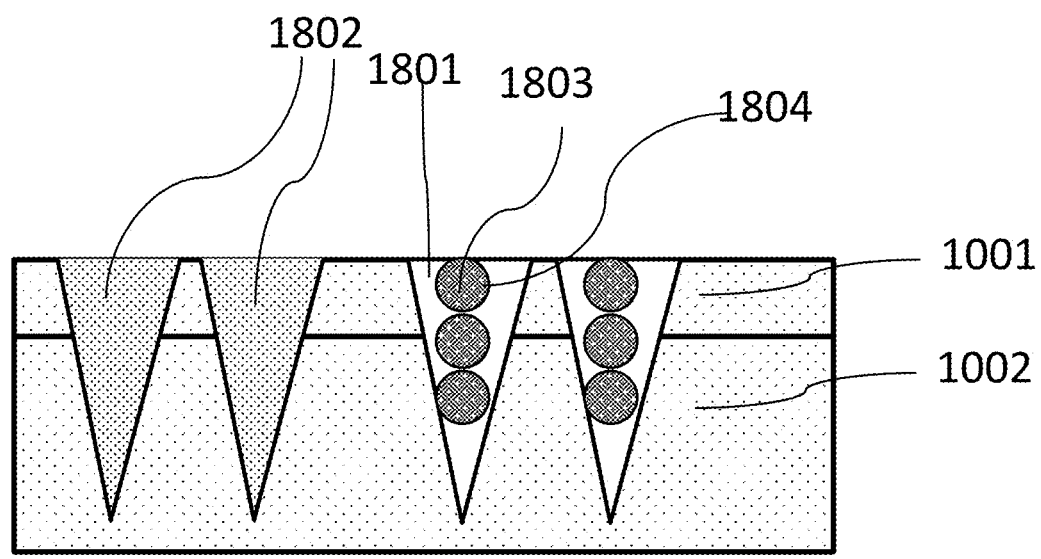
FIG. 18 shows partial schematic representation of microneedle array comprising the islets of Langerhans implanted in a skin tissue in accordance with one embodiment of the present invention.

FIG. 18 shows a partial schematic representation of microneedle array comprising the islets of Langerhans implanted in the skin tissue. 1801 shows an array of conical needle shaped artificial cavities in the skin tissue which are filled with insulin producing cells (islets of Langerhans) encapsulated in a semipermeable biodegradable or biostable polymer/hydrogel matrix (1802). The cells can exchange through the semipermeable matrix insulin, glucose, nutrients from the surrounding skin tissue for survival and metabolic waste products. The live cells can survive and produce insulin based on glucose concentration present in the skin tissue fluids. 1803 shows microencapsulated islets cell microspheres filled in the cavity 1801. 1803 are islet cells inside the microsphere and 1804 is spherical shaped semipermeable microencapsulation microsphere matrix which enables exchange of nutrients and cellular waste products but prevents immunoglobulins diffusion and offers immunoprotection.

Figure 19A:
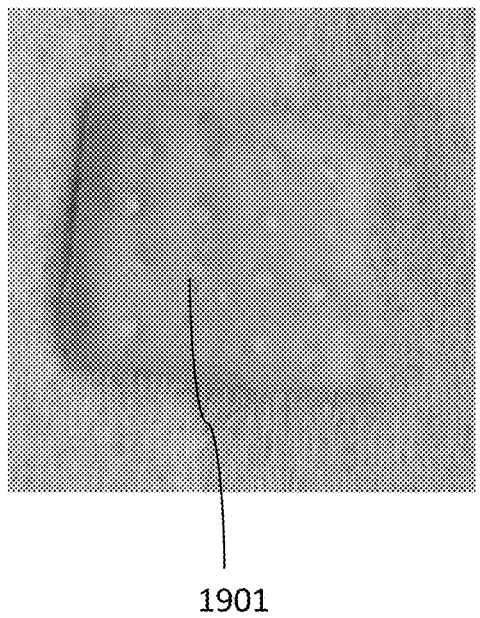
FIGS. 19A and 19B show exemplary photographic images of microimplant arrays created using methods and devices according to the present invention.
Figure 19B:
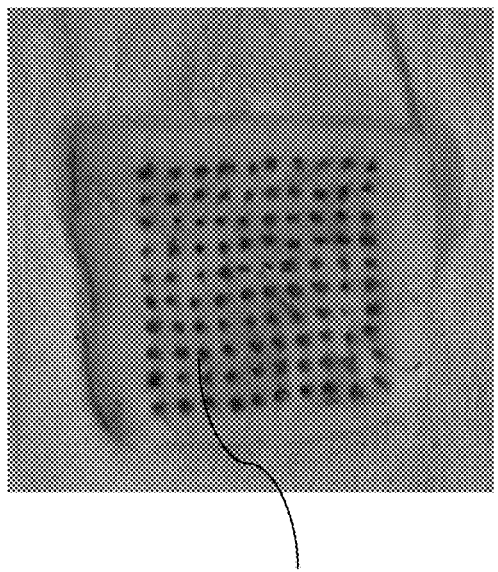

FIGS. 19A and 19B show exemplary images of microimplant arrays created using inventive methods and illustrative devices used to create such arrays. FIG. 19A shows image of 4 by 4 microimplant array made in the sheep skin. Array is an exemplary synthetic biodegradable crosslinked hydrogel gel (1901, white colored) containing magnesium carbonate encapsulated microparticles as visualization agent or as a biodegradable filler or as an exemplary drug encapsulated microparticles. FIG. 19B shows image of 10 by 10 liquid microimplant array made in sheep skin. Array is an exemplary liquid carrier vitamin E acetate containing tea stained magnesium carbonate (1902, red colored) added as visualization agent. The array is liquid at ambient/body temperature.

Figure 20:
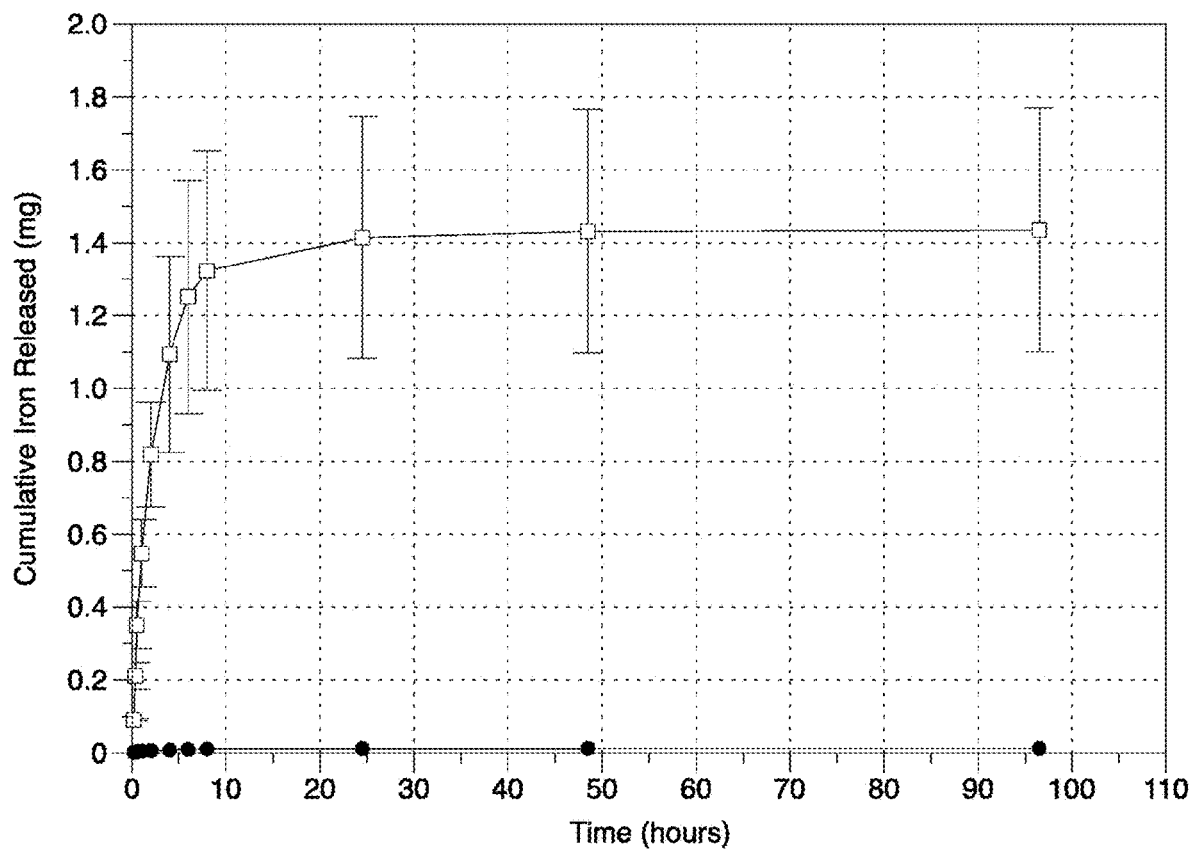
FIG. 20 shows a release profile of iron from the treated tissue, infused with ferric pyrophosphate and PLGA polymer and control sample is infused with PLGA polymer only.

FIG. 20 shows iron release profile of samples prepared according to Example 8. The ferric pyrophosphate particles are suspended PLGA solution in NMP and tattooed into sheep dermal tissue. Control sample is tattooed without ferric pyrophosphate. The release of iron from ferric pyrophosphate treated samples (rectangles) and control samples (no ferric pyrophosphate, solid circles) is shown in FIG. 20.

Figure 21A:
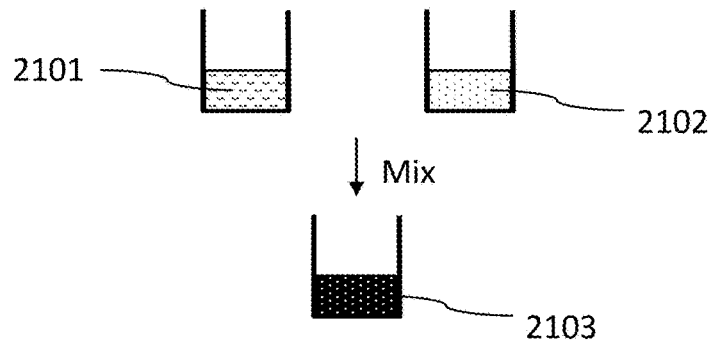
FIG. 21A shows partial schematic representation of a method for making in situ implant in the human or animal body comprising biodegradable fillers.
Figure 21B:
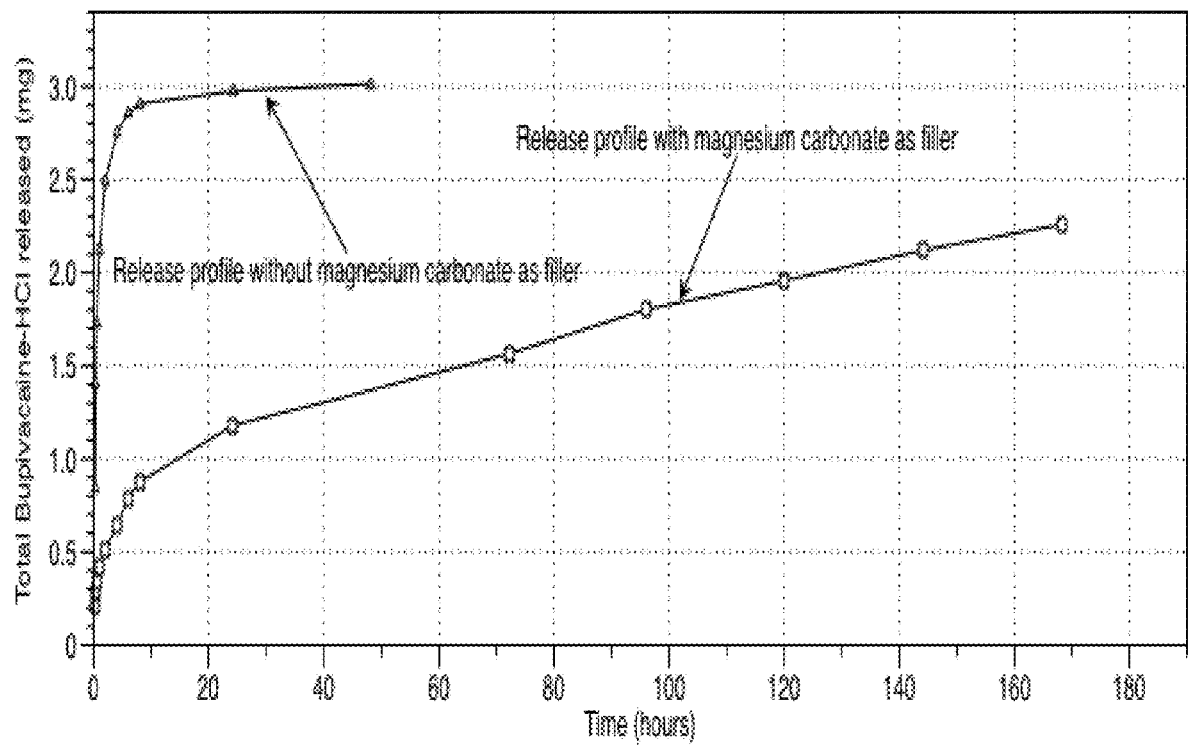
FIG. 21B shows release profile of bupivacaine hydrochloride from the in situ made PLGA array implant with and without magnesium carbonate as exemplary filler.

FIG. 21 shows a method for in situ implant formation in the human or animal body comprising biodegradable fillers. 2101 schematically represents an injectable composition comprising a drug and biodegradable polymer in water miscible organic solvent or crosslinkable precursor composition/s comprising a drug or a thermoreversible polymer composition in aqueous solution or polymer melt. 2102 comprises biodegradable, biocompatible inorganic or organic filler microparticles that are insoluble in the injectable composition 2101. The components of 2101 and 2102 are mixed to form a suspension/emulsion 2103 and injected into human or animal body via conventional syringe or using methods described in this invention to form implantable arrays. The injected composition undergoes physical and/or chemical change (precipitation, crosslinking, cooling, thermoreversible gel formation and the like) entrapping the drug and the filler in the formed gel/solid implant. The presence of filler is believed to provide nucleating sites for polymer precipitation as well as provide more surface area for the implant thereby altering drug release profile. Filler also changes the mechanical properties of the in situ precipitated polymer/gel which helps to push out from "array in array" apparatus described in this invention. FIG. 21A shows the steps involved in making the implant with filler and FIG. 21B shows release profile of bupivacaine hydrochloride from the in situ made PLGA array implant with and without magnesium carbonate as an exemplary filler.

Figure 22C:
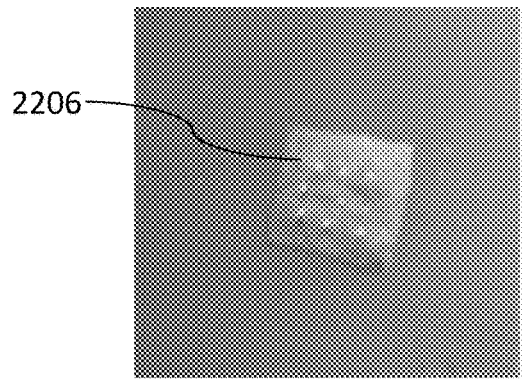
FIGS. 22A, 22B, 22C and 22D show exemplary photographic images of microimplant arrays created according to present invention.
Figure 22B:
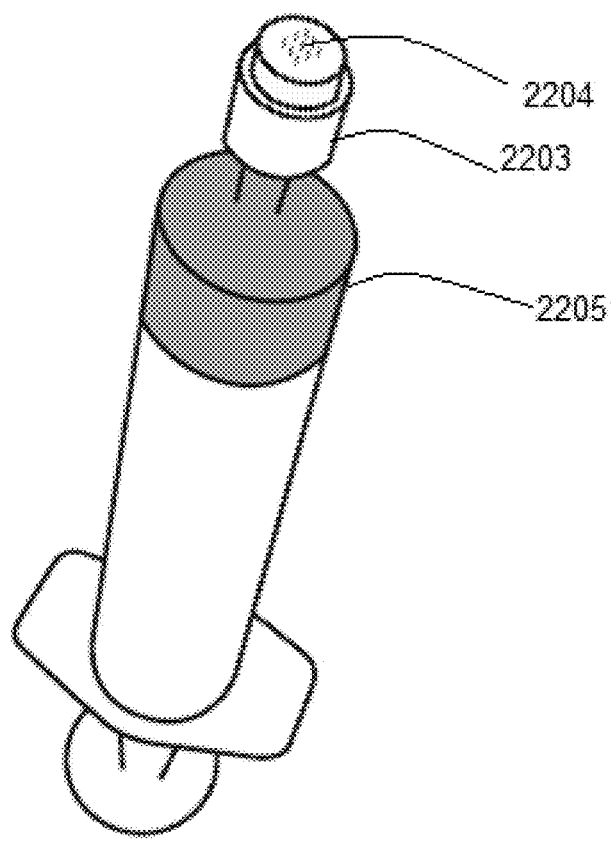
Figure 22D:
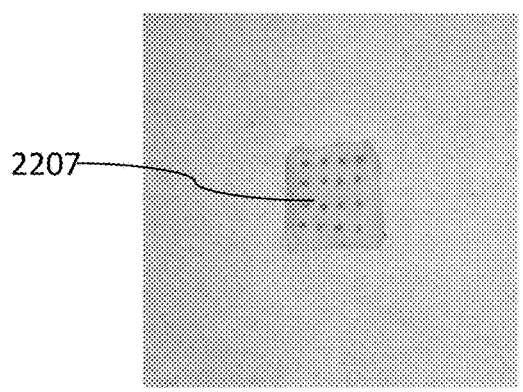
Figure 22A:
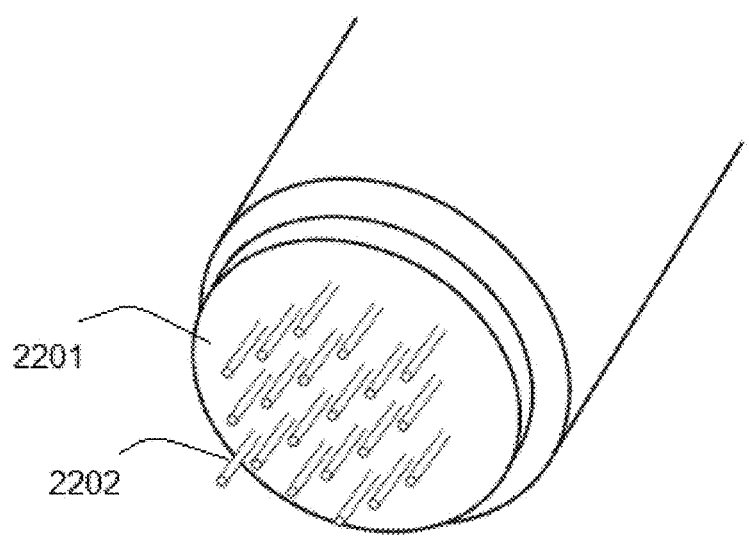

FIGS. 22A, 22B, 22C and 22D show exemplary schematic/images of microimplant arrays created using inventive methods and illustrative devices according to the present invention. FIG. 22A shows microneedle array (2201) containing 20 microneedles (2202) used to create 20 micro cavities per insertion in the tissue. FIG. 22B shows 33MP hollow microneedle array with 3 by 3 hollow microneedles array (2204) attached to a syringe via Luer hub (2203) containing injectable composition (2205, PDLG 5002 biodegradable polymer solution in DMSO with methylene blue as a visualization agent) to form microimplant array. FIG. 22C shows a 3 by 3 array of fluorescent biodegradable cylindrical rods (2206, 100 microns diameter and 1000 microns height prepared by slicing 100 microns diameter fluorescent fiber/thread) and is inserted in the tissue to form an array. FIG. 22D shows image of 4 by 4 microimplant array made in sheep skin. Array is an exemplary synthetic PEG-polylactone based biodegradable thermosensitive polymer hydrogel containing rifampin encapsulated microspheres (2207, red colored) for sustained drug delivery.

Figure 23A:
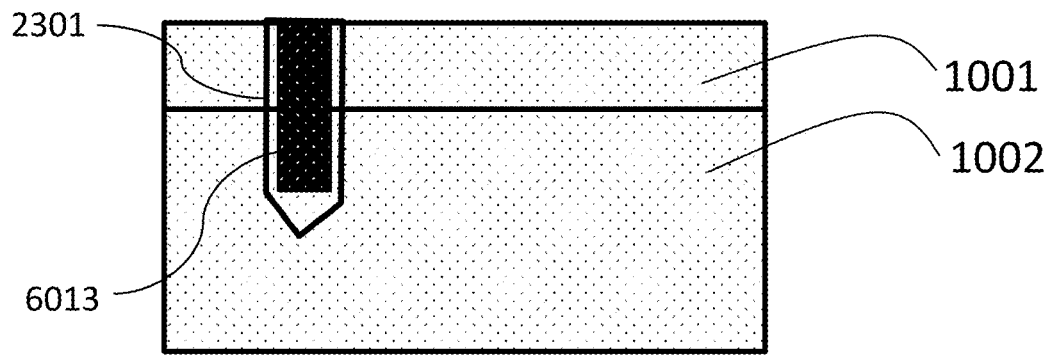
FIGS. 23A-23C shows schematic representation of use of expandable array needle in forming drug delivery microimplant array.
Figure 23B:
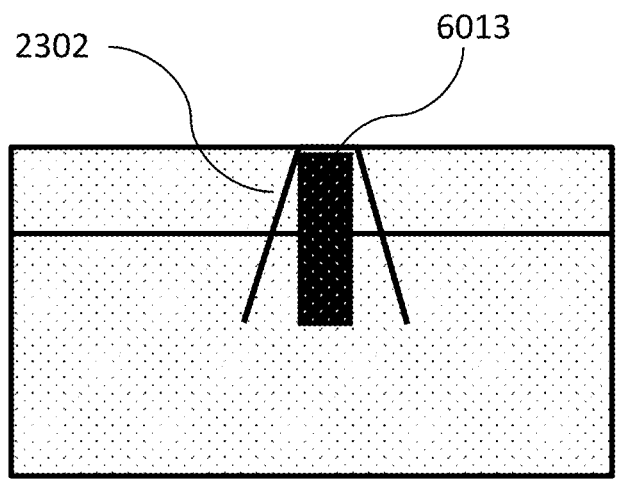
Figure 23C:
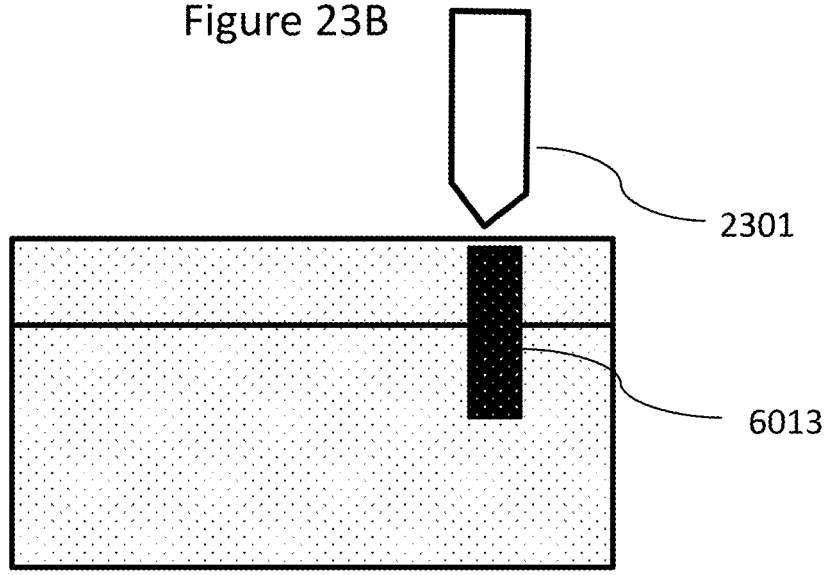

FIG. 23A to C show schematic representation of use of expandable array needle in forming drug delivery microimplant array. 2301 is an expandable needle/stent with hollow cavity for storage of drug/cell delivery microimplant and may have sharp edge at distal end. Plunger array needles used in AIA device described in this invention can be expandable needles such as 2301. The needle is present in the compact form in the base array cavity needle of AIA device. The base array cavity space prevents the expandable needle from expansion. FIG. 23A shows an expandable needle in compact form with microimplant (6013) in its cavity and is pushed out from the base array cavity into the skin tissue in unexpanded form but with implant in its cavity. FIG. 23B shows the expansion of needle/stent into an expanded shape or its memorized shape (2302). The expanded shape has been pre-memorized into needle/stent using a heat treatment of the Nitinol alloy. The expanded shape release the implant in the skin tissue and needle 2301 is then withdrawn in the base cavity array in compact form and then out of the skin tissue (FIG. 23C). Preferably during expansion of needle, the implant is pushed out in the skin tissue. The microimplant (6013) is left in the tissue in an array format for therapeutic action.

Figure 24:
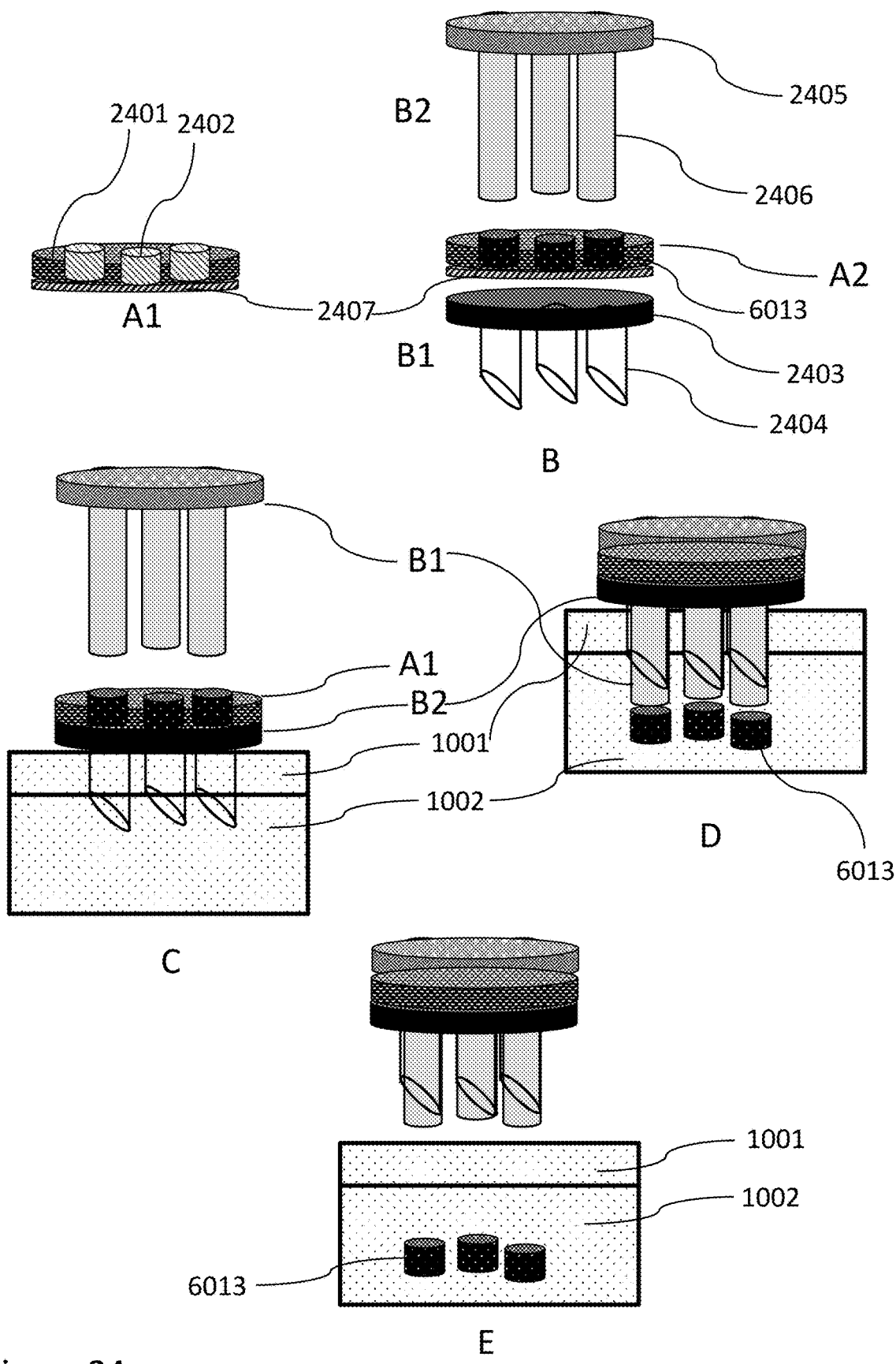
FIG. 24 depicts a partial schematic representation of another version of "array in array" device in an alternate embodiment.

FIG. 24 shows a partial schematic representation of another version of "array in array" device wherein a separate cartridge for holding microimplants is used. The cartridge can be aligned and placed between base array or outer array and plunger or inner array. The microimplants in the cartridge are then inserted into skin/tissue via base array cavities. FIG. 24A shows an exemplarily circular shaped cartridge wherein cartridge has a base plate (2401) with one or more holes/cavities (2402). The holes have openings on both sides of the plate 2401 surface (proximal and distal end). The holes 2402 can be filled with preformed or in situ formed microimplants (6013) with drug/cells (A2). The bottom and/or top surface of 2401 may be covered with protective cover (2407) which may be removed at the time of use. The 2407 prevents unwanted slippage of implant from the holes during storage and handling. B1 and B2 represent base array and plunger array respectively similar to described in FIG. 6 wherein 2405 is a base plate to which hollow sharp needles 2404 are attached. Proximal end of needles has opening on the base plate to load microimplants. B2 is similar to the plunger array described in FIG. 6 wherein 2405 is a base plate to which solid non-cutting needles (2406) are attached. The internal diameter of hollow needles (2404) is same as hole diameter in cartridge (2402). The external diameter of plunger needles (2406) is less than the diameter of holes (2402) and it can freely move up and down in the holes/cavities of 2402 and 2404. The number of needles and holes and their arrangement in the array is identical in A1, B1 and B2. FIG. 24C shows array B1 inserted in the skin tissue and cartridge A2 with microimplant is placed on top of array B1 with protective cover 2407 removed. The center of all the holes in FIG. 24A is aligned with the center of hollow needle opening on baseplate of B1. The center of plunger array needles in FIG. 24C is also aligned with center of holes in A2 and B2 but is not inserted in cartridge A2. FIG. 24D shows the insertion of plunger needles in the holes of cartridge A and cavities of B1 and pushing the implants from A2 via cavities of 2404 in the skin tissue. Both the arrays and cartridge is pulled from skin tissue leaving behind microimplant array with drug/cells for local or systemic therapeutic effect. The cartridge may be packaged and stored separately and used as described above or it may be packaged in the pre-aligned form in the AIA device and used for implantation. The cartridge, plunger array may have additional holes (not shown) and base array may have guiding posts (not shown) to help in alignment similar to described in FIG. 6.

Figure 25:
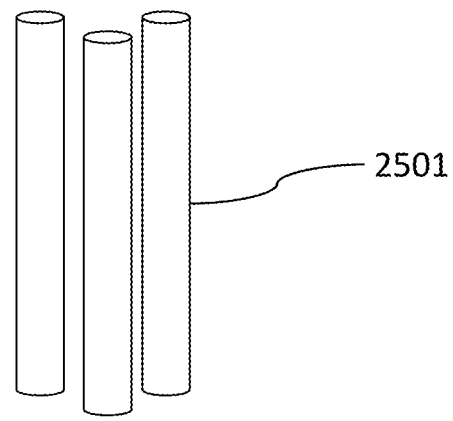
FIG. 25 shows a partial schematic representation method to make base or plunger array according to present invention.
Figure 25:
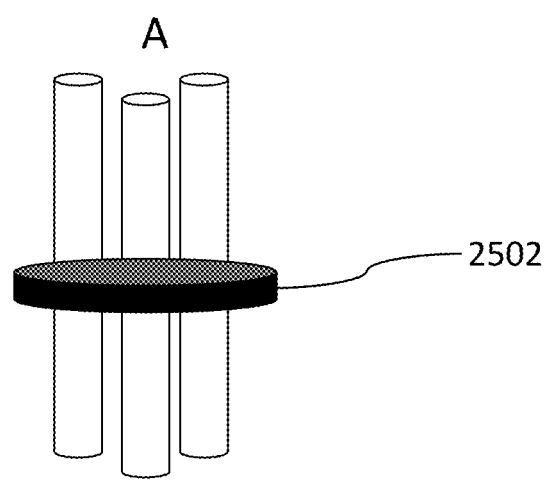
Figure 25:
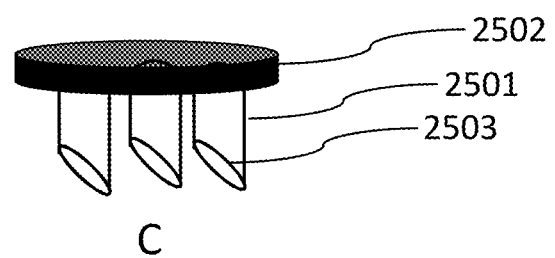

FIG. 25 shows partial schematic representation method to make base or plunger array as described in FIG. 6. Metal/plastic/ceramic preferably metal hollow tubes with a desired diameter and length are provided (2501). The tubes are encased in a plastic or metal plate (2502) via in situ casting of plastic resin or injection molding or wielding/adhesive bonding or other methods. The encasing of tubes acts as a circular base or plunger plate described in FIG. 6. The encased tubes are cut on the base plate surface (proximal end, straight cut) and angular cut at desired angle at distal end to produce sharp edged (2503) hollow microneedles at distal end. The sharp-edged microneedles (2503) protrude from the base plate (2502). The cut edges may be polished to produce a sharp edge. The opening on base plate surface (proximal end, not shown) is used for insertion of microimplant for forming/casting in situ implant. The hollow tubes may be substituted with solid rods to produce plunger array. Alternatively, plunger array can be entirely made by injection molding of commonly used medical thermoplastics. Alternatively, the needles may be first cut to desired length with sharp end and then encased in a plastic/metal/ceramic base plate (2502) to produce needles with sharp edges at distal end and opening in proximal end.

FIG. 26 shows partial schematic representation of various configurations of biodegradable metal based, preferably magnesium alloy based, microneedles and arrays that can be useful in making implantable drug delivery devices. FIG. 26A schematically shows a biodegradable magnesium alloy based hollow array needle (2601) with sharp distal edge (2602) for easy tissue penetration. The hollow cavity of needle is partially or completely filled with sustained drug delivery composition such as PLGA polymer with a drug like rifampin (2603). FIG. 26B shows a schematic of an illustrative array needle 2604 whose external surface is coated with biodegradable sustained drug delivery composition (2605). The composition 2605 may have one or more coating layers and one of them may be a release rate controlling layer without a drug. FIG. 26C shows a hybrid needle wherein the tip of the needle (2606) is made up using biodegradable metal for easy skin penetration and the drug delivery portion (2607) is made biodegradable polymer/hydrogel with sustained drug or live cell delivery composition. FIG. 26D shows schematics of illustrative biodegradable metal array needle with various configurations for infusing drug delivery compositions. Figure D1 shows a biodegradable metal array needle (2608) wherein wedge shaped micro pockets are created inside the needle surface and then filled with drug delivery composition (D1, 2609). In another variation (D2), rectangular portions have been cut out in the needle body to create a space for drug delivery composition filling material (2610). In another variation (D3), several artificial microcavities of various shapes (cylindrical in this illustrative case) or holes are created in the needle surface/body and the cavities/holes are then filled with injectable drug delivery compositions (2611). FIG. 26E shows illustrative microneedle implantable array device with biodegradable metal based microneedles attached to a flexible removable backing material. Four microneedles having holes/cavities filled with biodegradable drug delivery compositions (2611, D3) are attached using a pressure sensitive adhesive (2613) to flexible backing material (2614) in an implantable array format to create a biodegradable microneedle array based drug delivery device. The needle base is attached to the adhesive and free distal end with sharp edge is used for tissue penetration. The device is inserted in the skin tissue by pressing the backing layer with needles sharp ends facing the skin and implanted in the skin. The backing/adhesive material is removed leaving behind the array in the skin. The metal array and drug delivery compositions are biodegradable and provide a drug for local or systemic therapeutic effect.

This invention teaches methods and compositions for infusing injectable compositions, preferably with drug/cells or imaging agents in the body or skin or in the tissue of a bioprosthesis.

Different embodiments of the present invention are described by referring to various medical/industrial applications and examples as provided.

DESCRIPTION OF PREFERRED EMBODIMENTS

In this invention, the microimplant array, preferably biodegradable arrays are made in situ inside the tissue rather than in a controlled factory setting. Briefly, artificial porosity or microchannels or cavities are first created inside a live tissue or bioprosthesis tissue using a surgical procedure such as laser drilling or oscillating needle or microneedle array and the like or any other method known in the art or yet to be discovered. The pores or microchannels or cavities created by the microarray are then filled with an injectable drug delivery composition comprising a drug or bioactive compound or live cells. In preferred compositions, the drug and biodegradable carrier matrix are injected in a fluid state and cast or solidified in situ inside the pores to form microarray or microimplant like structure inside the tissue. Preferably the solid formed is a unibody implant. The solidified compositions in array form release the drug in a sustained manner for local or systemic therapeutic effect. In some embodiments, using specialized devices described in this invention, microimplant arrays are made in situ in the tissue using prefabricated microimplants. The comparison of conventional microarray based drug delivery systems and microarray like structures created inside the skin or tissue as described in this invention is shown in Table 1.

TABLE 1

Comparison of drug delivery arrays made externally and in situ generated array as described in this invention.

| Conventional Drug Delivery Array | In Situ Generated Drug Delivery Array |
|---|---|
| Externally fabricated. Limited in shape and material choice. Generally, must have sharp edges for easy penetration in the skin tissue. | In situ generated. No need to have sharp edges. The array shape is dependent on skin/tissue and artificial porosity/cavity shape created for the specific application. |
| Array material must be a solid for implantation and cannot be liquid in nature. | Can form liquid based microimplant arrays. |
| Generally, has external backing material for application of external force and ease of insertion. | Not applicable. |
| Cost associated with fabrication of array in factory setting and insertion mechanism. | Cost associated with porosity generation in the tissue and preparation and injection of injectable composition. |
| The microneedle array material must have hardness and mechanical strength to withstand resistance from skin/tissue for insertion. Soft elastomeric materials are not preferred/suitable. | No such requirement which enables to choose from wide variety of biocompatible materials. |
| Limited availability of size and dose due to external manufacturing. | More flexibility on microimplant size and drug dose. The size, number of microimplants in the array and their arrangement can be tailored for specific clinical application. |

Biodegradable implants can be made in situ for drug delivery applications (U.S. Pat. No. 5,567,435 cited herein for reference only). Generally, such methods are useful to fill a body cavity that is naturally present in the body. Though such methods are useful, these methods have limitations. A comparison of in situ formation of materials generally known in the art and inventive methods and compositions proposed in this invention are shown in FIG. 1 and Table 2. FIG. 1 shows partial and schematic representation of making in situ generated drug delivery implant made using conventional syringe based method and array based methods described in this invention. A partial schematic of muscular tissue is represented by 1003. The injectable composition is injected as a crosslinkable precursor fluid/liquid from a conventional syringe using intramuscular injection. The precursor liquid forms a gel or polymer in situ inside the intramuscular tissue as a single solid implant generally with irregular shape (1004) (FIG. 1A). The formed implant may have drug or cells entrapped in the implant. The implant (1004) is created without creating artificial cavity first. FIG. 1B shows an injectable composition comprising cell encapsulated microspheres (1004) injected into muscular tissue (1003). Some of the microspheres/cells in the 1004 or 1005 implants are in contact with itself and not with the surrounding tissue (middle portion of the implant). The middle portion of the implant is devoid of tissue fluids which can potentially affect the in vivo drug release profile or cell viability. This isolation of implant from the tissue can also prohibit cells to get required nutrients from the tissue potentially reducing cell viability. Microimplants drug delivery array (1005) formed using methods, compositions and apparatus described in this invention is shown in Figure C. The microarray implant formed according to this invention shows well defined shape and several microimplants are formed providing large surface area. Due to separation between each microimplant, each microimplant is surrounded by a tissue which enables drug extraction by tissue fluids and also enables to get nutrients for the cells from the tissue.

TABLE 2

Comparison of conventional injectable drug delivery systems and microimplant drug delivery array as described in this invention.

| Conventional injectable drug delivery systems made using in situ polymerization systems. Inject generally large volume, typically greater than 1 ml delivered using a syringe like device. | In situ generated drug delivery microimplant array described in this invention Deposits several small volume droplets in well-defined artificial cavities inside the tissue, typically using a microarray device. |
|---|---|
| No control over shape of the implant. For example, intramuscular injection of injectable composition generally, forms irregular shape implant. | Well defined cavity shapes are generally used to form/cast an implant. |
| Generally, forms one large body implant in situ. | Generally, forms several discrete small volume microimplants. |
| Limited area of the in situ formed implant exposed to the tissue for dispersion of drug in the tissue. In case of microspheres based drug delivery systems, each injected microsphere may not be in contact with tissue and therefore may have difficulty in drug elution in tissue fluids. | Microimplants array made according to this invention generally have large surface area due to small size and large number of implants. Each microimplant is in contact with tissue which enables better diffusion of drug in the tissue. |
| Can be used with commonly used device like syringe and needle. | May need a specialized device and special manufacturing process. |
| No need to create artificial cavity. | Must create artificial cavity generally with well-defined shape and size. |
| Removal of implant is generally difficult due to deep intramuscular injection and absence of visualization agent to locate the injected product. | Removal, destruction, laser induced vaporization or drug deactivation is possible if implanted under the skin and/or visualization agent can assist removal. |

In this invention, new methods and compositions to create or fabricate drug delivery devices/arrays in situ inside the live tissue or bioprosthesis tissue are disclosed. Briefly, porosity is first artificially created on live tissue surface such as skin tissue. The cavities created in the tissue are then filled with drug delivery compositions for sustained drug delivery and therapeutic effect. A partial and schematic representation of making in situ generated drug delivery array for sustained drug delivery is shown in FIG. 2. A partial schematic of skin tissue is represented by epidermis (1001) and dermis (1002) layers. Artificial porosity is first generated in the epidermis and/or dermis layer by many methods known in the art or described in this invention. Conical shaped cavities (2001) formed in the skin tissue are schematically shown. The cavities (2001) are then filled with fluid injectable drug delivery composition comprising drug/s or bioactive compound/s (2002). Optionally the fluid composition is converted into solid or semisolid or hydrogel (2003) by physical and/or chemical means and entrapping the drug in the in situ formed solid or gel. The drug is released from the solid or gel in the surrounding tissue by diffusion and/or biodegradation and/or bioerosion or combinations thereof processes.

Creation of Artificial Porosity in the Tissue:

The term porosity also includes voids, cavities, holes, surface grooves, indentations, channels, roughness and the like. Artificial tissue porosity is created first and is then used to store or fill the therapeutic agents or drugs or live cells. Many methods can be used to create porosity in the tissue. The porosity creation may involve surgical procedure, preferably MIS surgical procedure. Generally, up to 2-5000 microns, preferably up to 5-1000 microns, even more preferably 10-600 microns thick human skin layer is preferred because such tissue can be accessed easily and potentially does not involve any nerve endings, thus enabling a relatively pain free procedure. For greater than 600 microns deep tissue access, topical local anesthetics lotions or gels or injections may be used to reduce pain in creating artificial porosity. One preferred method involves use of physical means or mechanical methods such as use of metal, ceramic or polymer needles or microneedle array or coring needles or biopsy needles to create pores or microchannels or cavities in the skin tissue. In one exemplary embodiment, AdminStamp devices, which contain AdminPatch® Microneedle Arrays attached to an applicator, are used. The AdminPatch microneedle array is available in variety of needle lengths. For example, AdminPatch® 1500 product has thirty-one 1400 micron tall microneedles located within 1 sq. cm circular area. The entire device is 20 mm in diameter and is made of medical-grade SS316L stainless steel. This array is attached to a stamping tool which enables easy application of array on tissue surfaces and creates porosity. Other microneedle arrays, available commercially, have forty three 1100 micron tall microneedles; eighty five 800 micron tall microneedles; one hundred eighty seven 500 micron microneedles and seven hundred fifty two 250 um-tall microneedles located within 1 sq. cm circular area. In the exemplary embodiment, an AdminStamp 600 Microneedle Array Device, which contains AdminPatch® Array 0600 microneedle array attached to an applicator with six low-profile stainless steel screws, is used. This device has one hundred eighty seven 500 micron microneedles located within 1 sq. cm circular area. A 2 cm by 2 cm sheep skin tissue is used to create porosity. Briefly, the 10 cm by 10 cm sheep skin portion is cut, hydrated for 2 minutes in PBS; shaved to remove all hairs and the AdminPatch® Array 0600 microneedle array is applied on the tissue. Upon application of pressure, the needles penetrate the skin surface, creating one hundred eighty seven 500 micron size holes in the tissue surface. To assist visualization of holes created, Trypan blue staining dye solution or a PLGA polymer solution in n-methyl pyrrolidone (NMP, 10 percent weight/volume polymer in NMP) containing one percent coumarin (relative to polymer plus drug weight) as fluorescent dye as well as model drug is applied. The solution is incubated for 1 minute to 10 hours to enable penetration inside the cavities created. The excess solution is wiped off from the skin surface. To remove any surface polymer and dye, the surface was cleaned and wiped off with methanol which is a nonsolvent for the polymer. In the artificial cavities created by the stamp, the water in skin tissue dissipates the NMP from the solution, forcing the polymer to precipitate inside the artificial cavities along with fluorescent dye. The precipitated polymer in the cavity takes the shape of the cavity and form into polymer solid mass with entrapped dye. The precipitated polymer solids are observed using microscope under blue light. The coumarin is fluorescent under blue light which enables to see the presence of dye and the polymer in the cavity. Other microneedle stamps were used to create cavities/microarrays inside the tissue with depth ranges (the needle size, shape and length equals to shape and depth of cavity). If more cavities are needed, the same stamp is pressed at a different location on the tissue. For example, the same stamp is removed from the surface and reinserted at 1 to 2000 micron apart from the first location of insertion. In this way, the number of cavities created is multiplied and several hundred cavities can be created on the skin tissue.

In another variation of this method, a polymer solution is first applied on the skin surface and allowed to form a liquid layer of 0.5 micron to several mm thick. The microneedle stamp is then applied on the skin via the liquid layer. The microneedles carry the polymer and drug solution inside the tissue. In this method, the cavity creation and subsequent insertion of injectable fluid drug delivery composition is done almost at the same time. The needle surface area helps to drag/carry the solution inside the cavity space created during insertion. This concept is illustrated in FIG. 3. Partial and schematic representation of making in situ generated drug delivery array for sustained drug delivery is shown in FIG. 3. The skin tissue is covered with a fluid drug delivery composition such as 10 percent PLGA and coumarin solution (3002) in DMSO (coumarin is added as model drug, one percent relative to PLGA plus drug weight). The metal, polymer or ceramic microarray needle (3001) with sharp edges is placed on the skin and polymer solution, and is pressed against the skin to perforate the skin. During perforation, the needles of the array create a plurality of artificial cavities and also carry the drug delivery composition in the cavities (3003). Optionally the fluid composition is converted into solid or semisolid or hydrogel (3004) by physical and/or chemical means and entrapping the drug in the in situ formed solid matrix. The drug is released from the solid in the surrounding tissue by diffusion and/or biodegradation or combinations thereof processes. The use of polymer solution is for example only. Precursor of crosslinking compositions such as fibrin glue prior to gelling or crosslinking, neat liquid carrier of drugs and other fluid compositions may be forced into cavities and converted into solid and/or gels for drug delivery.

In another embodiment, a dissolvable microneedle array is used to create porosity. Various small compounds (with molecular weight below 2000 g/mole)/sugars can be used to make dissolvable microneedles or microimplants with drug and these include but limited to: xylitol, sucrose, maltose, mannose, cyclodextrin, stachyose, inositol, mallorol, melitose, iso-maltulose, dextran, lactulose, trehalose, turanose, fructose, icodextrin, raffinos, maltodextrin, glucose, lactose, sorbitol, mannitol, melezitose, palatinit, maltulose and the like or combinations thereof. Partial and schematic representation of making in situ generated drug delivery array using dissolvable array is shown in FIG. 4. A partial and schematic representation of making in situ generated drug delivery array for sustained drug delivery is shown in FIG. 4. A partial schematic of skin tissue is represented by epidermis (1001) and dermis (1002) layers. Artificial porosity is generated in the epidermis and/or dermis layer by using dissolvable microneedle array (array is made using hyaluronic acid or dextran and the like, 4001). The dissolvable array is pushed in the tissue and needle materials are allowed to dissolve in the body or tissue. The cavities created by the dissolution of needles (4002) are then filled with fluid injectable drug delivery composition/s comprising drug/s or bioactive compound/s or live cells (4003). Optionally the fluid composition is converted into solid or semi-solid or hydrogel (4004) by physical and/or chemical means and entrapping the drug/cells in the in situ formed solid or gel. The drug is released from the solid or gel in the surrounding tissue by diffusion and/or biodegradation or combinations thereof processes. Briefly, dissolvable microneedles are used to create porosity in the tissue. The dissolvable microneedles are designed to penetrate the tissue and are generally comprised of a therapeutic drug. Upon insertion, the needles dissolve in the physiological environment such as present in the human skin tissue (37 degree C., pH 7.4). The dissolution of the dissolvable microneedle array creates a space or cavity in the tissue which is then filled with the injectable compositions. The injectable compositions release the drug in a sustained manner. The injectable compositions also may undergo physical or chemical changes leading to formation of solid, semi-solid or gel like implant in the cavity. Many methods are known in the art to prepare dissolvable microneedle implants. Some manufacturers also supply dissolvable microimplant arrays for research use. In general, aqueous solutions of biocompatible water soluble salts/small molecules or macromolecules/polymers are used to make dissolvable microarray implants. Biocompatible, non-toxic materials like sugars (various types), cyclodextrin and its derivatives can be used. Water soluble polymers likes polyvinyl pyrrolidinone, carboxy methyl cellulose, polyvinyl alcohol, hyaluronic acid, dextran, chitosan, carboxymethyl cellulose, and the like may be used to make dissolvable microneedle array. Generally, arrays are made by casting the aqueous solutions of desired materials in the mold of desired size and shape. A casting mold can be made by the use of photolithography process, mechanical cutting and fabrication tools or other methods known in the art. Materials like silicone rubber are preferred because their elastomeric nature and chemical inertness. Mold materials like silicon (suitable for photolithographic process), polymethyl methacrylate, nylon and the like may also be used. The mold consists of several cavities arranged in the form of an array with desired shapes, volumes and sizes such as conical shape cavities. The desired array material is poured in the mold cavity and mold and cavity are generally subjected to centrifugal force to drive and fill the cavity. The water is generally evaporated and the array material is removed from the mold and used. In one illustrative embodiment, a silicone rubber mold is used to prepare 10 by 10 array with 700 microns height and 200 by 200 microns base size pyramid shaped needles prepared from carboxymethyl cellulose solution. The solution is poured, centrifuged and the solvent is removed by air drying to produce the array. In another example, an array made from polyvinyl pyrrolidinone is used. In another embodiment, a hyaluronic acid based dissolvable microneedle array implant is purchased from Micropoint Technologies and is used to prepare cavities.

In another embodiment, a 3 by 3 hollow needle array from Micropoint Technologies Pte Ltd, Singapore is used (referred as 33MP, FIG. 22B). The hub has a square needle shape with height of 1000 microns, rectangular base 300× 300 microns, inner diameter 150 microns, and needle pitch 700-1000 microns and needle's center-to-center spacing is 0.63 mm. Hollow Microneedle Hub (33MP) with a Luer-slip female hub which can be connected to syringe with injectable fluid. The needles of this microarray are hollow with a common reservoir for injectable fluid. The injectable fluid can be connected to a syringe with injectable liquid composition. The liquid from the syringe is transferred to the array reservoir via Luer-slip connector to the hollow needles which are used to deposit the liquid where it is needed. Generally, all 9 needles deposit liquid from the syringe at the same rate. The height of the microneedles is 1,000 microns and the needle's center-to-center spacing is 0.63 mm. The internal diameter of the microneedles is 150 microns. In some embodiments, the array was used on bovine pericardium or sheep dermal tissue or on gelatin gel (transparent tissue like model material) as an experimental material to create porosity. The array is used to create 3 by 3 array holes in the tissue with a cavity depth of 1000 microns and cavity diameter is same as external diameter/shape of the needle. The external shape of 33MP needle is rectangular pyramid which is a shape of cavity it creates. A PLGA polymer solution with coumarin is used to fill the cavity after its creation. Since the cavity created has pyramid like shape, the in situ formed implant has pyramid like shape.

In some situations, the hollow needle or hollow microneedle array used to create cavity may cut the tissue (tissue coring) and the cut tissue may occupy the space inside the needle cavity/hollow space. To prevent the tissue penetration inside the needle cavity, certain modifications may be made to create clean well defined space or cavity inside the tissue. In one illustrative embodiment, a 3 by 3 hollow needle array (33MP) needles are dip coated using 30 percent carboxymethyl cellulose solution and air dried. This forms a thin water soluble film on the outer surface of the needle surface including the hollow needle opening. The coated needle array is then inserted in the tissue. The coating on the needle opening pushes the tissue away from the needle and prevents it getting into hollow portion of the cavity. The injectable composition such as polymer solution or fibrin glue or precursor of crosslinkable composition is then deposited in the hollow needle cavity. Upon physical and chemical transformation of the composition in the cavity, and dissolution of poly carboxymethyl cellulose membrane, the needle of the array can be withdrawn from the tissue leaving behind the deposited composition in the artificial cavity created by the hollow needle. The water soluble membrane serves as temporary barrier for tissue to enter in the needle cavity and its dissolution enables withdrawal of the needle without pulling the injectable composition from the tissue. FIG. 5 shows partial schematic representation of creation of cavity using coated hollow needle of microarray and filling the cavity with injectable composition. 5001 denotes a hollow microneedle of array such as 33MP array. The tip of 5001 needle array is coated with water dissolvable coating or removable coating (5002). The applied coating and its thickness does not affect sharpness of the coating. The coated needle is inserted in the skin tissue (1001 and 1002). The coating prevents insertion of tissue and other material in the hollow space inside the needle. The hollow space in the needle inserted in the tissue (5004) is then filled with injectable composition such as fibrin sealant, DuraSeal sealant precursors or biodegradable polymer solution in water miscible biocompatible solvent (5005). The water in the tissue or components in the injectable material dissolve the coating 5003 which enables removal of the needle from the tissue without obstruction from the coating material. The injectable composition may undergo physical or chemical changes forming solid implant 5006. The injectable composition may undergo physical or chemical changes. Coating material used has a thickness of 10 microns or higher and preferably 10-1000 microns. It may be dissolvable in water under physiological conditions such that pH 7.4, temperature 37 degree C. The coating is strong enough to prevent tissue from inserting into hollow portion of needle cavity. The preferred material must be biocompatible and biodegradable. The preferred coating material may include but not limited to are: polycarboxymethyl cellulose, polyvinyl pyrolidonone, polyvinyl alcohol, polylactones or polyhydroxyacids such as PLGA, polycaprolactone and the like. Hydrophobic materials may need to be treated with biocompatible water miscible solvents like DMSO, NMP, PEDM, PEG to dissolve the coating prior to injecting the injectable composition. For example, the coating may be treated with 0.1 ml NMP to remove from the tip of needle. In some cases, the "array in array" device described in FIGS. 6A, 6B and 15, may be inserted in the tissue in a closed position (plunger array completely inserted inside base array, FIG. 15F). This can also prevent tissue entering into needle cavity space. The plunger array is withdrawn thus creating a space/cavity inside the base array needle which can be used to fill with injectable composition. The needles used in hollow microneedle array are preferably non-coring in nature. Generally, non-coring needles are specially designed to minimize coring action during skin tissue insertion. Becton Dickinson company sells Huber trademarked non-coring needles. The designs used in Huber needle may be preferentially used. Huber Needles feature a deflected point (the tip is raised above the centerline to minimize contact with tissue or media) which eliminates the potential to "core" a tissue during insertion process.

In another embodiment, instead of using the membrane coating, the hollow needle cavity is first filled with tissue dissolvable compositions such as carboxymethyl cellulose, low melting water soluble polymers like PEG and its derivatives, Pluronics, sugar based compositions, or ice or PBS solution that is in frozen condition and the like in the hollow cavity and inserted in the frozen state. Polymers like PEG molecular weight 2000 to 35000 g/mole or Pluronics and Tetronics are low melting (melting point below 60-70 degree C.) polymers with high water solubility. Such polymers may be melted first and then infused in the hollow portion of the needle cavity and cooled. The solid polymer formed in the cavity prevents tissue accumulation in the cavity, but is dissolved away in the body creating a space for filling the injectable composition. The use of frozen water (ice), frozen saline solution or frozen PBS (pH 7.4, 20 mM) may be used in frozen state in place of low melting polymers. Materials used in dissolvable microneedle array in dry form may also be used. These include but not limited to various sugars, polyvinyl alcohol, carboxymethyl cellulose, dextran, polyvinyl pyrrolidinone and the like. The needles with dissolvable composition are then inserted inside the cavity. With the dissolvable component in the needle, the needle temporarily becomes solid and does not stay hollow. The space occupied by the dissolvable composition does not permit the tissue to enter in the hollow space of needle cavity during insertion process. Upon insertion, the dissolvable composition such as ice or sugar or water soluble polymer dissolves in the tissue, creating space or cavity for injectable composition. The dissolved components may also be suctioned off or aspirated if needed to accelerate the cavity creation process. The injectable composition is then added in the space created by the dissolved composition which conforms to needle cavity shape and transforms into solid or gel like microimplant. The hollow needle is then withdrawn from the tissue, leaving behind the formed implant inside the artificial cavity.

In another illustrative embodiment, cavity creation in the tissue and filling is done at the same time. A polymer solution is first filled in the syringe and the syringe is attached to the array via Luer-slip female hub. The 3 by 3 array (33MP) as described above is then inserted in the tissue at full depth (1000 microns) and pulled back about 5 to 95 percent (50 to 950 microns in case of 33MP), preferably 5 to 95 percent and most preferably 20 to 80 percent. Upon pulling back, the empty space created in pulling the needle is then filled with the injectable composition fluid from the syringe. The syringe is pressed to inject the injectable composition such as polymer solution. The polymer solution occupies the cavity and the excess solution is oozed or transferred on the tissue surface. The array is removed, the excess solution from the tissue is wiped off and polymer solution is allowed to precipitate in the cavity. The NMP or DMSO which is used as water miscible organic polymer solvent is dispersed by the tissue and which leads to precipitation of the polymer in the cavity. The deposited polymer entraps the drug. If a volatile solvent such as acetone is used, then a combination of evaporation and tissue dispersion in any proportion may be used to precipitate/cast the polymer in the artificial cavities created. By choosing variables such as needle height; needle type (hollow or solid); needle shape; needle internal diameter; needle external diameter; spacing between each needle in the array; needle material type; number of needles per array; number of array insertion points and the like, many types of porosities/cavities with different size, shape and depth and number of cavities can be created for a given medical need. For example, height of the array needle may range from 5 microns to 3500 microns, preferably, 10 microns to 2500 microns, even more preferably 20 microns to 1300 microns. The number of needles per array may be greater than 3 or 4 or 5 or 6 and may range from 3 to 10000, preferably 4 to 2000. The needle shape may be cylindrical or conical or pyramidal or combination thereof with sharp edges for easy insertion in the tissue. The shape of the needle also could be, straight obelisk, negative-beveled obelisk, cylindrical, pyramidal, conical, trigonal, tetragonal, pentagonal, hexagonal, pyramidal, irregular and the like or combinations thereof. The shape of needle may be symmetrical or non-symmetrical. Preferably needle should have sharp edges for ease of insertion. Biocompatible and/or biodegradable lubricants such as vitamin E, silicone oil, coconut oil, mineral oil, oleic acid, liquid polymers like polyethylene glycol molecular weight 400 to 1000, polycaprolactone (molecular weight up to 1000), glycerol, detergent solutions like Tween 40 or Tween 80, hyaluronic acid and the like may be applied on needle surface and/or tissues to lubricate and for ease of insertion during cavity creation. The array used may be repeatedly inserted to create additional holes or cavities. The array could be inserted 2, 3, 4, 5, 6 or more times or could be used up to 2-1000 times, preferably 2 to 20 times to create more number of cavities in the tissue. It may be inserted at the same location to stabilize the already created cavity for 2 or more number of times or it may be inserted at a distance lager than the previous hole created. The distance between each array insertion may vary from 1 micron to 10 mm, preferably 2 to 3500 microns, even more preferably 10 to 3000 microns. The needle used in the array may be hollow or solid. If hollow, it may have two, three, four or more lumens to deposit two or more different injectable compositions at the same time. The average needle diameter may vary form 5 microns to 3500 microns, preferably 10 microns to 2000 microns. The needle array materials may be selected from but not limited to metallic, ceramic, glass, polymeric, silicon, solidified aqueous solutions such as ice (frozen, at temperature below zero degree C. and used at temperature below its melting point). The metallic materials used include but are not limited to: iron, copper, magnesium, zinc, stainless steel, titanium, brass, silver, gold or their alloys and the like. The commonly used polymers or plastic materials include but not limited to polyurethane (PU), polypropylene (PP), polyethylene (PE), polystyrene (PS), poly(methyl methacrylate) (PMMA), polycarbonate (PS), liquid crystal polymer (LCP), and the like. The microneedle implant arrays made using dissolvable compositions known in the art may also be used (B. Bediz et al., "Dissolvable Microneedle Arrays for Intradermal Delivery of Biologics: Fabrication and Application" Pharm Res., volume 31(1), page 117-135, 2014, cited herein for reference only). Rapidly dissolvable materials are preferred in some applications. The dissolvable microneedles such as described by B. Bediz et al. may be used to create micropores in the tissue. The advantage of such arrays is that the needles dissolve away upon insertion leaving behind the empty space or cavity which can be filled by injectable therapeutic compositions. Alternatively, surface of such dissolvable microneedles may be coated with injectable compositions like PLGA solution in NMP or PEG and then inserted in the tissue. The coated solution is carried away by the needle in the tissue. As the needle dissolves in the cavity, the aqueous environment precipitates the polymer and entraps the drug inside the polymer solution. The drug is released by the polymer in a sustained manner. Alternatively, as described before, dissolvable microneedle array may be applied through the polymer solution layer on the tissue as described before. Many dissolvable materials can be used which include but not limited to: sugars (fructose, trehalose, and raffinose) and polymeric materials included but not limited to: hyaluronic acid, polyvinyl alcohol, polyethylene glycol and its copolymers, polyvinylpyrrolidone, carboxy methylcellulose, hydroxypropyl methylcellulose, sodium alginate and the like. When using the array with polymer solution, the array material must be a non-solvent for the solvent used in injectable composition. Materials like sugars based dissolvable microarray may be unsuitable because they may get dissolved in solvent like NMP or DMSO. A list of solvents for polymers and other chemicals can be found out from chemistry literature, chemistry handbook and polymer handbook. Mechanical drilling may also be used in some situations, especially in some situations where hard materials like bone, skull and nails are involved. In one illustrative embodiment, a 1/64 inch size micro drill bit is used on a human nail (obtained from a human cadaver). 4 cavities, 100 micron dip, are created on the nail surface, with spacing between the cavities around 1000 microns each. A PLGA solution in acetone or ethyl acetate (10 percent polymer concentration) and 10 percent Terbinafine hydrochloride (relative to polymer plus drug weight, antifungal drug) is applied. The solvent is allowed to evaporate leaving behind the polymer and drug in the cavity and thus forming a 2 by 2 microimplant array. The release of Terbinafine hydrochloride is monitored over a period of 6 weeks in PBS at 37 degree C. In another embodiment, part of human nail is cut. 4 cavities in 2 by 2 array format are created using a syringe needle (average cavity diameter around 700 microns). A PLGA based polymer solution with D and C violet as an illustrative colorant and terbinafine hydrochloride as exemplary antifungal drug is then used to fill in the cavity. FIG. 16A shows a photographic image of part of human nail with artificially created cavities. FIG. 16B shows the cavities (as depicted in FIG. 15A) filled with PLGA based biodegradable composition with D and C violet as colorant. FIG. 16C shows in vitro terbinafine hydrochloride (an antifungal drug suitable for treatment of fungal nail infection) release profile from PLGA based experimental composition released from the array formed inside the nail.

In some embodiments, a syringe needle is used (an illustrative tool) to create cavities manually in the tissue. Approximately 15 mm by 15 mm dry pericardium tissue was used to make cavities by hand in 4 by 4 array format. A 24 gauge needle was used to core approximately 1 mm dip cavity by hand in the tissue. Total 4 cavities were made, 2 mm apart from each other, along the length of the tissue to make one row of cavities. Total four rows were made, 2 mm part to make a 4 by 4 cavity array where each cavity is separated by 2 mm. FIG. 8D shows a pericardial tissue with cavities in 4 by 4 array format as an illustration. Manual method for cavity creation can be useful but may not be preferred where large number of cavities are needed. Variables like the size of cavity, number of cavities made, distance between each cavity, needle size used, depth of cavity can be varied to obtain a suitable array structure. In another illustrative example, a 4 by 4 array was created manually by inserting 24-gauge needle at 100-300 micron depth in the human nail. FIG. 16A shows 2 by 2 array cavities created in the nail.

Oscillating needle such as tattoo needle may be used to create cavities in the tissue or skin. A commercial tattoo machine as described in the related application (U.S. Pat. No. 9,072,678, cited herein for reference only) is used. The 500-1000 micron size tattoo needle is used and the oscillation frequency was 10 to 12000 oscillations per minute. About 1 square centimeter area was treated with the tattoo needle for 1 minute. The pores created by the tattoo machine repeated needle insertion were used to fill the injectable composition such PLGA solutions with the drug as described before. Alternatively, polymer solution is first applied on the tissue surface to form a solution layer and then the tattoo needle is used to create holes through the solution. The needle goes in and out of the tissue surface and carries the solution with it inside the cavity created. The deposited solution inside the cavity is precipitated by the tissue fluids and the precipitated polymer releases the drug in a sustained manner. Additional information about tattoo based methods can be found on related applications cited herein for reference only. In one illustrative embodiment (Examples 6D, 17), bupivacaine base releasing microimplants array was prepared using oscillating needle to create porosity and infuse polymer solution in the porosity. Briefly 172 mg PLGA polymer (PDLG 5002) is dissolved in 1.75 ml DMSO. 0.75 ml of polymer solution and 23 mg of bupivacaine are mixed, and the solution is applied on the glutaraldehyde fixed bovine pericardium tissue. A commercial tattoo machine needle (permanent makeup machine needle) is used to create the porosity and drive the solution inside the tissue. The needle is moved on one square centimeter diameter area. The machine needle oscillated at 6000 times per minute. After about two minutes, the oscillating needle machine is stopped and excess bupivacaine solution is wiped off from the tissue surface. Care is taken to ensure that no polymer sample is precipitated on the tissue surface. A control sample is prepared/tattooed using identical conditions where only polymer solution in DMSO without drug is used for infusion. The treated areas (bupivacaine treated and polymer treated control) were cut from the tissue and were subjected to drug release in PBS at 37 degree C. for several days. The concentration of bupivacaine in the eluted samples is monitored using UV spectrophotometer. A bupivacaine release profile elution curve is shown in FIG. 13 along with polymer. The polymer solution was successfully infused by the oscillating needle. The DMSO is dissipated in the tissue leaving behind PLGA polymer along with hydrophobic bupivacaine. The release from the precipitated polymer is shown in FIG. 13. It is clear from the FIG. 13 that the sustained release of bupivacaine base is possible for several days. By changing type of polymer used, drug concentration in the polymer, polymer molecular weight, number of microimplants, implant shape and the like, a suitable drug release profile may be designed for a given medical condition.

A microneedle fractional radiofrequency (RF) device can also be used to create artificial cavities in the tissue. Such devices are commercially available from Lutronic Corporation or Cryomed Corporation. (Lutronic Corporation, Lutronic, North America, Burlington; Cryomed Corporation, Sydney, Australia). The array device available from suppliers as above or other vendors insert an array of microneedles (5 by 5 array as an example) in the skin tissue. Upon insertion of microneedle array in the skin tissue at a controlled depth (300 microns to 3.5 mm as an example), the needles are supplied with controlled RF power which is transmitted to the surrounding tissue causing controlled denaturation of the tissue surrounding the needles and also forms a micro cavity in the area surrounding the needle. The shape and size of the cavity formed generally depends on the variables like total RF power applied via array needles, needle depth, needle size and shape and the like. Additional information about the device and its use can be found in Byalekere S. C. et al. (J Cutan. Aesthet Surg., Volume 7(2), Page 93-97 (2014)) and references therein; cited herein for reference only. This type of method uses combination of both methods such as tissue displacement (during needle insertion) and tissue destruction (applying RF power to destroy or denature tissue) to create cavities.

In one embodiment, the needle penetration is controlled by the using the spacers. For example, a 500 micron thick polymer adhesive film is first applied on the tissue and a device like 33MP is used through the film. Because the polymer adhesive film has a thickness of 500 microns, the 33MP device needles with 1000 microns needle depth can only penetrate about 500 microns in the tissue. By changing the thickness of the spacer or polymer film, the depth of penetration can be controlled. In another embodiment, the array needles are placed in a "tube in a tube" like device wherein inner tube can be moved out of outer tube using a screw like movement or using a shaft of a linear motor. The needles are placed on proximal end of inner tube and it is moved out of outer tube at precise length. The inner tube array needles come out of outer tube at predetermined length (500 microns as an example). When outer tube is pressed against the skin tissue, the needles up to 500 microns go first into the tissue but cannot go further because of the outer tube prevents it from going it further. Thus the "tube in tube" arrangement of needles and movement of inner and outer tubes can be used to control the depth of penetration. A NuCell skin solution (a Dermapen like device, purchased from Amazon Inc. uses "tube in tube" like arrangement to control the depth of needle penetration. A 36 needle cartilage is inserted in the device and connected via Bayonet Coupling mechanism to the device and the outer tube of the device is rotated clockwise or anticlockwise to adjust the needle exposure or penetration depth. The device has a gauge to adjust the penetration depth from 250 microns to 2 mm. In another embodiment, a 36 pin Needle Cartridges for Derma Pen (micro-needling skin dermabrasion medical device). The Dermapen is an automated micro-needling device, with a disposable needle tip cartridge, that uses 9-42 microneedles array to vertically stamp the skin at high speed. The stamping action of the Dermapen's vertical tip creates micro-cavities in the skin. In one embodiment, A NuCell skin solution (a Dermapen like device, purchased from Amazon Inc.) is used to create cavities. The machine is fitted with 36 needle sterile cartilage (Purchased from Amazon, UPC code 601913872222) via Bayonet Coupling mechanism and the needle length is adjusted to 500 microns. The length adjustments protrude 36 needles out of the machine at the length of 500 microns. An outer plastic tube on the cartilage prevents the needle to go beyond 500 microns inside the tissue. The machine can be adjusted to penetrate from 250 microns to 2 mm in the skin tissue. The 36 needles with 500 microns penetration depth are stamped at the same location 10 times to create 36 artificial cavities in approximate one centimeter square circular area. In another embodiment, a 9 pin cartilage is used to create 9 cavities at 250 micron depth in the sheep skin tissue.

In some embodiments, it is envisioned that only some of the needles are programmed to penetrate the tissue out of several available needles. A 10 by 10 array needle containing 100 needles is used as an illustration. The mechanism wherein only one, or two or 3 or 4 or 10 or 20 needles can come out the array and used for injection. This type of mechanism/arrangement can help to control total drug dose given for a given surgical tissue or skin site. The pattern created by use of programmed insertion may be used to code certain information like type of drug used, its dose, date and time and the like.

In some cases, computer controlled machines may be used to create porosity and to fill cavities. Such machines may deploy microimplant array based devices as described in this invention. Exemplary machines such as da Vinci® Surgical System (Intuitive Surgical, Inc. Sunnyvale, Calif.) or other MIS surgical based instruments known in the surgical art may be preferentially used to deploy microimplant array based devices and compositions described in this invention. The advantage of robotic machine based cavity creation is that more closely space cavities of precise depth and diameter can be made in a reproducible fashion for a given medical need.

Another preferred way to prepare porosity in the tissue is to use laser based methods already practiced in the medicine. For example, ophthalmologists use laser based systems to correct nearsighted vision correction generally referred as LASIK procedure. Laser based tools used in LASIK surgery may be used to drill holes or create cavities in the live or bioprosthesis tissue. Ablative fractional laser therapy is used to treat variety of skin conditions including drug delivery. In one literature reference, cited herein for reference only, E. H. Tudor et al. (Lasers in Surgery and Medicine, volume 46, Page 281, 2014 and references therein) describe the use of erbium yttrium aluminum garnet laser (Er:YAG; 2940 nm) to create several size micro-channels or holes or cavities in the pig skin. The authors were able to create conical shaped channels/holes with ablation width 22 microns to 488 microns and 16 microns to 1348 microns ablation depth (E. H. Taudorf et al., Table 2 in the reference). The shape of cavities created can be seen in histology (E. H. Taudorf et al., FIG. 1 in the reference). The authors modified various instrument parameters (laser power, beam width, laser pulse rate, number of stacks to achieve to control cavity diameter and depth. Many types of ablative fractional lasers (AFXL) instruments are commercially available and are used in modern medicine practice. These machines could be used to create micro-porosity in the live tissue, preferably in the skin tissue or in bioprosthesis tissue. Erbium:yttrium aluminum garnet laser (Er:YAG; wavelength 2940 nm), carbon dioxide laser ($CO_2$; wavelength 10600 nm), yttrium scandium gallium garnet laser (YSGG; wavelength 2970 nm) and the like are some of the most commonly used lasers in medicine practice. These laser instruments emit laser light in infrared range and target water in the tissue. The energy for the laser beam is absorbed by the water present in extracellular matrix in tissues, which leads to evaporation of water and surrounding tissue producing a void or channel or cavity in the tissue. Variables such as laser wavelength, laser spot size, laser power level, laser pulse duration, laser pulse repetition rates, number of stacked pulses and the like can be controlled to obtain cavities with various shapes and sizes in the tissue. Those skilled in the art will understand that many variations are possible and ultimate parameters will depend on desired cavity diameter/size, shape and depth. In general, lasers used in infrared wavelength potentially may create local thermal injury. UV based laser on the other hand, do not create thermal injury and generally provide a clean cut. However, UV radiation can penetrate only at a small depth and generally useful of creating shallow cavities with small size of diameter. UV laser can create much smaller diameter holes than infrared laser and therefore may be preferred where small diameter channels (1 to 100 microns) are desired. In modern laser based instruments, generally the machine parameters are controlled by the computer software. The focused laser beam is scanned across desired tissue area. The laser beam diameter is a function of optics used in the instrument as well as wavelength. UV based laser can be focused on a much smaller diameter as compared to infrared or visible light lasers. The laser energy delivered to the tissue is a function of residence time of laser beam on the tissue surface, total laser power and repetition of laser pulse frequency and the like. Depending on porosity desired, laser wavelength, laser power, laser pulse frequency and other instrument parameters may be varied to obtain a suitable porosity level and cavity size.

There are many methods that can be used to generate porosity in the tissue and preferred methods are discussed above. Those skilled in art understand that porosity preparation methods known in the art or yet to be discovered may also be used. Water jet drilling based methods, ultrasonic energy based methods, particle bombardment based methods and the like could also be used in preparing artificial porosity in the tissue. Among these, porosity preparation using laser based methods, oscillating needle, mechanical drilling and microneedle array based methods are most preferred. Among the microarray based methods, use of dissolvable microarray or hollow metal microneedle array is most preferred.

The artificial cavities created by methods discussed above may create pores or cavities with various shapes, volumes and sizes. The average diameter of cavity prepared may range from 0.5 microns to 3500 microns, preferably 1 micron to 2500 microns, even more preferably 10 microns to 2000 microns. The depth of cavity prepared may range from 1 micron to 5000 microns, preferably 5 microns to 3000 microns, even more preferably 10 microns to 2000 microns. The shape of the cavity created may range from straight obelisk, negative-beveled obelisk, cylindrical, pyramidal, conical, trigonal, tetragonal, pentagonal, hexagonal, pyramidal, irregular and the like or combinations thereof. The distance between each cavity may range from 1 micron to 10 mm, preferably 3 microns to 3500 microns, even more preferably 5 microns to 2000 microns. The volume of each cavity may range from $1\times10E-12$ to 0.05 ml, preferably $1\times10E-10$ to 0.03 ml, even more preferably $1\times10E-10$ to 0.01 ml. Total number artificial pores or cavities created may be greater than 4 per square centimeters or may range from 4 to 6000 per square centimeter. Total number artificial pores or cavities created may be greater than 3 or may range from 3 to 20000, preferably 3 to 15000, most preferably 3 to 10000 per treatment area. The microimplants created by in situ casting of injectable compositions in the cavities described above will have similar dimensions and shapes similar to the cavities created as above. Preformed implants of similar size and shape as above can be inserted in cavities to create microimplant array. The preformed implants may be porous in nature.

When using microneedle array for creating porosity, generally the needles are inserted at 90 degree angle (perpendicular) to the surface. In some applications, that angle may be shifted and could be changed to 30 to 80 degrees, especially implanting prefabricated implants as described in this invention. For example, needle of microneedles may be specially designed such that during tissue insertion, the needles may penetrate at 45 degree or 30 degrees relative to the skin surface. Some of the devices described in this may have microneedles that can insert inside the tissue at 20-80 degree angle, preferably 30-60 degree angle.

When using microneedle array for creating porosity, generally the use of applicator to apply the array on the skin/tissue is desirable. The applicator is specifically designed to apply definite force in the range of 15 N/CM². This enables better insertion of array needles in the tissue. Generally commercial suppliers of array materials can provide an applicator for obtaining highly reproducible results while using their array product. Human hand when used properly can be used without the applicator if trained properly. A specific applicator may also be designed and used for a given microneedle array. A robotic machine may be programmed to exert force in the range of 5 to 30 N/CM², preferably 10 to 20 N/CM² and even more preferably 15N/CM² force. Similar amount of force may be used in inserting AIA device needles.

The porosity creation as described above may involve either tissue displacement or tissue destruction or combination of both. Use of dissolvable microneedle array generally involves tissue displacement and this type of porosity generally does not remove or destroy the tissue. Methods such as micro-drilling in bone tissue or infrared laser burning of tissue and the like, physically remove the tissue from its existing space and create a space or cavity. The choice of cavity creation will depend upon the clinical need and desired outcome. In general, methods using non-destructive removal of tissue such as use of dissolvable microarray needle array are preferred or use of specialized devices such as "array in an array" type described in this invention may also be used. Methods that displace the tissue rather than destroy the tissue also are most preferred.

Infusion of Injectable Compositions in the Artificial Porosity
Methods of Filling the Artificial Cavities The artificial cavities created as described in previous sections are filled with injectable compositions that can provide sustained release of drugs. The filling materials are generally in a fluid state or in the liquid state and have ability to flow in the tissue cavity or porosity. The liquid composition may be a low to high viscosity. Viscous injectable liquids, preferably with low viscosity (1 to 500 Centipoise) to medium viscosity (500 to 10000 Centipoise) are preferred. The liquid composition injected may be solution, emulsion or suspension or combination thereof comprising a carrier matrix and bioactive compound or drug or may comprise live cells. The fluid composition may be applied on the cavities and it is pulled into cavity via gravity. If needed, additional pressure/force may be applied on liquid composition to force the composition in the cavity. The pressure may be applied using a gas or liquid means. For example, the liquid composition may be first applied on top of the porous area and the area is enclosed using an enclosure device. The enclosure device is connected to a gas line such as carbon dioxide, oxygen or other biocompatible gas. The enclosure is then filled with gas and gas pressure is increased in the enclosure. The pressurized gas transfers its pressure on the injectable composition on top of cavities which helps the composition to enter in the cavities and fill the cavities with the composition. In one embodiment, a pressurized gas stream coming out from a 19-gauge syringe needle is used to drive the injectable composition in the artificial cavities. Instead of gas, biocompatible fluids such as PBS or other biological biocompatible aqueous buffers may be used to apply pressure and inject the compositions. Biological fluids that may be used include but not limited to are: phosphate buffer pH 7.2, triethanol amine buffer pH 7.2, HEPES buffer pH 7.2 and the like. Care is taken to ensure that the liquid used does not affect the injectable composition or does not prematurely precipitates before going in the cavities. In some case, injectable composition may be sprayed or atomized and the fine droplets are forced into artificial cavities. Other energy based methods such as use of magnetic force, ultrasonic waves, laser radiation and the like may also be used in filling injectable compositions in the cavities. Alternatively, injectable compositions may be filled using syringe like device and injected in the cavities with or without pressure. Those skilled in the art understand many methods can be used in assisting in filling the cavities; the ultimate choice will depend on the injectable compositions, its viscosity and other injection parameters. The cavities may be filled partially (1 percent to 99 percent, preferably 10 to 90 percent of cavity volume occupied by the composition) or completely with injectable compositions. It is preferred that at least 10 percent or higher cavity space is occupied by the composition. It is not necessary to fill all the cavities. Depending on the desired clinical outcome, drug concentration, 1 to 99 percent, preferably 10-90 percent of available cavities may be filled with the injectable composition.

The injectable compositions may be filled in the cavity with one, two, three, four or more layers and each layer may have a different drug/cells or biodegradable polymers or combinations thereof. Two or more injectable compositions may be filled in layers to form a multi layered implant. Each layer may have a drug or cell or visualization agent. The multilayer approach may be used in some cases to achieve a desired release rate. In a three layered implant the top and bottom layer may have biodegradable polymer without drug and the middle layer has a drug. The drug diffuses through the top and bottom layers and affects its release profile. Alternatively, top and/or bottom layers may contain a visualization agent such as fluorescent or colored compound. A prefabricated multi-layered implant may be also inserted in the cavity to form an array.

Microfluidics is the science of manipulating fluids at micron and submicron levels. Many microfluidics devices are available commercially that can be used for variety of scientific and technical applications. Please refer to review of microfluidics devices by L. Y. Yeo et al. (Small, 2011, Volume 7(1), Page 12-48, (2011) and R. G. Willaert et al. (Fermentation, Volume 1, Page 38-78 (2015) and references therein; cited herein for reference only for additional information. In one embodiment, a glass or silicone rubber based microfluidic array with 9 fluid channels is designed and each output of the channel is fed to a microneedle of 3 by 3 array using a specially designed connector. This way, small volumes of injectable compositions can be used to inject via microfluidic array into the artificial cavities. Commercial firms like uFluidix (Toronto, Canada); Fluigent Inc. (Lowell, Mass.) can also help to design and make desired microfluidic device for a given use. Injectable compositions comprising drug/cell encapsulated microparticles A partial and schematic representation of in situ generated drug delivery array comprising drug encapsulated microparticles is shown in FIG. 7. A partial schematic of skin tissue is represented by epidermis (1001) and dermis (1002) layers. Artificial porosity is generated in the epidermis and/or dermis layer (7001). Conical cavities (7001) formed in the skin tissue are schematically shown. The cavities (7001) are filled with fluid injectable drug delivery composition comprising microparticles encapsulated/coated with drugs (7002). The drug is released from the microparticles in the cavity and in the surrounding tissue. Example 14C provides an illustrative method for infusing rifampin loaded microspheres in the skin tissue. FIG. 14 shows a drug release profile of rifampin encapsulated microspheres from microimplants array formed in the tissue using a microneedle array. The artificial cavities are formed through the rifampin microspheres suspension in glycerol on the sheep skin tissue surface by the microneedle array. The array needles are pressed on the tissue through the suspension. As the needle penetrates the tissue and form a cavity, the suspension is carried along with it. The glycerol is dissipated in the tissue leaving behind rifampin microspheres in the artificial cavities. Microspheres without rifampin were also incorporated in the tissue and used as a control. Rifampin release profile from the tissue and from the control (lower curve, solid circles) is shown. As expected the rifampin microspheres showed a sustained release of rifampin in the tissue and control microspheres did not show rifampin release (solid circles, bottom curve).

The composition may be biodegradable or biostable microparticles encapsulated or coated with drugs or bioactive compounds. In one illustrative embodiment, PLGA microspheres (average size 1-100 microns) containing 10 percent rifampin as a model drug is suspended in aqueous medium such as PBS or in glycerol and then filled inside the cavity. It is understood that the cavity size must accommodate the microparticle size distribution. For example, in the illustrative example, the particle size is in the range of 1-100 microns. The cavity size must be at least 5 percent larger than the largest size of microparticles present in the injectable composition. In this case, the average diameter of cavity must be 105 microns (5 percent of 100) or higher preferably 120 microns (20 percent higher) or higher even more preferably in the range of 105-400 microns (5 to 400 percent higher). This will enable to fill the cavity with microparticles. The microparticles will release the drug to the surrounding tissue for systemic or local therapeutic effect. Please refer to the U.S. Pat. No. 9,072,678, and references therein, cited herein for reference only; for preparation of microparticles with drug. It is preferred that fluid composition comprises visualization agent which helps to see the composition during cavity filling operation. The composition can be visualized by aided or unaided human eye or with the help of medical imaging equipment such as x-ray machine (for radio-opaque composition) or magnetic resonance imaging machine (for paramagnetic composition) or ultrasound imaging machine. The preferred visualization agent is colored or fluorescent in nature. In some preferred embodiments, the visualization agent is incorporated in the microparticles. For preparation of colored microparticles, please refer the U.S. Pat. No. 9,072,678, and references therein. The cited patent provides various compositions and methods for obtaining colored microparticles.

It is preferred that drug particles are encapsulated in the microparticles, preferably in biodegradable microparticles or microspheres. Many methods are known in the art to make biodegradable particles. U.S. Pat. No. 9,072,678, and references therein. Some preferred methods are given in U.S. Pat. No. 9,072,678, Table 2. One embodiment teaches to encapsulate F D and C dye and drug in a same microparticle. Another embodiment teaches making colored and drug coated microparticles separately and using the mixture of these two particles in any proportion to obtain suitable drug loading and color depth. Drug and color compound loading in particles is controlled to obtain a suitable drug release rate or color depth. The drug/color compound loading in the biodegradable polymer used for encapsulation may range from 1 to 50 percent relative to the weight of polymer, preferably from 5 to 30 percent. Colored microparticles may also be obtained by staining the biodegradable polymer particle or may be obtained by encapsulating within the polymer. In one case the drug (rifampin) itself has a mild color and serves as drug as well as coloring agent. In another embodiment, the drug particles are stained with staining compound and used without encapsulating in the polymeric carrier. Poorly water soluble drugs such as chlorhexidine, paclitaxel, silver chloride and the like which have water solubility less than 5 g/100 g water are especially useful for this application. Microparticles/microspheres and even more preferably with biodegradable polymer microspheres can be useful for local drug delivery applications. The definition of biodegradable polymer is included in the definition section. The preferred biodegradable polymers used for encapsulation of drug are: polyhydroxy acids, polyester, polylactones, PEG, polytrimethylene carbonate or their copolymers or blends. Hydrogels, biostable or biodegradable polymers could also be used as drug delivery vehicles. Some preferred embodiments provide methods and compositions for preparing hydrogel based drug delivery systems. The drug particles must be suspended in the liquid medium such as PBS (pH 7.2). Other aqueous solutions include saline solution; water alcohol, water glycerine, water PEG, water protein (albumin) mixtures and the like may also be used. Water with biocompatible buffers is a preferred medium. Additives that may be added to the particle formulations may include but not limited to: wetting agent to remove air from particle surface; dispersing agent or surfactant to form a stable suspension; and a liquid medium that maintains the particles in a fluid form. An additive that improves the loading of drug suspension in the needle may also be used. The type of drug used will depend on the medical condition being treated. The list of drugs is clearly defined in the definition section including additional list drugs cited in the reference may be used. The list of drugs is not limited to drugs mentioned in the definition sections. Other drugs compounds cited in U.S. Pat. No. 8,067,031 could also be used, cited herein for reference only. Biodegradable microspheres/microparticles can be fabricated using variety of methods and can be formulated to release drugs at a certain rate (kinetics of drug release). The drug may be released by diffusion and/or biodegradation mechanism or combination of both. The preferred rate of release is a zero order release where a constant or nearly constant rate of drug over a long period of time is obtained. Polymer molecular weight, type of polymer used, microparticle size and shape, double or single walled particle, drug loading in the microparticle, porosity of the particles and the like are some of the variables that can be used to obtain desired rate of release for a given therapeutic or bioactive compound. If needed combination of two or more microparticles may be used to obtain burst release and/or zero order release of drugs. Please refer to U.S. Pat. No. 6,599,627 and cited art and cross references therein to make biodegradable microspheres, cited herein for reference only. There may be other methods known in the art to make biodegradable microspheres, such methods could be used or methods yet to be developed could also be used. By mixing two or more colored particles, preferably primary color particles, a desired color shade may be created. Many types of biodegradable polymers could be used to make color particles. The list is exhaustive but preferred polymer include polymer, copolymers of polylactones or polyhydroxyacids, and polytrimethylene carbonate. PEG-polylactone PEG-polycarbonate polymers are also preferred. Among hydrogel polymers, the PEG based crosslinked hydrogels and protein based hydrogels are preferred carriers for colored substances. In some applications hydrogels may be preferred because hydrogels in dry state can form very small size particles and once injected can absorb up to 0.1 to 20 times or even more to its original weight water which increases their size and therefor are unlikely to move away from injection site. Hydrogels that absorb 10 to 10000 percent water upon injection are most preferred. Some embodiments in this invention illustrate methods to obtain hydrogel microspheres (Example 4 and 5). Such microspheres may be dried or dehydrated and used. PEG based hydrogels are prepared by crosslinking PEG based macromonomers or crosslinking reactive precursors. Methods of preparing biodegradable hydrogels are known in the art (please refer to U.S. Pat. Nos. 5,410,016 and 6,566,406 and references cited therein, cited herein for reference only) and such methods may also be used. Methods described in the cited patents can be used to obtain biodegradable hydrogels with different amount of in vivo degradation time. Methods described in these patents could also be adopted to make hydrogels microspheres. Methods provided in U.S. Pat. No. 6,599,627 and cited art and cross references therein, cited herein for reference only may also be used to make colored biodegradable microspheres.

In another embodiment, islet encapsulated microspheres are made (Example 18) and live cell containing microspheres are used to fill the artificial cavities in the tissue. The microencapsulation matrix used is semipermeable allowing critical nutrients from surrounding tissue and maintaining cell viability. The matrix also protects the cells from immune reaction by preventing diffusion of immunoglobulins. The matrix is also permeable to insulin which is produced for live cells in response to glucose concentration in the tissue fluids.

Examples 3-5 show illustrative methods to make drug encapsulated microparticles. Additional methods are given in U.S. Provisional application 62/378,662 filed on Aug. 23, 2016 and its related applications. Methods such as spray drying method, freeze-drying method, melt method can also be used to make encapsulated microparticles. Artisans can understand that many modifications can be done to these methods to obtain drug loaded microparticles, preferably microspheres that have desired size, distribution and drug loading. In addition, compounds such as coloring agent may be added during particle preparation to obtain a drug loaded microparticle with color. Example 3 teaches one illustrative method for obtaining colored and drug encapsulated composition in the same particle. Microparticles with drugs and microparticles with coloring agent can be mixed together to obtain a desirable color as well as release profile. The mixing can be done in any proportion to obtain desirable color and drug loading. Two or more colored particles may be mixed to obtain a desirable color shade. One embodiment teaches the preparation colored hydrogel based composition. Alternatively, many commercial companies/entities provide biodegradable microspheres for a given clinical application, such companies may be contracted to provide an encapsulated microparticle composition. Companies like Octopus N.V. Netherlands, Nanomi B.V, Netherlands; Polysciences, Inc. Warrington Pa., Alkermes plc Waltham Mass., Ramannco Inc., and the like could be used to make custom based sustained release microparticle compositions, preferably biodegradable microspheres for a given application.

Injectable Compositions Comprising Polymer Solutions and Drug.

In this invention, the artificial porosity in the tissue is filled with a polymer solution with or without a drug. Partial and schematic representation of making in situ generated drug delivery array for sustained drug delivery is shown in FIG. 2. A partial schematic of skin tissue is represented by epidermis (1001) and dermis (1002) layers. Artificial porosity is generated in the epidermis and/or dermis layer by many methods known in the art or described in this invention. Conical cavities (2001) formed in the skin tissue are schematically shown. The cavities (2001) are then filled with fluid injectable drug delivery composition comprising drug/s or bioactive compound/s (2002) and biodegradable polymer dissolved in a water miscible organic biocompatible polymer solvent. The fluid composition is converted into solid or semisolid or hydrogel (2003) by precipitating the polymer and entrapping the drug in the in situ formed solid or gel. The drug is released from the solid or gel in the surrounding tissue by diffusion and/or biodegradation or combinations thereof processes. The deposited polymer entraps the drug which is released in a sustained manner for local or systemic therapeutic effect. Both the biostable and biodegradable polymers can be used to deposit in the cavity, but biodegradable polymers are preferred. In one illustrative embodiment, PLGA, (polylactide-co-glycolide) (lactide:glycolide (50:50)), molecular weight 10000 to 15000 g/mole, ester endcapped) an exemplary synthetic biodegradable polymer that is water insoluble is used as a carrier for the drugs. The polymer is dissolved in n-methyl pyrrolidone (NMP), an illustrative biocompatible water miscible polymer solvent along with coumarin as a model drug or rifampin as exemplary therapeutic drug and methylene blue as a colorant. The polymer solution at 10 percent drug loading (relative to polymer plus drug weight) is sterile filtered using an inert Teflon or polypropylene based syringe filter. The solution is then applied on the porcine or sheep dermal tissue skin where nine (300 micron diameter and 1000 micron height) cavities were created by using hollow stainless microneedle array (33MP). The polymer solution is incubated with the cavities for 10 minutes to fill the cavities. In one embodiment, a nitrogen jet (via glass capillary tube or stainless steel syringe needle, 20 psi) is used to force the solution inside the cavity. In another embodiment, where cavities are relatively large, a syringe and needle is used to fill each cavity manually. The needle size of the syringe preferred to be smaller than the cavity size. The excess solution is wiped off and NMP is allowed to dissipate in the tissue. The polymer precipitates in the cavity entrapping the coumarin or rifampin. The presence of rifampin is clearly seen in the precipitated polymer due to its mild yellow/red color. The precipitated polymer cannot be removed by manually wiping down. The presence of polymer in the tissue is later confirmed by conducting histology of treated tissue. The polymer presence is also confirmed by observing the precipitated polymer with the necked eye under blue light (coumarin produce green fluorescent light when observed under blue light, FIG. 8C, 8004). The red color of rifampin is seen by the necked eye. The treated areas are cut and incubated in 3 ml PBS at 37 degree C. and the fluid is exchanged at 10 minutes, 30 minutes, 1 hour, 2 hours, 6 hours, 12 hours, 24 hours, 1 day, 2 day, 3 day, 7 day and twice a week up to 30 days. The drug concentration in the fluid is monitored by UV-VIS spectrophotometer. A drug release profile is generated and cumulative drug released is plotted against cumulative time. Red color of rifampin and green fluorescence is only seen in areas where cavities are created and not in other areas. This experiment demonstrates that PLGA polymer array can be formed by making the cavities first and then forming the PLGA implant in situ inside the cavity via in situ precipitation of polymer solution. The formed implant does not require sharp edges or backing material to make the array implant. In another embodiment, 1 ml of 10% PDLG 5002 polymer solution in n-methyl pyrrolidone (NMP) is mixed with 200 mg of Eosin stained MgCO3. The solution/suspension is filled in the syringe and manually injected in the cavities of sheep tissue (cavities were manually created by syringe needle, 4 by 4 format). The excess solution is wiped off and the polymer is allowed to precipitate in the cavities to make a 4 by 4 microimplant array (8007, FIG. 8E). The biodegradable PLGA based microimplant array (8007) is fluorescent under blue light due to eosin in the microimplant and its image is shown FIG. 8E.

Example 14B illustrates the creation of PLGA based moxifloxacin releasing microimplant array in the tissue. The release profile of Moxifloxacin released from the created array is shown in FIG. 10. The array of microcavities were prepared first and then filled with polymer solution comprising PLGA. The solvent diffuses in the tissue and the polymer encapsulated moxifloxacin releases the drug for several hours indicating successful encapsulation of drug in the precipitated polymer. Example 14A illustrates the use of direct injection of exemplary PLGA polymer solution in DMSO or NMP with Moxifloxacin as an illustrative drug and methylene blue as illustrative colorant. The direct injection was made using 3 by 3 hollow needle array (33MP). The array was used to create porosity/cavities and inject the polymer solution cavities. Polymer in the artificial cavities is precipitated encapsulating the moxifloxacin. The release of moxifloxacin from the precipitated polymer (PLGA array formed in the tissue) is shown in FIG. 12. The drug is released over a period of 200 hours. Example 14C illustrates the use of polymer solution layer to form implant array in the tissue. The PLGA and moxifloxacin solution in DMSO was poured on the tissue first to form a liquid solution layer on the tissue surface. A 3 by 3 hollow microneedle array (33MP) was pressed on the tissue via polymer solution layer 15 times on different locations on the tissue. As the array needles penetrate the tissue and they form cavities inside the tissue, the solution was then carried in the cavities (135 total cavities). The excess surface solution was wiped off with a tissue paper. The infused solution is converted into precipitated polymer in the artificial pores created by the microneedles. The release profile of moxifloxacin from the formed PLGA implants in the cavity over 10 days is shown FIG. 11.

FIGS. 8A, 8B, 8C, 8D and 8E show representative images of cavities formed in tissue and gelatin gel and then filled with polymers with drug and/or visualization agent. A microimplant array is formed in the model tissue like material (gelatin gel, 8001) and sheep skin tissue (8005) or pericardial tissue (8008). A 3 by 3 array (33MP) is used to create porosity in transparent gelatin gel (8801) which is then filled with PLGA polymer containing methylene blue as a colorant and/or drug. An illustrative image of 33MP array device and attached syringe with blue colored solution PLGA is shown in FIG. 22B. The precipitated PLGA polymer and its blue color in 3 by 3 microimplant array form (8002) are shown in FIG. 8A. The gelatin gel has blue tint due to leakage of colorant in the gel from the PLGA microimplant array. FIG. 8B shows gelatin gel with 3×3 microimplant array made from PLGA polymer solution and coumarin as fluorescent dye using 33MP array. The 3 by 3 PLGA implant array formed in situ which is fluorescent under blue light (8003) is shown in FIG. 8B. A PLGA polymer with coumarin microimplant array were formed by direct injection in the sheep dermal tissue (8005) using 33MP array at 3 separate locations is shown in FIG. 8C. The formed microimplants are fluorescent under blue light (8004). FIG. 8D shows cavities (8009) created in pericardial tissue (8008) before infusion of injectable composition. FIG. 8E shows sheep skin tissue (8005) infused with 4×4 array (8007). The microarray 8007 is made by infusing PLGA polymer solution containing magnesium carbonate stained with eosin. The implanted microarray 8007 is pictured under blue light wherein eosin in the array is fluorescent.

In another embodiment, a PEG-PLA block copolymer is dissolved in ethanol and injected inside the cavity. In another embodiment, a polycaprolactone polymer dissolved in dimethyl sulfoxide is used as injectable polymer solution. Several biodegradable polymers are known in the art and can be used for sustained delivery. A partial list of preferred biodegradable polymers is provided in the definition section. The preferred polymers are synthetic biodegradable polymers which include, but are not limited to, polymers, dendramers, copolymers or oligomers of glycolide, dl-lactide, d-lactide, l-lactide, caprolactone, dioxanone and trimethylene carbonate; degradable polyurethanes; polyamides; tyrosine-derived polycarbonates, tyrosine-derived polyacrylates, polyesters; polypeptides; polyhydroxyacids; polylactic acid; polyglycolic acid; polyanhydrides; and polylactones; polyethylene glycol-polyhydroxy acid or polyethylene glycol-polylactone copolymers (PEG-PL copolymers); polyvinyl alcohol co-polylactone copolymers are among the hydrophobic synthetic polymers could also be used. These polymers can be dissolved in biocompatible organic solvents. Each polymer used can have its own set of organic and water based solvents. List of solvents that can be used for a given polymer can be found in Polymer Handbook. Alternatively, solubility can be determined experimentally prior to using. In general, water miscible solvents are most preferred. Among these, solvents that can be tolerated by live tissues are mostly preferred. The partial list of solvents and mixtures in any proportions that can be used include but not limited to: tripropionin (triprop), tetraglycol, pyrrolidone-2, ethyl lactate, triacetin, triethylene glycol dimethyl ether (triglyme), glycerol formal, dimethyl sulfoxide, ethylene glycol monoethyl ether acetate, benzyl alcohol, n-methyl pyrrolidone, N-ethyl-2-pyrrolidone, tributyrin, benzyl benzoate, acetone, methyl ethyl ketone, acetic acid, ethanol, isopropanol, diethylene glycol dimethyl ether (Diglyme), ethyl benzoate, dimethyl isosorbide (DMI), polyethylene glycol dimethyl ether, glycofurol, glycerol, ethyl acetate, polyethylene glycol (low molecular weight), 1,3 propane diol, 1,4 butane diol, 1-6-hexane diol, tetrahydrofuran, triethanol amine, water, buffered water solutions with pH ranging from 6 to 8, preferably pH around 7 and their mixture and the like. If water based solutions are used, it is preferred that the solutions are osmotically balanced and appropriate pH and buffer to maintain the pH is used. Among these, polyethylene glycol, ethyl benzoate, polyethylene glycol dimethyl ether (preferred molecular weight 500-35000 g/mole, linear or branched), glycofurol, ethanol, dimethyl sulfoxide, acetone, water and n-methyl pyrrolidone and their mixtures in any proportion are most preferred. The polymers concentration in the solvent may range from 0.1 to 60 percent depending the molecular weight of the polymer, the structure of the polymer and the solvent used. In general, polymer-solvent systems that provide low viscosity (1-500 centipoise) or medium viscosity (500-5000 Centipoise) solutions are preferred. High viscosity solutions, can be used but are difficult to inject and therefore may be less preferred. When using polymer solution, it is understood that polymer-solvent combination chosen may precipitate in vivo in few minutes to several hours depending on the polymer solvent combination chosen. Several factors affect polymer precipitation which include polymer molecular structure, hydrophobicity of polymer, polymer molecular weight, water solubility of polymer solvent chosen, amount of water present in tissue site or environment (infected oozing wounds tissue sites or bleeding wounds may have significantly more water than normal skin tissue) and the like). The appropriate polymer-solvent combination must be chosen depending on the desired medical application in mind. Factors like biocompatibility of solvents and polymer, how fast the polymer precipitation is desired, tissue site and the like are considered in choosing a proper polymer-solvent combination. Polymer-solvent combination that precipitates in 0.1 to 40 minutes, preferably 0.5 to 30 minutes, and most preferably precipitates in 1 to 20 minutes is most preferred. The list of solvents for a given polymer can be accessed from Polymer Handbook or general polymer chemistry literature or can be determined experimentally. The preferred average molecular weight of polymer may range from 1000 to 200000 g/mole, even more preferably 5000 to 100000 g/mole. Polymers with molecular weight greater than 200000 g/mole can be used but their solutions may form high viscosity solutions and their tendency to precipitate quickly can limit their utility.

The list of drugs that can be used is given in definition section of this document. The drug may be dissolved, suspended or emulsified before injecting. The concentration of the drug in the polymer (relative to polymer plus drug weight) may range from 0.1 percent to 50 percent, preferably 1 to 40 percent and most preferably 10 to 30 percent. The drug may be dissolved or dispersed or emulsified in the polymer solution. If drug is insoluble in the polymer solvent system, fine particulates (particle size 0.1 microns to 500 microns) may be used. The particle size chosen should be less than the needle size of the injecting device or artificial cavity size. The polymer may be added a medical imaging agent or colorant to help the delivery/deposition process. The colorant may be dissolved or suspended in the polymer solution, preferably dissolved in the polymer solution. Many biocompatible colorants can be used and these include but not limited to: many FD and C dyes or D and C dyes that FDA has permitted to be used in approved medical devices. Colorants that have been used in absorbable surgical sutures or contact lens materials are most preferred. Partial list of coloring agents or coloring compositions is given in the definition section of this document. The in vivo biodegradation time for the polymer may be from few hours to few years, preferably few days to 12 months. The deposited particle may release the drug in a sustained manner. The delivery of the drug may last for few hours to several months, preferably 3 days to 180 days. The release rate of the drug may follow zero order rate release (constant release over a period of time) or may follow standard diffusion model or combination of both. The drug may be released via diffusion and/or erosion mechanism of the carrier. Various copolymers of polylactones have different in vivo degradation times. For example, PLGA (PDLG 5002) is generally suitable for 30-90 day delivery, PLGA with higher PLA content will have 6 month to one year degradation time. Polycaprolactone based polymer generally have 1-2 year in vivo degradation time. Its copolymer with polyglycolide has intermediate degradation time depending on the copolymer composition. Some PEG based polylactones have very short degradation times, less than 30 days. Those skilled in the biodegradable polymer art will recognize that many types of biodegradable polymers can be chosen with range of degradation time and ultimate choice will depend upon the desired clinical application. Hydrogels based polymers, especially crosslinked PEG based hydrogels are generally more suited for protein based drugs. Pluronics, Tetronics and its derivatives gels may be used for short term delivery up to few hours to few days.

In one illustrative embodiment, a sugar based dissolvable array is used to create porosity and infuse polymer solution with drug as described above to create holes as well as to infuse the solution. Briefly, hyaluronic acid dissolvable array, either purchased from commercial sources or made by casting sodium hyaluronate solution in PBS in silicone rubber mold. The needles of the array are coated with polymer solution (PLGA dissolved in ethyl acetate or polyethylene glycol dimethyl ether molecular weight around 550 g/mole) is coated on the needles and then inserted into the skin tissue. The polymer solvent chosen should be non-solvent for needle material. In this case, NMP is a non-solvent for hyaluronic acid. A combination of polymer solvent and non-solvent for needle material can be found using a polymer handbook or chemistry handbook. Laboratory solubility tests may be done to make sure that the polymer solvent chosen does not affect/dissolve the microneedle material. The water in the tissue dissolve the hyaluronic acid based needles and create a space for polymer solution to occupy and precipitate in situ forming an implant in situ. The precipitated polymer releases the drug for local and systemic therapeutic effect. Alternatively, the PLGA solution is first applied on the skin tissue and dissolvable microneedle array then pressed on the skin through the solution. The needles insert the skin tissue and drag the solution with it. After dissolution of needles in the tissue, the dragged solution occupies the space created by the needle forming in situ implant for sustained drug delivery. Arrays made from low molecular weight sugars (molecular weight less than 5000 g/mole) are preferred because they quickly diffuse into tissue and the space created by them can be used as described before.

Injectable Compositions Comprising Neat Liquids

The fluid compositions that can be injected in the cavities may comprise liquid carrier and/or drug. The compositions stay in liquid state in the array where drug is either suspended or dissolved or combinations thereof. The fluid carrier used to fill the cavities may be an oil, polymeric or non-polymeric liquid. The liquid carrier is substantially liquid at room temperature or around body temperature (37 degree C.). Biocompatible liquid carriers may be hydrophobic or hydrophilic. The liquid can be oils such as sucrose acetate isobutyrate, vitamin E and its derivatives; fatty acids like oleic acids and its derivatives; fatty alcohols; liquid non-ionic surfactants like polysorbate, Tween® 40 or Tween® 80; polymers like liquid polylactones, liquid polyhydroxyacids, liquid PEG-polylactone copolymers, PEO-PPO-polylactone copolymers, liquid polytrimethylene carbonate and its copolymers, liquid polyorthocarbonates, and its copolymers or combinations thereof and the like are preferred. Biodegradable liquids are most preferred. The liquid carriers along with drugs (either dissolved or suspended or emulsified) are delivered in the cavity via injection or other methods described previously. The biodegradable liquids/microparticles used in this invention may last in the body from 3 hours to few years, preferably from 24 hours to 360 days, even more preferably from 24 h to 90 days. The drug loading in liquid carriers may range from 0.01 percent to 50 percent, most preferably 0.1 percent to 40 percent, even more preferably from 1 to 30 percent. In one illustrative embodiment, sucrose acetate isobutyrate is used a biocompatible liquid carrier and rifampin as a model drug. The mild color of rifampin is used as a visual aid to deposit the liquid in the cavities. The liquid deposited in the cavity delivers the drug in a sustained manner. In another embodiment, an herbal therapeutic like turmeric is loaded in a vitamin E (loading at 1-10 percent concentration) in the cavities created in the skin tissue.

In another embodiment, non-polymeric liquid sucrose acetate isobutyrate is used as a liquid carrier. In some cases, viscosity-modifying agents such as biocompatible organic solvents like ethanol, DMSO and the like may be added in any proportion (generally 1 to 99 percent, preferably 5-90 percent, most preferably around 20 percent) to adjust the viscosity of the non-polymeric liquid carrier like sucrose acetate isobutyrate. The lower or higher viscosity can help the liquid carrier to penetrate cavity space created. Other additives such as antioxidants, UV stabilizers, generally found in pharmaceutical preparations may also be added.

In one embodiment, a liquid biodegradable polymer like polycaprolactone or PLGA is used as a liquid carrier. Liquid polymeric carriers are especially useful for sustained delivery of therapeutic drugs. Many liquid polymeric carriers are known in the art and could be used. For example, U.S. Pat. Nos. 5,631,015 and 5,411,554 and references therein, cited herein for reference only, disclose various biodegradable liquid polymer compositions and methods of their preparation. Such compositions could be deposited in artificial pores. The viscosity of the liquid polymers may be adjusted using biocompatible water miscible solvents such as water or aqueous buffers, dimethyl sulfoxide, n-methyl pyrrolidone, ethanol, glycerol, polyethylene glycol, acetone and the like. Biocompatible polymers, preferably biodegradable polymers may also be added to increase the viscosity if needed. The list of preferred biocompatible solvents is given in earlier section. The solvent could be added in any proportions; preferably at a concentration of 1-99 percent preferably 10-90 percent. After deposition in the artificial cavities, the solvent is dispersed by the tissue (if water soluble) leaving behind the liquid polymer droplet the liquid polymers comprising polyethylene glycol are most preferred in many applications. One embodiment (example 10J) teaches synthesis of PEG polylactone polymer. By changing the molar ratio of PEG hydroxy group and cyclic lactone during the synthesis, the degree of polymerization lactone in the PEG-polylactone polymer is changed. The molar ratio is adjusted in such a way that the polymerized product is liquid at ambient or body temperature. Some PEO-PPO copolymers, preferably PEO-PPO-PEO copolymers (Pluronic® or reverse Pluronic® or Tetronic® polymers from BASF) or their reaction products with cyclic lactones that are liquid at room temperature could be used.

In one illustrative embodiment, a sodium hyaluronate based dissolvable microneedle array is used to make cavities. The liquid PEG-PLA (Example 10J) or liquid polycaprolactone polymer based compositions are used to infuse the compositions inside the skin tissue for local drug delivery.

In another illustrative embodiment, 1 g of vitamin E acetate is mixed with 100 mg of magnesium carbonate stained with tea stain. The dark colored suspension is used to fill cavities of 10 by 10 array created in sheep tissue. The cavities were first made in the tissue and then filled with the colored injectable compositions based on Vitamin E. FIG. 19B shows an image of liquid (vitamin E acetate) microimplant array with red colored liquid microimplants arranged in 10 by 10 array format. The stained magnesium carbonate is added as a biocompatible biodegradable visualization agent.

The vitamin E used herein is for example only. Other liquid carriers may also be used. Microimplant array size, shape, height, diameter, volume, density and the like can be changed depending on clinical application as mentioned in earlier sections.

Example 10J shows some illustrative embodiments where liquid carriers are used to fill artificial cavities in tissue or model materials like gelatin with or without drugs. The arrays formed have liquids, preferably hydrophobic liquids used as carriers for drugs. Generally liquid carriers can help to release drugs for a short duration of time, typically less than 30 days. However, this should not be considered as a limitation of this invention.

Injectable Compositions Comprising Thermoreversible and/or pH Sensitive Gels

This invention discloses formation of thermoreversible gels in situ wherein the thermoreversible gel microimplants are made inside the artificial tissue cavities. The injectable compositions having thermoreversible gelation property are used to make microimplant array. The cavities are made first and then thermoreversible compositions comprising drugs and/or cells are injected in the cavity. The injected compositions undergo insitu gelation due to thermoreversible gelation property of the composition. The injectable composition may also be loaded inside the injection device capable of injecting the composition at 10 to 12000 injections per minute if used with oscillating needle. During each injection, the device can deliver 1.0E-02 to 1.0E-16 ml of injectable composition. The composition is either heated (below 60 degree C.) or cooled (0-20 degree C.) to make it fluid prior to injection. In one illustrative embodiment, a 33MP array is used to inject thermoreversible compositions. After injecting the composition, the composition undergoes temperature induced gelation at the injection site due to normal body temperature (37 degree C.). The injectable composition reservoir of the oscillating needle device can be cooled or heated to make the composition fluid and injectable. The temporary reservoir may be thermally insulated to keep the injectable composition in the fluid state. Cold or warm fluid thermoreversible composition layer may be first formed on the tissue and while in cold or warm fluid state, the fluid composition can be then inserted in the artificial cavities as described before. The body temperature (37 degree C.) will generally convert such compositions into thermoreversible gel which can release the drug in a sustained manner.

In one exemplary embodiment (example 10H), a solution or liquid that shows thermosensitive gelation behavior may also be used to infuse under the skin or in the dermis or in the bioprosthesis surface. The thermosensitive composition is delivered using oscillating needle apparatus or tattoo machine apparatus as described before. Such liquids may be preferentially colored prior to the infusion as described earlier. The thermosensitive liquids normally are fluid during injection but undergo gelation as a result of change in temperature. For example, Pluronic F127 copolymer (a PEO-PPO-PEO copolymer with molecular weight of 12000 g/mole) dissolves in cold PBS (below 10 degree C. at concentration of 20 to 50 percent). At 20 percent or higher (w/v) concentration and at warm temperature (37-45 degree C.), the F-127 solution forms a physically crosslinked hydrogel from a cold solution. This process of gelation is called as thermoreversible gelation because when the gel is cooled, it reverts back to Pluronic liquid solution. Pluronic F-127 solution (30 percent W/V in PBS along with eosin Y as red dye for visualization (0.01 percent) along with drug Rifampin (one percent, w/v) is injected as a cold liquid (0-10 degree C.) using tattoo machine apparatus as described before or using microneedle array such as 33MP array. The Pluronic liquid undergoes thermosensitive gelation at body temperature and forms a gel, which releases rifampin in a controlled manner. If necessary, the machine may be modified to keep the needle and machine cold during injection. The injecting machine may be kept cooled by blowing cool air on the needle to prevent premature gelation inside the needle or on the tissue. The color of Rifampin and Eosin Y serve as coloring agents which helps to see the injected liquid or polymer. In another embodiment, Pluronic F127, chlorhexidine acetate an antibacterial and methylene blue as a coloring agent are dissolved in cold PBS wherein Pluronic F127 concentration in the PBS is around 33 percent. At this concentration, Pluronic F127 is liquid at 0-15 degree C. but forms a gel at body temperature. The cold liquid is injected in the tissue where a change in temperature (0-15 degree C. to 37 degree C.) causes F127 solution droplets to from gel particles. The gelled particles deliver the drug compound in a sustained manner. Pluronic F127 is generally useful to deliver the compound from few hours to few days. F127 shows thermoreversible gel property at certain concentration range, generally around 15-45 percent w/v concentration range. The gelation temperature can vary depending on the solutes and drug added, drug concentration, pH and buffers used and polymer concentration. Artisans can understand that a formulation must be developed for a given drug and thermosensitive polymer wherein the polymer will show gelation property at body temperature upon implantation. It is important that many water based compositions described in this invention are osmotically balanced wherein such solution does not create any osmotic imbalance when injected inside the body. Some polymers such as some gelatin grades or PEO-polylactone copolymers undergo gelation when injected as a hot solution (less than 65 degree C., preferably less than 50 degree C.) and cooled as to body temperature (37 degree C.) or at ambient temperature may also be used. Many other types of thermosensitive polymers are known in the art. Among these biodegradable or biodissolvable polymers (polymers that dissolve in the human body and removed safely from the body without harmful effect) are preferred. The thermosensitive polymers that can be used include but not limited to are: Pluronic or PEO-PPO copolymers; reverse Pluronics; polyacrylamides such as poly-isopropyl acrylamide and their copolymers; gelatin (various grades); chitosan based compositions and its derivatives, cellulose derivatives, various PEG-polylactone copolymers, PEG-PLA, PEG-PLHA, PEG-polyhydroxy copolymers, and the like. U.S. Pat. Nos. 6,004,573 and 7,740,877, US patent application 20140256617 and references therein, cited herein for reference only, disclose thermosensitive gel compositions. Such compositions may also be used for deposition inside the artificial cavities. In one illustrative embodiment, a Jeffamine lactide based thermoreversible composition comprising rifampin encapsulated microspheres is injected in to 4 by 4 array of artificial cavities created in a sheep skin tissue. The compositions form a thermoreversible gel in the cavity forming microimplant array containing rifampin encapsulated drug (FIG. 22D). The rifampin is released from the microimplant array in a sustained manner.

In another illustrative embodiment, a Pluronic or PPO-PEO-PPO based copolymer (Jeffamine, molecular weight 1900 g/mole) is first reacted with dl-lactide in presence of stannous octoate to make a Jeffamine-polylactide copolymer (Example 10H). The copolymer synthesized has thermosensitive gelation properties. A 20-40 percent of Jeffamine-lactide polymer solution in PBS forms gel at 30-40 degree C. and is liquid/fluid around zero degree to 10 degree C. The cold solution of this polymer along with rifampin loaded microspheres as visualization agent as well as sustained drug delivery carrier is used for filling the artificial cavities. The cavities are first made in an array form and the ice cold composition (around zero degree C.) is filled in the cavities using a syringe and needle. At body temperature (37-40 degree C.), the polymer exists as a solid gel with entrapped microspheres. The microspheres release the drug for local or systemic therapeutic effect. FIG. 22D shows the sheep skin tissue with 4 by 4 microarray implant containing Jeffamine lactide copolymer thermosensitive gel (an exemplary thermosensitive gel array) and rifampin microspheres entrapped in the gel (red colored 2207).

The thermosensitive compositions described herein can deliver variety of drugs including protein drugs. The drug may be microencapsulated in a biodegradable matrix for better control over release profile. The detailed list of drugs is given in the definition section of this document. Up to 0.1 percent 30 percent drug may be loaded (relative to gel weight) in the thermosensitive composition. Actual loading will depend upon the type of drug used, drug solubility, type of thermosensitive polymer used and the like. As stated before, coloring or medical imaging agent may be added to the thermosensitive composition to assist in the delivery of the composition and to follow its degradation after implantation. U.S. Pat. No. 7,790,141, cited herein for reference only, discloses radio-opaque compositions and such compositions may be added and used for local delivery as described before.

The illustrative compositions described above are especially useful for delivery of cells due to physical nature of thermoreversible gelation process. The temperature induced transition is generally well tolerated by the cells and therefore can be used for therapeutic use. Osmotically balanced solution of thermosensitive polymer in appropriate cell culture medium or PBS is used to entrap cells in the microimplant array as discussed before and entrapped cells in array can be used for therapeutic use. The microneedle implant array gel compositions with cells as described above may be added with cryopreservative, cast as microneedle array and frozen at −80 degree and then implanted in frozen state in the body to form microimplant array with cells.

In some embodiments, pH sensitive polymer gelation property is used to form a gel in situ inside the cavity. Temperature and pH sensitive polymers are known in the art (M. Rizwan et al., Polymers, volume 9, page 137, 2017, cited herein for reference only) and such polymers can also be used to make injectable compositions. Buffered aqueous solutions of pH sensitive polymers are present as a liquid under mildly acidic (pH 4-6.9) or basic aqueous conditions (7.5 to 9) but form gel around pH 7.2 or physiological pH. When mildly acidic or basic aqueous solutions are exposed to physiological pH such as pH around 7.4, the polymer in the solution forms gel and this property can be used in making injectable implants to form gel based array. Collagen is soluble in mildly acidic solution but forms a gel when exposed to neutral pH. Copolymers of n-alkyl acrylamide, particularly n-isopropyl acrylamide with monomers containing acidic or basic groups show pH and temperature sensitive gelation. Such systems or polymer systems reported by M. Rizwan et al. may be used in making injectable polymers. Certain blends of chitosan polymers are also known for pH sensitive gelation and such polymers may also be used.

Injectable Compositions Comprising Precursors of Crosslinkable Compositions.

The invention discloses methods and compositions for making microimplant array in situ inside the live tissue or inside a bioprosthesis tissue. The injectable compositions are precursors of crosslinkable compositions which are injected in the artificial cavities to form crosslinked microimplant array. The crosslinked microimplant array may comprise a drug and/or live cells for therapeutic use. In one illustrative embodiment, precursors that form crosslinked polymer preferably crosslinked hydrogel structures with or without cells or cellular components or drugs are disclosed. The precursors are formulated as injectable compositions with or without cells or drugs and then injected in the tissue using oscillating needle apparatus or hollow microneedle array such as 33MP. The precursors react with themselves or components in the tissue and/or with external stimulus such as light that trigger a chemical reaction or crosslinking reaction forming crosslinked polymers in the artificial cavities. The crosslinking reaction converts the injected compositions into solids or hydrogels entrapping cells and/or drugs. The encapsulated cells or drug provide therapeutic benefit. Preferably the crosslinked structures are biodegradable.

In one illustrative embodiment (example 10D), a biodegradable macromonomer is synthesized and then formulated to make an injectable composition which can be initiated by long UV light or visible light. A polyethylene glycol based water soluble biodegradable macromonomer (precursor) is prepared by initiating a cyclic lactone polymerization from the hydroxyl groups of PEG starting material. The PEG lactate polymer is then endcapped by with polymerizable acrylate group. This is achieved by reacting the PEG-lactate diol with acryloyl chloride using triethyl amine as a base catalyst. The PEG-lactate-acrylate is designed to be water soluble (PEG to lactide weight ratio is kept high to maintain water solubility) and can undergo polymerization at 10 percent or higher concentration (above its critical micelle concentration in water) in water or water based buffers such as PBS buffer (pH 7.4). The PEG-lactate-acrylate solution is mixed with photoinitaitor solution (either UV light photoinitaitor or visible light photoinitaitor). The precursor solution along with photoinitiator is sterile filtered and deposited using a tattoo machine or other oscillating needle apparatus or using hollow needle array or using standard syringe and fine needle. The machine deposits small droplets of mixture in the tissue (dermis tissue) if used with oscillating needle. The composition can also be infused in artificial cavities created using methods as described before. The polymerization of composition in the cavities is triggered by illuminating the composition with long UV light or with visible light (514 nm). The compositions can be irradiated with light during deposition process as long as liquid compositions in the device are protected from light. The illustrative composition undergoes polymerization and crosslinking triggered by light and photoinitaitor in 5 to 400 seconds. The polymerization reaction converts the liquid composition into solid crosslinked biodegradable hydrogel particles entrapping the drug or cells in the crosslinked hydrogel. The crosslinked hydrogel degrades in 2-9 months due to hydrolysis of lactate group. One advantage of photopolymerization systems is that the system can be used to deliver live cells for therapeutic use without damaging them. The cells could be therapeutic cells or stem cells or any other cells as described in the definition section. The cells also could be used for tissue engineering application. The degraded hydrogel fragments are safely removed by the body. U.S. Pat. Nos. 5,529,914 and 5,410,016, cited herein for reference only, can provide additional compositions and methods for photopolymerizable, biodegradable or biostable hydrogels and their use in cell encapsulation. Many polymerizable precursors are known in the prior art and can be deposited and crosslinked using the method described in this invention. Protein based macromonomers such as collagen, keratin or albumin can be modified with photopolymerizable groups and crosslinked in situ using methods described in this invention.

In another exemplary embodiment, 200 mg of PEG 35K-lactate-acrylate macromonomer prepared according to procedure shown in Example 10D is dissolved in 800 mg PBS. After complete dissolution, 200 mg of magnesium carbonate is added as opacity creation agent or as a visualization agent. 300 mg Irgacure 2959 is dissolved in 700 mg n-methyl pyrrolidone. 5 microliters of Irgacure 2959 solution is added to the macromonomer solution. The sterile solution (precursor solution) is then filled in the array of cavities (4 by 4 array, manually created using 24 gauge needle) using syringe needle in the sheep tissue, excess solution is wiped off and exposed to long UV ultraviolet light (Black-Ray UV lamp, 360 nm light, 10000 mW/cm2 intensity) for 5 minutes to photopolymerize and crosslink the macromonomer solution to form a crosslinked hydrogel. Crosslinked biodegradable hydrogels 4 by 4 microimplant array in sheep tissue is shown in FIG. 19A. The crosslinked hydrogel 4 by 4 hydrogel array with magnesium carbonate as visualization agent/filler (2401) is clearly seen in the image. In another embodiment as above, magnesium carbonate is replaced with fibroblast cell pellet with 1000000 human foreskin fibroblasts cells and the mixture is filled in the artificial cavities of the array and exposed to UV light to form crosslinked gel with live cells.

Another embodiment (Example 10E) describes condensation polymerization of precursors, preferably PEG based precursors. In this illustrative embodiment, NHS ester of PEG and albumin or trilysine are mixed to form a precursor solution. The mixed solution is then deposited inside the tissue cavities using microneedle array or tattoo machine like device or oscillating needle apparatus. The deposition is done prior to complete crosslinking or change in viscosity or gelling the solution. Premature crosslinking can prevent the deposition and is generally avoided. It is preferred that the composition is mixed just prior to infusion and used immediately. In the preferred embodiment, the precursor solutions are mixed inside the oscillating needle apparatus in a mixing chamber and used immediately for the infusion inside the tissue cavities. In one illustrative embodiment (Example 10E), PEG NHS ester and albumin solutions are mixed in PBS (pH 7.2) and used. The composition that forms gel in 30-60 seconds and is injected using this apparatus before gelation. A small amount of triethanol amine may be added to accelerate the gelation process. Many types of condensation polymerization systems are known in the art and such reactions can be used making gel particles in situ as described in this invention. U.S. Pat. Nos. 6,887,974, 7,592,418, and 6,323,278 and cited references therein, cited here for reference only, can provide various compositions that can be polymerized in situ using condensation polymerization method. Other precursors that can be used for in situ polymerization used include but not limited to: precursors that form crosslinking by the reaction of isocyanate and alcohols or amine and epoxide or acrylate and amine, acrylate and thiol and the like may also be used. In general, precursors have nucleophilic and electrophilic reactive groups and the total number of reactive groups in the precursors must be greater than or equal to five. Ionic crosslinking such as crosslinking of sodium alginate solution (0.2 percent solution in deioinzed water) with calcium chloride solution (2 percent in distilled water) can also be used. In this case, a two-needle delivery system is used or multilumen needle is used. One needle or lumen delivers the 1 percent sodium alginate solution and another needle/lumen delivers calcium chloride solution. The interaction of two droplets triggers ionic crosslinking of sodium alginate forming crosslinked calcium hydrogel particle in situ.

In another embodiment (Example 10F), the precursors react via enzymatic pathway to form a crosslinked (physically and chemically crosslinked) compositions. Fibrin glue based microimplant arrays are used as an illustration of enzymatically formed microimplant array. In this illustrative embodiment fibrin glue microimplant arrays are formed in situ. Briefly fibrin glue precursors are deposited prior to gelation in the tissue cavities or using tattoo machine inside the tissue. The precursors compositions react with each other forming fibrin glue hydrogel microimplants in situ inside the artificial cavities in tissue. Fibrin glue formation is a complex enzymatic reaction. The solution of concentrated fibrinogen and factor XIII are combined with a solution of thrombin and calcium. Once the thrombin/calcium is combined with the fibrinogen/factor XIII, a fibrin clot forms in few seconds to few minutes, depending on the thrombin concentration, temperature, calcium ion concentration, fibrinogen concentration and the like. The fibrin glue components are mixed and deposited inside the tissue cavity prior to gel or clot formation (within few seconds). The factor XIII in the formulation continues to act for several days leading to covalently crosslinked fibrin gel. If drugs are entrapped in the fibrin clot, those are then released from the fibrin clot via diffusion and/or biodegradation process. In the preferred formulation, the fibrin glue is colored for improved visualization. Alternatively, precursors of fibrin glue can be delivered using multilumen needle or bi-needle based oscillating machine similar to described for alginate gel making. Fibrin glue and PEG based biodegradable hydrogels described above are especially useful for delivery of protein drugs like growth factors or therapeutic cells. U.S. Pat. No. 8,557,535 and references and cross-references therein; describe some fibrin glue compositions, cited herein for reference only. Such compositions could also be used for local delivery of fibrin glue based compositions described above. The precursor solutions may be preferably deposited using a multilumen needle as described before. For example, solution comprising fibrinogen may be fed via one lumen and the solution comprising thrombin may be fed by another lumen. Both the solutions may exit at the same time, mixed in situ and react to form a crosslinked material in situ. Fibrin glue may be especially suitable for delivery of cells. The therapeutic cells such as stem cells may be mixed with fibrinogen solution and the solution is crosslinked by reacting with thrombin as described above. The entrapped cells in the crosslinked network may provide therapeutic effect. The crosslinkable precursor compositions described as above may also be deposited using hollow microneedle array such as 33MP array as described previously. The compositions are delivered The amount of drug that can be injected may range from 0.1 percent to 30 percent, preferably 1 to 10 percent depending on the drug to be delivered and disease that has been addressed. The size of hydrogel particles will depend on the artificial cavity size.

Injectable Compositions Comprising Cells In some embodiments, the technology described herein can be implemented by using injectable compositions that comprises live cells, preferably live mammalian cells, or cellular elements thereof. Cellular elements, which can be used for therapeutic use, include, but are not limited to mammalian cells including stem cells; cellular components or fragments, enzymes, DNA, RNA, and genes may also be included as bioactive components or drugs. A method for local delivery of an injectable composition can include obtaining precursors that form crosslinked compositions in situ wherein the volume of crosslinked composition formed is less than 1.0E-02 ml. The crosslinked compositions may comprise of cells, drugs, or imaging agents. The injectable composition(s) are loaded inside the injection device capable of injecting the composition at 10 to 12000 injections per minute. During each injection the device can deliver 1.0E-02 to 1.0E-16 ml of injectable composition. After injecting the composition, the injected precursors undergo ionic, physical, chemical or enzymatic reaction such as polymerization, ionic or covalent crosslinking, and thermoreversible gelation and the like forming a physically, ionically or chemically or enzymatically crosslinked material and entrapping the cells without substantially affecting their viability. The crosslinked material could be hydrophobic or hydrophilic or hydrogel. The crosslinked material formed as above could be biostable or biodegradable.

The invention discloses methods and compositions for making encapsulated microspheres/microspheres in situ inside the tissue or inside a bioprosthesis tissue. In one embodiment, precursors that form crosslinked polymer preferably crosslinked hydrogel structures with or without cells or cellular components or drugs are disclosed. The precursors are formulated as injectable compositions with or without cells or drugs are injected in the tissue using oscillating needle apparatus as small droplets. The precursors react with themselves or components in the tissue or with external stimulus such as light that trigger a chemical reaction or crosslinking reaction forming a crosslinked structures. The crosslinking reaction converts the injected droplets into solids or gels entrapping cells or drugs. The encapsulated cells or drug provide therapeutic benefit. Preferably the crosslinked structures are biodegradable. The crosslinked structure could be hydrophobic or hydrogels or hydrophilic.

One advantage of photopolymerization systems is that the system can be used to deliver live cells for therapeutic use. The cells could be therapeutic cells or stem cells or any other cells. The cells also could be used for tissue engineering application. The degraded hydrogels are safely removed by the body. U.S. Pat. Nos. 5,529,914 and 5,410,016, cited herein for reference only, can provide additional compositions and methods for photopolymerizable biodegradable or biostable hydrogels and their use in cell encapsulation.

Many polymerizable precursors are known in the prior art and can be deposited and crosslinked using the method described herein. Protein based macromonomers such as collagen, keratin or albumin can be modified with photopolymerizable groups and crosslinked in situ using methods described in this invention.

Fibrin glue and PEG based biodegradable hydrogels described above are especially useful for delivery of protein drugs like growth factors or therapeutic cells. U.S. Pat. No. 8,557,535 and references and cross-references therein; describe some fibrin glue compositions, cited herein for reference only. Such compositions could also be used for local deliver of fibrin glue based compositions described above. The precursor solutions may be preferably deposited using a multilumen needle as described before. For example, the solution comprising fibrinogen may be fed via one lumen and the solution comprising thrombin may be fed by another lumen. Both the solutions may exit at the same time, mixed in situ and react to form a crosslinked material in situ. Fibrin glue may be especially suitable for delivery of cells. The therapeutic cells such as stem cells may be mixed with a fibrinogen solution, and the solution is crosslinked by reacting with thrombin as described above. The entrapped cells in the crosslinked network may provide therapeutic effect. In some embodiments, a method of forming an implant in a tissue can include: providing an injectable composition including live mammalian cells suspended in an aqueous solution; and injecting the injectable composition into the tissue at the rate of about 10-12000 injections per minute. In some aspects, the aqueous medium is a phosphate buffered solution or Minimum Essential Medium. In some aspects, the aqueous medium is osmotically balanced. In some aspects, the aqueous composition comprises a visualization agent. In some aspects, the visualization agent is a colored compound, a fluorescent compound, an x-ray imaging agent, or a MRI agent. In some aspects, the colored compound is dye or pigment/microparticle that is biocompatible. In some aspects, the colored compound is water soluble preferably at physiological pH (PH around 7.2). In some aspects, the colored compound is selected from the group comprising methylene blue; Eosin Y; fluorescein sodium; ferric ammonium citrate; D&C Blue No. 9; D&C Green No. 5; FD&C Blue No. 2; D&C Blue No. 6; D&C Green No. 6; D&C Red No. 17; D&C Violet No. 2; D&C Yellow No. 10; indocyanine green; rose bengal; phenol red and phenolphthalein. In some embodiments, the derivatives of biocompatible colored compounds as above with biocompatible polymeric materials like dextran, hyaluronic acid, albumin or polyethylene glycol and the like may be used as colored or fluorescent compound. Such derivatives may be made by using complexation, covalent bonding or electrostatic interactions with the polymeric materials. In some respects, colored biodegradable microparticles described in this invention may also be used as coloring composition.

In some aspects, the method includes injecting the injectable composition by a microneedle. In some aspects, each injection of the injectable composition per microneedle includes about 1 to about 10 million live mammalian cells. In some aspects, each injection of the injectable composition per microneedle includes about 1 to about 10,000 live mammalian cells. In some aspects, the live mammalian cells have a viability from about 30% to about 100%. In some aspects, the live mammalian cells have a viability of live mammalian cells from about 35% to about 99.5%. In some aspects, the live mammalian cells have a viability of live mammalian cells from about 40% to about 99%. In some aspects, the cell comprising injectable composition is injected in a tissue that is a live tissue or a bioprosthetic tissue. In some aspects, the live tissue includes: adrenal gland tissue, duct cell tissue, sensory transducer cell tissue, placental tissue, iris tissue, cancellous bone tissue, pia-arachnoid tissue, cardiac valve tissue, pituitary gland tissue, fibrocartilage tissue, spleen tissue, bone marrow tissue, compact bone tissue, peritoneal tissue, liver tissue, retinal tissue, cardiac muscle tissue, tendon tissue, pericardial tissue, pain sensitive tissue, gastrointestinal gland tissue, ectodermal tissue, squamous tissue, neuronal tissue, pleural tissue, lymph gland tissue, ependymal tissue, mesodermal tissue, endodermal tissue, germ cell tissue, thyroid gland tissue, lymphatic duct tissue, synovial tissue, epididymis tissue, intervertebral disc tissue, blood cell tissue, sclera tissue, gall bladder tissue, renal tissue, cochlear tissue, dental tissue, hyaline cartilage tissue, adipose tissue, thymus tissue, blood vessel tissue, serosal tissue, autonomic neuron tissue, peripheral nervous system tissue, optic tissue, ocular lens tissue, stem cell tissue, pulmonary tissue, vas deferens tissue, testicular tissue, respiratory gland tissue, smooth muscle tissue, dural tissue, fetal membrane tissue, umbilical tissue, cranial nerve tissue, ligament tissue, choroid plexus tissue, autologous tissue, parathyroid gland tissue, ciliary tissue, ovarian tissue, elastic cartilage tissue, skeletal muscle tissue, glial tissue, heart tissue, and combination thereof. In some aspects, the live mammalian cells are human foreskin fibroblasts. In some aspects, the human foreskin fibroblasts are included in a carrier matrix as the injectable composition. In some aspects, the carrier matrix includes a fibrin sealant, a water soluble polymer or monomer thereof or macromonomer thereof, or a thermosensitive gel. This invention discloses several illustrative embodiments wherein live cells are entrapped/encapsulated in the artificial cavities created in the live tissue. Several exemplary embodiments in Example 15 disclose preferred methods and compositions comprising live cells in the artificial cavities. The type of cells and other variables used in the Example 15 is for illustration only and does not limit the invention to specific embodiments. Example 15 discloses use of illustrative cells for therapeutic use. Mammalian cells like human foreskin fibroblasts (HFF) are isolated and grown using standard mammalian tissue culture techniques known in the mammalian/human cell culture art. The cells are typically grown on tissue cultured flasks which have special surface treatments that enable these cells to grow on the flask surfaces. The techniques for growing and culturing human cells is well known in mammalian tissue culture/engineering prior art. The HFF cells are isolated and suspended in an exemplary carrier matrix like fibrin sealant or synthetic materials like PEG based macromonomers or thermosensitive gels. The cell suspension is mixed with precursor of fibrin glue or PEG based macromonomer precursors. The suspension is then injected in the live tissue or bioprosthesis tissue like sheep dermal tissue using hollow microneedle array. A 3 by 3 array (33MP) is used as an example. This array has 9 microneedles and common reservoir for all the needles to access to and inject. The cell suspension is filled in the syringe and attached to the array hub via its female Luer lock. The array needles are inserted inside the live or bioprosthesis tissue where they create cavity first and cells are injected in the cavities created by the array. The size of the cavity created is same as the size of the needle and depth of penetration is the height. The precursor of fibrin glue undergoes physical/chemical change (crosslinking reaction) to form a fibrin clot (a reaction product of fibrinogen, thrombin, Factor 8, calcium and other materials present in the precursor composition). The entrapped cells injected in vivo can survive the cavity filling operation and can form a microimplant array in the tissue with live cells. The live tissue provides necessary nutrients for cell to function and produce a therapeutic effect. In some cases, carrier matrix used does not provide therapeutic effect, but is added to provide mechanical integrity and volume to the cells. Cell suspension containing 40-100 percent, preferably 80-100 percent viable live cells in biocompatible medium like PBS, MEM and the like may also be used with or without carrier matrix like fibrin glue or PEG based crosslinked matrix. Each injection of cell suspension per microneedle may comprise 1 to 10 million live cells, preferably 1 to 1 million cells, even more preferably 1-10000 cells in a suitable medium such as PBS or cell culture medium. The viability of cells used may range from 30 to 100 percent, preferably 35 to 99.5 percent and even more preferably 40 to 99 percent. The HFF cells may proliferate and form a collagen rich tissue which may be helpful in application like healing burn wounds or other type of wounds or may be useful in cosmetic application. HFF based cells are currently grown outside in the lab and cells and its extracellular matrix is used as burn dressing. This process is expensive and requires several days of culturing and specialized sterile handling. In this invention, cells are cultured inside the tissue cavity for therapeutic effect, thereby eliminating the culturing and growing of cells in the laboratory and its sterilization and packaging costs for the consumer.

Live cells may be injected in the bioprosthetic or live tissue which include but not limited to: adrenal gland tissue, duct cell tissue, sensory transducer cell tissue, placental tissue, iris tissue, cancellous bone tissue, pia-arachnoid tissue, cardiac valve tissue, pituitary gland tissue, fibrocartilage tissue, spleen tissue, bone marrow tissue, compact bone tissue, peritoneal tissue, liver tissue, retinal tissue, cardiac muscle tissue, tendon tissue, pericardial tissue, pain sensitive tissue, gastrointestinal gland tissue, ectodermal tissue, squamous tissue, neuronal tissue, pleural tissue, lymph gland tissue, ependymal tissue, mesodermal tissue, endodermal tissue, germ cell tissue, thyroid gland tissue, lymphatic duct tissue, synovial tissue, epididymis tissue, intervertebral disc tissue, blood cell tissue, sclera tissue, gall bladder tissue, renal tissue, cochlear tissue, dental tissue, hyaline cartilage tissue, adipose tissue, thymus tissue, blood vessel tissue, serosal tissue, autonomic neuron tissue, peripheral nervous system tissue, optic tissue, ocular lens tissue, stem cell tissue, pulmonary tissue, vas deferens tissue, testicular tissue, respiratory gland tissue, smooth muscle tissue, dural tissue, fetal membrane tissue, umbilical tissue, cranial nerve tissue, ligament tissue, choroid plexus tissue, autologous tissue, parathyroid gland tissue, ciliary tissue, ovarian tissue, elastic cartilage tissue, skeletal muscle tissue, glial tissue, heart tissue and combination thereof.

In another illustrative embodiment, a PEG based macromonomer is used as a precursor and as a synthetic hydrogel carrier to encapsulate cells in the artificial cavities created by the array. PEG based macromonomers that are biodegradable and used for cell encapsulation have been reported in U.S. Pat. Nos. 5,801,033 and 5,626,863 and references therein, cited herein for reference only. Compositions and methods reported in U.S. Pat. Nos. 5,801,033 and 5,626,863 may be used to encapsulate cells and inject in the artificial cavities. In one illustrative embodiment (Example 15), the macromonomer solution with visible light initiator and co-catalysts and comonomers along with cells are injected in the artificial cavities created by the array. The cavities may be partially or completely filled with the injectable composition with cells. The cavity volume may be filled 5 to 100 percent, preferably 10 to 95 percent even more preferably 70-95 percent with injectable composition. The macromonomer liquid composition is exposed to green laser light to initiate polymerization and crosslinking reaction which form crosslinked degradable gels and entraps the cells. The polymerization and macromonomers do not significantly affect the viability of cells before and after encapsulation. The size/shape of the implant is generally same as the size/shape of cavity of microneedle of the array. It is preferred that the hydrogel composition used will not swell (hydrogel absorbs water from the surrounding tissue) excessively after crosslinking reaction or gel formation. It is understood that by changing variables like the array needle size, number of needles, needle internal diameter, needle length, number of injections made and the like, variety of microimplant array size can be created inside the live or bioprosthesis tissue. Stem cells which can be converted into any type of cells provided proper chemical and biological stimulus is given. Stem cells are most preferred for therapeutic use. Hollow array like device used in illustrative embodiments is for example only and is not a limitation. Other devices and methods described in this invention, known in the art or yet to be discovered may also be used. Dissolvable or biodegradable polymer based microneedle arrays, hollow microneedle array, laser based cavity creation methods are preferred methods for cell based therapies.

The use of fibrin glue, gelatin and PEG macromers for cell encapsulation in the artificial cavities is for illustration only. Other methods known in the cell encapsulation art such as sodium alginate and calcium ion crosslinking chemistry, chitosan, protein or peptide based gelation systems and the like known in the art or yet to be discovered may also be used as long as such methods are able to infuse the cells in cavities without affecting their viability and encapsulation matrix is biocompatible and/or biodegradable.

Some embodiments disclose methods and compositions for preparation of mammalian cell containing dissolvable array. In one illustrative embodiment, a mammalian cell suspension (suspended in tissue culture medium or PBS containing 10 percent dimethyl sulfoxide as a cryopreservative agent) is poured into silicone rubber mold (Watch Microneedle array mold as an example), which has cavities that can create microneedle arrays. The suspension may be centrifuged to fill the cavities completely. The mold with liquid suspension is then frozen below the melting point of liquid (PBS or saline solution) to form frozen solid matrix without forming ice crystals without significantly affecting cell viability. The cells can survive freezing process for short period of time. The frozen cell containing array is removed from the mold and is then inserted in the frozen condition in the skin tissue. The body temperature dissolves the water in the array needle and cells are released inside the dermal or epidermis or other tissue layers. In some embodiments, non-toxic biocompatible additives such polyethylene glycol, hyaluronic acid sodium salt, carboxy methyl cellulose and other materials used in dissolvable microarray can be used. Such additives help to improve mechanical properties of frozen solids without affecting cell viability. Including all additives and injectable composition materials, the cell suspension should be generally osmotically balanced to maintain cell viability. Majority of the culture medium contain water which can be hard when frozen. The sharp needle shape and its hardness enable the frozen microneedles to penetrate the tissue surface and deliver the cellular cargo upon melting inside the tissue.

Mammalian cells can be preserved by freezing (also generally referred as cryopreservation) and reused by thawing. Generally, mammalian cells are best preserved at −80 degree C. or lower, and at −50 to −70 degree for shorter period of time. Preserved cells are usually stored in liquid nitrogen or around that temperature. The freezing operations must be done carefully and conditions may vary for type of cells used. A use of cryopreservation agent such as dimethyl sulfoxide is generally considered as essential when cells are subjected to cryopreservation. It is generally added at 5-10 percent concentration in the PBS or culture media without no magnesium, calcium, or phenol red. The amount of agent added will depend on the type of cryopreservation agent used. The cryopreservation agent is believed to prevent ice crystallization in the live cell structure which can lead to cell death and affect viability of frozen cells. Many cryopreservation agents can be used which include but not limited to: dimethyl sulfoxide, glycerol, polyvinyl pyrrolidinone, polyvinyl alcohol and the like. Among these, dimethyl sulfoxide is most preferred. Commercial cryopreservation medium such as Recovery™ Cell Culture Freezing Medium or Synth-a-Freeze® Cryopreservation Medium from Gibco or other vendors may also be used.

It is preferred that cells entrapment is done at the time of therapy or during a surgical procedure. Specialized sterile kits that can handle cells and injectable compositions may be designed and supplied to be used during a surgical procedure.

In some embodiments, thermoreversible compositions as described previously may be used to encapsulate cells. Thermoreversible compositions based on PEG-polylactones, Jeffamine-lactide, gelatin, chitosan based compositions, and poly-n-alkyl acrylamide or poly-n-isopropyl acrylamide may be used for cell delivery inside the cavity.

In one embodiment, a PEG based macromonomer (Example 20B or Example 21) is dissolved in Synth-a-Freeze® Cryopreservation Medium from Gibco or PBS containing 10 percent DMSO Ail operations are carried out in sterile condition and all solutions are sterilized prior to use. Eosin, vinyl pyrrolidinone and triethanol amine are added as visible light initiator and cocatalyst. The macromonomer solution is cooled in refrigerator (4-10 degree C.). Live cell suspension is first centrifuged for 100-200×g for 5 to 10 minutes, supernatant medium is removed almost completely leaving behind mostly cell pellet. The cell pellet is re-suspended in cold precursor solution as above and filled in the cold silicone based microneedle array mold (Watch Microneedle array) which is precooled to 4 degree C.) and exposed to visible light for 30-120 seconds to polymerize and crosslink the precursor to form a crosslinked hydrogel with encapsulated cells. The array with cells is frozen to −80 degree C. at the rate of one degree per minute. At the time of use, the array is removed in frozen state, thawed to −10 to zero degree C. (using a polyester adhesive backing tape) and pressed in the skin tissue and the backing tape is removed leaving the array inside the tissue. The frozen state provides shelf life for the cells as well as hardness to the hydrogel matrix which is sufficient to penetrate the tissue. The cryopreservation agent helps to maintain cell viability in frozen state. The crosslinked hydrogel provides Immunoprotection (the crosslinked network prevents diffusion of immunoglobulins (molecular weight range around 150000 Daltons) to the cells but allows diffusion of small molecular weight nutrients and cellular waste products. Mammalian cell containing arrays can be used for variety of therapeutic use.

Microimplants comprising live cells may be formed first and then implanted using AIA device as discussed before. Briefly cell and injectable cell encapsulation matrix are mixed together and filled inside the mold of suitable size and shape wherein the mold size is smaller than AIA device cavity. The encapsulation matrix forms a gel without substantially affecting the viability of cells. The formed implants with live cells are then loaded in the AIA device and deployed/implanted in the tissue as discussed in this invention (pushed using plunger array). Alternatively, cells may be microencapsulated in the microspheres (size generally less than 500 microns, preferably less than 300 microns), The encapsulated cells are then injected in the artificial cavities or in porous microimplants and then implanted. Live cells may also be grown on porous microimplants such as EDC crosslinked collagen or gelatin, fibrin glue and the like and such implants may be deployed and implanted using AM device as discussed in this invention.

Microneedle Array Comprising Crosslinked Biodegradable Hydrogels or Polymers

Biodegradable hydrogels have found several medical applications. In the microneedle array format, the hydrogels can be more easily delivered under the skin. However, most hydrogels have poor mechanical properties. Hydrogel materials commonly used in the art are not degradable but dissolve away after implantation. The synthetic polymers used in the prior art such as polyvinyl pyrrolidinone, must have low molecular weight. High molecular weight polyvinyl pyrrolidinone (molecular weight greater than 100000), polyethylene glycol (molecular weight greater than 35000) cannot be eliminated from the body and therefore cannot be used in array preparation where substantial biodegradation is necessary. Generally, strength of array depends on its molecular weight. In this invention, methods and compositions are provided wherein higher molecular weight synthetic polymers such as polyethylene glycol can be used in making array materials. The implantable array materials are made using very high molecular weight crosslinked materials and are biodegradable in nature. Such array materials, when fabricated and implanted under the skin, undergo biodegradation and/or hydrolysis which converts crosslinked materials into small molecular weight fragments which then can be eliminated from the human or animal body.

In one illustrative embodiment, Example 20, a biodegradable macromonomer made using 10000 molecular weight polyethylene glycol linked to polylactide which is linked to polymerizable acrylate group at both the terminal ends. The solution of this macromonomer is added in molds of microarray cavities. The macromonomer in the solution is polymerized via acrylate group increasing its molecular weight several times, typically greater than 2-100 times. The crosslinked gel is dried, removed from the mold. The array has better mechanical properties than its monomer counterpart due to increased molecular weight via crosslinking reaction. The array is implanted in the skin tissue and the polylactate undergoes hydrolysis upon implantation which reduces the molecular weight of the crosslinked polymer to its monomer fragment which then can be eliminated from the tissue. The crosslinked polymer hydrogel also can entrap variety of drugs, especially protein based drugs which could be released in a sustained manner upon implantation. U.S. Pat. No. 6,306,922, cited herein for reference only, discloses additional macromonomer based compositions which produce crosslinked hydrogels that could be crosslinked and used to make implantable microneedle array. By changing the molecular weight of macromonomers polyethylene glycol or biodegradable polymer unit; its biodegradable polymer type (polylactide is changed to polycaprolactone or to polyglycolate or to polytrimethylene carbonate or combinations thereof) and number of polymerizable groups per macromonomer, crosslinked hydrogels with various degradation time and molecular permeability can be synthesized.

In another embodiment, crosslinked polyethylene glycol based crosslinked hydrogels made using condensation polymerization method is used. PEG derivative with degradable glutarate group and terminal reactive group (n-hydroxysuccinimide, NHS, exemplary electrophilic group) is reacted with equimolar quantities with PEG derivative with terminal amine groups (exemplary nucleophilic group). The polymerization and crosslinking reaction is carried out under equimolar concentration of reactive groups in water under close to physiological conditions (pH around 7.4, total reactive groups greater than or equal to 5 for crosslinking to occur) in silicone mold cavities for array preparation. PEG amine and NHS groups react forming amide bonds and increase the molecular weight via condensation polymerization and crosslink to form a gel. The gel is dried, removed from the mold and array is inserted in the body. Upon implantation, the glutarate ester bond in the crosslinked hydrogel undergoes hydrolysis in the body reducing the molecular weight of crosslinked hydrogel. The hydrolyzed fragments are removed from the body. Additional examples of crosslinked degradable materials can be found in U.S. Pat. Nos. 7,009,034 and 6,534,591, cited herein for reference only. The crosslinked compositions with wide range of degradation profile from few days to few years can be made by proper choice and number of nucleophilic and electrophilic group, PEG molecular weight, reaction conditions (time, temperature, buffers etc.) and use of different degradable esters like succinate, glutarate, adipate, suberate or their combinations and the like. The polymerized/crosslinked gels as described above can be made with various degradation profiles suited for variety of drug delivery applications.

In some embodiments, arrays were made from natural polymers like collagen, gelatin. These polymers could be used as crosslinked or non-crosslinked materials and their array upon implantation degrades via enzymatic degradation pathway.

The crosslinked polymer disclosed could also be hydrophobic and biodegradable. The hydrophobic structures include crosslinkable polymers such as hydrophobic macromonomers made by polymers or copolymers of polylactones or polyhydroxyacids and polycarbonates. Such polymers are may be oligomers of polylactones which are endcapped with polymerizable groups such as acrylate or methacrylate group and generally present as neat liquids. These neat liquid oligomers crosslink via polymerizable groups producing crosslinked hydrophobic polylactone based crosslinked network. Additional examples of hydrophobic liquid oligomers that can be polymerized by free radical polymerization can be found in U.S. Pat. No. 6,352,667, cited herein for reference only. The liquid precursors of such polymers are poured into silicone mold cavities as discussed before and then crosslinked. Prior to precursor crosslinking a formulation compatible visualization agent may be added to aid array implantation. The crosslinking of hydrophobic precursors produces hard sharp edged microneedle biodegradable array which can be used for therapeutic drug delivery. This invention is not limited to application on skin tissue. Minimally invasive surgical devices (MIS) based methods can also be used to create porosity at a local site accessed using MIS and then accessed site can be treated using compositions and methods described in this invention. For example, porosity may be created using angioplasty balloons attached with flexible microneedles. Injectable compositions then can be applied on the surface and then infused using the needles on angioplasty balloons. Laparoscopy based methods may be used to treat areas in abdominal cavity. It is understood that a MIS device modifications may be made for a given disease that is managed and such modifications are considered as part of this invention.

Injectable Compositions Comprising Biocompatible and Biodegradable Inorganic and Polymeric Fillers:
Polymer Solutions Based and Thermoreversible Gelling Compositions Comprising Fillers:

The biodegradable polymer solution in water miscible organic solvent can be used for sustained drug delivery. Such compositions can be delivered using syringe and injected via intramuscular injection. The injected polymer undergoes precipitation forming implant in situ after dissipation of water soluble solvent in the tissue. In this invention, the injectable composition comprising polymer solution is improved by addition of biodegradable and biocompatible filler particles in the injectable composition. FIG. 21 shows schematic of a method for in situ implant formation in the human or animal body comprising biodegradable fillers. 2101 schematically represents an injectable composition comprising a drug and biodegradable polymer in water miscible organic solvent or crosslinkable precursor composition/s comprising a drug or a thermoreversible polymer composition in aqueous solution or polymer melt. 2102 comprises a biodegradable, biocompatible inorganic or organic filler microparticles that are insoluble in the injectable composition 2101. The components of 2101 and 2102 are mixed to form a suspension/emulsion and injected into human or animal body via conventional syringe or using methods described in this invention to form implantable arrays. The injected composition undergoes physical and/or chemical change (precipitation, crosslinking, cooling, thermoreversible gel formation and the like) entrapping the drug and the filler in the formed implant. The presence of filler is believed to provide nucleating sites for polymer precipitation as well as provide more surface area for the implant formation/precipitation thereby altering drug release profile. Filler also change mechanical properties of the precipitated polymer which helps to push out from "array in array" apparatus described in this invention. The filler can also affect localized pH changes depending on the type of filler used. For example, magnesium carbonate provides local basic environment.

FIG. 21A shows steps involved in making the implant with the filler. In one embodiment, magnesium carbonate (particle size less than 300 microns) is used as an illustrative filler. PLGA polymer (PDLG 5002) is dissolved in DMSO along with methylene blue as a colorant. The polymer solution is mixed with bupivacaine hydrochloride as a model drug and magnesium carbonate powder (fine powder sieved to collect fraction below 300 microns in size) as a biocompatible and biodegradable exemplary filler and the mixture was vigorously vortexed for 5 minutes. The magnesium carbonate suspension was infused/tattooed using an oscillating needle in 1 cm square area. Excess solution from the tattooed surface was wiped off. The light blue tattoo with magnesium particles was clearly seen the unaided naked eye. In another embodiment, polyglycolic acid (PGA) microparticle is an exemplary biodegradable polymeric filler. In another embodiment, cat gut suture based microparticles (mostly collagen based) were used as filler. In another embodiment, crosslinked gelatin or PEG based biodegradable microspheres are used as filler material. The crosslinking prevents dissolution of the microparticles in the injectable medium. All the illustrative fillers used were insoluble in the organic water soluble solvent used. The insolubility leads to suspension or emulsion formation. The injected solution precipitates or forms a gel in the aqueous environment present in the tissue. It is hypothesized (invention is not necessarily bound by the hypothesis) that during precipitation step, the filler particles provide large surface area for polymer precipitation thereby accelerating precipitation and also provide a larger area for controlled drug release. Filler can also alter mechanical properties of the precipitated polymer. As the filler dissolve or degrade, they can create/alter localized chemical environment such as pH of the surrounding area. The change in localized pH may also affect the release profile of drug. It is hypothesized (invention is not limited and bound to the hypothesis) that the magnesium carbonate creates a localized mild basic environment which may convert drug salts like bupivacaine hydrochloride into bupivacaine base which has a much lower water solubility in water than bupivacaine hydrochloride salt. This change in drug solubility can potentially affect the sustained release profile of the drug. The basic nature of filler can also neutralize the hydroxyacids created during biodegradation of polylactones or polyhydroxy acids such as PLGA. Filler like PGA microcylinders or microparticles can produce localized acidic environment and may also alter the drug properties during degradation progress. Irrespective of mechanism of filler action, fillers can be useful additives for local sustained release of therapeutic drugs when used with in situ gelation systems like polymer solution in water miscible organic solvent.

FIG. 21B shows release profile of bupivacaine hydrochloride from the in situ made PLGA array implant with and without magnesium carbonate as an exemplary filler. The filler particles are insoluble organic solvent and have fine particle size. The data shows that the addition of magnesium carbonate has extended the release of bupivacaine hydrochloride from one to two days to several days. The average size of fillers used may vary from 0.1 microns to 500 microns, even more preferably 0.5 microns to 300 microns. The preferred inorganic/organic fillers have low water solubility and produce localized pH around 7.4 (close to physiological pH). Salts that can be used as filler include but not limited to: calcium benzoate, calcium citrate tetrahydrate, calcium hydroxide, calcium sulfate, gadolinium(III) sulfate octahydrate, magnesium carbonate dihydrate or trihydrate, silver acetate, zinc formate dihydrate, ferrous ammonium sulfate, calcium gluconate, magnesium tartarate, calcium lactate, calcium tartarate and the like. The preferred compounds include inorganic salts and organic salts and salts of magnesium and calcium metal. Salts of hydroxy acids, monoacids, di-acids, tri-acids and polyacids are most preferred. Organic salts with C1 to C22 carbons are even more preferred. Salts of organic monoacids such as, lactic acid, formic acid, oleic acid, steric acid, acetic acid, propionic acid, butyric acid, valeric acid, caproic acid, benzoic acid and the like may be used. Diacids such as malonic acid, succinic acid, glutaric acid, adipic acid, pimelic acid, suberic acid, azelaic acid, sebacic acid, maleic acid, fumaric acid, itaconic acids, oxalic acid, aspartic acid, glutamic acid, tartaric acid, terephthalic acid, citric acid, undecanedioic acid, dodecanedioic acid, glutaconic acid, traumatic acid, muconic acid; polyvinyl pyrrolidinone-co-polyacrylic acid, polyacrylic acid copolymers, polyaspartic acid, hyaluronic acid, protein or peptide sequences comprising two or more acid resides; ethylenediaminetetraacetic acid, methanetetracarboxylic acid, 1,2,3,4-butanetetracarboxylic acid, PEG derivatives with acid end groups and the like. Di or polyacids containing unsaturated groups like fumaric acid, maleic acid, itaconic acid and the like may also be used. The preferred salts used must be biodegradable, biocompatible and non-toxic otherwise they cannot be used. One illustrative preferred salt is hydroxy acids such as calcium gluconate, which has a kPa around 6-7. Salts with pKa value around 7 are most preferred. In bone related applications, calcium salt based compositions are preferred. Salts like hydroxy apatite, calcium sulfate, calcium phosphate and the like are preferred.

Apart from inorganic particulate filler, biodegradable polymer or hydrogel microparticles/microspheres may also be used as filler material in the in situ gelation systems as described above. Optionally filler may be stained or encapsulated with visualization agent like coloring agent or fluorescent agent to assist deposition in the tissue. Several embodiments in this or related application or in cited art provide compositions and methods for preparation of biodegradable polymer or hydrogel microparticles/microspheres. Such methods can preferentially be used to make biodegradable polymer or hydrogel microparticles/microspheres for use as filler in this application. Microparticles comprising synthetic biodegradable polymers are most preferred. Microparticles comprising PEG based crosslinked hydrogels or PEG-polylactone based polymers are most preferred.

Devices for Making Microarrays Comprising Drug/Cell

In this invention, specialized devices have been disclosed which enables to implant preformed microimplants or in situ formed microimplants in an array format. The inventive devices enable to form implanted microarray without having sharp cutting edge to the implanted material or without having a backing material. The devices also enable to use materials like soft hydrogel in hydrated form as array microimplant materials. The inventive device uses two microneedles arrays (an outer and inner array, also referred as "array in array") wherein inner array can be inserted in the outer array. The microimplants present in the outer array are pushed out of outer array once the inner array is inserted in outer array. If the arrays are inserted in the tissues, then the microimplants in the outer arrays can be inserted in the tissue to form microarray of implants.

The inventive devices use arrays made of hollow and/or solid microneedles. Materials for hollow microneedle array are made out of metal or plastic or ceramic with sharp edges and are capable of penetrating the tissue with little pressure or force. The hollow cavity in the needle is used to store/carry the desired drug/cell delivery implant. Upon insertion of hollow needle in the skin/tissue at desired depth, the microimplant in the hollow cavity is pushed out in the tissue and needle is withdrawn from the tissue leaving behind the implant for therapeutic use. An illustrative "array in array" device is described in FIGS. 6 and 15, more specifically in FIGS. 6A, 6B, 6C, 6D and 15A to 15F. FIGS. 6A and 6B show partial schematic representation of "array in array" apparatus (AIA apparatus) useful in forming microimplant array in the skin or tissue. The apparatus comprises two parts namely "base array" or "outer array" with hollow microneedles and "plunger array" or "inner array", both schematically shown in FIG. 6A and FIG. 6B respectively. The base array has a base plate with plurality of sharp hollow microneedles protruding perpendicular from the surface of the base array plate. The plunger array (positioned on top of the base array) also has a plunger plate with a plurality of solid needles protruding perpendicular to the plunger plate from its bottom surface. The arrangement, length/size and shape of plunger array and base array needles is identical except the plunger array needle fits smoothly inside the hollow cavity of base array needle and can move freely inside the cavity up and down as needed. Panel 6C-1 shows plunger array on top of base array, with center of both corresponding needles are aligned but not inserted. The spacer lock (6024) prevents the plunger array being inserted completely. Panel 6C-2 shows plunger array on top of base array inserted completely after removal of spacer lock. Plunger array needles occupy space in the base array cavity. Panel 6D-1 shows base array cavities filled with preformed or in situ generated implants (6013) with drug and/or cells and is ready for implantation. 6013 microimplant could be porous and its porosity could be partially or completely filled/coated or impregnated with injectable compositions with drug/cells described in this invention. Panel 6D-2 shows base array is inserted in the skin tissue and plunger array plunger needles are used to push the implant in the skin tissue and form an implanted array in the skin tissue. Both the arrays are removed from the tissue leaving behind the implanted array with drug/cells in the skin tissue.

"Array in array" (AIA) devices described above have many variations and can be modified to form different types of arrays. In one illustrative working apparatus prototype was prepared according to FIG. 6 and is used to form microimplant array in the gelatin gel which is used as a model tissue substrate to conduct laboratory experiments. Use of gelatin helps to reduce number of animal experiments in designing suitable formulation for a given drug or cell type. The partial description and images of working prototype are given in FIG. 15 for illustration only and does not limit in terms of number of needles in the array, size of needles, needle arrangement, volume of cavity, materials used and the like. FIG. 15 shows a schematics of a working prototype of illustrative "array in array" apparatus as described in FIGS. 6A and 6B. FIG. 15A shows base array (1501) with top view showing 5 by 5 hollow microneedle array created in stainless steel metal plate. Length and breadth of plate is 20 mm and thickness is 1 mm. Outside diameter (OD) of the hollow microneedles is 0.55 mm while internal diameter (ID) of hollow cavity is 0.31 mm. The opening of hollow needles in 5 by 5 format (proximal end of hollow needle 1502 with cavity ID 0.31 mm) on the plate surface is clearly seen. The base array plate has 4 guiding posts (1503) with diameter 2.5 mm. Distance between each needle is 2 mm. FIG. 15B shows the side view of same base array (1501) showing base metal thickness and hollow microneedles (1502) protruding out of the base plate surface. The outer needle edge (distal end of hollow needle) is cut at 30 degree angle and cut needle is polished to get sharp edges for ease of insertion in the tissue. FIG. 15C shows plunger array (1505) with top view showing 5 by 5 microneedle array with solid plunger needles (1508) created in stainless steel metal. Length and breadth of base plate is 20 mm and thickness is 3 mm. Outside diameter (OD) of the solid microneedles is 0.3 mm and length is 2 mm. The plunger array plate has 4 guiding holes (1507) with diameter 2.6 mm. Both the array needles have identical arrangement (5 by 5 array format). Distance between each needle is 2 mm. FIG. 15D shows the side view of plunger array 1505 showing base metal thickness and solid needles protruding out of the base plate surface. The solid needles at distal end do not have cutting edge but a smooth flat surface useful for pushing the implants and the proximal end is attached the plunger array plate. FIG. 15E shows the plunger array 1505 placed on top of base array 1505 (not inserted but aligned and ready for insertion) wherein center of each needle of plunger array is aligned with center of base array needle. FIG. 15F is same as FIG. 15E where plunger array needles are completely inserted in cavities of base array needles and both arrays base plates are touching each other. FIG. 15G shows PLGA based cylindrical microimplant with coumarin as model drug and fluorescent agent is formed in situ inside hollow cavities of base array first and then pushed inside gelatin gel using plunger array as shown in FIGS. 15E and 15F. The green fluorescence of implanted array (FIG. 15G, 5 by 5 array) under blue light is clearly visible. This shows that the device can form biodegradable polymer based microimplants arrays in tissue (gelatin used as model tissue material).

Figure H shows catgut suture based cylindrical microimplants with coating inserted in sheep skin tissue in an array format. The preformed coated cylindrical microimplants (fluorescent coating is on the implant surface along the height of the cylinder but not on the base surface) are placed in hollow cavities of base array and then inserted in the sheep skin tissue using plunger array as described above. The inserted microimplant show green fluorescent coating on the outer edge of the implant under blue light. The apparatus used in making arrays (FIGS. 15G and 15F) is one of the several prototypes made and are described in FIGS. 6A, 6B, 6C and 6D. Base array with metal needles and plastic base plate and plunger array entirely made of plastic material is preferred.

Example 22A teaches illustrative methods by which the AIA apparatus is made. The method is given for illustration only and does not limit this invention to this example only. Those skilled in the art know that other methods such as carving the needle and base plate using modern CNC machines or other tools are possible and may also be used. Lithographic methods to etch a given pattern in silicon or metal known in semiconductor chip manufacturing process can also be used. Three dimensional manufacturing/printing methods such as methods used in sintering of metal/plastic powders or use of melted polymer or photocrosslinked polymers to form 3 dimensional objects (also known as stereolithography or 3D printing) may also be used. The choice will depend on cost, ease of manufacturing, acceptable tolerance of each part of the device and other business variables considerations. In one illustrative embodiment (Example 22, Design 3), a rubber based base plate is used to provide flexibility to the AIA apparatus. This flexibility helps to adjust/conform to skin or tissue surfaces with curvature. The hollow needles array and plunger needle array may also be injection molded along with the needles with flexible plastic or thermoplastic elastomer materials as base plate similar to commercial array shown in FIG. 22A. Flexible metal based band designs such as used in wrist watch may also be used. The thickness of the base plate (t) may be 100 microns to 5 mm, preferably 0.5 mm to 3 mm. Size and shape of base plate will depend on number of needles, cost and ease of processing and other factors. Base plate shape may be square, circular, triangular, rectangular, square, oval, hexagonal, pentagonal and the like. The area of the base plate may be 0.1 cm square to 100 square cm, preferably 0.5 square cm to 20 square cm. The material of the base plate can be ceramic, plastic or metal. Choice will depend on cost, ease of processing, dimensional stability and ease of use and manufacturability. Disposable materials like commonly used thermoplastics like polyethylene, polypropylene, polyurethanes and the like or thermoplastic elastomers like polyurethanes are preferred. Materials that provide high dimension stability, easy to sterilize are preferred. Commonly used medical device materials, particularly materials that are resistant to organic solvents are preferred. In some cases, the organic solvent may be used to cast implants in the needles and solvents used may be exposed to the base plate and needle materials. In such case, material should withstand such solvent exposure. The hollow needles may be made out of ceramic, metal or plastic. Plastic or metal are preferred. Chemically inert plastics such as polypropylene, polytetrafluoroethylene and the like are preferred. Metal based needles such as stainless steel needles are most preferred. If desired, the inside surface of the needle may be lubricated with biocompatible lubricants such as vitamin E, Vitamin K, oleic acid, silicone oil, polyethylene glycol, glycerol and the like. The choice will depend on the implant materials being used in the array. The lubrication reduces friction and therefore provides smooth pushing of microimplants, preferably unibody microimplants in the tissue with minimum force. The base array needles design and edge is chosen in such way that minimum force is needed to push it in the skin or tissue. The force required will be different depending on the type of tissue used, number of needles in the array, needle cutting edge design, needle sharpness, angle of force application and the like. Generally base array needles may be able to penetrate the skin tissue with a force per needle in the range of 5 to 50 $N/CM^2$, preferably 10 to 20 $N/CM^2$. The force may be further reduced by lubricating the needle external surface with lubricants such as silicone oil or glycerol or other needle lubricants known in the art. Preferably the injectable composition ingredients should not dissolve or chemically react with the lubricant used. The inside surface of the needle may be lined or coated with inert or non-stick material like PTFE for ease of insertion. For hydrophilic materials, a hydrogel based surfaces may be more useful. The needle length for both arrays, base and plunger, may vary from 40 microns to 5 mm, preferably 60 microns to 3.5 mm, even more preferably from 100 microns to 2 mm. The most preferred length is 100 microns to 1500 microns. The thickness of the hollow needle is important. The preferred thickness is the minimum thickness required to penetrate the tissue without bending or damaging. The wall thickness of the base hollow needle can be 10 microns to 1000 microns, preferably 20 microns to 700 microns and even more preferably 50 microns to 500 microns. The stronger and harder materials would enable to use needles with minimal wall thickness. Titanium or titanium alloys, Nitinol, aluminium alloys, stainless steel, other cobalt, iron and nickel based alloys and the like may be used to make thin walled microneedles for the base array. The base array hollow microneedle used must have sharp edge at distal end for smooth tissue penetration. The distal sharp edge which penetrates the tissue during implantation can have various shapes such as taper point, blunt taper point, cutting edge, reverse cutting edge, taper cut and spatula curved and the like. The needle at the distal end (tissue cutting edge) may be cut at 10 to 70 degree angle, preferably 30-45 degree angle α. The average internal diameter of base array hollow microneedle, d, may vary from 1 micron to 3500 microns, preferably 5 microns to 2500 microns, even more preferably 20 microns to 2000 microns. The shape of base array microneedle may include but not limited to straight obelisk, negative-beveled obelisk, cylindrical, pyramidal, conical, trigonal, tetragonal, pentagonal, hexagonal, pyramidal, and the like or combinations thereof. The pyramid and cylindrical shape is preferred. The distance between each microneedle in the base array is 1 micron to 10000 microns, preferably 3 microns to 3500 microns, even more preferably 5 microns to 2000 microns. The volume of base array hollow needle (β) may range $1\times10E-12$ to 0.05 ml, preferably $1\times10E-10$ to 0.03 ml, even more preferably $1\times10E-10$ to 0.01 ml. Total number of needles per array may be greater than 3 or 4 per square centimeters or may range from 3 or 4 to 6000 per square centimeter, even preferably 3 or 4 to 1000 and most preferably 3 or 4 to 200 per centimeter square of base plate area. Total number of needles per array (n) may range from 3 to 10000, preferably 3 to 1000 even more preferably 4 to 300. The arrangement of microneedles in the array is preferred like a matrix which has m number of rows and n number of columns. Each needle in the array can be identified as respective number of rows and column. The plunger array also has a base plate and solid needles designed to hold or push the microimplants from the base array needle. The materials used in plunger array base plate and its size are similar to base array plate as described above. The number of needles in plunger array (n') may vary but must be equal to or less than base array needles (n). If n equals or is less than n', then the position of plunger array and base plate needles on respective arrays must match with each other so that plunger array needles can be inserted inside the cavities of base array needles at the same time. Number of needles (n') can be same or equal to number of needles in one column or row. In illustrative array such as shown in FIG. 6 or 15, the number of needles in one row or column is five (C1 to C5 or R1 to R5) When such arrangement exists, then plunger array needles can be inserted in each column or each row to push the implants out per row or column at a time in the tissue. It is preferred that number of needles of base array, n, is equal to number of plunger array needles. The purpose of plunger array microneedles is to push the implant out of base array cavity. It generally has smooth surface without sharp edge/s at distal end and should not be able to pierce/tear the in situ formed implant or preformed implant present in the base array needle cavity. The materials used could be metal, plastic, glass, rubber/elastomeric or ceramic, but soft plastic material with flat surface is preferred. The average diameter/size of plunger array needle is less than the diameter/size of base array hollow cavity diameter (e' is less than d). This enables insertion of plunger array needles in the cavity of base array needles. It is preferred that it is a tight fit with smooth up and down movement of plunger array needle in the cavity of base array needle. The value of e' could be 1 to 80 percent less than the value of d, preferably 5 to 60 percent less. The length of the plunger array needle (b') is generally same as length of base array needle (b).

The length b' could be smaller or larger than the base array needle. The needle length b' could be larger and in some cases, it can be 1.1 to 6 times longer, preferably 2 to 3 times longer than base needle. In one embodiment, 3 times longer plunger needle array is used to remove the implant from the AIA apparatus in the skin tissue. The base array of AIA apparatus with preformed implant in the hollow cavity is first inserted in the skin tissue (Panel 6D-1). The plunger array with 3 times the length of base array is then inserted in the hollow array cavities until the plunger array needles touch the microimplants top surface in the base array cavity. The plunger array is held in that position and base array is lifted up along the length of the plunger array needle and out of the tissue. The extra length of plunger array needle enables this upward movement. The plunger array is also removed from the tissue leaving behind the implant in the skin tissue. In this method, the implant is not pushed but is held in place by the plunger array in the tissue while the base array is being removed from the skin tissue. The plunger array holds the implants in place in the tissue while base array is completely removed from the tissue. About three times the length of plunger provides sufficient space along the axis of the array needle to be removed from the tissue and thus it enables to move the base array needles out of skin surface. A combination of pushing or holding as described in any proportion may be used to insert the microimplant in tissue.

Array needles may have caps or packaging features that helps them to protect the needles during normal handling and storage of the AIA device. Since the device features are small, the package must protect it from dust and other particulate matter which can get inside the needle cavities and can potentially block the passages. The needles on both arrays can be bent or damaged during manufacturing and transportation operation. Specialized protective coverings or caps may be designed to protect the needles from such damages. The protection may especially be needed for sharp edged needle array to maintain sharpness for tissue insertion. The protective covering may be removed easily at the time of use.

In some embodiments, the plunger or inner array needle has a passage or tube (6022) along the axis of the needle length and injection port (6023). The purpose of passage and port is to use the plunger array to deliver injectable compositions (polymer solutions, crosslinkable precursors compositions, thermosensitive gel based compositions and the like) comprising drugs/cells in the tissue or in the cavity of base array needle. The average diameter of passage tube/opening is 10 to 70 percent of diameter of the plunger needle, preferably 15 to 60 percent and even more preferably 20 to 50 percent. The passage and port may also be used to apply air or other gas pressure to push the implant in base array cavity. Any biocompatible gas can be used but biocompatible gases such as carbon dioxide or oxygen are preferred. It can also be used to inject biocompatible liquids (which may be pressurized) such as PBS solution, saline solution and the like to push the implant in the tissue. The injectable port may be like a Luer lock type port where syringe or catheter with injectable compositions can be connected and injected in the tissue via passage 6022 into in the cavity space β. Injectable port may also house microelectronic accessary and sensors which enable movement of plunger array needle up and down so that each needle array movement can be controlled by a machine or computer program. If movement of individual needle is controlled by a machine, then it is possible to choose a desired pattern of implanted array in the tissue. In one illustrative embodiment, a syringe needle connected with pressurized nitrogen gas is inserted manually in each cavity of the array (base array with prefabricated implant, FIG. 15B). The pressured gas pushes the implant from the base array needle cavity in to the tissue. The manual pushing of microimplants, one at a time, can potentially give more control over drug dose to be given per human/animal subject but may be time consuming and susceptible to human errors.

The AIA apparatus has features that ensure alignment of array needles. This alignment ensures entrance of all the plunger array needles in the base array cavities at the same time. In one illustrative embodiment, guideposts and guide holes are used as an alignment feature. The base plate of the base array has four guide posts (FIG. 6) and plunger array base plate have 4 holes (FIG. 6) at corresponding location and the size of holes is greater than size of guiding posts. The guide posts also help to hold/handle the array by hand during insertion in the skin tissue. It is necessary that all the centers of needles of the plunger array must be aligned with centers of base array needle cavity/openings (opening on the base plate surface). If plunger array needles are not properly aligned, they may potentially get damaged or bent during improper insertion and therefore cannot function to push microimplants in the tissue. The guide posts help to achieve this alignment. The base array and plunger array may also have additional markings on their surfaces such as arrow/s or line/s or number/s that assists in proper orientation while inserting plunger array. Alternatively, guide posts may be on added on plunger array and holes may be added on base array, however, guideposts on the base array are preferred. The use of guide post is optional but alignment feature on AIA device is believed to be helpful to the user. Other methods of alignments or other alignment features such as laser based instrumentation known in the medical/automobile instrumentation art, electronic or mechanical methods known in the engineering art may also be used. The alignment of both array needles is more important than how it is achieved. In one illustrative embodiment 4 guide posts and holes have been used. Number of guide posts and corresponding holes could be one, two, three, four or more depending on the space available, cost and other variables.

FIG. 25 shows partial schematic representation method to make base or plunger array as described in FIG. 6. This is one of the several methods that can be used to make the AIA device. Metal hollow tubes with a desired cavity diameter (ID) and wall thickness and length are provided (2501). Hypodermic needles are normally made from a stainless-steel tubes, which pass through a process known as tube drawing where the tube is drawn through progressively smaller dies to make a tube of desired size. The tubes are encased in a plastic or metal plate (2502) via in situ casting of plastic resin or injection molding or wielding/adhesive bonding or other methods. The encased tubes are cut on the base plate surface (proximal end, straight cut to create a tube cavity opening on the surface) and also cut at distal end and beveled to create a sharp pointed tip letting the needle easily penetrate the skin. Standard bevel, medium short bevel or short bevel may be used to form a cutting edge. The angular cut at desired angle at distal end produces sharp edged (2503) hollow microneedles at distal end. The cut needle edges may be electropolished to make the cutting surface smooth. The sharp-edged microneedles protrude from the base plate (2501). The cut edges may be polished to produce a sharp edge. The opening on base plate surface (proximal end, not shown) is used for insertion of microimplant. The hollow tubes may be substituted with solid rods to produce plunger array. A laser beam may also be used to cut the tubes and produce sharp edged needle in combination with polishing or electro polishing. Alternatively, base and plunger array, preferably plunger array can be entirely made by injection molding of commonly used medical thermoplastics. Alternatively, the needles may be first cut to desired length with sharp end and then encased in a plastic/metal/ceramic base plate (2502) to produce needles with sharp edges at distal end and opening in proximal end. Base array alone or in combination with plunger array is used to form microimplant array in the skin or tissue. The apparatus as described above may be used to form implant in situ inside the tissue or may be able to inject a preformed implant with well-defined shape and size and drug release profile may be used. The preferred microimplant (either formed in situ or preformed outside in a factory setting) has a visualization agent. The preferred visualization agent is a biocompatible and biodegradable colored or fluorescent compound. The color or fluorescence of the injectable composition or implant helps to see the array during and after implantation procedure. In one exemplary embodiment (Example 22B), the AIA array is used to form in situ implant in a gelatin gel which can be used as a model tissue substrate because it is transparent in nature and helps to optimize implantation conditions and compositions. 5-15 percent gelatin solution is cast into 4 mm thick 1 inch diameter gel. The array in "array in array" device similar to device described in FIG. 6 or 15 is used. The base array device such as shown in FIG. 15B and plunger array plunger device such as shown in FIG. 15D are used. The plunger array (PA array) with 25 needles is inserted in the base array corresponding base array cavities (such as shown in FIG. 15F). In this arrangement, most of the hollow cavity space in the base array needles is occupied by the plunger array needles. The device (similar to shown in FIG. 15F) is inserted in gelatin gel or skin to create 5 by 5 array holes. The tissue/gelatin gel cannot enter in the cavity space of base array needles because the space is preoccupied by the plunger array needles. Upon complete insertion, the plunger array is removed from the base array and the space/volume created by the removal of plunger array microneedles is then filled by an injectable composition. Briefly, 1 g of PLGA (50:50 lactide:glycolide, PDLG 5002) polymer and 10 mg of coumarin and 9 ml n-methyl pyrrolidone are mixed until complete solution. The green solution is injected using a syringe in each base array needle cavity (ß, 25 total cavities). After filling cavities, excess solution is wiped off. The cavity is exposed to 2 ml PBS solution to accelerate precipitation of the polymer in the cavities. Using a plastic rod with size less than size of the hollow needle cavity, each precipitated microimplant is individually pushed into gelatin gel. Alternatively, plunger array is inserted to push all implants at once. The advantage of individual insertion of implant is that the number of implants and the array design/arrangement can be controlled.

Generally, the drug amount per microimplant per array needle is very small and each implant can be individually inserted, enabling to deliver small dose per microimplant. If needed, the total dose can be further increased by inserting additional microimplants from the array. Also, it may be possible to leave certain position in the matrix unimplanted and such positions can be used to encode certain information. The location the implant where it is present is encoded as one and the location without the implant is encoded as zero. The combination of zero and one can be used in encoding information similar to the used in modern computers. Another advantage of individual insertion of implant in an array is that the pattern implanted array can be chosen for a given medical need. For example, if needed, the implants in the first row (R1C1, R1C2, R1C3, R1C4 and R1C5 per FIG. 6A) can be inserted in the tissue out of 25 implants in the 5 by 5 format (FIG. 6A). If a microimplant in R1C1 can deliver a drug for one day, then each implant in the array (25 total implants in 5 by 5 array) can be programmed to be inserted per day. This way 25 day sustained drug delivery can be managed. The programming can be machine controlled or can be done manually. In another embodiment, if each microimplant in the array can deliver a drug for one week, then the entire array can be used to deliver 25 weeks sustained drug delivery. It is preferred that the needles are in the tissue for a short period of time during implantation time only, otherwise they can be on the skin/tissue surface but not inserted. Thus, by controlling variable like number of microimplants in the array, amount of drug per implant, duration of delivery per implant, insertion of number of implants per day and the like a sustained drug delivery composition, its dose and its duration can be controlled using this device.

The gelatin gel with PLGA microimplants is cut into rectangular shape and is photographed under blue light (FIG. 15G). The 5 by 5 array of PLGA based microimplants is clearly visible in gelatin gel and is fluorescent in nature (FIG. 15G). The use of polymer solution in water miscible solvent is used as illustrative injectable composition. Other injectable compositions described in this invention may also be used. The list of biodegradable polymers, biostable polymers, solvents for polymers, list of drugs that can be used is described elsewhere. In another exemplary embodiment (Example 22B), the AIA device is such as shown in Panel 6C-2 or FIG. 15F (plunger array is completely inserted in base array cavities) is inserted in the porcine skin tissue to create 5 by 5 array holes. The presence of plunger array needles in the hollow needles prevents the tissue coring or insertion in the hollow tissue cavity of base array. The plunger array is removed from the base array and the created space in the base array needle cavity is filled with injectable composition comprising live cell suspension and crosslinkable precursors solution such as fibrin glue or macromonomer solution (Example 15 and Example 10D). The precursor solution is crosslinked in situ encapsulating live cells in the crosslinked gels. The formed microimplants take the shape of base array cavity. The formed implants are then pushed inside the skin tissue with the plunger array thus forming microimplant arrays with live cells in the skin tissue.

In another embodiment and modification of AIA device, one microimplant at a time is pushed or injected in the tissue from base array cavity using a mechanism similar to used in firing bullet from a pistol or revolver. Generally, revolver/pistol is a repeating handgun that has a revolving cylinder containing multiple chambers and at least one barrel for firing. The revolver enables the user to fire multiple rounds without reloading. Each time the user cocks the hammer, the cylinder revolves to align the next chamber and round with the hammer and barrel. A similar mechanism can be used to fire/push implant wherein the chambers of barrel (cavities in base array) are used to store microimplant and the firing/pushing is done by plunger of the array needle or similar mechanism. In some cases, the tissue used for cavity making has a tendency to recoil due to elastic nature of the tissue. The recoiling may change or reduce the size/volume of the cavity or close the entrance of the cavity. In such circumstances, the cavity created inside the device (AIA device described in this invention) may be used or the composition may be injected prior to elastic response. For example, the hollow microneedle hollow needle array used in some embodiments (33MP array) can be inserted in the tissue and then withdrawn from the disuse. During the partial needle withdrawal, the injectable composition can be injected before the tissue recoils in the cavity created by needle.

Alternatively, tissue destruction can be used in place of tissue displacement. Those skilled in the art will realize that the choice of method will depend on the medical need, cost, ease of use and other variables.

In another embodiment of the AIA device, use of expandable array needle in forming drug delivery microimplant array has been shown. The needle of the AIA device (base and/or plunger, preferably plunger array) can be expandable. FIG. 23 shows schematic representation of use of expandable array needle in forming drug delivery microimplant array. 2601 is an expandable needle/stent with hollow cavity for storage of drug/cell comprising microimplant. The needle is present in the compact form in the base array cavity needle in AIA device. The base array cavity space prevents the expandable plunger array needle from expansion. FIG. 23A shows an expandable needle in compact form with microimplant (6013) in its cavity and is pushed out from the base array cavity into the skin tissue in unexpanded form but with implant in the cavity. FIG. 23B shows the expansion of plunger array needle/stent into an expanded shape or to its memorized shape (2302). The expanded shape has been pre-memorized into needle/stent using a heat treatment of the Nitinol alloy. The expanded shape releases the implant in the skin tissue and is then withdrawn in the base cavity array in compact form and then out of the skin tissue (FIG. 23C). The microimplant (6013) is left in the tissue in an array format for therapeutic action. The use of Nitinol based shaped memory alloys for making stent like devices is well known in stent based medical device art. The Plunger array needle device can be made using Nitinol alloy. The needle of the plunger array has two shapes. A compact shape and an expanded shape. Compact shape (2601) has cavity for storage of drug delivery microimplant. The Expanded shape such as conical shape (2602) is memorized into Nitinol alloy by heat treatment. The Plunger array with microimplants in its cavity is inserted in the base array cavity in compact form. The base array cavity's limited space prevents the expansion of compact form to expanded form at room temperature or body temperature. When base array and plunger array is inserted in the tissue, the plunger array needle is pushed out of base array needle cavity and body temperature causes the plunger array needle to expand and release the drug delivery microimplant in the tissue (FIG. 23B). The plunger array is pulled back in to base array cavity and then out of skin tissue leaving behind the drug delivery implant for therapeutic action. The use of Nitinol materials for expandable needle is used for illustration only and is not a limitation to this invention. Other expandable designs such as known in the stent medical device art like balloon expandable stent may also be used. The micro-balloon suited for the expandable needle may need to be specifically designed for the needle expansion and then used.

The AIA apparatus also can be used to implant preformed microimplants made in a factory setting. The microimplants can also be made outside using well established polymer processing techniques like extrusion, injection molding, solution casting, sintering and the like. In one embodiment, microcylindrical implants coated with drug delivery compositions are formed. The size and shape of the implant is chosen in such way that they can fit inside the cavity of AIA base array needles or inside cavity of plunger array expandable needle. In one embodiment, cat gut based fibers/threads are first coated with PLGA and coumarin based compositions as described before to obtain a coated fiber. The coated fiber is then cut into several microcylindrical rods or microimplants. Average length of cut microcylinder is 496 microns and PLGA coating has a thickness of approximately 40 microns (FIG. 15H). The cut microcylindrical rods are placed inside the cavity of base array. The plunger array is placed on top of base array with 2 mm polyethylene sheet as a spacer lock (6024). The device is then transported on top of porcine/sheep skin and bottom array needles are inserted completely in the skin. The spacer sheet is removed and the plunger array is pushed in the base array cavities. The plunger array pushes the implant in the skin. Both base array and plunger array are removed from the skin tissue leaving 25 implanted rods in array format. The implanted array can provide sustained drug delivery and fluorescent coating helps to visualize the implants in the skin. FIG. 15H shows coated microcylindrical rods in the skin tissue imaged under blue light. The implants did not have sharp cutting edge but can be implanted in the tissue using AIA apparatus. The microneedles of base array can do the cutting and insertion in the function. The illustrative FIG. 15H image shows 5 by 5 matrix type implantation arrangement in the skin tissue with fluorescent green coating. In some cases, a pressurized saline is used to push the implant from the base array cavities in the tissue. The illustrative array shows only cylindrical implant. The shape of the implant can vary and could be pyramidal, hexagonal and the like, as long as the size of the implant can fit inside cavity of base array. The sterile saline solution is attached to 22 gauge needle and 0.5-10 psi pressurized saline is discharged from the 22 gauge needle in the base array cavity to dislodge the implant from the array into tissue. In some cases, pressurized gas such as air, nitrogen, oxygen or carbon dioxide is used in place of saline to push the implant. In one exemplary embodiment, a 22 gauge needle is connected to carbon dioxide cylinder and preformed cylindrical implants is pushed using the pressurized fluid coming out of 22-gauge needle. Conical shape implants with sharp needle edge (Example 8, 16, 20 FIG. 9B2) may also be used as prefabricated implants (Panel 6A-3-2, 6013). Such implants are useful to push inside the tissue when pushed by air or gas pressure or plunger. Conical shape implants with sharp needle edge made from biodegradable polyester like PLGA can be useful in some applications.

The AIA device and its methods of use enables to deliver the drug in a solid form without forming drug solution or suspension. This can have several advantages over injectable drugs that are made in to solution prior to use. Table 3 compares the delivery of drug in a solid state as described in this invention and drug injection such as Botox injection.

TABLE 3

Comparison of conventional injectable drug solution administrated as a solution and delivering the same using microimplant array as described in this invention.

| Conventional liquid/solutions injectable | Drugs administrated as solid microimplant array as described in this invention. |
|---|---|
| Generally, drug is provided as a sterile solid along with its specially designed liquid diluent (water for injection as an example). | No need to provide liquid diluent. Drug is provided as a solid in the form of microimplant array. |
| The diluent must be measured, mixed in a sterile manner. Chance of human error in measurement or accidental needle pricks or loss of sterility during preparation or measurement. | Not applicable. Reduced chance of errors due to elimination of human steps. |
| Requires a sterile syringe and needle for administration. | Requires AIA device for administration. |
| Requires proper storage and disposal of used syringe and needles. | Requires proper storage and disposal of AIA device. |
| Distribution of drug in tissue generally cannot be visually seen. | Potential for visualization of administered microimplant array. |
| Can be painful. | Potential for pain free application. |
| Generally, treatment cannot be reversed once injected. | In some cases, potential to remove/denature/destroy the microimplants after administration if administered under the skin. |
| Injected liquid can have different tissue contact area of tissue contact. | Tissue contact area of the implanted array is generally well defined. |
| Injection area is generally limited. | Injection area can be large depending on the array design used. |

In one embodiment, collagen foam based fluorescent microimplants (fluorscein covalently linked collagen) containing 0.1 unit of Botox per microimplant are made first and then filled in the base array cavities (25 microimplants in 5 by 5 array format) and then pushed in the skin tissue as above using a plunger array and both arrays are removed leaving behind collagen based implant with Botox. The array provides 2.5 units of Botox per array in the skin tissue. The blue light exposure of skin tissue shows green fluorescence of collagen indicating successful implantation. If the length of base array needle is less than 600 microns, it could be a relatively pain free procedure for Botox delivery. This method also delivers Botox drug in the solid state (lyophilized state) without dilution with saline. Collagen is used as an illustrative biocompatible biodegradable bulking material in a solid state. The bulking agent provides bulk or volume to the Botox drug (an illustrative solid state drug) to form a microimplant with unibody properties or unibody microimplant with desirable mechanical integrity which can tolerate routine processing and device based implantation process. Other biocompatible and biodegradable natural and synthetic materials such as albumin (human or bovine), sugar of various types used in making dissolvable microarray implants, hyaluronic acid, polyvinyl pyrrolidinone, polyethylene glycol, polyvinyl alcohol, hydroxymethyl cellulose, hydroxypropyl cellulose, biodegradable polymers like polylactones or combination thereof and the like may be used as a carrier for Botox drug. Botox drug is used for illustration only, the same technique can be applied to deliver other drugs or vaccines which can be delivered in the solid state form without making a liquid solution. If the drug has high enough molecular weight, and its amount/mass used is sufficient to form a unibody microimplant, then it may not need bulking agent as described before. Botox has high molecular weight but is used in extremely small amount per vial, which may not be sufficient to form a unibody microimplant of desired size, therefore human serum albumin or hyaluronic acid or collagen is used as a bulking agent to provide unibody implant properties. For many small molecular weight compounds like rifampin or bupivacaine, or for drug encapsulated microspheres, a bulking agent or binding agent may be needed to form a unibody microimplant structure which then can be implanted in artificial tissue cavities or implanted using AIA device. In some cases, the bulking agent is first made into appropriate size microimplant and the implant is impregnated with drug solution prior to implantation or it may also be impregnated in factory setting and solvent is removed. If using just prior to implantation, the care is taken that the drug solution will preserve unibody properties of the implant. In one illustrative example, glutaraldehyde or EDC crosslinked collagen or gelatin foam is cut or fabricated into microcylindrical implants, loaded in AIA device cavities. The foam is then impregnated with 1-5 microliter of Botox solution having 0.1 unit of Botox drug is added on the implant. The implant does not lose its unibody structure with the addition of small drug solution. Crosslinked structure helps in maintaining unibody properties and prevent dissolution. The Botox impregnated implant is then implanted in the tissue as described before. In many cases, the microimplant is produced with the protein drug in factory setting and then implanted in an array format using AIA device as described before. This is done by mixing the drug and bulking agent in aqueous buffer or solvent to form a solution or suspension, filling the solution in a mold of desired size and lyophilizing/evaporating to remove water/solvent and to form unibody microimplant with drug. The unibody implant is then used to form microarray implant in the skin/tissue. In many cases, the solution is added in the base array cavities, centrifuged for uniform filling and lyophilized/evaporated the solvent in a factory setting. Alternatively, bulking agent and drug are formed into a solid sheet like material of desired size (10 cm length by 10 cm width and 500 microns thick as an example). The microimplant is then cut/stamped out (300 microns size diameter and 500 microns height cylindrical implant as an example) and then deployed in artificial tissue cavities or deployed using AIA device to form a microimplant array in the skin/tissue as described before.

In another illustrative embodiment, according to the "array in array" arrangement where the device is inserted in the skin/tissue in closed position (such as illustrated in FIG. 15F) wherein the plunger array or inner needle substantially or completely occupy the space inside outer needle or base array needle. Tissue/skin insertion in a closed position prevents tissue from going inside (tissue coring) the base array needle cavity during insertion step because most of the cavity volume is preoccupied by the plunger needle. The inner needle has a relatively small opening to inject polymer solutions or other injectable composition and it does not affect the ability of tissue to go inside the needle. The sharp edge of the outer/base array needle enables easy penetration inside the tissue. Once inside, the inner/plunger tube/needle is pulled up like a piston moving inside a tube, which creates a cavity in the base array needle. The cavity is then filled using the passage or tube present inside the inner needle. The inner tube (6022) which pushes injectable fluid, may be multilumen tubing so that two different liquids can be injected in the cavity via each lumen. This could be useful to add compositions like fibrin glue whose precursors may be added inside the cavity and each precursor may be added via each lumen present in the tube. The injectable composition occupies the cavity, partially (10 to 90 percent) or completely. The injectable composition undergoes chemical or physical transitions and "sets" inside the cavity. The outer device can be withdrawn from the tissue leaving behind the set polymer. For example, a low melting polymer can be melted and injected in the cavity and cooled to form solid implant. Crosslinkable precursors like fibrin glue precursors or precursors present in DuraSeal surgical sealant may be added and allowed to crosslink and form a biodegradable synthetic crosslinked gel. Injectable composition could be polymer dissolved in water miscible organic solvent and solvent is allowed to dissipate inside the tissue, which leads to polymer precipitation and forming a solid implant. Prefabricated microimplants with drug/cells may also be loaded in device cavities and then pushed into skin tissue. The FIGS. 6A-6D and 15A-H show a cylindrical cavity being formed inside the device, but it could be of any shape, preferably symmetrical shape, as long as the inner and outer tube can be removed without affecting the set implant. The shape could be cubical, cuboid, prism and the like.

The hollow needle used for deployment of implants should not have narrow opening at the distal end (d1 is less than d) because upon casting, the cast implant cannot be pushed out from the narrow opening. This is also true for deployment of solid prefabricated implant through the device. The average diameter of cast implant or prefabricated implant must be smaller than the smallest of the needle diameter (d or d1). If d1 is smaller than d, the cast or prefabricated will require excessive force to squeeze out through the narrow opening and such situations should be avoided. It will also impede the removal of needle from the tissue and can pull back the cast implant with it. The average internal diameter of hollow needle (d) is preferably less than or equal to d1, except in case of expandable needle shape described elsewhere. Those skilled in the art can understand the choice of shape and size of the prefabricated microimplant or in situ case implant must be chosen such that it can be easily pushed out from the distal end of the needle. Those skilled in the art understand that needle shape and size must be chosen in a way that it should not hinder the removal of device needles from the skin/tissue. Those skilled in the art recognize that many variations are possible with the illustrative embodiments presented herein. Variable like needle shape; needle internal diameter (d and d1); needle external diameter; spacing between each needle in the array; needle material type; number of needles per array; number of array insertion points and the like may be used to make variety of microimplant arrays in the tissue. The embodiments illustrated and described herein may be shown to have a narrowed opening relative to the lumen of the hollow microneedle, however, any of these embodiments should be understood to also allow for the entirety of the lumen of the hollow microneedle and outlet at the tip to have the same cross-sectional profile and cross-sectional dimensions in order for a solid microimplant within the lumen to be capable of being pushed out of the lumen by the plunger shaft (e.g., solid microneedle that is blunt tipped.). Accordingly, during removal of the microneedle, the microimplent will be retained in the medium (e.g., live tissue or bioprosthesis tissue). However, if the distal opening at the tip of the microneedle is narrowed relative to the shaft lumen, the composition may be malleable or compressible so that it may be pushed out the narrowed opening during or after withdrawal of the microneedle from the medium so that the formed cavity receives the microimplant therein while allowing withdrawal of the microneedle from the medium.

In another modification of AIA device, a separate cartilage containing unibody microimplants is made and used. The cartridge is either shipped with an AIA device as a kit or it may be used as a single package comprising base array, plunger array and microimplant cartridge. The cartridge is specifically designed to work for a specific AIA apparatus design. If AIA design changes, then cartilage must be redesigned to work with modified redesigned AIA device. FIG. 24 shows a partial schematic representation of illustrative "array in array" device wherein a separate cartridge for holding microimplants is used instead of space in hollow cavity of the base array. The cartridge can be aligned and placed between base outer array and plunger or inner array. The microimplants in the cartridge are then inserted into skin/tissue via base array cavities. FIG. 24, item A1 shows an illustrative circular shaped exemplary cartridge. The cartridge has a base plate (2401) and has one or more holes/cavities (2402). The holes have openings on both sides of the cartridge plate surface 2401 (proximal and distal end). The holes 2402 can be filled with preformed or in situ formed microimplants (6013) with drug/cells (FIG. 24 item A2). Optionally bottom and/or top surface of 2401 may be covered with protective cover (2407) which may be removed at the time of use or it may implantable and/or biodegradable. The protective cover prevents unwanted movements of implant from the holes. FIG. 24 item B1 and FIG. 24 item B2 represent base array and plunger array respectively similar to described in FIGS. 6A-6D wherein 2405 is a base plate to which hollow sharp needles are attached and proximal end of needles has opening on the base plate to load microimplants. FIG. 24 item B2 is similar to the plunger array described in FIGS. 6A-6D wherein 2405 is a plunger plate to which solid non-cutting needles (2406) are attached. The internal diameter of hollow needles (2404) is same as hole diameter in cartridge FIG. 24 item A1 (2402). The external diameter of plunger needles (2406) is less than the diameter of holes in FIG. 24 item A1 and hollow needles in FIG. 24 item B1 and it can freely move up and down in the holes/cavities of FIG. 24 item A1 and FIG. 24 item B2. The number of needles and holes and their size, shape and arrangement in the array is identical in FIG. 24 items A1, B1 and B2. FIG. 24 item C shows array B inserted in the skin tissue and cartridge A2 with microimplant is placed on top of array B1 with protective cover 2407 removed. The center of all the holes in FIG. 24 item A1 is aligned the with the center of hollow needle opening on base array plate FIG. 24 item B1. The center of plunger array needles in FIG. 24 item C is also aligned with center of holes in FIG. 24 item A2 and FIG. 24 item B2 but is not inserted in cartridge A2. FIG. 24 item D shows the insertion of plunger needles in the holes of cartridge A (2402) and cavities of B1 (2404) and pushing the implants from them in the skin tissue. Both the arrays and cartridge are pulled from skin tissue leaving behind the microimplant array with drug/cells for local or systemic therapeutic effect. The cartridge may be packaged and stored separately and used as described above or it may be packaged in the pre-aligned form in the AIA device and used for implantation. The cartridge, plunger array may have additional holes (not shown) and base array may have guiding posts (not shown) to help in alignment similar to described in FIGS. 6A-6D. A drug/cell loaded unibody microimplant may be manufactured, sterilized and packaged separately than the AIA device or it may be pre-inserted, pre-aligned and deployed along with AIA device. In one illustrative embodiment (Example 22, Design 4) a cartridge that has a base plate with holes to store drug/cell implants and optionally a protective covering on top and bottom plate to prevent movement of implant during storage and handling is made. A stainless steel rectangular plate 500 microns thick and 20 mm length and 20 mm width is used. At the center of the plate 25 holes with 0.29 mm diameter are drilled in the 5 by 5 matrix format. The matrix position and format is same as base array needle format as shown in Example 22, design 2 or array used in FIGS. 15A-15H. The plate is kept on Teflon sheet and the holes of the plate are filled with PEG based macromonomer solution with photoinitiator (Example 10) and bupivacaine loaded PLGA microspheres (20 percent loading). For aqueous solutions, hydrophobic surface like Teflon surface prevents droplet spreading which helps to stay the solution inside the cavity. The monomer solution/suspension is exposed to long UV light (360 nm). The polymerization forms biodegradable hydrogels inside the holes with drug loaded microspheres. The water in the hydrogel may be removed by lyophilization. A protective polyester sheet is placed at the bottom of cartridge plate. The plate with solid lyophilized microimplants with diameter 0.29 diameter is placed on top of base array plate with center of holes matching the center of base array cavity holes and the protective cover is removed. The base array needles are then inserted in the sheep skin tissue and the plunger array is kept on top of cartridge array where center of plunger needles aligns the center of cartridge implant. The plunger array is pushed downward which pushes the hydrogel implant via base cavity array into tissue. The base array along with cartridge and plunger array are removed from the tissue leaving the hydrogel implant for local or systemic drug therapy. The stainless-steel plate of cartridge can have holes for alignment which can be used with guiding posts on the base array surface. In another variation, prefabricated cylindrical implants such as shown in FIG. 15H are used. To hold the implant in place, the base plate bottom surface has been spray/dip coated with collagen or gelatin film foam or other film forming biodegradable biocompatible polymer. The part of the protective covering may be made from water soluble and/or biodegradable biocompatible polymer. The implants are pushed and the coated film/foam is removed just prior to use. In another embodiment same as above, the protective foam cover is not removed but is cut/stamped out by the plunger array and is transported inside the tissue and implanted (in this case plunger array needles have a cutting edge to stamp out the foam). The gelatin/collagen is safely removed by the body by biodegradation process. In another embodiment, biodegradable polymer implant (PLGA implant) is cast from a solution in situ, solvent is removed and the microimplant is inserted in the tissue as discussed before. In another variation, stainless steel base plate in the cartridge is substituted with silicone rubber sheet with holes for guide posts for alignment. In another variation, a biodegradable foam such as collagen foam with same size as base plate of cartridge base plate (500 micron thick) that is infused with drug/cells is used as a cartridge. The foam is placed on top of base array plate and a plunger array is inserted in base array cavities via foam. The plunger array needles cut/stamp the foam and the cut foam portion of the foam is pushed via base array needle cavity into skin/tissue as described before. In this embodiment, plunger array needles distal end is designed such that it can easily stamp out the foam material with little pressure or force.

Oscillating plunger needle that implants/pushes one microimplant per insertion at 30-120-degree angle, preferably 90-degree angle from cartridge is also envisioned. The implants are inserted at frequency of 1-200 implant per minute from the cartridge via base array needle into skin/tissue. Each implant is inserted in predetermined new location at predetermined depth on the skin to form a microarray of desired shape and size. The micro implants will be loaded in a cassette like arrangement wherein one implant will be loaded from the cassette into oscillating needle prior to skin insertion. The cartridge or base cavity holes may be filled with biodegradable polymer solution with drug, degassed and optionally centrifuged to fill uniformly. The solvent is removed by evaporation or by lyophilization or other means leaving behind the biodegradable polymer and drug in the cartridge or base array cavity. The molecular weight of the polymer is and other properties are chosen such that the implant formed has unibody structure. The unibody implant is then inserted in the skin/tissue as discussed before for local or systemic drug therapy.

Number of microimplants that can be formed with AIA device include but are not limited to 1, 2, 3, 4 5, 6 and up to 100 per square centimeter or higher. The implant formed is biodegradable and preferably contains drug/cells and/or visualization agent. The device materials could be metal, polymers or plastics or ceramics or glass. The most preferred materials are stainless steel, titanium, gold, silver, polyethylene, polypropylene, nylon, polytetrafluoroethylene or their alloys and combinations thereof. Among these stainless steel is the most preferred. The device materials should be compatible with solvents and other components in the injectable composition; for example, DMSO used in injectable compositions can dissolve common plastics like polymethyl methacrylate and thus such materials are not preferred as device components. Materials described above generally work for aqueous based non-corrosive compositions.

Another advantage of this inventive method is that there is no need for sharp edges for microimplant materials to be implanted. The base array material needle can serve the function of tissue insertion. In conventional biodegradable or dissolvable microneedle for drug delivery, the needle must have sharp edges for easy insertion in the tissue along with its backing material and the same material is used as a carrier of drugs. The conventional array needle serves as a tissue penetration device as well as it provides sustained drug release properties for the drug. This requirement of needle sharpness and mechanical strength for tissue penetration with small force limits the type of materials that can be used for drug delivery. In this invention, the sharpness and mechanical strength are separated from the drug delivery aspect of the implant. The metals have the best combination of toughness and hardness and thus are preferred in piercing the tissue (stainless steel metal used in the preferred embodiment shown in FIG. 15). The hollow cavity of the needle is used as a carrier of precast microimplant of desired shape and size in the tissue as long as the shape chosen can easily pushed out of the cavity. The precast implant does not need sharp edge at distal end for tissue penetration. This approach enables the use of materials that are not mechanically strong but are useful for sustained drug delivery or hydrogel soft materials that can encapsulate live cells and therefore allows use of wider variety of materials. This also enables to eliminate the use of adhesive tapes and specialized applicator used to push the microneedle array inside the body. This method enables to use liquid drug carriers like vitamin E or sucrose acetate which cannot form conventional microarrays by themselves.

FIG. 22C shows a 3 by 3 microimplant array of fluorescent biodegradable cylindrical microimplants. The microimplants are inserted in the tissue to form microimplant array (2206). The microimplant array prepared as above (2206) does not have sharp needle like edge but is implanted in the tissue using AIA devices as described above. The implanted array can provide sustained drug delivery or cells for therapeutic use. The array 2206 was created by making the fluorescent cylindrical microimplants (size 100 mm diameter and 1000 mm height) by slicing a fluorescent 100 micron diameter thread. The exemplary tissue is first treated with microneedle array or syringe needle to create array of artificial 150-300 microns size cavities (cavity size must be larger than implant size. The cylindrical implant is then inserted individually one by one by hand or all at once using an array in array device as described before. The array formed is imaged under blue light to visualize the microimplant array. The inserted implants may further be immobilized by applying tissue adhesive/sealant like DuraSeal or fibrin glue sealant or adhesive tape like band aid tape on top of the array to prevent its migration from the cavity.

In some embodiments, a unibody implant or combination of 1 to 10 unibody implants are preferred. The unibody implants have continuous solid structure which enables to use them in AIA device. Unibody implants are easy to push by the plunger array. If implant is not unibody type, for example a loose powdered particles or drug encapsulated particles, it may be difficult to push those using plunger array needles. Some of the particles may reside in the device which may result into lower drug dose than desired. However, the particles may be converted into unibody implant by sintering them or fusing them to form a sintered body which has uniform solid structure. The particles may also be bound using a binder additive and compacted under pressure to produce a unibody "green body mass" which can be pushed into body without leaving any residue into the device. The particles may also be encapsulated in a hydrogel matrix such as PEG based biodegradable hydrogels produced from PEG based macromonomers or PEG based crosslinkable precursors to form a unibody implant.

The array in array device described herein may be provided as a kit wherein microimplants and/or injectable compositions and AIA device may be packaged together as a kit. The implants or injectable solutions are loaded in the AIA devices just prior to use.

In some cases, the implants delivered by the AIA device may undergo change in shape in contact with tissue or tissue fluids. For example, hydrogel based implant may increase in volume by absorbing water in the tissue and increase its volume by 1 percent to 10000 percent. In some cases, the device may shrink in size if the hydrogel is lyophilized under stretched conditions or under strain. Microimplants can be designed or made to change their shape after implantation. Change in volume in one example for hydrogels. Biodegradable materials that can change the shape are known in the art and such materials can also be used in preparing microimplants as discussed in this invention. The advantage of shape changed materials is that the implants cannot migrate or come out of skin tissue once implanted. The change in shape is not a requirement for this invention to work but can provide additional benefit if it is desired.

A comparison of conventional microneedle arrays made externally and microimplant array made using devices and methods described above is shown in Table 4.

TABLE 4

Comparison of conventional microneedle arrays made externally and microimplant array made using devices and methods described above.

| Conventional microneedle array used for Implantation | Microneedles implanted using devices and method described as above. |
|---|---|
| The implanted microneedles must have sharp edge at distal end for easy skin insertion. This limits the shape of the implant. Cannot use cylindrical implant with no sharp edge at distal end. | The microimplant does not need have sharp edge. Can be used to implant cylindrical and other shaped materials. Enables wider choice of implant shapes and materials. |
| Microneedle must have certain hardness and mechanical strength for tissue penetration. | No hardness and mechanical strength requirement for the microimplant. |
| Limited to materials choices. Cannot be used with soft hydrogel materials like gelatin hydrogel at ambient temperature or liquid drug carriers like sucrose acetate. | Enables the use of wide range of materials. Can be used with soft materials and liquid carriers. |
| Difficult to use with live cells due to harness and solid state nature of the implant. | Can be used with live cells to form live cell microarray implants. |

Preparation of Prefabricated Porous Microimplants Coated/Infused with Drug/Cells for Implantation in Microarray Format This invention uses prefabricated microimplants, preferably unibody microimplants that can be implanted using AIA device or in artificially created cavities. Some embodiments use prefabricated microimplants that are porous in nature. The porosity may be filled with or porous microimplant surface may be coated with sustained drug release compositions or live cells for therapeutic use. The solid or polymers used in porous microimplant may also provide structural support to act as unibody implant which may help in pushing the implant via plunger array needles as discussed before. The increased area created by the porosity, enables more surface area for the drug loading which enables more efficient utilization of microimplant surface. The total porosity of the implant may range from 5 to 95 percent, preferably 10-90 percent of the microimplant volume. The surface area of solid cylindrical microimplant can be substantially increased by creating artificial cavities or porosity. In one embodiment, several 0.005 cm diameter and 0.01 cm dip cavities are drilled on the 0.1 cm diameter and 0.2 cm height cylindrical microimplant. By creating 1 to 2000 cylindrical cavities (0.005 cm diameter and 0.01 cm height) on the surface, approximately 10 to 400 percent area (relative to the original area) of the implant can be increased. If a drug is released at 10 nanograms per square cm area, then increased surface area would lead to substantially increased drug concentration of the drug. The porous microimplant used may be biostable or biodegradable. The artificial porosity may be created in many ways as known in the polymer foam preparation art. The porosity preparation methods include but not limited to: creating a gas source inside the solid matrix such as carbon dioxide gas used to make bread porous via fermentation or by decomposition of sodium bicarbonate; removal of solvents by freeze drying or other methods; knitting or weaving of fibers; adding a porogen such as water soluble salt and leaching it out from the solid matrix and the like. For the purpose of illustration, two exemplary methods of porous implant preparation have been provided. It is understood that other methods in the polymer foam preparation or tissue engineering scaffold preparation art, either known or yet to be discovered, can also be used without limitation. In one illustrative example, biodegradable poly (L-lactide-co-caprolactone copolymer porous polymer is prepared by adding sodium chloride as a porogen. Briefly, poly(L-lactide-co-caprolactone copolymer is dissolved in organic solvent such as tetrahydrofuran or dioxane. Dioxane is preferred because it can be removed by freeze-drying process. The dioxane solution of the polymer is mixed with sodium chloride crystals to make a suspension. The sodium chloride crystals are ground by mortar and pastel or any other means and sieved to obtain a desired particle size and distribution fraction. The polymer and salt suspension is stirred to mix the crystals uniformly and frozen quickly using liquid nitrogen to form a frozen solid matrix. The frozen solid is subjected to lyophilization or freeze-drying process to remove the solvent by sublimation process. The freeze-drying is conducted at temperature around −10 to zero-degree C., typically around −5 degree C. The dried solid is exposed to water to dissolve out the sodium chloride in the water and thus forming a solid polymer structure with empty space vacated by leaching out sodium chloride and solvent dioxane. By changing the amount of solvent, sodium chloride and its particle size and shape, a wide variety of porous implant structures with varying degree of porosity can be created. For example, salt may be added up to 95 to 5 percent, preferably 90 to 10 percent and even more preferably of the 70 to 20 percent of the volume of microimplant. Many water soluble or organic solvent soluble porogen or leaching agents may be used and these include inorganic or organic salts, prefabricated microspheres with uniform particles size, organic and macromolecular substances like polyethylene glycol and the like. The preferred materials include materials that have well defined particle size and distribution which may include but not limited to: commonly used salts and compounds such as sodium chloride, potassium chloride, sugar, glucose, and the like. In choosing the porogen, it is essential that it can be extracted without affecting the polymer in which it is incorporated. For example, extraction solvent must be a non-solvent for the polymer being used. In one embodiment, poly(L-lactide-co-caprolactone copolymer is used which is water insoluble and therefore water extractable porogen such as sodium chloride may be suitable to make the porosity. For hydrophilic or water soluble polymers like collagen or gelatin or poly(vinyl alcohol), polyvinyl pyrrolidinone, hydroxy ethyl cellulose, hydroxy propyl cellulose and the like sodium chloride may not be preferred because it can also dissolve/swell the water soluble polymer. Organic solvents such as methanol acetone, which are non-solvent for collagen or gelatin, may be used for porogen extraction. In one exemplary embodiment, methanol soluble microspheres are used as a porogen and are removed from methanol extractions. The list of solvents and non-solvent for many polymers can be found in Polymer Handbook. For water soluble polymers and macromolecules such as collagen or gelatin, the water itself may be used to create porosity. The free water in the aqueous polymer solution can be removed by lyophilization to create porosity in the polymer. In another illustrative example, ethyl methacrylate microspheres, which can be removed by methanol extraction, have been used. The microspheres create spherical voids in the polymer solid. Solvent may be added from 0.1 to 60 percent relative to polymer weight depending on the solvent used. Generally polymer is dissolved 1 to 50 percent relative to solvent weight, preferably 5 to 30 percent. Many types, beads/microspheres that may be useful are commercially available from suppliers like Polysciences, USA. Porous structure may be created in many biostable and biodegradable polymers as defined previously. The polymers may be hydrophobic or hydrophilic. The polymers may be crosslinked or thermoplastic. In general polymers must be biocompatible and suitable for implantation in the human or animal body. Among biodegradable polymers, synthetic or natural polymer or macromolecules as discussed in earlier sections may be used. The preferred biostable polymers include but not limited to aliphatic and aromatic polyurethanes, polycarbonate polyurethanes, polyether polyurethanes, silicone polyurethane block copolymers, silicone rubbers, polydimethyl siloxane copolymers, polytetrafluoroethylene, expanded polytetrafluoroethylene, polyethylene, polypropylene, polyamide, polyamide block copolymers and the like. In another exemplary embodiments, methanol or water extractable PEG is used as a porogen to make a porous structure. In one exemplary embodiment, a natural hydrophilic natural polymer is used to create porosity via PEG extraction. A collagen solution is frozen with poly (ethyl methacrylate) beads as a porogen and lyophilized. The freeze-dried collagen-bead composite is then subjected to methanol extractions to remove the microspheres and create porosity in the collagen. The collagen porous implant may be crosslinked with 1-Ethyl-3-(3-dimethylaminopropyl)-carbodiimide (EDC) or glutaraldehyde or PEG based water soluble crosslinkers to improve its degradation time in the body. Treating the porous collagen porous implant with 0.1 M EDC solution in 50 percent acetone for 8 hours can form crosslinks in the collagen. By changing EDC concentrations and reaction time, collagen degradation time in the body can be changed. EDC crosslinked porous collagen also serves as exemplary crosslinked hydrophilic polymer based porous implants suitable to be used as drug carriers. Other carbodiimide based crosslinkers may also be used.

Loading of Drug/Cell Comprising Compositions in the Porosity of Prefabricated Porous Microimplant to Form Microarray:

Once the porous structure is obtained, the porous structure can be partially, substantially or completely filled or coated with drug releasing compositions, which may comprise, a drug or drug with carrier or live cells. The list of drugs that can be used is provided in the definition section. The carrier may be non-polymer, ceramics, minerals, polymers or macromolecules that may be suitable for use in the human or animal body. The carrier may be liquid, solid, waxy, gels, semisolids, or viscous liquids. The preferred carrier may be biostable and biodegradable polymers. The polymers may be hydrophobic or hydrophilic. The polymers may be cross-linked, non-crosslinked or thermoplastic. In general polymers must be biocompatible and suitable for implantation in the human or animal body. Among biodegradable polymers, synthetic or natural polymers/macromolecules may be used. The biodegradable polymers may be hydrophobic or hydrophilic. The biodegradable polymers may be crosslinked or non-crosslinked. The crosslinking may be done via condensation polymerization or via free radical polymerization. The polymers may be random or block or graft copolymers. The polymers may be linear, graft or branched. The hydrophobic polymers include, but are not limited to, polymers, dendramers, copolymers or oligomers of glycolide, dl-lactide, d-lactide, l-lactide, caprolactone, dioxanone and trimethylene carbonate; degradable polyurethanes, polyamides, polyesters, polypeptides, polyhydroxyacids, polylactic acid, polyglycolic acid, polyanhydrides, and polylactones. Hydrophobic polymers also include polyhydroxyalkanoates which are polyesters produced by microorganisms such as poly-(3-hydroxybutyrate), 3-hydroxyvalerate, 4-hydroxybutarate, 3-hydroxyhexanoate, 3-hydroxyoctanoate. Preferred hydrophilic polymers include, but are not limited to, polyethylene glycol-polyhydroxy acid or polyethylene glycol-polylactone copolymers (PEG-PL copolymers), polyvinyl alcohol co-polylactone copolymers, and derivatives of cellulose, collagen, gelatin, albumin, fibrinogen, keratin, starch, hyaluronic acid and dextran. The PEG-PL copolymers are most preferred. PEG-PL copolymers such polyethylene glycol-polylactone copolymers can have a range of properties from hydrophobic to hydrophilic depending on the amount of PEG incorporation in the copolymer and molecular weight of PEG and polylactone. In one exemplary embodiment, drug solution is infused in the body of a porous implant without the use of carrier polymer. The drug loading can be 1 to 40 percent relative to the weight of the polymer or the drug can occupy 1 to 90 percent of the pore volume. In another exemplary illustration, a synthetic biodegradable polymer is used as drug carrier for the drug. The drug and biostable polymer or biodegradable polymer is dissolved in a common solvent and the solution of the polymer is exposed to the porous implant. The solvent for the polymer and drug infusion should be a non-solvent for the porous implant. In the illustrative example, 10 ml tetrahydrofuran or 1,4-dioxane, 900 mg of poly (PLGA, lactide-co-glycolide) (lactide:glycolide (50:50), molecular weight 30000 to 60000 g/mole.) and 100 mg (approx. 10 percent loading relative to weight of polymer) Latanoprost are mixed until homogeneous solution. A porous collagen implant or commercial collagen microimplant from Odyssey Medical, Inc. (size 0.4 mm diameter×1 mm length) is used as a substrate. 25 dry collagen porous microimplants are incubated in the PLGA and drug solution in organic solvent such as dioxane or THF and after complete penetration of the solution into the pores, the excess solution is removed and the implants are added in 10 ml PBS solution in glass vial to precipitate the polymer in the pores of the implant.

After incubating for 6 h, (PBS solution is changed every hour), the implants are lyophilized. Alternatively, after complete penetration of dioxane-polymer-drug solution in the pores, the implant is taken out, wiped to remove excess solution from the surface and frozen immediately using liquid nitrogen and lyophilized to remove the solvent. The pores in the microimplant now has biodegradable polymer with drug. The drug-polymer is either precipitated in the pore or freeze-dried in the pores. If the pore volume is high, then large amount of volume is occupied by the drug releasing composition. The implants are loaded and deployed in the array format using AIA device as described before. The drug is released in a sustained manner due to diffusion and/or bioerosion/biodegradation of the biodegradable polymer. The release rate will depend on the biodegradation rate of the polymer used, drug solubility in the polymer, drug loading in the polymer (2 to 60 percent, preferably 5 to 40 percent relative to weight of the biodegradable polymer). Since dioxane is a non-solvent for the porous implant, the porous implant can maintain its mechanical integrity which is helpful in pushing the implant in the tissue using AIA device. In some embodiments, a biocompatible liquid carrier may be infused in the porosity of microimplants. The liquid carriers that may be used include but not limited to: vitamin E or its derivatives, vitamin E acetate liquid polylactone or polyhydroxy polymers or copolymers or copolymers, PEG-polylactone copolymers, PEO-PPO-PEO polylactone copolymers, sucrose acetate, natural or synthetic oils and fats, fatty acids, fatty alcohols, oleic acid and its derivatives and the like. The porous implant provides a matrix and unibody properties for the microimplant and liquid carrier and drug infused/coated in the porous structure provides sustained release of drug. In another exemplary embodiment, the drug compositions may be injected directly into pores or artificial cavities created in the implant body.

The unibody microimplant array formed is preferred to be colored or fluorescent or combination thereof. The color or fluorescent enables to see the implanted array after it has been formed or implanted in the tissue. Color may also help to encode/decode certain information such as manufacturing batch number, expiry date of the product and the like. Colored compounds could be added in many ways. Color could be covalently bound, ionically bound, stained or physically mixed with the microimplant composition. Preferably, the colored compound is biocompatible and biodegradable. Even more preferably the colored compound used is selected from the compounds which have history of use in human or history of use in medical devices or pharmaceutical compositions. The percent of colored or fluorescent compound could be added in microimplant may range from 0.05 percent to 10 percent, preferably 0.1 to 5 percent relative to the weight of microimplant. Color also could be added as colored biodegradable microparticles or microspheres.

In some cases, the color or fluorescent compound is added to the microimplant or hydrogel matrix used in the microimplant array. In one illustrative embodiment, fluorscein is covalently attached to collagen or bioprosthesis tissue. This was achieved by treating/reacting the fluorscein and collagen/bioprosthesis tissue in presence of N-(3-Dimethylaminopropyl)-N'-ethylcarbodiimide hydrochloride (EDC) as a catalyst at ambient temperature in aqueous buffered modicum around pH 6 to 7. The fluorscein linked to the collagen chains via ester or amide bond. The fluorscein bound collagen or tissue shows green fluorescence when exposed to blue light. Color or fluorescent compound can also be covalently bonded to synthetic hydrogel biostable or biodegradable matrix used in microimplant array formation. Preferably the synthetic hydrogel matrix is a biodegradable hydrogel comprising PEG or PEG based crosslinked hydrogel.

Implantable Biodegradable Metal Based Arrays for Drug Delivery

This invention discloses microneedle based drug delivery arrays derived from biodegradable metal. Since metals offer the best combination of mechanical properties for easy skin penetration, we have discovered that microneedles made from biodegradable metals could be useful in drug/cell delivery application. This invention discloses biodegradable microneedle arrays made using biodegradable metal. The inventive arrays have microneedles with sharp edge. The microneedles are made using biodegradable metal. The array also has a backing layer wherein needles temporarily are attached to the backing layer via adhesive layer, preferably a pressure sensitive adhesive layer. The purpose of the backing layer is to hold the array needles in place temporary until implantation and detach itself easily once array needles are implanted in the skin. The adhesive layer is attached to a flexible polymer film, leather or woven/knitted textile fibers or rubber like materials. The needles are attached perpendicular to the backing layer and the sharp edge is pointing away from the backing layer surface. Preferably the needles are attached in a matrix array format. The microneedles attached to the adhesive backing layer make the implantable drug delivery device array. FIG. 26 shows partial schematic representation of various configurations of biodegradable metal based, preferably magnesium alloy based, microneedles that can be useful in making implantable drug delivery arrays. FIG. 26A schematically shows a biodegradable magnesium alloy based hollow array needle (2601) with sharp distal edge (2602) for easy tissue penetration. The hollow cavity of needle is partially or completely filled with sustained drug delivery composition such as PLGA polymer with a drug (2603). FIG. 26B shows a schematic of an illustrative array needle 2604 whose external surface is partially or completely coated with biodegradable sustained drug delivery composition (2605). The composition 2605 may have one or more coating layers and one of them may be a rate controlling layer without a drug. FIG. 26C shows a hybrid needle wherein the tip of the needle (2606) is made up using biodegradable metal for easy skin penetration and the drug delivery portion (2607) is made biodegradable polymer/hydrogel with sustained drug/cell delivery composition. FIG. 26D shows schematics of illustrative needles with artificially created porosity for drug delivery. The illustrative configurations create artificial porosity to increase surface area and to create a space for drug delivery compositions. Figure D1 shows a biodegradable metal array needle (2608) with distal sharp edge wherein wedge shaped micro pockets are created inside the needle surface and then filled with drug delivery composition (D1, 2609). In another variation (D2), rectangular portions have been cut out in the needle body to create a space for drug delivery composition filling material (2610). In another variation (D3), several artificial microcavities of various shapes (cylindrical in this illustrative case) or holes are created by the needle surface/body and the cavities/holes are then filled with injectable drug delivery compositions (PLGA with rifampin as an example, 2611). FIG. 26E shows illustrative microneedle array device with biodegradable metal based microneedles attached to a flexible backing material. Four microneedles with holes/cavities filled with biodegradable drug delivery compositions (2611, D3) are attached using a pressure sensitive adhesive (2613) to a flexible backing material (2614) in an implantable array format to create an exemplary biodegradable microneedle array device. The needle base is attached to the adhesive and free distal end with sharp edge is used for tissue penetration.

The device is inserted in the skin tissue by pressing the backing layer with needles sharp ends facing the skin and implanted in the skin. The backing/adhesive material is removed leaving behind the array in the skin. The metal array and drug delivery compositions are biodegradable and provide a drug for local or systemic therapeutic effect.

In one illustrative and non-limiting embodiment, a 100 mm length, 100 mm width and 500 micron thick magnesium alloy (AZ31, Magnesium 96 percent, Aluminum 3 percent and Zinc one percent) foil from Goodfellow Corporation, Coraopolis, Pa., USA (product code 343-198-08) is used to make an implantable array (Example 25). In another embodiment, a hollow microneedle based needle is used to prepare an array device (Example 25). The hollow cavity of the microneedle is filled with sustained drug delivery compositions. Yet in another embodiment, a magnesium alloy based microcylinder is coated with drug delivery composition with multiple layers and the microcylinder is implanted using AIA device described in this invention.

In all the cases, a biodegradable metal is used in variety of different designs and configurations to make the implantable array based drug delivery device (Seitz J et al., Adv. Healthcare Mater., volume 4, page 1915-1936, 2015). The biodegradable metal used could be any metal that degrades safely in the body in a period from few days to few years, preferably in 7 days to 270 days. Many alloys of calcium, magnesium, aluminium, zinc, manganese, iron and other metals are known to degrade safely upon implantation. Preferred metals do not create extreme basic or acid local environments upon implantation and is safely removed by the body via biodegradation process such as hydrolysis or other corrosion type mechanism. Metal alloys based on magnesium are preferred due to its long history of use. The metal only serves as a structural part in the inventive device. The drug delivery function is done using a biodegradable polymer or hydrogels in the device. The biodegradable polymers and hydrogels along with drug/s can be coated on the needle surface or may be infused in the hollow cavities of the microneedles. Hydrogel in dry form or dehydrated may also be used. The drug delivery compositions may be infused in the grooves, wedges, or holes created in the microneedle surface or the body. In one exemplarity embodiment, a hollow microneedle is used to create a microneedle array and the hollow cavity is filled with biodegradable polymer composition with rifampin as model drug. In another embodiment, the surface of the microneedle array is coated with one or multiple layers of biodegradable polymers and the coatings are used for sustained drug delivery. Some layers in the coating are used to control the rate of release of the drug. In another illustrative embodiment, several holes are created in the microneedle array body and the holes are used to load the drug delivery compositions. The holes could be filled in two or more layers of drug delivery compositions. The embodiment uses cylindrical holes or grooves but any shape can be used.

Cylindrical, triangular, square, rectangular, pentagonal, hexagonal or irregular shaped holes or grooves may be used. Cylindrical holes/grooves are most preferred.

In some embodiments, porous magnesium alloy based arrays may be prepared by sintering alloy powders and the porosity is then filled with injectable composition comprising drugs/cells. Porosity may also be created using methods such as laser drilled holes as discussed before. Compositions comprising drugs/cells may be infused in the porosity or may be coated on the needle surface as lyophilized powders or solids or liquids or semisolids or as injectable compositions discussed in this invention.

The physical size and dimensions of microneedles in the exemplary embodiments is for illustration only. Those skilled in the art can recognize that microneedles with variety of sizes, shapes, heights, volumes, number of needles per array, total area of the array and the like can be made to obtain a microneedle array of desired size and shape. The average diameter of microneedle in the array may range from 1 micron to 3500 microns, even more preferably 5 microns to 2600 microns. The height of the needle in the array may range from 5 microns to 5000 microns, preferably 10 microns to 3000 microns, even more preferably 10 microns to 2000 microns. The shape of array needle may range from straight obelisk, negative-beveled obelisk, cylindrical, pyramidal, conical, trigonal, tetragonal, pentagonal, hexagonal, pyramidal, irregular and the like or combinations thereof. The distance between each needle in the array may range from 1 micron to 10000 microns, preferably 3 microns to 5000 microns, even more preferably 5 microns to 2000 microns. The volume of each needle may range from $1\times10E-12$ to 0.05 ml, preferably $1\times10E-10$ to 0.03 ml, even more preferably $1\times10E-10$ to 0.01 ml. Total number of needles may be greater than 4 per square centimeters or may range from 4 to 500 per square centimeter. Total number of array needles may be greater than 4 or may range from 4 to 6000, preferably 4 to 2600, most preferably 4 to 1000 per array. The array has a backing attached to the base which provides an area where mechanical force or pressure is applied so that all needles of the array can be inserted in the tissue at the same time. Variety of base materials for backing materials known in the art can be used. These include but not limited to: nylon, cotton, different woven textile materials, metals and ceramic and the like. The microneedle array needle with backing material is a one of the several preferred designs. Devices such as "array in array" or AIA devices, described in this invention, may also be used to infuse biodegradable metal based microimplants in the skin. The microneedles may be loaded in hollow cavity of the base array needle and injected in the skin tissue either individually, or one row at a time or one column at a time or whole array at once. A special applicator may be designed for each type of insertion and used to implant biodegradable metal based arrays disclosed in this invention.

Applications of Methods and Compositions Proposed in this Invention

Following are some of the clinical applications where the methods and compositions described in this invention may be useful. The proposed applications do not in any way limit this invention to other medical applications. Many embodiments use skin tissue as a main tissue. The advantage of skin tissue is that it is external and with large surface area. In some cases, if microimplants need to be removed due to allergic reaction to the drug or some other medical factors, the removal may be possible for skin inserted microimplants. Such a removal is not possible with conventional injection of sustained drug delivery biodegradable microspheres in intramuscular tissue. The medication or implant materials may be removed using methods such as laser treatment similar to used in tattoo removal procedures. The laser induced heat treatment can also destroy and/or denature and/or eliminate biological activity of the drug. The implant may also be removed by surgical procedure if present in the skin surface.

Encoding Information in the Array

In one illustrative embodiment, one cylindrical microimplant with radio-opaque properties, one cylindrical implant with fluorescent properties and 7 PLGA microimplants with moxifloxacin are obtained. Fluorescent and radio-opaque microimplant may not have drug but are designed to help to identify and tag the array after implantation. The implants are loaded in the array form using AIA apparatus as described in this invention (3 by 3 array). During loading, radio-opaque implant is loaded at the center and fluorescent microimplant is located at one of the four corners. The positions of the radio-opaque and fluorescent microimplants can be used to code and decode certain information, like type of surgery used, gender of the patient and the like. Thus, the use of array format and its location in the array could be used to convey or relay certain information which may be relevant to the doctor administering the treatment, government regulating agency, patient and the like. The use of visualization agent and its location in the array can be used to convey or relay that information. Variables like position or location in the array, fluorescence wavelength (red verses green fluorescence), radio-opacity, ultrasonic imaging visibility, MRI imaging visibility and the like can be used to code and decode certain useful information in the array. The embodiment described above is for illustration only. Those skilled in the art can recognize that many variations are possible such as number of microimplants in the array, geometry of array (circular versus rectangular array as an example), shape of microimplant and the like can be used to relay useful information that can be used to improve medical treatment and/or its service and regulatory component. Some of the spaces or positions in the microimplant array may be used to load certain sensors such as temperature sensor, pressure sensor, insulin sensor, radio frequency identification tags (RFID), cell viability indicators, pH sensors, chemical sensors, biological entity sensor, bacterial activity sensor, viral activity sensor and the like. Generally greater than 10 percent, preferably greater than 50 percent and preferably greater than 95 percent positions in the in the microimplants array described in this invention may be used for implants with drugs or cells. Remaining other positions may be used to load microimplants with visualization agents or sensors and can be used in coding and decoding certain information.

Nail and Bone Infections

It is generally well known that bone infections are difficult to manage. The infected area in the bone and nail may be first accessed, a porosity is created in the affected area and surrounding area and the antibiotic compositions such as PLGA microparticles with antibiotic or PLGA solutions with antibiotic may be used to fill the porosity. Anti-fungal drugs may be given via cavity filling process to manage fungal nail infections.

Pain Management

Local anesthetic agents such as bupivacaine can potentially be used in managing local pain. A pain associated with surgical wound may be managed by directly forming a microarray based implants in areas of local pain or surgical wound site. Local anesthetic such as bupivacaine is released via in situ formed biodegradable microarray for 1 to 5 days until surgical wound is healed.

Cardiovascular Applications

The damaged heart tissue is extremely difficult to regenerate. Stem cells therapies can help but distribution of cells in affected areas is difficult to manage. The cells delivery via in situ microimplant formation may be useful as described in this invention. Several microimplants containing stem cells which can be converted into heart muscle cells may be implanted via in situ generated microimplants as disclosed in this invention or preformed implants with cells. The size of implant, number of implants, and depth of implants may be tailored for a specific need of a patient. The damaged heart tissue may be exposed to laser based method to create micro-porosity and the holes may be filled with stem cells and encapsulated in fibrin glue matrix or other suitable biodegradable hydrogel matrix. The encapsulated stem cells reproduce in the cavity and produce new heart muscle which may help in improving cardiovascular function of the heart. Alternatively, cell containing microimplants can be made just prior to surgery and implanted using devices described in this invention. Also, microneedle arrays containing frozen stem cells may be implanted in treated area under frozen conditions (cryopreserved cells) as described in this invention. Many methods and compositions for delivering stem cells are described in this invention, ultimate choice will be determined by the end user and best desirable clinical outcome. The cell suspension in PBS or tissue culture medium may also be infused into the heart tissue using oscillating needle apparatus as described in this invention. This way large area of the organ can be infused in a relatively short period of time and with uniform distribution of therapeutic cells. The experimental conations used must provide live cells after implantation.

Therapeutic arrays or coated biodegradable threads reported in this invention may be used to deliver anti-restenosis drug like paclitaxel, everolimus, sirolimus which may be delivered at the vascular graft anastomosis sites during vascular graft implantation procedures or coronary bypass surgery procedure.

Ophthalmic Drug Delivery

The inventive compositions can be useful in many ophthalmic indications including but not limited to reducing inflammation and pain after cataract and other ophthalmic surgery, controlling viral and bacterial infections, age-related macular degeneration and the like. In one illustrative embodiment, a drug and polymer solution is applied on scleral tissue and tissue is perforated using a microneedle array. The solution is deposited in artificial cavities created by the array. The deposited solution precipitates in the scleral tissue entrapping the drug which is then released in a sustained manner. In another embodiment, a hollow microneedle array such as 33MP array is used to deposit a polymer and drug solution or suspension containing biodegradable microspheres containing dexamethasone as exemplary drug. The deposited drug is released in to eye in a sustained manner. In another embodiment, preformed cylindrical PLGA microimplants containing total of 0.4 mg dexamethasone are deposited in 5 by 5 array format in scleral tissue using AIA device described in this invention. The implanted array releases the dexamethasone in a sustained manner over period of 14-30 days. Preferably the array is colored or fluorescent for easy visualization and monitoring.

Diabetes Management

Pig islets are available in abundant supply and insulin produced by pig islets is well tolerated by the humans. Microimplant array containing approximately 1 million pig islets are believed to be sufficient to act as artificial pancreas for humans. The pig islets can be implanted under the skin with or without immunoisolation. Depending on the density of array, 1 million pig islets can be implanted using up to 15×15 cm area of the skin. Example 15 and 16 provide several illustrative embodiments that can be used to implant islets under the skin. It is preferred an immunoprotective matrix is used in the array for islet encapsulation and the encapsulation matrix forms a minimum amount of scar tissue. The scar tissue can potentially prevent insulin diffusion from the islets and may also limit the nutrient supply which is necessary for survival of cells. PEG based hydrogel surfaces are known to reduce scar tissue formation and are therefore are preferred in this application. The implanted islets can continuously monitor glucose concentration in the tissue fluid and release insulin necessary to control the glucose in the tissue fluid. This way, better control over glucose managements is possible. Depending on the immunoprotection provided, the patients may need to take immune suppressing drugs to protect islets from immune system. Since this implantation is done in the skin tissue, adverse reaction developed by animal cells may be reduced/eliminated by destroying or denaturing the cells in the skin implant using laser based methods or surgical based methods as discussed before. Alternatively, drugs such as insulin and other drugs that control level of sugar in the blood may be used to form microimplant arrays as described in this invention. Such drugs may be encapsulated in biodegradable polymers and released in a sustained manner for better control of sugar in the blood.

Management of Iron Deficiency

Iron deficiency or anemia associated with lack of iron in the blood is one of the most important health issues in the world today, especially, in the third world countries. Iron deficiency is caused by many factors which include mensural cycle in females, GI bleeding, malnutrition, premature birth, parasitic infection and the like. Iron deficiency affects cognitive development of children from infancy through to adolescence. Iron deficiency is believed to be associated with increased morbidity rates. Certain oral medications have also tendency to reduce iron content in the blood. Iron deficiency is generally managed through oral supplements and is not considered to be very reliable method to manage anemia. Oral therapy has lower bioavailability of iron and has side effects such as constipation. Oral therapy also has compliance issue because patients may not complete the prescribed oral dose. Severe iron deficiency can be managed via intravenous route but requires careful monitoring in hospital settings and has certain risks such as anaphylaxis, and cardiovascular complications. U.S. Pat. No. 8,821,945 reports iron complexes delivery using iontophoretic method. Iontophoretic method uses electric current to drive iron complex across skin barrier. The use of electric current may have potential to cause burn and other types of injury. Iron can be delivered using compositions and methods described in this invention. The iron complex, such as ferric pyrophosphate is transported across the skin barrier and delivered in the skin tissue. Once transported, the complex is believed to be absorbed by the surrounding tissue and used in reducing iron deficiency by variety of known and unknown biological mechanisms. In one illustrative embodiment, aqueous ferric pyrophosphate or iron sucrose complex solution is injected in the skin tissue using an oscillating needle and using hollow microneedle array. An image of treated tissue with iron sucrose complex is shown in FIG. 9A. The treated tissue has dark brown color due possible tattooing effect of the drug. The tattooing effect is believed to be caused by the insoluble oxidation products caused by reaction of free iron ions with tissue proteins. The infusion of ferric pyrophosphate generally did not cause significant tattoo effect indicating the iron remain complexed with pyrophosphate ion and does not provide free iron for tattooing effect. In another embodiment, the ferric pyrophosphate solid powder is ground, sieved to provide 300 microns or less particle size. The sieved powder is suspended/dissolved in glycerol and tattooed using oscillating needle. The solid powder has higher density than the solution and thus may help to reduce the amount of materials that needs to be delivered across the skin tissue. In another embodiment, a PLGA solution in NMP is mixed with sieved iron pyrophosphate powder. The suspension is injected using tattoo needle in the skin tissue. The NMP is dissipated in the tissue, entrapping iron pyrophosphate in the PLGA polymer which is released in a sustained manner. A release profile of iron released from the precipitated polymer is shown in FIG. 20. As seen from the figure, iron is released in a sustained manner over a 4 day period. The encapsulation of iron is believed to reduce the interaction of iron from the skin tissue proteins and hence may further help to reduce tattooing effect. The illustrative embodiments use two iron compounds ferric pyrophosphate or iron sucrose complex, but the use of iron pyrophosphate is preferred due to its stability and its ability to convert into useful iron complex that can be used in reducing iron deficiency. The iron complex could be either ferrous or ferric salts of iron. Iron complexes that can be used and may include but not limited to: ferric carboxy maltose, ferric trisglycinate, ferrous gluconate, iron-dextran complex, iron-dextrin, ethylenediamineedetate iron complex, ferric ammonium citrate, ethylenediaminesuccinate iron complex, ferric citrate, ferric manganese citrate, iron-sorbitol-citric acid complex, ferrous fumarate, ferric gluconate complex, glycol ether diaminetetraaceticacid iron complex and the like. Additional list of ferrous or ferric complexes can be found in U.S. Pat. No. 8,821,945, cited herein for reference only. The preferred amount of iron that can be infused in the tissue may range from 5 to 100 mg, preferably 10 to 50 mg, even more preferably 10-30 mg. The dose of iron will depend on the patient factors such as weight and deficiency of iron and the like.

Iron also can be delivered using hydrogel based dissolvable array. In one illustrative embodiment, a sodium hyaluronate based dissolvable with ferric pyrophosphate array was made (FIGS. 9B1 and 9B2). The array can easily penetrate in skin tissue and dissolves in the skin tissue under 10 minutes. The dissolved array delivers ferric pyrophosphate in the tissue. The dose of the iron can be managed by iron concentration in each needle and number of needles/arrays inserted in the tissue.

Arrays Containing Botulinum Toxin and Other Protein Drugs/Vaccines

Drug Delivery without Making Drug Solution.

Delivering Drug in a Solid State and in the Unibody Microimplant Form.

Botox® is a trade name for Botulinum toxin. Botox is neurotoxic protein produced by the bacterium *Clostridium* and is sold to treat variety of medical conditions. Biodegradable arrays can be made comprising Botulinum toxin and delivered in the solid state into skin tissue without the use of dilution and injection. The use of Botox array can be made for specific medical application with each array containing 0.1 to 30, preferably 0.5 to 20 units of Botulinum toxin. Preferably such arrays are colored or fluorescent so that their implantation can be monitored and/or documented. The distribution of the drug can be achieved over a large surface areas under the arm pit for excessive sweat management or on the face for wrinkle management. The application of Botulinum toxin array can be relatively pain free for the patient. The recommended shelf life of Botox solution is 48 hours and this can potentially lead to waste of expensive drug if not used immediately. Since this delivery of method does not involve solution preparation, the wastage of Botox during application can be potentially eliminated. It is preferred that each Botox microimplant is present as a unibody which can be pushed using the methods and devices described in this invention. Vaccines may be delivered using the same manner as Botulinum toxin as discussed before.

Botox is generally sold as a dry lyophilized protein powder with each vial containing 50 or 100 units dose of the drug. The Botulinum toxin concentration is generally present at around 1 nanogram level which is hard to detect and manage in solid state. In this invention, a bulking agent is added to increase the mass of the total solids present in the device. In one illustrative embodiment, the Botox vial containing 100 units is diluted with sterile 0.1 ml of 0.1 percent sodium hyaluronate (mechanical property enhancer and bulking agent) or human serum albumin (10 percent solution) in PBS buffer (pH 7.4) and 0.1 mg sodium fluorscein (as a coloring/fluorescent agent) or F and D and C blue number 2 as a colorant. The 3.53 microliter of the Botox solution is loaded 100 cavities of base array of 10 by 10 AIA apparatus as discussed in Example 22. The apparatus has 100 cylindrical cavities with 500 micron height and 310 micron diameter cavities. The filled solution is frozen and lyophilized in the cavities. A 10 by 10 plunger array of the AIA apparatus is applied on top of the base array aligning its needle but not inserted. A polyethylene 2 mm spacer lock is kept between the bottom and top array to prevent accidental insertion of plunger array in the base array. Each 100 microneedle array contains approximately 3.53 units of Botulinum toxin (0.0353 units per microimplant, total 100 microimplants). In case of Botox, most of the solid in the implant, preferably over 80 percent, preferably greater than 50 percent of the implant volume is occupied by the bulking agent such as hyaluronic acid or human serum albumin or compounds like sugars and polymers used in making dissolvable array. Generally, the bulking agent and other pharmaceutical additives such as colorant, antioxidant, stabilize, lyophilization agent and the like may occupy up to 1 to 99 percent of total implant volume, preferably 5 to 95 percent of the total implant volume. The amount of Botulinum toxin per implant is generally higher than 0.01 units per microimplant and may range from 0.01 units to 30 units per implant, preferably 0.01 to 20 units per implant and even more preferably 0.01 to 10 units per implant. The device is terminally sterilized and used on the skin tissue. During the usage, the base array needles are inserted in the tissue, spacer is removed and the plunger array is pushed to inject the fluorescent implant in the tissue. Once injected, both the arrays are taken out leaving behind the implant in the tissue. Under blue light, implantation of the injected microimplant array is visible as green array. Multiple arrays may be used to treat more areas on the skin if needed. The sodium hyaluronate and fluorscein dissolve away leaving behind Botulinum toxin for therapeutic effect. This method delivers Botulinum toxin in the solid state without dilution in saline as used in current practice. If Botulinum toxin containing arrays are delivered using AIA device/apparatus as discussed in this invention, the microimplants with Botulinum toxin can be pushed out in the skin tissue one implant at a time from the base array, or one row/column at a time or all implants can be pushed at once. Alternatively, implants can be delivered at a predetermined sequence if the plunger array movement is controlled electronically by computer algorithm. The ultimate choice will determine the dose of Botulinum toxin per implant and total dose needed per treatment site. In some cosmetic applications, the fluorescence and color of the implant is only visible under blue light and not under normal condition. This way the presence of the implant does not alter cosmetic appearance of the subject. This is achieved by many methods but in one illustrative example, minimal amount of fluorscein is used and due to high solubility, the dye disperses quickly in the tissue. In some embodiments, the preformed solid microimplants may be impregnated using a sterile Botox solution of desired concentration and then impregnated implant in solid state is then inserted in the skin tissue as described before. However, microimplants that are infused/encapsulated with Botox drug in a manufacturing setting are preferred because solution preparation step is not required during implantation step.

Other protein/biologics drugs such as vaccines (Influenza vaccine as an example) can be delivered in the solid state using similarly to Botox as described before. Many biologics drugs such as Etanercept (Enbrel®) or Adalimumab (Humira®) are injected as solutions to treat rheumatoid arthritis and such drugs also may be formulated into unibody microimplants in solid state and then implanted in an array format as described in this invention.

Adrenalin or Epinephrine or Adrenaline is a drug used to treat severe life threatening allergic reaction approved (anaphylaxis). Epinephrine auto-injectors such as EpiPen® is used by a person with a history of a severe allergic reaction. Adrenalin could be formulated into microimplants that can be implanted in microarray format as described in this invention to provide a total dose of 0.3 or 0.15 mg per array to treat severe life threatening allergic reaction.

In an embodiment, a drug delivery microneedle array device comprises two microneedle arrays; a) i) first array comprises one base plate with top and bottom surface and x number of hollow microneedles with internal diameter d protruding from bottom base surface wherein x is grater than 3; ii) the hollow microneedles have sharp cutting edge at distal end and proximal end opening on top surface; b) i) second array comprises one base plate with top and bottom surface and x number of solid microneedles with diameter 5 percent or more smaller than d and protruding from bottom base surface wherein x is greater than 3; ii) the solid microneedles have non-cutting surface at distal end; iv) the matrix arrangement of needles is identical to first array needles; c) the second array needles can be inserted in hollow cavity of first array via needle opening on top surface of first array after aligning center of needles of both the arrays.

In an embodiment, a drug delivery microneedle array device comprises two microneedle arrays and one cartridge for holding of microimplants with drug/cells; a) i) first array comprises one base plate with top and bottom surface and x number of hollow microneedles with internal diameter d protruding from bottom base surface wherein x is greater than 3; ii) the hollow microneedles have sharp cutting edge at distal end and proximal end opening on top surface; b) i) second array comprises one base plate with top and bottom surface and x number of solid microneedles with diameter 5 percent or more smaller than d and protruding from bottom base surface wherein x is greater than 3; ii) the solid microneedles have non-cutting surface at distal end; iv) the matrix arrangement of needles is identical to first array needles; c) i) the cartridge comprises a base plate with top and bottom surfaces with x number of holes in both surfaces and x is greater than 3; and the arrangement and internal diameter of holes is same as first array.

In an embodiment, a drug delivery microneedle array device comprises; 3 or more hollow microneedles arranged in an array format attached to a solid base plate and each microneedle has an piercing element at the distal end that is configured to pierce the human or animal skin tissue and proximal end is attached to a base plate wherein the proximal end of hollow microneedle is exposed on the base plate; the hollow microneedle space in at least 3 microneedles is partially or completely occupied by a solid sustained drug delivery unibody microimplant composition wherein the unibody composition is devoid of piercing element and the unibody microimplant composition can be pushed in the skin tissue by application of gas or liquid pressure or mechanical force.

In an embodiment, a drug delivery microneedle array device comprises two microneedle arrays wherein one array comprises an injectable unit that comprises x number of hollow microneedles attached to a base plate and arranged in an array format wherein x is greater than 3 and each hollow microneedle has a piercing element at the distal end that is configured to pierce the human or animal skin tissue and proximal end is attached to a base plate wherein the hollow cavity of microneedle is exposed on the base plate; the hollow microneedle space is partially or completely occupied by a solid sustained drug delivery unibody microimplant composition; the other array has Y number of solid non-piercing microneedles attached to a base plate and arranged in the same array format as hollow microneedle array and y is less than or equal to x; and the solid microneedles can be inserted in hollow space of hollow microneedle array via exposed hollow cavities on the base plate and can push the unibody microimplant composition out of the hollow cavity and in to skin tissue. In an embodiment, a sustained drug delivery unibody microimplant array composition in a live or bioprosthesis tissue can include: i) each microimplant has a non-piercing edge at proximal end; ii) the number of microimplants in the array is greater than or equal to 3; ii) each microimplant is separated by a spacing of by more than 10 microns; iii) each microimplant is implanted at a depth of 50 microns to 5 mm in the tissue; iv) and the volume of each microimplant is less than 0.05 ml. In an embodiment, a method for forming drug delivery microimplant array formed in a live or bioprosthesis tissue includes: i) forming 3 or more artificial cavities in the tissue in array format; ii) each artificial cavities is separated by a spacing of between 10 microns to 5 mm; iii) partially or completely filling 3 or more cavities with a polymer solution having an effective amount of polymer dissolved in a biocompatible, water-soluble organic solvent; iv) precipitating the polymer from the injected polymer solution in the cavities.

In an embodiment, a method for forming microimplant array in the live or bioprosthesis tissue comprises: a) forming 3 or more artificial cavities in the tissue in array format; b) filling the cavities partially or completely with an injectable fluid composition comprising a drug wherein: i) the number cavities formed is greater than or equal to 3; ii) each cavity has a volume of 1×10E-10 to 0.03 ml; iii) each cavity is separated by a spacing of between 10 microns to 5 mm; v) each cavity is formed by displacing or destroying tissue or combination thereof.

In an embodiment, a microimplant array composition with live mammalian cells in a live or bioprosthesis tissue wherein: ii) the number of microimplants implanted is greater than or equal to 3; ii) each microimplant is separated by a spacing of between 10 microns to 5 mm; iii) each microimplant is implanted at a depth of 50 microns to 5 mm in the tissue; iv) the volume of each microimplant is 1×10E-10 to 0.03 ml.

In an embodiment, a method for forming microimplant array with live mammalian cells in the live or bioprosthesis tissue comprises: a) forming array of 3 or more artificial cavities in the tissue; b) each cavity has a volume of 1×10E-10 to 0.05 ml; iii) each cavity is separated by greater than 10 microns; and iv) filling the cavities with an aqueous injectable composition comprising 1 to 10000000 live cells per ml of injectable composition.

In an embodiment, a microimplant array composition comprises live mammalian cells formed in a live or bioprosthesis tissue wherein: i) each microimplant has 1 to 10000000 live cells; ii) the number of microimplants in the array is greater than or equal to 3; ii) each microimplant is separated by a by 10 microns; iii) each microimplant is implanted at a depth of 50 microns to 5 mm in the tissue.

In an embodiment, a method for delivering an injectable composition at a local site in a tissue comprises: providing an aqueous injectable composition having 1 to 1.0E 7 live mammalian cells per ml; and injecting the injectable composition into the tissue at the rate of 10-12000 injections per minute and/or at an amount of 1.0E-02 ml to 1.0E-16 ml per injection In an embodiment, a method of forming an implant in the tissue, the method comprises: providing a polymer solution having an effective amount of polymer dissolved in a biocompatible, water-soluble organic solvent and mixing the polymer solution with a biodegradable filler to form a suspension or emulsion; injecting the polymer solution in the tissue; dissipating the biocompatible, water-soluble organic solvent in the tissue; and precipitating the polymer from the injected polymer solution so as to form the implant.

In an embodiment, a method of delivering a drug in a solid state form without forming a solution includes: a) providing 3 or more solid unibody microimplants comprising effective amount of drug encapsulated or coated on a biodegradable unibody forming matrix; b) implanting 3 or more implants simultaneously in a live tissue or bioprosthesis tissue to form a microimplant array c) each microimplant is separated by a spacing of between 10 microns to 5 mm; d) each microimplant is implanted at a depth of 50 microns to 5 mm in the tissue; f) the volume of each microimplant is 1×10E-10 to 0.03 ml.

In an embodiment, a method of delivering a Botulinum toxin in a solid state form without forming a solution comprises: a) providing 3 or more solid unibody microimplants comprising effective amount of Botulinum toxin encapsulated or coated on a biodegradable unibody forming matrix wherein each microimplant has at least 0.01 units of Botulinum toxin; b) implanting the drug in a live tissue or bioprosthesis tissue to form a microimplant array; c) each microimplant is separated by a spacing of between 10 microns to 5 mm; d) each microimplant is implanted at a depth of 50 microns to 5 mm in the tissue; iv) the volume of each microimplant is 1×10E-10 to 0.03 ml.

A method of delivering a vaccine in a solid state form without forming a solution, the method comprising: a) providing 3 or more solid unibody microimplants comprising effective amount of vaccine encapsulated or coated on a biodegradable unibody forming matrix; b) implanting 3 or more implants simultaneously in a live tissue or bioprosthesis tissue to form a microimplant array; c) each microimplant is separated by a spacing of between 10 microns to 5 mm; d) each microimplant is implanted at a depth of 50 microns to 5 mm in the tissue; iv) the volume of each microimplant is 1×10E-10 to 0.05 ml.

In an embodiment, a method of delivering a bioactive compound comprising iron in a solid state form without forming a solution includes: a) providing 3 or more solid unibody microimplants comprising effective amount of iron compound coated or encapsulated in a biodegradable unibody forming matrix; b) implanting 3 or more implants simultaneously in a live tissue or bioprosthesis tissue to form a microimplant array; c) each microimplant is separated by a spacing of between 10 microns to 5 mm; d) each microimplant is implanted at a depth of 50 microns to 5 mm in the tissue; iv) the volume of each microimplant is 1×10E-10 to 0.05 ml.

A method of treating nail infection, the method comprising: i) forming an array of 3 or more artificial cavities in the nail; ii) each artificial cavities is separated by a spacing of between 10 microns to 5 mm; iii) partially or completely filling 3 or more cavities with a polymer solution having an effective amount of polymer dissolved in a biocompatible, water-soluble organic solvent and an effective amount antifungal drug; iv) precipitating the polymer from the injected polymer in the cavities and entrapping the antifungal drug in the precipitated polymer.

c) the second array needles can be inserted in hollow cavity of first array via needle opening on top surface of first array via cartridge holes after aligning center of needles of both the arrays and cartridge holes.

In an embodiment, a process for sustained drug delivery in tissue through an array created in situ can include steps: creating an artificial porosity of predetermined geometric configuration and dimensions, filling the artificial porosity with fluid injectable drug delivery compositions, releasing the drug in the surrounding tissue by diffusion or biodegradation, wherein the artificial porosity comprises of a plurality of cavities having predetermined volume, shape and surface area and created in predetermined quantity and pattern with a specific tissue area and depth.

A process can include the artificial porosity being created by means such as displacing or destroying the tissue, including water jet drilling based methods, ultrasonic energy based methods, particle bombardment based methods, laser based methods, oscillating needle, mechanical drilling and microneedle array based methods.

A process can include the array having a configuration of at least a 2×2 matrix.

A composition can be provided for local sustained delivery of a drug present in the form of a micro array in a tissue, wherein such compositions comprise of drug encapsulated microimplants that are made or implanted in situ and deliver the drug in a sustained manner.

A microimplant array can be created in an artificial cavity in a tissue comprising a combination of a biodegradable polymer and a drug.

A microimplant array can be formed in a plurality of artificial cavities in a tissue comprising a combination of a hydrogel and live mammalian cells.

A device can be provided for creating a microimplant array for sustained drug delivery, wherein the device enables to form one, two, three, four, five, six or several microimplants in the tissue.

An "array-in-array" device can be provided for creating a microarray of implants for sustained drug delivery, wherein the device comprises of a plurality of first micro needle array and a plurality of second micro needle array, such that the plurality of first micro needle array is disposed concentrically within the plurality of second micro needle array.

A device can have the microneedle being hollow, solid or bioerodable.

A microneedle array patch can be provided for sustained drug delivery comprising 4 or more hollow microneedles per centimeter square, wherein the said microneedles cavities are loaded with microimplants for sustained drug delivery and each implant has a volume of 1×10E-10 to 0.03 ml.

A metal, plastic or ceramic hollow microneedle array patch can be provided for sustained drug delivery or for mammalian cell delivery with four or more hollow microneedles per $cm^2$ microneedles, wherein the said microneedles comprising a structure comprising a base at a proximal end and a vertex or tip with sharp edge that enables tissue insertion; and the hollow cavity of microneedle is partially or completely filled with solid or hydrogel implant wherein the implant has a volume of 1×10E-10 to 0.03 ml per needle.

A method of making a microimplant array for sustained drug delivery can include: providing a hollow microneedle patch with four or more hollow microneedles per $cm^2$ and cavity volume of 1×10E-10 to 0.03 ml per needle; filling the hollow cavity with a biostable or biodegradable polymer solution and drug; and removing the solvent from the solution and precipitating the polymer and drug in the cavity; inserting the array in the tissue and dispensing the implant from the needle cavity in to the tissue.

A method of making an array of sustained drug delivery implants in the tissue can include: providing a hollow microneedle patch with four or more hollow microneedles per cm2 and cavity volume of 1×1.0E-10 to 0.03 ml per needle; filling the hollow cavities of microneedles with a biostable or biodegradable polymer solid implant that can fit inside the cavity of the needle; inserting the needles of the array in the tissue and dispensing the implant from the cavity in to the tissue.

A method of forming an implant in the tissue can include: providing a polymer solution having an effective amount of polymer dissolved in a biocompatible, water-soluble organic solvent; injecting the polymer solution in the tissue using hollow microneedle array patch with four or more hollow microneedles per $cm^2$; dissipating the biocompatible, water-soluble organic solvent in the tissue; and precipitating the polymer from the injected polymer solution so as to form the implant.

A method of making an array of implants with live mammalian cells in the tissue can include: providing a hollow microneedle patch with four or more hollow microneedles per $cm^2$ and cavity volume of 1×10E-10 to 0.03 ml per needle; filling the hollow cavities of microneedles with a biostable or biodegradable hydrogel implant comprising live mammalian cells that can fit inside the cavity of the needle; inserting the needles of the array in the tissue and dispensing the implant from the cavity in to the tissue.

A microneedle array can include mammalian live cells and frozen matrix that has a vertex or tip with sharp edge at distal end that enables tissue insertion; base at proximal end; wherein the frozen matrix comprises cryopreservative.

An array in array device for sustained delivery of drugs or live cells in tissue, the drug composition being in the form of a unibody microimplant, can include: a base array, the base array further comprising a base array plate, having a top surface and a bottom surface, and a plurality of hollow microneedles provided in an array format and protruding from the bottom surface of the base array plate, said hollow microneedles having a piercing element at the distal end that is configured to pierce the skin tissue, a proximal end that is attached to the base array plate, and a hollow cavity capable of containing a unibody implant, a plurality of guiding posts protruding from the bottom surface of the base array plate; a plunger array, the plunger array further comprising a plunger array plate, having a top surface and a bottom surface, and a plurality of solid microneedles provided in an array format on the bottom surface of the plunger array plate, said solid microneedles characterized by a non-piercing element at the distal end, a proximal end that is attached to the plunger array plate, and capable of pushing the unibody implant contained in the hollow cavity of the hollow microneedles, a plurality of guiding holes provided on the plunger array plate at predetermined locations; a plurality of spacer locks; wherein: the plunger array is capable of coaxial vertical movement within the base array, the plurality of solid microneedles of the plunger array is less than or equal to the plurality of hollow microneedles of the base array, the base array and the plunger array being vertically aligned above the tissue, and dimensionally characterized such that the plurality of solid microneedles of the plunger array is smoothly inserted in the plurality of the hollow microneedles of the base array.

A device for sustained delivery of drugs or live cells in tissue, the drug composition being in the form of a unibody microimplant, can include: a plurality of hollow microneedles arranged in an array format, a base member, wherein each microneedle has an piercing element at a distal end that is configured to pierce the tissue and a proximal end that is attached to the base member, wherein the hollow cavity of microneedle is exposed on the base plate; the hollow microneedle space is partially or completely occupied by a solid sustained drug delivery unibody microimplant composition wherein the unibody composition is devoid of piercing element and the unibody microimplant composition can be pushed in the skin tissue by application of gas or liquid pressure or mechanical force.

An array of unibody microimplants, disposed within a live or bioprosthesis tissue at a predetermined depth and in a predetermined pattern, can include: said array comprises of a plurality of unibody implants characterized by non-piercing edges, the plurality of unibody microimplants is at least three, and has a separation distance between a pair of unibody microimplants in the range of 10 microns to 5 mm, the predetermined depth is in the range of 50 microns to 5 mm, the volume of each unibody microimplant is at most 0.05 ml, and the composition of each unibody microimplant is obtainable from a combination of a bioactive agent, live cells, one or more biodegradable polymers, a porous coating material, a crosslinking agent, a hydrogel, an injectable fluid and a visualization agent.

An array of unibody microimplants, disposed within a live or bioprosthesis tissue at a predetermined depth and in a predetermined pattern, can include: said array comprises of a plurality of unibody microimplants for sustained delivery of a bioactive agent in a solid state form, and each unibody microimplant is characterized by non-piercing edges, the plurality of unibody microimplants is at least three, and has a separation distance between each unibody microimplants in the range of 10 microns to 5 mm, the predetermined depth is in the range of 50 microns to 5 mm, the volume of each unibody microimplant is at most 0.05 ml, and the composition of each unibody microimplant is obtainable from a combination of a protein based bioactive agent, a biodegradable polymer, a porous coating material, a crosslinking agent, a hydrogel, an injectable fluid, a visualization agent and an encoding agent.

A ready-to-inject microneedle array device can include a plurality of hollow microneedles arranged in an array format, and preloaded with a corresponding plurality of unibody microimplants, wherein: each unibody microimplant is obtainable from a combination of a protein based bioactive agent, a biodegradable polymer, a porous coating material, a crosslinking agent, a hydrogel, an injectable fluid, a visualization agent and an encoding agent, the plurality of microneedles is at least three, the microneedles are inserted in into the tissue to a depth, and the volume of each unibody microimplant is at most 0.05 ml.

A method for delivering a vaccine or a protein based drug in a solid state form, in a live tissue, as an array of unibody microimplants can include: providing a drug composition in a biodegradable microneedle array, creating an artificial porosity of predetermined geometric configuration and dimensions, filling the artificial porosity with a plurality of unibody microimplants disposed within the biodegradable microneedle array, releasing the drug composition in the live tissue by diffusion or biodegradation, wherein the artificial porosity comprises of a plurality of cavities having predetermined volume, shape and surface area and created in predetermined quantity and pattern with a specific tissue area and depth.

A method for delivering live cells as an array of unibody microimplants, in a live tissue, can include steps: providing a dissolvable, hollow microneedle array, filling the cavities of hollow microneedle array with hydrogels comprising live cells, inserting the dissolvable hollow microneedle array containing live cells inside the tissue; pushing hydrogels comprising live cells out of the hollow microneedle array into the tissue; removing the hollow microneedle array from the tissue leaving behind the hydrogel array comprising live cells inside the tissue.

A method for sustained drug delivery in tissue through an array created in situ can include steps: creating an artificial porosity of predetermined geometric configuration and dimensions, filling the artificial porosity with fluid injectable drug delivery compositions, releasing the drug in the surrounding tissue by diffusion or biodegradation, wherein the artificial porosity comprises of a plurality of cavities having predetermined volume, shape and surface area and created in predetermined quantity and pattern with a specific tissue area and depth.

A microneedle array patch for sustained drug delivery comprising three or more hollow microneedles per centimeter square, wherein the said microneedles cavities are loaded with microimplants for sustained drug delivery and each implant has a volume of 1×10E-10 to 0.05 ml. A metal, plastic or ceramic hollow microneedle array patch for sustained drug delivery or for mammalian cell delivery with four or more hollow microneedles per $cm^2$ microneedles, can include said microneedles having a structure comprising a base at a proximal end and a vertex or tip with sharp edge that enables tissue insertion; and the hollow cavity of microneedle is partially or completely filled with solid or hydrogel implant wherein the implant has a volume of 1×10E-10 to 0.05 ml per needle.

Materials and Methods

Microneedle array are purchased from AdminMed (Sunnyvale, Calif.), Micropoint Technologies Pte Ltd. Singapore or Amazon (UPC code 601913872222). Tissues like bovine pericardium, porcine pericardium, porcine submucosa, porcine aortic root, porcine meniscus tissue, porcine cornea and bovine thoracic arterial tissue, bovine cornea, porcine blood and porcine plasma are acquired or purchased from commercial sources such as Animal Technologies, Tyler, Tex. or obtained from local abbotair or slaughter house. Submucosa tissue is obtained after cleaning and removal of tunica mucosa, muscular tissue and serous layers from the fresh porcine, sheep or bovine small or large intestinal tissue. Polyethylene glycol can be purchased from various sources such as, by way of example, and not limitation, Nektar Therapeutics (formerly Shearwater Polymers), Dow Chemical's (Union Carbide), Fluka and Polysciences. Various protein crosslinkers especially diacid or polyacid n-hydroxysuccinimide esters or n-hydroxysulfosuccinimide esters may be purchased form Sigma-Aldrich or Thermo Fisher Scientific (Pierce). Multifunctional hydroxyl and amine-terminated polyethylene glycol are purchased from Nektar Therapeutics, Dow Chemicals, Huntsman Corporation and Texaco. Amine-terminated polyethylene glycols also can be synthesized using methods known in the prior art or may be purchased from Aldrich (Jeffamine® ED-2003). Other specialized polyethylene glycol derivatives may also be purchased or custom synthesized from Nektar Therapeutics, BOC Sciences, Shirley, N.Y., or Laysan Bio, Inc. AL. DL-lactide, glycolide, caprolactone and trimethylene carbonate can be obtained from commercial sources like Purac, DuPont, Polysciences, Aldrich, Fluka, Medisorb, Wako and Boehringer Ingelheim. N-hydroxysulfosuccinimide can be purchased from Pierce or Aldrich. All other reagents, solvents are of reagent grade and can be purchased from commercial sources such as, by way of example, and not limitation, Polysciences, Fluka, ICN, Aldrich and Sigma. Most of the reagents/solvents are purified/dried using standard laboratory procedures such as, by way of example, and not limitation, described by Perrin et al. Small laboratory equipment and medical supplies can be purchased from Fisher or Cole-Parmer. Cell culture experiments are performed using a standard mammalian tissue culture laboratory or microbiology laboratory capable of handling and growing mammalian and human cell cultures.

General Analysis

Chemical analysis such as, by way of example, and not limitation, structural determination is done using nuclear magnetic resonance (proton and carbon-13) and infrared spectroscopy and mass spectrometry. High-pressure liquid chromatography or UV-visible spectrophotometry is used to determine drug elution profiles. Gel permeation chromatography is used for molecular weight determination. Thermal characterization such as, by way of example, and not limitation, melting point, shrink temperature and glass transition temperature is done by differential scanning calorimetric analysis. The aqueous solution properties such as, by way of example, and not limitation, self-assembly, micelle formation, and gel formation are determined by fluorescence spectroscopy, UV-visible spectroscopy and laser light scattering instruments. Drug release studies are conducted in PBS under sink conditions at 37 degree C. and the drug elution is monitored by HPLC or UV-VIS spectrophotometer.

General methods about biodegradable microparticles and microspheres can be found in relevant prior art. Some examples of biodegradable microparticles and microspheres can also be found in previously filed US provisional applications U.S. Provisional Patent Application No. 62/378,662 filed on Aug. 23, 2016 and U.S. Provisional Patent Application No. 62/363,839 filed on Jul. 19, 2016 and U.S. Pat. No. 9,072,678 cited herein for reference only.

Biodegradation and Biocompatibility of Implants

In vitro degradation of the polymers is monitored gravimetrically at 37 degree C., in aqueous buffered medium such as, by way of example, and not limitation, phosphate buffered saline (pH 7.2).

In vivo biocompatibility and degradation life times are assessed after subcutaneous implantation of tissue samples. The implant is surgically implanted in the animal body. The degradation of the implant over time is monitored gravimetrically or by chemical analysis. The biocompatibility of the implant is assessed by standard histological techniques.

Example 1

Preparation of In Situ Implant for Sustained Drug Delivery Using Biodegradable Filler
Use of Filler in Injectable Polymer Solution Systems
Use of Magnesium Carbonate as an Exemplary Biodegradable Inorganic Filler.

100.2 mg PDLG 5002 polymer is dissolved in 1.0 ml DMSO. 10 microliters of methylene blue stock solution (10 mg methylene blue in 2 ml DMSO) is added to the polymer solution as a colorant. Infusion solutions are prepared using the following method: 15.2 mg bupivacaine hydrochloride and 0.50 ml polymer solution are mixed until drug is completely dissolved. 50 mg magnesium carbonate powder (fine powder sieved to collect fraction below 300 microns in size) is added as a biocompatible and biodegradable filler in the drug solution and the mixture is vigorously vortexed for 5 minutes. The magnesium carbonate suspension is infused/tattooed using an oscillating needle in 1 cm square area of sheep skin tissue. Excess solution from the tattooed surface is wiped off. The light blue tattoo with magnesium particles is clearly seen the by unaided naked eye.

Similarly, a polymer solution without magnesium carbonate is prepared and infused/tattooed in the sheep skin tissue as above. The infused tissue sample is cut and used in controlled release experiment.

The cut samples are placed in 3 mL of PBS (pH 7.4). The drug eluted PBS is collected at several time points. Fresh PBS is added to replace the eluted PBS solution. The collected PBS is analyzed using a UV spectrophotometer to determine the drug concentration. Cumulative total drug released from the tissue is plotted against elution time and drug elution profile is shown in FIG. 21B. The sample with magnesium carbonate showed much longer sustained release as compared to samples without magnesium carbonate.

Example 2-A

Preparation of In Situ Implant Using Biodegradable Polymeric Particulate Filler.
Use of Polymeric Particulate Filler in a Biodegradable Polymer Solution in Water Miscible Solvent.
Use of Polyglycolic Acid (PGA) Microparticles as an Exemplary Biodegradable Polymeric Filler in a Biodegradable Polymer Solution in Water Miscible Solvent.

200.1 mg PDLG 5002, 2.0 ml polyethylene glycol dimethyl ether and 20 microliter methylene blue stock solution (as a colorant) are mixed until polymer is completely soluble in the solvent. 15.1 mg bupivacaine base and 0.5 ml polymer solution as above is mixed until complete solution. The solution is sterile filtered and is then mixed with 20 mg sterile PGA microcylinders (150 microns in diameter and 200 microns length), prepared by cutting the fibers/filaments/threads. The PGA particles are insoluble in the polymer solution and form suspension upon vigorous mixing. 0.3 ml of the suspension is injected into chicken leg muscle using standard 3 ml syringe and 16 gauge needle. The polymer precipitates in the injected area leaving behind precipitated polymer entrapping drug and PGA microparticles.

In a similar experiment, microcylinders made using commercial colored catgut suture thread (Ethicon, chromic gut, colored, suture USP size 6-0) and length 100 microns are used in place of PGA particles. The color of particles may be used as a colorant in place of methylene blue. The rifampin coated microspheres incorporated in thermosensitive gel in Example 10H can be considered as biodegradable filler incorporated in thermosensitive gel. Similarly, inorganic filler such as magnesium carbonate may be added as a filler in thermosensitive gel precursor solution prior to injection and gelling.

In another illustrative example, inorganic biocompatible, biodegradable fillers such as magnesium carbonate, calcium sulfate, and the like may be mixed with crosslinkable polymer solution such as PEG 35K-lactate-acrylate macromonomer solution (Example 10D) or PEG10KARM glutarate NHS ester and trilysine (Example 10E) are polymerized and crosslinked with light to entrap the filler in the gel. The entrapped filler can be used to alter the local chemical/physical environment of the crosslinked gel (pH, osmolality, surface area and the like) which may help to tune the sustained drug release of drugs (FIG. 19A).

Example 2-B

Use of Polymeric Particulate Filler in a Biodegradable Polymer Solution in Water Miscible Solvent.
Use of Polyvinyl Alcohol or Protein (Collagen or Albumin) Microparticles.

50.4 mg PDLG 5002, 0.5 ml polyethylene glycol dimethyl ether (PEGDME) as a polymer solvent 5.0 microliter methylene blue solution as a colorant (10 mg methylene blue dissolved in 2.0 ml DMSO) are mixed until polymer is completely dissolved. 7.5 mg Bupivacaine base (approximately 30 percent of polymer weight) and 0.25 mg polyvinyl alcohol (PVA) powder as a biodegradable filler (sieved, PVA particle size less than 300 microns) are added to 0.25 ml polymer solution as above. The filler weight is approximately same as PDLG polymer weight (1:1). The PVA powder is insoluble in polymer solution but the drug Bupivacaine base is soluble. The suspension is infused in the bovine pericardium tissue in 1 square centimeter area using oscillating needle to form a drug delivery array/implant. The infused polymer precipitates in the hydrated tissue after dispersion of PEGDME solvent in the tissue, entrapping drug in PDLG polymer. PVA filler is also entrapped. The PVA filler is believed to provide large surface area for polymer precipitation. The control solution (without Bupivacaine base) with PDLG and PVA in DMSO as above is also infused in bovine pericardium tissue. The release of Bupivacaine base is monitored from control and treated tissue. In this illustrative example PVA acts as a biodegradable insoluble filler.

In another modification of above embodiment, PVA filler is replaced with crosslinked gelatin microspheres (size less than 300 microns). Crosslinking prevents solubility in common water miscible organic solvents used for biodegradable polymer solution preparation.

In another modification of above embodiment, PVA filler is replaced with crosslinked PEG based biodegradable microspheres (size less than 300 microns) made by polymerization of PEG-hydroxyacid based macromonomers similar to described in Example 10D. Cross slinking of PEG based hydrogel particles prevents their solubility in common water miscible organic solvents used for biodegradable polymer solution preparation. The biodegradable bonds such as ester bonds present in the crosslinked particles enables biodegradation.

In another modification of above embodiment, PVA filler is replaced with crosslinked PEG based biodegradable microspheres (size less than 300 microns) made by condensation polymerization of PEG based precursors with nucleophilic and electrophilic groups, similar to described in Example 10E.

Example 3

Preparation of Colored and Drug Encapsulated Microspheres
Preparation of Synthetic Biodegradable Polymer Encapsulated Microspheres Comprising Rifampin.

0.5 g Poly(lactide-co-glycolide) copolymer (PLGA)(PURAC Biochem, Netherlands, PDLG 5002 polymer) is dissolved in 4.5 ml ethyl acetate to make approximately 10 percent solution. In a 15 ml glass vial, 10 mg of Rifampin is added to 1 ml PLGA ethyl acetate solution and vortexed until complete dissolution of the drug. In a 50 ml beaker, 5 ml PVA solution (1 percent in distilled water, Sigma Aldrich, catalog no P8136, 30000-70000 g/mol, 87-90 percent hydrolyzed) and magnetic stir bar are added. The solution is stirred and while stirring, drug solution is added dropwise using disposable plastic dropper. After complete addition, the solution is transferred to 50 ml PP centrifuge tube and vortexed for 2 minutes. The drug suspension is then added to 40 ml PVA solution stirred vigorously using magnetic stirrer in a 250 ml beaker. The stirring is continued overnight to remove ethyl acetate. Next day, the red drug suspension is transferred to 50 ml polypropylene centrifuge tube (approximately 35 ml suspension). The suspension is centrifuged at 2500 rpm for 10 minutes. The supernatant is removed and the rifampin pellet is resuspended in 35 ml distilled water and vortexed vigorously for 2 minutes. The suspension is observed under microscope and the red colored microspheres are clearly observed floating in the suspension. The process is repeated one more time and supernatant is removed almost completely. The microspheres are lyophilized and recovered as red colored powder.

In another embodiment, 1 g PDLG 5002 polymer and 0.2 g rifampin is dissolved in 100 ml dichloromethane and the mixture is spray dried using a standard lab based spray drier. The rifampin encapsulated microspheres are collected, characterized and stored at −80 degree C. until use.

Example 4

Preparation of Hydrogel Based Biodegradable Polymers Protein Based Colored Biodegradable Microspheres.

0.2 g Gelatin is Dissolved in 1.8 ml 0.1 M MES Buffer, PH 5.5. To this Solution, 100 mg Eosin Y, 0.3 g n-hydroxysuccinimide and 0.3 g EDC are added. After complete dissolution, the mixture is added to 100 ml mineral oil and stirred vigorously. The crosslinking reaction and stirring is continued for 12 hours. The gelatin microspheres are separated by filtration and washed with hexane to remove traces of mineral oil. The eosin stains as well as forms covalent links to the gelatin. Using a similar procedure, fluorescein (free acid form) can be chemically bound to the crosslinked albumin to make it fluorescent.

Example 5

Preparation of Hydrogel Based Biodegradable Microspheres with Drugs 1 g bovine albumin is dissolved in 3 ml PBS. To this solution 100 mg of chlorhexidine gluconate is added. The solution/suspension is stirred and transferred to 10 ml syringe with 22 gauge needle. The albumin solution is dispensed from the syringe or sprayed from a sprayer into 1000 ml liquid nitrogen. The frozen droplets are collected. Liquid nitrogen is evaporated. The frozen microspheres are exposed to 0.25 percent glutaraldehyde solution at zero degree C. for 30 minutes in PBS pH 7.2 to crosslink albumin. The crosslinked microspheres are washed with PBS 3 times and then lyophilized. The crosslinked hydrogel microspheres may be vacuum dried at room temperature to dehydrate them. The dehydrated microspheres can have smaller size or more relative to its hydrated size and can regain the original size by abortion of water.

In a modification of above procedure, the albumin is crosslinked with 20 mg/ml in PBS pH 7.2 disulfosuccinimidyl suberate for 12 h.

In a similar experiment, chlorhexidine is replaced by 100 mg rifampin to make rifampin loaded colored microspheres.

Example 6

Preparation of Porosity in the Tissue or Model Tissue Like Materials Such as Gelatin Gel.
Preparation of Porosity Using Metal Microneedle Array.
Porosity Creation in Sheep Dermal Skin.

Example 6A

Artificial Porosity Created Using a Metal or Plastic Solid Microneedle Array

A sheep skin is freshly procured from the local abattoir. One side is shaved to remove all the hairs and other side is (dermis layer side) is used for making artificial porosity. AdminStamp 600 Microneedle Array Device is used to create micropores in the skin tissue. This device has 187 five hundred microns tall stainless steel microneedles on 1 square centimeter (circular shape). Briefly, the needles are applied (needle are positioned perpendicular to the facing skin surface) on the dermis side of the skin tissue. The stamp is rotated 180 degrees three times to make a circular hole in the skin tissue. The same area is treated three times. This stamped area in the skin created 500 microns tall 187 cylindrical holes in the tissue. These artificial cavities are used further to infuse injectable compositions.

In another experiment, a gelatin gel is cast in a plastic petri dish. Briefly, 10 g food grade gelatin (Knox Original Unflavored Gelatin) is dissolved in 90 g distilled water and the solution is heated to 70 degree until complete solution. The solution is poured in the petri dish and the dish is cooled in refrigerator. Upon cooling, the gelatin is converted into soft transparent gel and is used as a model flesh/tissue material to optimize porosity creation experiments. Due to its transparency, it may be desired in some cases to optimize porosity method development and injectable formulation development. AdminStamp 600 Microneedle Array Device is used to create 500 microns tall 187 cylindrical holes.

In another similar experiment, AdminStamp 777 Microneedle Array Device is used. This device has 121 seven hundred micron tall microneedles on one square centimeter circular microneedle array. In another similar experiment, eighty-five 800 micron tall microneedles arranged in one square centimeter circular microneedle array is used. Yet in another experiment forty-three 1100 microns tall microneedles arranged in one square centimeter circular microneedle array are used. Yet in another experiment thirty-one 1400 microns all microneedles arranged in one square centimeter circular microneedle array are used. This example shows different types of cavities with various cavity densities and different heights can be created by using commercially available metal microneedle arrays.

Example 6B

Artificial Porosity Created Using a Hollow Stainless Steel Microneedle Array

A 3 by 3 stainless steel hollow microneedle hub is obtained from Micropoint Technologies Pte Ltd. (Singapore) (referred as 33MP). The hub has a square base pyramidal shaped needle with height of 1000 microns, rectangular base 300×300 microns, internal diameter 150 microns, needle pitch 1000 microns and needle's center-to-center spacing is 0.63 mm. The hub has a stainless steel female Luer lock connector which can be connected to a syringe with male Luer Lock connector. All the needles in the device can inject liquid when injected via Luer Lock and syringe. The empty hub is connected to a syringe which is filled with a saline. The hub is inserted in the sheep skin tissue to create array of 3 by 3 holes in the tissue. Total 9 holes created in one insertion. The same hub is used to make two sets of 3 by 3 holes on the same tissue. Total 27 holes are created. The holes had same dimensions as external shape of the needles on the hub. To visualize the holes, gelatin gels are used instead of skin tissue to make the cavities. The size on the holes in gelatin is measured using the optical travelling microscope. In a similar experiment, a hub with 10 by 10 array with 700 micron needle height is used for injection.

Example 6C

Artificial Porosity Created Using Dissolvable Array
Casting of Dissolvable Array Using Silicone Rubber Mold.

Silicone base MPatch™ Microneedle templates are procured from Micropoint Technologies Pte Ltd. (Singapore). The mold has following characteristics: 20 mm dia and 4 mm height. 10 by 10 microneedle array holes, 700 microns cavity height (square pyramid shaped cavities) with 200 by 200 microns base, 500 microns pitch and distance between each needle is 500 microns (center to center). The mold is washed with mild soap and dried under nitrogen. 0.5 g low viscosity carboxymethyl cellulose sodium salt (CMC, Sigma Catalog number C5678) and 1 mg of sodium fluorscein as a colorant/or florescent agent are dissolved in 1.5 ml distilled water. The polymer is added in several small quantity steps to dissolve it completely (24 to 48 hours for dissolution). The solution is centrifuged to 2000 g for 40 minutes to remove entrapped air under closed and humidified conditions to prevent moisture loss. The air free solution is transferred on silicone mold surface. The mold and solution is spun for 4700 rpm to drive the solution in the cavities and fill them completely. The solution is dried while rotating for 8 h or air dried at room temperature (30%-45% RH) for 4-48 hours. After drying, an adhesive tape is applied on the mold (base of the needles) and the array is removed gently from mold. The array is then inserted in the sheep skin tissue or gelatin gel as mentioned previously. The polymer in the array dissolves in the tissue fluid which can be aspirated or suctioned. The cavities created can be used for filling with various injectable materials as described previously. In this example, it is believed that the needle displaces the tissue to create a space for itself.

In another modification of this embodiment, CMC solution is replaced with polyvinylpyrrolidone (molecular weight 55000) solution (25 percent). In another modification maltose is used instead of CMC. The advantage with sugar is that it is dissipated by the tissue and no removal of polymer may be needed prior to cavity filling.

In another modification of this embodiment, 20 mM PBS (Ph 7.4) solution containing 10 percent dimethyl sulfoxide as cryopreservative is degassed by freezing and thawing under vacuum is used to fill the mold cavity with little excess to form a 3 mm thick layer on top of mold. The water and mold is centrifuged and while being centrifuged, the mold and water is cooled below −80 degree to form frozen solid. The mold is separated from the needles (in cold chamber below −10 degree C.) to prevent melting of frozen microarray needles. The top 3 mm layer forms a block of ice on which ice needles are attached. The array in frozen state is applied on top of porcine dermal tissue held at 37 degree C. to mimic body temperature. The frozen block helps to apply pressure and push the needle in the skin. The frozen needles penetrate in the tissue and melt inside the tissue first due to higher temperature of the tissue and form cavities inside the tissue. The frozen block holding the needle does not melt during the experimental time frame due to larger volume/mass and not in direct contact with the tissue. After melting the needles, the frozen block is removed. The melted composition or PBS is dispersed in the tissue. The cavities formed can be used to fill injectable compositions. Other aqueous solutions such as distilled water, osmotically balanced solutions such as 0.9 percent sodium chloride solution in water, HEPES buffer, triethanol amine buffer solutions pH 7.4, solutions containing amino acids, tissue culture medium and the like may be used in frozen form or state to penetrate the tissue and form cavities. The use of cryopreservative like DMSO is preferred when working with mammalian cells. Alternatively, methods described by B. Bediz et al., "Dissolvable Microneedle Arrays for Intradermal Delivery of Biologics: Fabrication and Application" Pharm Res., volume 31(1), page 117-135, cited herein for reference only, may also be used.

Hyaluronic based dissolvable microarray can also be purchased from Micropoint Technologies Pte Ltd. (Singapore). MPatch™ Mini is hyaluronic acid based microneedle patch along with its proprietary applicator can also be used in making micro-cavities in the skin tissue. Upon application on skin tissue, the patch usually dissolves in 1-10 minutes depending on the location producing micropores in the skin tissue.

Example 6D

Artificial Porosity Created Using Oscillating Needle.

An oscillating coring needle (500 micron internal cutting diameter, stainless steel) is attached to a tattoo machine or permanent makeup tattoo machine. The needle is oscillated at 10-12000 times per minute, typically at 600-1000 times per minutes with penetration distance kept at 500 microns. The machine is used on a porcine dermal tissue or bovine pericardium to create pores. Briefly the tattoo machine is set to go only 500 micron dip in the tissue. The skin tissue is applied with a lubricant such as vitamin E and the needle is slowly moved on skin tissue. As needles goes in and out of skin tissue, it creates 500 microns diameter size and 500 dip holes in the tissue. The needle is moved on the tissue surface so that each insertion point is different on the tissue surface and the movement is followed predetermined matrix pattern such as 10 by 10 matrix.

Example 6E-1

Artificial Porosity Created Using Mechanical Drill

In this method, a micro drill bit is used to create 2 by 2 array cavities using a drilling method. Hard tissue such as bone, skull or nail may be drilled to create artificial porosity of desired size and shape. A 1/64 size micro drill bit is attached to a standard drilling machine. A portion of cut human nail is used as model substrate to create holes. 4 holes (about 400 microns diameter) and 200 microns deep are drilled into nail. In another example, a fresh cow femur bone is isolated from local slaughter house. A 1/32 inch size micro drill bit and drill machine is used to drill 3 by 3 array (9 holes separated by 2 mm) holes on bone surface. The hole diameter is about 800 microns and depth is 200 microns.

Example 6E-2

Artificial Porosity Created by Syringe Needle

In another embodiment instead of drill, a fine syringe needle is used manually to create a cavity array in the tissue. Approximately 15 mm by 15 mm dry pericardium tissue is used to make 4 by 4 array of cavities. A 24 gauge needle is used to core approximately 1 mm dip cavity by hand in the tissue. Total 4 cavities are made, 2 mm apart from each other, along the length of the tissue to make one row of cavities. Total four rows are made, 2 mm apart each to make a 4 by 4 cavity array where each cavity is separated by 2 mm. FIG. 8D shows image of a bovine pericardial tissue with cavities in 4 by 4 array format. Manual method for cavity creation can be useful but may not preferred where large number of cavities are needled. Variables like the size of cavity, number of cavities made, distance between each cavity, needle size used, depth of cavity can be varied to obtain a suitable array structure. In another illustrative embodiment, instead of cavities, holes are created in the tissue in 4 by 4 matrix pattern. In this case tissue thickness (around 1 mm) is the height of cavity and diameter is same as external diameter of 24 gauge needle (approximately 565 microns). Alternatively, a coring needle may be manually used to core holes. A modified breast biopsy or coring needle and instrument is used to create 2 by 2 array holes (4 holes, 500 microns diameter and 1000 micron dip) on 1 cm square rectangular area.

Example 6F

Artificial Porosity Created Using Laser Irradiation.

A bovine pericardium tissue or porcine dermal tissue is used to create laser irradiated porosity. Harmony Elite Laser machine from Alma Lasers™, Buffalo Grove Ill., US is used in creating porosity. The machine parameters are set using manufacturer recommendations and literature references (E. H. Tudor et al., Table 1) for similar type of machine. Briefly following experimental parameters are used to create porosity (array of cavities) in the pericardium or dermal tissue. Wavelength 2940, spot size 225 microns, density 5%, power levels 1.15-2.22 W, pulse durations 50-225 microseconds, pulse repetition rates 100-500 Hz, and 2, 20, or 50 stacked pulses. These conditions resulting in pulse energies of 2.3-12.8 mJ/microbeam and total energy levels of 4.6-640 mJ/microchannel. Variables like total power, spot size and shape, pulse repeating rate, number of stacks and the like are used to create array of 5 by 5 array cavities in one square centimeter separated by 1 mm.

Example 7

Example 7A

Infusion of Injectable Compositions in the Artificial Porosity Direct Infusion in the Artificial Cavities.

In this method, the injectable composition such as PLGA drug microspheres suspended in PBS buffer or PLGA solution in n-methyl pyrrolidone (10 percent weight by weight, and 10 percent (relative to PLGA plus solvent weight) rifampin as drug and/or visualization agent, is applied or exposed on the newly created porosity in the tissue. The composition is inserted in the porous space via capillary force action, gravity if incubated for sufficient amount of time (1 to 60 minutes incubation). The insertion can be further assisted by applying external energy/force or pressure. For example, a jet of nitrogen gas or carbon dioxide gas via a 14 gauge syringe needle may be used to force the fluid composition in the cavity. A fiber or rod or array needles may be used to sweep the injectable composition or mechanically "stuff" the composition in the cavities. Care is taken to ensure that polymer is not prematurely precipitated on the skin surface if used as a polymer solution. Upon insertion in the cavity, the composition can undergo further transformation (either physical or chemical) which enables to entrap the drug and release it slowly over a period of time. In another modification, the PLGA solution as above is added in the cavity via syringe and needle. The 30-34 gauge syringe needle is used to infuse solution in each cavity individually and excess solution is wiped off from the surface.

The solution may also be sprayed/atomized and the droplets may be collected in the cavities.

Example 7B

Creation of Artificial Porosity and Infusion of Injectable Compositions in the Artificial Porosity.

Application of microneedle array via injectable composition layer on skin/tissue surface to create porosity and inject composition in the porosity at the same time.

In this method, injectable fluid composition such as PLGA solution with rifampin in NMP or rifampin microsphere suspension in PBS or in glycerol is applied on the tissue or skin to form a layer of injectable composition. 1 g of PLGA (50:50 lactide:glycolide, molecular weight 15000 g/mole) polymer and 100 mg of moxifloxacin base and 0.1 mg of methylene blue as a colorant is dissolved in 9 g of methyl pyrrolidone (NMP). The solution is sterile filtered using 0.2 micron PTFE syringe filter. This solution is applied on the porcine or skin dermal tissue to form a liquid layer. The thickness of layer is may be greater than one micron thick, typically 10 microns to 3000 microns thick. The porosity is creation is done through this layer. For example, a microneedle array AdminStamp 600 as an example or 3 by 3 stainless steel microneedle hub from Micropoint Technologies (33MP) is applied on the skin through the injectable composition layer. The needles of the array contact the solution layer first and then skin tissue. As needles pierce the tissue and make the cavity, the injectable composition is carried along with the needles and is deposited inside the newly created cavities. The needles are retrieved from the tissue leaving behind the injectable composition in the cavities. The process may be repeated multiple times to fill the cavities completely. If the injectable compositions have drug encapsulated microparticles, they are carried inside the cavity for local and sustained drug delivery. If the polymer solution is used as an injectable composition, then the solvent from the composition in is dispersed in the tissue and polymer is deposited in the tissue. If the composition contains precursors of crosslinkable composition, then the precursor composition undergoes in situ polymerization and/or crosslinking inside the cavity and form a crosslinked material/hydrogel inside the cavity.

Example 7C

Creation of Artificial Porosity and Infusion of Injectable Compositions in the Artificial Porosity at the Same Time. Use of Hollow Needles Array to Create and Fill Porosity.

1 g of PLGA (50:50 lactide:glycolide, molecular weight 15000 g/mole) polymer and 100 mg of moxifloxacin base and 0.1 mg of methylene blue as a colorant is dissolved in 9 g of methyl pyrrolidone (NMP) or dimethyl sulfoxide (DMSO). The solution is sterile filtered using 0.2 micron PTFE syringe filter. The sterile solution is loaded into sterile syringe. The syringe is attached to sterile 3 by 3 stainless steel hollow microneedle hub from Micropoint Technologies (33MP). The solution is infused in the sheep skin tissue and/or on gelatin gel. After inserting the needle array in the tissue, the syringe solution is pushed inside the tissue. The array is pulled away from the tissue and the solution is pushed in the cavities created by the array as it is pulled away. The excess solution is wiped from the skin surface. The array is used a total of 3 times at nearby tissue creating 27 cavities filled with the PLGA solution. The blue solution in the cavity is clearly seen to the naked eye. The polymer is precipitated in the cavity after NMP is dispersed in the tissue. The precipitated polymer traps moxifloxacin in the polymer. The treated tissue is cut off and is used to monitor the release of moxifloxacin in 3 ml PBS at 37 degree over several hours. The PBS is exchanged at every time point of drug release study.

Another illustrative embodiment teaches that artificial space (cavity) is first created inside the tissue which is isolated by the needle wall. The space created by the array needle is then filled with injectable composition. When the 3 by 3 stainless steel microneedle hub is inserted in the tissue, it displaces the tissue and creates the space in the tissue. This space is isolated in the tissue from the needle wall. The artificially created space in the tissue which is isolated by hollow needle wall is then filled with injectable composition such as PLGA solution with moxifloxacin. Upon removal of the needle, the polymer stays in the tissue cavity forming an array of implant (27 microimplants) in situ. Other injectable compositions such as precursors of crosslinkable compositions, drug encapsulated microparticles, neat liquid based compositions, low melting compositions may also be used in place of polymer solution as described here.

Example 7D

Creation of Artificial Porosity and Infusion of Injectable Compositions in the Artificial Porosity. Use of Dissolvable Microarray.

In this embodiment, a dissolvable microneedle array such as hyaluronic or sugar based microneedle array is used for creating and filling cavity. 1 g of PLGA (50:50 lactide:glycolide, molecular weight 15000 g/mole) polymer and 100 mg of moxifloxacin base and 0.1 mg of methylene blue as a colorant is dissolved in 9 g of polyethylene glycol dimethyl ether, molecular weight 550 or ethyl acetate). The solution is sterile filtered using 0.2 micron PTFE syringe filter. This solution is applied on porcine dermal sheep tissue to create a liquid layer of 10 to 100 microns thick. The dissolvable microneedle array is applied through this layer. (caution, the solvent used for polymer solution must be a non-solvent for the microneedle array material. For example, carboxymethyl cellulose or polyvinyl pyrrolidinone based materials are not soluble in ethyl acetate or polyethylene glycol dimethyl ether, molecular weight 550). The available list of polymer solvent can be found in Polymer Handbook. The solvent and needle material are removed by the tissue water by dissolution or evaporation process or combination thereof. The polymer precipitates in the artificial cavities created by the needle.

In another embodiment, 1 g of PLGA (50:50 lactide: glycolide, molecular weight 15000 g/mole, ester endcapped) polymer is dissolved in 9 g ethyl acetate. The needles of the carboxymethyl cellulose microarray are then dip coated with the PLGA solution and the solvent is evaporated. The PLGA solutions forms a coating on the array needle. The coated array is inserted in the tissue where water dissolvable portion of the array is dissolved upon insertion leaving behind the PLGA coated film and the space created by the dissolved array. If needed PBS solution or other biocompatible aqueous buffer solution is used to dissolve away the needle. The space created by microarray dissolution remains isolated in the tissue due to PLGA film. This space is then filled with the injectable compositions such as fibrin glue or liquid carriers like vitamin E acetate or sucrose acetate isobutyrate, thermosensitive gel like Pluronic gel and the like described in this invention.

Example 8

Compositions for Treating Iron Deficiency.
Infusion of Iron Based Compositions in the Tissue.

Venofer® or its generic version (iron(III)-hydroxide sucrose complex) is a 20 mg iron/ml solution is procured from local pharmacy. 0.2 ml of this solution (0.2 mg) is tattooed into 2 square centimeter of sheep skin tissue. Please refer to U.S. Pat. No. 9,345,777 for additional details on the use of tattooing process to deliver drugs into tissue. The treated tissue showed red color after infusion into the skin tissue.

In another method, soluble ferric pyrophosphate is obtained from Sigma-Aldrich Inc. (St. Louis, Mo.). The powder is ground and sieved to obtained less than 300 micron particles. 150 mg of sieved powder is suspended in 1 ml glycerol or polyethylene glycol 400 as biocompatible water soluble carrier. The 0.2 ml suspension is tattooed into 2 square centimeter area of the tissue (15 mg per square centimeter).

In another variation of this process, the sieved particles (150 mg) are suspended in one ml of PLGA (50:50 lactide: glycolide, molecular weight 15000 g/mole, ester endcapped) solution in n-methyl pyrrolidone (NMP). Methylene blue (small amount) is used as a colorant. 0.2 ml of the suspension is tattooed in sheep dermal tissue and blue color of the tattooed portion is clearly visible. The excess solution during tattooing process is wiped off from the tissue. The PLGA undergoes precipitation in the tissue after dissipation NMP in the tissue. A control sample without ferric pyrophosphate is prepared and tattooed as described above. The entrapped iron is released from the precipitated polymer in the skin tissue. The release of iron from the treated tissue is monitored at 37 degree C. for 5 days. The iron is analyzed using a spectrophotometric method wherein a collected sample is mixed with 1.6 ml 10% hydroxylamine hydrochloride solution, 0.4 ml 0.2 M sodium acetate solution and 2.0 ml 0.25% phenanthroline solution and diluted up to 10 ml using distilled water. Absorbance is recorded at 515 nm. The sustained release of iron from treated and control sample is provided in FIG. 20.

Silicone rubber based MPatch™ Microneedle templates are procured from Micropoint Technologies Pte Ltd. (Singapore); 10 by 10 microneedle array cavities with 700 microns needle height cavities with 200 microns by 200 microns base and 500 microns pitch. The mold is washed with mild soap and dried under nitrogen and sterilized using 70 percent isopropanol. 15 mg ferric pyrophosphate+0.5 ml 1% sodium hyaluronate are mixed, sterile filtered and added to the mold cavities. The water is removed by air drying and the microneedle array containing hyaluronic acid and ferric pyrophosphate is removed using a polyester tape at the base. FIG. 9B1 shows the dissolvable array containing hyaluronic acid and ferric pyrophosphate (902). FIG. 9B2 shows the microscopic image of one of the needles of the arrays showing sharp edges and needle point (903). The array is pressed against the skin tissue and the needle dissolved in the tissue releasing ferric pyrophosphate in the tissue.

In another variation, cylindrical microimplants comprising ferric pyrophosphate are created first and then implanted using hollow microneedle array or "array in array" device described in this invention. Briefly a finely sieved powder (size less than 300 microns) of ferric pyrophosphate and dextran are mixed and compacted to produce microcylinders of various size suitable for inserting in base array cavity of AIA device described in this invention. The dextran acts as a binder and helps to form a unibody microimplant structure upon compaction under pressure which enables to inject the ferric pyrophosphate as a unibody implant. The dextran dissolves away in the body leaving behind the ferric pyrophosphate for therapeutic effect.

Example 9

Compositions for Treating Nail Infection

Human nail fragments are procured from human volunteers. A 1/64 inch micro drill bit is used to drill 3 cavities along the width of the nail. The nail cavities had depth around 20-100 microns depending on the nail thickness. Care is taken not to drill hole all the way through the nail. 100 mg Terbinafine hydrochloride, and 0.9 g, PLGA (50:50, dl-lactide:glycolide) are dissolved in 10 ml ethyl acetate or tetrahydrofuran or acetone. The polymer solution is applied on the cavities on the nail. All cavities are filled completely by the PLGA solution. The nail is allowed to dry in air overnight. The release of drug from the nail is monitored in vitro in 3 ml PBS (pH 3.0) for 7 days. In a similar experiment, the cavities are created by the laser drilling process as described before. The cavities created by laser drilling are coated/filled with PLGA solution with antifungal drug as described before.

In another embodiment, a 3 by 3 array hollow needle array (33MP) is used to create cavity and fill the cavities at the same time. The array has 1000 micron height. The array is applied with 700 micron PTFE spacer on top of the microneedles to limit the penetration of array to 300 microns only. The PLGA solution with Terbinafine hydrochloride solution is sterile filtered and injected via array to make cavities and fill the cavities at the same time. Excess of solution is wiped off from the surface. The treated area is exposed to PBS solution for 10 minutes to accelerate the precipitation process in the cavity. The deposited drug in cavities release the drug in a sustained manner. This array creates 300 micron dip cavities in the nail.

In another embodiment, part of human nail is cut. 4 cavities in 2 by 2 array format are created using a 24 gauge needle (average cavity diameter around 600-700 microns). A PLGA based polymer solution with D and C violet as colorant and terbinafine hydrochloride as antifungal drug is then used to fill in the cavity. FIG. 16A shows a photographic image of part of human nail with artificially created cavities FIG. 16B shows FIG. 16A cavities filled with PLGA based biodegradable composition with D and C violet as colorant. FIG. 16C shows in vitro terbinafine hydrochloride (an antifungal drug suitable for treatment of fungal nail infection) release profile from PLGA based experimental composition.

Example 10

Delivery of Injectable Synthetic Biodegradable Polymer Solution in Tissue.

Example 10A

Formation of In Situ Biodegradable Microimplants in the Live Tissue or Bioprosthesis Tissue.
Creating a Porosity First and then Filling the Pores with Injectable Composition (Polymer Solution in the Second Step.
Part 1: Preparation of Sterile Injectable Synthetic Biodegradable Polymer Solution with Drugs Suitable for Injection in the Live Tissue. Use of Water Miscible Organic Solvent In a 50 ml glass beaker, 20 ml dimethyl sulfoxide (DMSO), 1.8 g Poly (PLGA, polylactide-co-glycolide) (dl-lactide:glycolide (50:50), molecular weight 13000 to 20000 g/mole.) and 200 mg (approx. 10 percent loading relative to weight of the polymer plus drug) moxifloxacin base and 1 mg of methylene blue as a colorant are mixed until homogeneous solution. The solution in the beaker is sterile filtered (filter has PTFE membrane and polypropylene housing which is not affected by the DMSO solvent). The sterile filtered solution is used an injectable solution to fill artificial cavities. Part 2: In situ delivery of the polymer drug solution using solid metal microarray About 2 cm by 2 cm portion rat back skin is shaved to remove hairs. Iodine solution is applied to sterilize the area. Sterile filtered vitamin E acetate oil is applied on the shaved skin area, which acts as a lubricant for the metal microarray needle. AdminStamp 600 Microneedle Array Device is used to create micropores in the skin tissue. This device has 187 five hundred micron tall stainless steel microneedles on 1 square centimeter (circular shape). The array is inserted in the tissue, rotated 180 degrees for 3 times and removed. The sterile PLGA solution is applied on the skin and a sterile nitrogen get pressurized stream is applied on the solution. The solution is allowed to incubate with the porous area for 10 minutes. The excess solution from the tissue is wiped off using sterile gauze.

About 10 treated areas are treated in a similar fashion. The treated tissue is cut and some tissue subjected to histological processing to see the presence of deposited polymer in the tissue. The other tissue is used to monitor the release of moxifloxacin from the tissue. Briefly the cut tissue is incubated in 3 ml PBS and drug release is monitored several times for 30 days. PBS is changed every time when drug solution sample is collected to maintain sync conditions.

Creating Porosity and Filling Injectable Composition at the Same Time.
Applying the Injectable Composition (Polymer Solution) First as a Fluid/Liquid Layer and then Applying Microneedle Array or Oscillating Needle to Form Pores and Fill the Cavity.

Bovine pericardium tissue (5 cm by 5 cm) is procured freshly and is decellularized. The tissue is incubated for 24 hours in PBS to hydrate it completely. The pericardial tissue can be considered as exemplary surgical bioprosthesis patch or wound dressing. The sterile moxifloxacin solution from part 1 as above is first applied on the tissue (about 2 square centimeter area, (about 0.1 to 1 mm solution layer thickness) and the sterile AdminStamp 600 Microneedle Array Device is applied on the solution and pressed into tissue. The needles penetrate the tissue and its needle carry solution with it inside the tissue. The solution is transferred by the microneedles inside the tissue. The needles are removed from the tissue and reinserted in the same area. This is repeated 2 or more times. The excess solution is wiped off. About 10 areas are treated this way. The treated tissue is incubated in PBS for 2 h to accelerate precipitation of the polymer inside pores. The polymer in the tissue precipitates entrapping the drug inside the precipitated PLGA. Methylene blue provides blue color, which helps to visualize the treatment. The infused portion is clearly visible on the white tissue background. The infused section is observed under scanning electron microscope and regular microscope to confirm the presence of polymer microimplants. The treated tissue section is cut from the tissue and sent for histology analysis to confirm the formation of PLGA microimplants at the treatment site. In another experiment the infused section is cut from the tissue is incubated in 3 ml PBS at 37 degree C. Fresh 3 ml PBS is exchanged at following time intervals: 30 minutes, 60 minutes, 12 h, 24 h, 2 day, 3 day, 5 day, 7 day, 14 day, 28 day time period. The drug eluted sample are protected from light and stored in refrigerator until HPLC or UV spectrophotometer analysis. The eluted moxifloxacin in PBS solution is analyzed using UV spectrophotometer.

In another modification of this embodiment, 20 ml dimethyl sulfoxide, 1.4 g Poly (PLGA, lactide-co-glycolide) (dl-lactide:glycolide (75:25), molecular weight 30000 to 60000 g/mole.) and 600 mg (approx. 30 percent loading relative to weight of the polymer plus drug) bupivacaine base is used and the solution is infused in pericardial tissue using 20 needle array as shown in FIG. 22A. The infused drug is eluted in PBS as mentioned above and is analyzed using UV visible spectrophotometer or HPLC.

In another modification of this embodiment, 20 ml dimethyl sulfoxide, 1.6 g polycaprolactone (molecular weight 70,000-90,000 g/mole.) and 400 mg (approx. 20 percent loading relative to weight of the polymer plus drug) rifampin is used and the solution is infused hollow microneedle 3 by 3 microneedle array (33MP). The infused drug is eluted in PBS as mentioned above and is analyzed using UV visible spectrophotometer.

In another modification of above examples, gentamycin is replaced with rifampin, or chlorhexidine diacetate salt hydrate. In another modification, moxifloxacin in the above examples is replaced with coumarin 6 a fluorescent visualization agent and model drug.

Example 10B

Formation of Artificial Porosity Using Oscillating Needle and Depositing the Polymer Solution in the Cavity.
Formation of In Situ Biodegradable Microimplant Array in the Tissue Using Oscillating Needle Method.
Part 1: Synthesis of Polyethylene Oxide (PEO)-Polypropylene Oxide (PPO)-Polyethylene Oxide Lactate Copolymer (PEO-PPO-PEO Lactate Copolymer)

20 g of Pluronic F127 (PEO-PPO-PEO block copolymer) is dried under vacuum at 100 degree C. for 24 h. 20 g of dry Pluronic F127, 4.61 g of dl-lactide and 30 mg of stannous octoate are charged into 100 ml Pyrex pressure sealing tube. The tube is then connected to argon gas line and sealed under argon. The tube is then immersed in oil bath maintained at 140 degree C. and the reaction is carried out for 16 h at 140 degree C. The polymer from the tube is recovered by breaking the Pyrex tube. The polymer is then dissolved in 100 ml chloroform and precipitated in 2000 ml cold hexane or ether. The precipitated polymer is recovered by filtration and dried under vacuum for 1 day at 60 Degrees C.
Part 2: Injection of PEG Copolymer (PEO-PPO-PEO Lactate Copolymer) in the Prosthetic Tissue Using Microarray In a 50 ml beaker, 20 ml n-methyl pyrrolidone, 1.8 g PEO-PPO-PEO lactate copolymer and 200 mg (approx. 10 percent loading relative to weight of the polymer plus drug) rifampin are added until solution is formed. The solution is sterile filtered using PTFE based filter in a clean sterile polypropylene tube. The solution is first applied on the tissue surface to form a 100-900 micron thick liquid layer on the surface. The tattoo machine needle is used to insert the solution on the tissue to form a cavity as well as to insert the solution in the cavity. The needle goes in and out of the tissue at 10-12000 minutes per minute. The solution spreads on the needle surface and penetrates in the tissue and deposits in the tissue where needle has inserted. The deposited solution precipitates in the tissue cavity and form drug delivery microimplant in situ. Total one centimeter square area of the tissue is treated for 1 minute. The infused drug is eluted in PBS as mentioned above and is analyzed using UV visible spectrophotometer. The needle penetration area is chosen in such way that a microimplant array is formed. In this method, no microneedle array is used to create a microimplant array.

In another modification of above example in Part 1, 20 g of polyethylene glycol (molecular weight 20000) g/mole is reacted with 14.4 g lactide and 30 mg stannous octoate are reacted at 140 degree C. for 16 h to produce PEG-polylactide high molecular weight polymer (molecular weight 30000 to 40000 g/mole). A 10 percent of this polymer solution in acetone is used for infusion with tattoo machine.

In another embodiment of above example in Part 1, 2.00 g polyethylene glycol (molecular weight 2000 g/mole), 7.2 g of dl-lactide, 5.7 g caprolactone and 30 mg of stannous octoate are reacted at 140 degree C. for 16 h to produce PEG-co-polylactide-co-polycaprolactone copolymer. A 10 percent of this polymer solution in DMSO is used for infusion using oscillating needle in part 2.

The molar ratio of cyclic lactone and hydroxy groups in the PEG or Pluronic polymers is used to control the molecular weight (degree of polymerization) in the copolymer. The PEG-polylactone ratio may be changed 5-90 percent to obtain polymers with wide range of properties including thermoreversible properties, water solubility, solid/liquid nature at room temperature and the like. Some of PEG-polylactone polymers are water soluble and some of them are water insoluble.

In another modification of above examples, rifampin is replaced with gentamycin, chlorhexidine diacetate salt hydrate. In another modification, rifampin in the above examples is replaced with coumarin 6 as a fluorescent additive and model drug.

Example 10C

Delivery of Injectable Synthetic Biodegradable Polymer Solution in the Artificial Porosity.
Delivery of Water Soluble Synthetic Biodegradable Polymer.
Part 1: Synthesis of Water Soluble Polyethylene Glycol Lactate Copolymer (PEG-Polylactate-10)

In a 500 ml flask, 20.0 g of PEG 10000 (molecular weight 10000 g/mole), and 200 ml toluene is added. Approximately 80-100 ml toluene is distilled of and the solution is cooled. 5.4 g of dl-lactide and 30 mg of stannous octoate are added in the flask and the solution is refluxed for 24 h under nitrogen atmosphere. The flask is cooled and the solution is precipitated in 2000 ml cold hexane or ether. The precipitated polymer (PEG-LACTATE-10) is recovered by filtration and dried under vacuum for 1 day at 60 degree C.
Part 2: Injection of PEG Copolymer Lactate Copolymer (PEG-Polylactate-10) in the Tissue Using in the Artificial Porosity.

In a 50 ml beaker, 6 ml PBS, 2.0 g (PEG-polylactate-10) and 100 mg (approx. 5 percent loading relative to weight of the polymer plus drug) rifampin are added until complete solution. The solution is sterile filtered using PTFE based filter in a clean sterile polypropylene tube. 1 ml of solution is poured on 2 cm by 2 cm sheep dermal tissue and the solution is infused by inserting AdminStamp 600 microneedle device or 3 by 3 hollow microneedle array from Micropoint Technologies (33MP). A surgical sealant such as Fibrin sealant or DuraSeal is applied on top of treated area or band aid type adhesive tape or silicone rubber based wound dressing is applied to prevent the injected solution to come out of cavities. The concentration of polymer in PBS is above its critical micelle concentration and therefore it forms micelles in PBS, which can entrap hydrophobic drugs. The drugs in the micelles are released in a sustained manner. This example can be treated as micellar drug delivery system wherein drug is incorporated in the micelles and the micelles are then injected artificial pores of the tissue. Each micelle can be considered as nano size drug loaded microparticle. In another modification, rifampin in the above examples is replaced with coumarin 6 as a fluorescent additive and model drug.

Example 10D

Delivery of In Situ Forming Crosslinkable Compositions Microarray Device.
Delivery of Composition that Crosslink Using Free Radical Polymerization
Part 1: Synthesis of Polyethylene Glycol Lactate Copolymer In a 500 ml flask, 20.0 g of PEG 10000 (molecular weight 10000 g/mole), and 200 ml toluene is added. Approximately 80-100 ml toluene is distilled of and the solution is cooled. 2.68 g of dl-lactide and 30 mg of stannous octoate are added in the flask and the solution is refluxed for 24 h under nitrogen atmosphere. The flask is cooled and the solution is and precipitated in 2000 ml cold hexane or ether. The precipitated polymer (PEG-LACTATE-5) is recovered by filtration and dried under vacuum for 1 day at 60 degree C. It then immediately used in next reaction.

Part 2: End-Capping of PEG-LACTATE-5 with Polymerizable or Crosslinkable Group (PEG-LACTATE-5-Acrylate)

In a 500 ml reaction flask, 20 g of PEG-LACTATE-5 is dissolved in 300 ml dry toluene. About 50 ml of toluene is distilled out to remove traces of water from the reaction mixture. The warm solution is cooled to room temperature. 0.39 g of triethyl amine and 0.34 g acryloyl chloride are added. The reaction mixture is then stirred for 6 h at 50-60 degree C. and filtered. PEG-LACTATE-5-acrylate macromonomer is precipitated by adding the filtrate to 2000 ml cold hexane or ether. The precipitated polymer is recovered by filtration. It is then dried under vacuum for 12 h at 50 degree C.
Part 3: Polymerization and Crosslinking of Deposited Solutions in the Artificial Cavities.

Separately 3 g of PEG-LACTATE-5-acrylate diacrylate prepared as above is dissolved in 9 g PBS. 300 mg Irgacure 2959 is dissolved in 700 mg n-methyl pyrrolidone. 50 microliter of Irgacure 2959 solution is added to the PEG-LACTATE-5-acrylate solution and 100 mg heparin as model water soluble drug is added to the solution. The solution is sterile filtered using 0.2 micron filter. The sterile solution (precursor solution) is filled inside a sterile syringe and the syringe is attached to sterile 3 by 3 stainless steel hollow microneedle hub from Micropoint Technologies (33MP). The microarray is inserted inside the sheep skin tissue completely. The needle is pulled approximately 80 percent out and the space created during pulling is filled with the sterile precursor. The infused solution used then exposed to the long UV ultraviolet light (Black-Ray UV lamp, 360 nm light, 10000 mW/cm2 intensity) for 5 minutes to photopolymerize and crosslink the infused precursor solution in the tissue. The PEG-LACTATE-5-acrylate polymerizes and crosslinks to form biodegradable hydrogel particles inside the tissue. This leads to formation 3 by 3 array of microimplants in the tissue. The process is repeated at 10 locations on the tissue to increase amount of implant material formed in the tissue. The entrapped crosslinked hydrogel release the drug in a sustained manner.

In another modification as above, 30 g PEG 10000 (tetrafunctional, one terminal hydroxy group per PEG branch, total four branches) is reacted with 8.460 g dl lactide in first part and 1.668 g acryloyl chloride and 1.882 g triethyl amine in second part. The macromonomer formed has four acrylate groups per molecule which upon polymerization and crosslinking produce crosslinked hydrogels that have higher crosslinking density than its bifunctional counterpart produced as above.

In another modification as above, 30 g PEG 20000 is reacted with 2.130 g dl lactide in first part and 0.501 g acryloyl chloride and 0.565 g triethyl amine in second part to produce PEG 20K-lactate-acrylate macromonomer.

In another modification as above, 30 g PEG 35000 is reacted with 1.234 g dl lactide in first part and 0.295 g acryloyl chloride and 0.333 g triethyl amine in second part to produce PEG 35K-lactate-acrylate macromonomer.

By changing PEG molecular weight, number of acrylate groups per PEG and polylactones as indicated above, crosslinked hydrogel networks with variety of degradation times and molecular permeability can be made and can be used in variety of drug delivery and cell encapsulation applications. In case of islet encapsulation, molecular permeability is adjusted by variables mentioned as above so that molecules with 100000 g/mol molecular weight can go in and out of the islet encapsulated hydrogels matrix, but will not allow to permeate/diffuse immunoglobulins (IgG, molecular weight around 150000 g/mole) to diffuse through the crosslinked hydrogels.

In another experiment, a 500 micron thick spacer (500 micron thick paper, Teflon or polyester film is placed between needle and hub where needles are attached. The spacer limits the depth of penetration from 1000 microns to 500 microns. Alternatively, a 500 microns tall needle array specifically fabricated for this purpose and used. Other spacers of various thickness (50, 100, 900 microns and the like) may be applied to limit the depth of penetration of needle in the tissue and hence depth of artificially cavity.

In another modification as above, a visible light photopolymerization is used to crosslink the injected precursor solution in the cavities. In 100 ml beaker 3 g of PEG-LACTATE-5-acrylate diacrylate prepared as above is dissolved in 9 g PBS. In another 10 ml glass vial, 300 mg eosin Y is dissolved in 700 mg n-vinyl pyrrolidinone. 30 microliter of eosin Y solution, 1 ml of 5 M triethanol amine in PBS are added to PEG-LACTATE-5-acrylate solution and the solution sterile filtered and protected from light using aluminum foil. The precursor solution is infused in the pericardial tissue or porcine dermal tissue using a tattoo machine like oscillating needle at a depth of 10-1000 microns or inserted in to 3 by 3 cavities created by 33MP array. The infused solution is crosslinked by photopolymerization by exposing it to the 512 nm laser (argon laser) light or high intensity white floodlight. The light polymerizes and crosslinks the PEG-LACTATE-5-acrylate monomer and forms gel particles in situ inside the cavity. In another modification of same example, about 1 million fibroblast cell suspension (1 million cells suspended in 0.2 ml of are added to 1 ml of sterile filtered precursor solution prior to injecting in the tissue in the dermal tissue or live tissue. The injected solution is crosslinked using visible light (512 nm Laser). The 512 nm light can penetrate up to 1000-3000 micron dip in the tissue and is therefore is capable of polymerization and crosslinking the precursor formulation without damaging the cells. The polymerized cells in the crosslinked materials may be used in cell based therapy.

In another embodiment, 200 mg of PEG 35K-lactate-acrylate macromonomer prepared as above is dissolved in 800 mg PBS. After complete dissolution, 200 mg of magnesium carbonate is added as opacity creation agent or as visualization agent or as a filler. 300 mg Irgacure 2959 is dissolved in 700 mg n-methyl pyrrolidone. 5 microliters of Irgacure 2959 solution is added to the macromonomer solution. The sterile solution (precursor solution) is filled in the array of cavities (4 by 4 array) created in sheep tissue, excess solution is wiped off and exposed to long UV ultraviolet light (Black-Ray UV lamp, 360 nm light, 10000 mW/cm2 intensity) for 5 minutes to photopolymerize and crosslink the macromonomer solution to form crosslinked hydrogel. FIG. 19A shows crosslinked biodegradable hydrogel 4 by 4 microimplant array in sheep tissue. The crosslinked hydrogel with magnesium carbonate as visualization agent or filler (1901) is clearly seen in the image. In another modification of above embodiment, 100 mg tissue plasminogen activator (TPA, an exemplary protein drug) is added in place of cells. The TPA is entrapped in a hydrogel particle and is then released in a sustained manner when the crosslinked PEG-LACTATE-5-acrylate degrades in vivo.

In another modification, inorganic biocompatible, biodegradable fillers such as magnesium carbonate, calcium sulfate, and the like may be mixed with crosslinkable polymer solution such as PEG 35K-lactate-acrylate macromonomer solution as above and polymerized and crosslinked with light to entrap the filler in the gel. The entrapped filler can be used to alter the local chemical/physical environment of the crosslinked gel (pH, osmolality, surface area and the like) which may help to tune the sustained drug release of drugs.

Example 10E

Microarray Made Using In Situ Crosslinkable Compositions Composition that Crosslink Using Condensation Polymerization 500 mg PEG10KARM glutarate NHS ester obtained from commercial sources; (molecular weight 10000 g/mole, 4 arm star shaped, with terminal NHS groups and glutarate as degradable ester, Laysan Bio Inc., Arab, Ala.) is dissolved in 9.5 ml PBS (20 mM pH 7.2) until complete dissolution (precursor A solution). 2 g albumin and 10 mg methylene blue is dissolved in 9 ml PBS (precursor B solution). Both precursor solutions are sterile filtered. 1 ml of PEG10KARM glutarate NHS ester solution and 1 ml albumin are loaded in duel syringe [(Duel syringe Product code 6B23-3 ml×3 ml, 1:1 Ratio, with 2 mm×8 Element mixer tip) from Pals-Pak Industries, Inc., Norwich, Conn., USA] is used. The output of duel syringe is fed to 3 by 3 hollow microarray from Micropoint Technologies, 33MP. The gel time for this solution is about 20-180 seconds. The array is inserted into sheep dermal tissue and the precursors solutions are pushed from both the syringes, which are mixed and infused into tissue cavities created by the array. The array is removed from the surface leaving behind empty space filled with crosslinkable composition. The infused precursor mixture undergoes condensation polymerization and crosslinking (total reactive functional groups in the precursors must be greater than 5 and each precursor must have greater than 2 functional groups). The precursors react with each other forming gel particles at the injection site. If the precursors are loaded with drug, the drug is entrapped in the crosslinked gel and is released in a sustained manner.

The drug should not have functional group capable of reacting with precursors under crosslinking conditions.

In another embodiment, PEG10KARM glutarate NHS ester and trilysine are mixed in molar equivalent quantities. The gel time of the precursors are adjusted using various buffers that provide pH in 6 to 8 range such as PBS buffer with PH 7.8 or sodium acetate buffer with 6 and the like). In general, acidic pH is preferred. Some of the formulations gels in few seconds and therefore may be preferentially used by mixing in situ inside the duel syringe device before injecting in the tissue via 3 by 3 microneedle array.

Another modification of above example, albumin is replaced with gelatin or collagen solution (1-5 percent in PBS or 0.1 M acetic acid) to form a crosslinked gelatin or collagen gels.

Another modification of above example, albumin is replaced with PEG 10000 tetrafunctional amine terminated polymer (PEG10K-4Amine, molecular weight 10000 g/mole, 4 arm, terminal amine groups, available from Laysan Bio, Inc. AL). Molar equivalent quantities of PEG10KARM glutarate NHS ester and PEG10K-4Amine are mixed in PBS pH 7.8 and injected in tissue using 33MP array. The solutions are allowed to react in the cavity for 10 seconds to 300 seconds. The crosslinked gel array is used for drug delivery. In another modification of same embodiment, rifampin microspheres made in Example 3 are mixed with PEG amine and then reacted in situ in the cavities to form a gel the PLGA microspheres embedded in the gel. The rifampin is released from the gel in a sustained manner.

Example 10F

Delivery of In Situ Forming Crosslinkable Compositions Using Oscillating Needle Device or Hollow Microneedle Array.
Delivery of Composition that Cross Slink Via Enzymatic Pathway.
Formation of Fibrin Gels Particles In Situ Using Cavity Filling Technique.

A commercially available EVICEL® from Ethicon or TISSEEL from Baxter may be used. The components of fibrin glue (fibrinogen, thrombin, factor 8, calcium ions and the like) are supplied as a two component mixture. The components of commercially available as fibrin sealant and are mixed in a sterile cup (total volume of mixed components 1-2 ml). To this solution 5 drops ophthalmic sodium fluorscein solution are added or 10 mg of indocyanine green dye added as a fluorescent/coloring agent. If no color is desired, the formulation can be used without the use of coloring agent or dye. The colored fibrin formulation is then loaded in a sterile syringe and it is connected in the 3 by 3 stainless steel hollow microneedle hub from Micropoint Technologies and injected into pericardial tissue or in live peritoneal tissue. The excess solution on the tissue surface is wiped off. The injected solution in the 3 by 3 array cavities undergo enzymatic polymerization/crosslinking and form fibrin glue/gel particles in situ inside the artificial cavities created inside the tissue. If desired, the components of fibrin glue are delivered via a duel syringe apparatus and then connected to hollow needle microarray hub. The precursor components are mixed in the mixing chamber and then delivered to microarray needles. Care is taken to inject the formulation before the fibrin glue forms gel (usually 1-2 minutes). If components prematurely gel, then a new mixture is prepared and used quickly before gelling. The fibrinogen solution may be diluted using PBS to slow the gelation process. Alternatively, a modified duel syringe based device [(Duel syringe Product code 6B23-3 ml×3 ml, 1:1 Ratio, with 2 mm×8 Element mixer tip) from Pals-Pak Industries, Inc., Norwich, Conn., USA] may be used wherein the components are mixed inside the device just prior to injection and injected by the hollow microarray needles. The colorant or fluorescence of particles or droplets provides visual clue on the amount of injected solution at each injection site. A drug may be added to the composition. Drugs that interfere with the fibrin glue formation such as TPA or heparin cannot be used for local delivery using this method. Many drugs can be used with fibrin glue system. Live cell suspensions may be added to the fibrin glue components to deliver live cell based compositions. A multilumen needle may be used to deliver fibrin glue precursors (one lumen for fibrinogen solution) and another lumen for thrombin solution. The components are injected simultaneously and crosslinked in situ.

Example 10G

In Situ Formation of Water Insoluble Drug Solids in the Artificial Porosity.
In Situ Microimplants Made Using In Situ Precipitated Drug Crystals.

In a 50 ml glass baker, 1 g of chlorhexidine diacetate salt hydrate and 10 mg ethyl eosin or methylene blue as a colorant are dissolved in 20 ml ethanol. The solution is sterile filtered. The solution is deposited in the skin tissue using 3 by 3 hollow microarray from Micropoint Technologies as described previously. Upon deposition in the tissue and under physiological conditions (37 degree C., pH 7.4), the ethanol in the solution is dispersed in the tissue and leaving behind substantially water insoluble chlorhexidine diacetate as solid crystals at the injection site or in the artificial cavity space created by the array.

In another variation of above embodiment, 10 mg of paclitaxel, an anticancer drug is dissolved in 10 ml dimethyl sulfoxide or ethanol along with 10 mg of methylene blue or ethyl eosin or turmeric as a colorant. The DMSO solution is injected in using hollow array (33MP) as described above leaving behind paclitaxel crystals upon dissipation of DMSO by the tissue. This creates a 3 by 3 array of cavities filled with paclitaxel crystals which dissolves slowly for local therapeutic effect.

Example 10H

Delivery of Thermosensitive Compositions in the Artificial Cavities.
Preparation of PEG Based Thermosensitive Polymer In 250 ml connected to a condenser and nitrogen inlet, 2.55 g (propylene glycol)-block-poly(ethylene glycol)-block-poly(propylene glycol) bis(2-aminopropyl ether) (Jeffamine® XTJ-502, Molecular weight 1900 g/mole, Aldrich) is dissolved in 100 ml toluene. About 30 ml toluene is distilled off and cooled. 5 g dl-lactide (Aldrich) and 0.2 ml stannous octoate is added and the mixture is refluxed for 4 hours under nitrogen atmosphere. The mixture is cooled and poured into cold hexane to precipitate the Jeffamine-lactide copolymer. The product is isolated by and dried under vacuum and stored in desiccator until use. The A 20-30 percent of Jeffamine lactide solution in PBS shows thermoreversible gelation around 30 to 40 degree C. 1 ml of 30 percent of Jeffamine lactide solution is mixed with 200 mg of rifampin microencapsulated microspheres (Example 3) and the suspension is infused into 4 by 4 microarray microcavities created manually on a sheep skin tissue. FIG. 22D shows the sheep skin tissue with 4 by 4 microarray implant containing Jeffamine lactide copolymer thermosensitive gel (an exemplary thermosensitive gel array) and rifampin encapsulated microspheres entrapped in the gel (red colored 2207).
Preparation of Pluronic Based Thermosensitive Polymer In a 250 mL glass beaker, 20 g of Pluronic F127, 0.5 g of chlorhexidine acetate or chlorhexidine gluconate and 10 mg of methylene blue are dissolved is 40 g cold PBS solution (0-10 degree C.). The F127 is a PEO-PPO-PEO block copolymer that has thermoreversible gelation properties. The cold polymer solution is sterile filtered (temperature held at 0-10 degree C. during filtration). The cold solution is used for deposition in the artificial porosity as described before. The solution is filled in the syringe and kept cold using an ice bath to maintain its fluid state. The solution is deposited using 3 by 3 hollow needle array from Micropoint Technologies (33MP). Briefly, syringe with cold solution is attached to 3 by 3 array hub (33MP) which is precooled to around zero degree C. in the ice bath. The array is then inserted in the porcine dermal skin or Alumax™ Surgical Graft (size 16 by 20 cm size) from C. R. Bard Inc. and the cold solution is injected in the tissue. The tissue is then incubated at 37 degree C. for 5 to 30 minutes to convert the cold solution into Pluronic gel in the injected space. The gel formed releases the drug in a sustained manner. In another modification of above example, the cold Pluronic solution is applied on ice cold tissue to form a liquid layer on the tissue. A 33MP array as above or AdminStamp 600 Microneedle Array is pressed on cold solution through the solution to form micro cavities in the tissue as well as to drive the solution inside the formed cavities. The tissue is warmed to 37 degree C. and the liquid in the cavities undergo thermoreversible gelation and form a gel inside the cavities. The same experiment can be carried on live human on porcine skin tissue. The cold solution is applied on the skin tissue and is forced into cavities using the microarray device. Due to warm body temperature of live pig or human skin, the Pluronic solution is converted into Pluronic gel and stays inside the cavities as a gel. If drug is loaded in the Pluronic gel, it is released in the cavity in a sustained manner. Care is taken so that the Pluronic solution stays in liquid state and not in gel state during application. If it forms a gel on the skin due to warm body temperature, then it may be cooled to less than 10 degree C. to using ice pack to liquefy the gel to a solution and forced into cavity while in liquid state.

In another modification of the above example, a thermoreversible polymer that forms solution when warmed around 40-65 degree C. but forms gel when cooled to body temperature or room temperature is used. A gelatin grade that is soluble in hot water but not in cold or body temperature water is used. Briefly 10 g of gelatin, 90 g PBS and 10 mg indocyanine green as a green colorant is used. The hot gelatin solution (40-60 degree C.) of gelatin is deposited inside the tissue using hollow microneedle array as above.

Some PEG-polylactone polymers (known in the prior art) also show thermoreversible gelation similar to gelatin or Pluronic 127 and such polymers may also be used to deposit in the tissue as described above. Variables such as concentration of polymer in the solution, gel transition temperature and the like may be determined experimentally or can be found using polymer chemistry literature.

Example 101

Delivery of Low Melting Compositions in the Artificial Porosity.
Delivery of Compositions that Form Microarray In Situ In a 250 mL glass beaker, 20 g of Pluronic F127 and 0.1 g of chlorhexidine acetate or gluconate and 10 mg of ethyl eosin are added and mixed. The mixture is heated to 60 degree C. in an oil bath until F127 polymer melts. The melted polymer is mixed thoroughly with chlorhexidine diacetate salt hydrate and cooled and pulverized using mortar pastel. The melted drug polymer composition is re-melted in an oil bath maintained at 60 degree C. and used for deposition in the artificial cavities of bioprosthesis tissue or in the live tissue. Briefly, about 3 g of Pluronic F127 and chlorhexidine composition as above transferred in the syringe. The syringe and 3 by 3 microarray hub from Micropoint Technologies (33MP) are preheated to 60 degree C. The polymer is allowed to melt completely. The hot polymer melt forms a low viscosity liquid at 60 degree C. The hot array hub is connected to the syringe via Luer Lock connector on the hub. The array is completely inserted in the porcine dermal tissue and pulled back about 90 percent of the needle length. The cavity created by pulling back is filled by pushing the syringe and pushing the melted polymer in the cavities. The excess melted polymer on surface is wiped off. If needed, band aid or surgical sealant or fibrin glue or cyanoacrylate glue and the like may be applied on treated surface to prevent migration of implant from the injected space. The polymer is allowed to cool to room temperature or to body temperature. The cold polymer solidifies in the injected artificial cavity and entraps the drug. The drug is released from the cooled solid in a sustained manner. If necessary, hot air may be blown using a hair dryer on the array hub and or syringe to prevent the premature solidification of the composition in the hub or apparatus. In another modification of above example, Pluronic F127 is replaced with lower molecular weight Pluronic F68. In another modification, chlorhexidine acetate is replaced with rifampin or coumarin 6.

In another modification of the above example, polycaprolactone polymer (molecular weight 2000 g/mole) is used for drug delivery and deposition using microneedle hub as described above. Briefly, in a 100 ml beaker, 9.9 g polycaprolactone polymer, 0.1 g rifampin and 10 ml dichlormethane are added until complete homogenous solution (drug weight percent is 1 percent relative to polymer plus drug weight). The methylene chloride is removed by air drying inside the hood leaving behind the polymer and drug. The polymer is vacuum dried over night at 40 degree C. The polymer is heated in oil bath to melt the polycaprolactone at 50-60 degree C. The liquid polymer is then filled inside the syringe and deposited inside the pericardial tissue using the hollow microneedle hub as described above. The excess polymer on the tissue surface is wiped off. The deposited liquid polymer cools and forms solid microparticles inside porous cavities created by the hub.

In another modification of the above embodiment, a bone wax is used in place of polycaprolactone. The wax melts around 60 degree C. and can be injected and cooled to form wax particles. The composition is a biostable non-polymer or oligomeric low melting composition.

In another modification of the above embodiment, a D-α-Tocopherol polyethylene glycol 1000 succinate is used as low melting polymer is used in place of polycaprolactone.

In another modification of the above embodiment, steric acid is used as a non-polymeric solid in place of polycaprolactone.

In another modification of the above embodiment, a low melting (below 60 degree C.) PEG-polylactone or PEG-polycaprolactone polymer is used in place of polycaprolactone.

Example 10J

Delivery of Biocompatible Liquid Compositions in the Artificial Porosity in the Tissue.
Liquid Sustained Drug Delivery Arrays Formed In Situ.

In a 250 mL glass beaker, 20 g vitamin E acetate and 1 g of rifampin are added. The non-polymeric liquid carrier (vitamin E acetate) is then filled in the artificial cavity space or arrays created in the tissue. Briefly, 3 ml of vitamin E acetate with rifampin as above is transferred in disposable syringe without needle with male Luer lock. A 3 by 3 hollow microneedle array from Micropoint Technologies (33MP) with female Luer lock is attached to the syringe. The array is then inserted in the porcine dermal tissue. It is pulled back 80 percent of the needle length and the vitamin liquid is pushed from the syringe via array in the tissue cavity created by pulling back the needle array. The liquid is deposited and excess liquid is pushed off from the array. The array is removed and the excess liquid on the tissue is wiped off. The liquid filled cavities in the injected areas release the drug from liquid carrier Vitamin E acetate. If desired a band aid type layer may be applied on the treated area or tissue sealant like fibrin glue (TISSEEL® or EVICEL®) or DuraSeal® surgical sealant available commercially. The sealant may prevent unnecessary movement of the liquid microimplant array during routine physical activity like walking, running and the like.

In another embodiment, 1 g of vitamin E acetate is mixed with 100 mg of magnesium carbonate stained with tea stain. The dark colored suspension is used to fill cavities of 10 by 10 array created in sheep tissue. FIG. 19B shows a picture of liquid (vitamin E acetate) microimplant array with red colored liquid microimplants arranged in 10 by 10 array format. The stained magnesium carbonate is added as a biocompatible biodegradable visualization agent or filler.

In another modification of the above example, a biodegradable polymeric liquid (polycaprolactone polymer; molecular weight 520 g/mole) is used for drug delivery and deposition using hollow needle array. The polymer is liquid at ambient or body temperature. Briefly, in a 100 ml beaker 9 g polycaprolactone polymer and 100 mg rifampin are added until complete homogenous solution/suspension is formed (drug weight percent is 10 relative to polymer plus drug weight drug weight). The liquid polymer is then filled inside the artificial cavities as described above (using hollow microneedle array 33MP) or in this invention. The excess polymer liquid is wiped off from the tissue surface. The deposited liquid polymer delivers the drug in a sustained manner. The liquid polymer is removed from the tissue by the biodegradation process.

In another modification of the above embodiment, sucrose acetate isobutyrate solution in ethanol or NMP, a non-polymeric liquid is used in place of polycaprolactone. The solvent NMP or ethanol is added to modify the viscosity of the sucrose acetate isobutyrate. Only small amount (1-20 percent) solvent is added to make it suitable for injection using the array 33MP. The solvents used (DMSO, ethanol, NMP and the like) preferably are water miscible, biocompatible and biodegradable.

In a 500 ml flask, 18.0 g of PEG 1000 (molecular weight 1000 g/mole), and 200 ml toluene is added. Approximately 80-100 ml toluene is distilled of and the solution is cooled. 2 g of dl-lactide and 30 mg of stannous octoate are added in the flask and the solution is refluxed for 24 h under nitrogen atmosphere. The flask is cooled and the solution is and precipitated in 2000 ml cold hexane or ether. The precipitated liquid polymer (PEG1000-LACTATE) is recovered by decanting the solvent and drying under vacuum for 24 h. The PEG molecular weight and molar ratio or PEG to lactone (1-lactide, dl-lactide, glycolide, caprolactone or trimethylene carbonate) is varied to obtain liquid (liquid at 37-40 degree C.) PEG-polylactone polymers of various viscosities and degradation times. The polymers can be used as liquid carriers as mentioned previously.

In another modification of the above embodiment, oleic acid, a non-polymeric liquid is used in place of polycaprolactone. This carrier also could also be used with water miscible solvents as described above to adjust its viscosity.

In another embodiment as above, rifampin is replaced with coumarin 6 as model hydrophobic and fluorescent drug and colorant.

Example 11

General Method for In Situ Array Formulation Development.
Porosity Creation
  Porosity Creation Using Microneedle Array:
    Microneedle Array Device Variables: Device material (metal, polymeric, proteins, natural macromolecules, glass, silicon, ceramic, ice, sugars and the like), microneedle length, needle angle while tissue penetration, microneedle shape, microneedle edge shape, dissolvable or inert, number of needles, distance between needles in the array, needle volume, needle porosity (hollow or solid); microneedle backing material, array shape, array area size, density of array (needles per centimeter square or area).
  Laser Induced Porosity Variables:
    Wavelength (ultraviolet or visible or infrared), laser spot size, laser power, laser pulse frequency, pulse repetition rates, number of stacked pulses.
  Oscillating Needle Based Variables:
    Needle size and shape, oscillation frequency, needle edge, number of needles, needle materials (metal, ceramic or polymeric), tissue penetration length;
  Mechanical Drilling Based Variables:
    Drill bit size (diameter), drill bit material type, drill rotation speed, drill penetration depth.
    Injectable Composition Variable: Type of polymer, polymer molecular weight, polymer concentration in the solvent, type of solvent, solvent concentration, viscosity of composition, drug concentration, wetting agents type and amount added, microparticle size, microparticle shape and microparticle porosity, microparticle color, crosslinking chemistry, crosslinking type, precursor concentration and the like.
    Drug type (synthetic or natural organic molecule, protein, synthetic peptides), molecular weight, water and organic solvent solubility, partition coefficient, biological activity, stability in the composition, drug concertation in the composition, compatibility with non-bioactive portion of the composition.
Array in Array Device Variables:
Base Array
  Device material including base plate and needle (metal, polymeric, proteins, natural macromolecules, glass, silicon, ceramic, ice, and the like), hollow microneedle length, needle angle while tissue penetration, microneedle shape, microneedle distal edge shape and cutting angle, number of needles, distance between needles in the array, needle cavity shape and volume, lubricant on needle cavity surface, array shape, array area size, density of array (needles per centimeter square), number of guide posts and their size, protective cap for needles and its material type, spacer lock shape, dimensions and material type, force required to penetrate tissue and the like.
Plunger Array
  Device material including base plate and needle (metal, polymeric, proteins, natural macromolecules, glass, silicon, ceramic, ice, and the like), solid microneedle length, microneedle shape, microneedle distal edge shape and cutting angle, number of needles, hollow passage shape and dimension, injection port on proximal end (size and type), distance between needles in the array, needle cavity shape and volume, lubricant on needle wall surface, array shape, array area size, density of array (needles per centimeter square or area), number of holes for guide posts and their size, protective cap for needles and its material type and the like.
  Pre-formed microimplant in base array cavity or in implant holding cartridge Implant size and shape, drug concertation, number of live cells and cell type, number of live cells per unit volume, unibody materials type (hydrogel, solid, biodegradable, biostable and the like), porosity, porosity filling material, visualization agent and its concentration, other formulation specific non-drug additives like stabilizer, antioxidant and their concentration, drug encapsulation matrix, drug release rate from the implant, in vivo implant biodegradation time, implant volume, surface area and the like.

Test Substrate: Pericardial tissue, transparent or semi-transparent thermoreversible gel like gelatin gel (Jell-O like gel cast in a petri dish), sheep or porcine skin tissue, tissue based hernia or surgical patch, chicken leg muscle, cow femur, freshly harvested bovine or porcine explanted organs like eyes, hearts, arteries, and the like.

Observations that can be recorded or made by changing various variables as described above include but not limited to: The amount of composition injected per injection per needle, injection volume per injection per needle, microimplant size, microimplant shape formed, implant depth of penetration, distribution and spacing of implant formed, drug concentration in the implant, drug release rate in the injected area and the like.

The injected composition in the tissue may be assessed by histology techniques. Briefly the injected area of tissue may be cut and subjected to histological techniques (encapsulating in wax or acrylic cement or frozen tissue), drying, slicing, staining and observing microimplant size by microscope or scanning electron microscope or electron microscope. A reconstruction of 3 dimensional distribution of microimplant array size can be made from histological data.

The tissue with injected composition or gelatin gel may be dissolved in 4 percent pepsin solution 0.1M HCL for 24 h at 37 degree C. to recover implants formed in situ. The recovered implants may be analyzed for size and distribution. Laser light scattering or SEM may be used to assess particle size, distribution and shape. The gelatin gel or thermoreversible gels may be heated at around 60-70 degree C. or cooled below 10 degree C. to liquefy the gel. The implants in the liquefied gel may be filtered and analyzed.

The injected tissue with microimplant array may be isolated and incubated in PBS under sink condition at 37 degree C. to elute encapsulated drug of a period of time. The eluted drug may be analyzed by HPLC, UV-VIS spectrophotometer or other means. Rate of release (drug elution over a period of time) is then constructed from the observed data.

A statistically designed experiment (DOE) may be used to test many variables discussed above, which can help to reduce the number of experiments needed to develop a suitable drug/cell delivery array as described in this invention.

The list of variables and resulting data described above is a partial list only and should not be considered as a limitation of this invention.

Example 12

Ophthalmic Drug Delivery Composition
In Situ Deposition of Sustained Drug Delivery Composition in Corneal or Scleral Tissue Ten fresh bovine or porcine eyes are obtained from local slaughterhouse. 100 mg PLGA (50:50, molecular weight 8000-10000 g/mole or PDLG 5002 polymer), 5 mg coumarin 6 as fluorescent colorant or moxifloxacin base a model hydrophobic drug and 0.9 ml polyethylene glycol dimethyl ether are mixed in 15 ml glass vial. After complete dissolution of all components, the solution is warmed to 37 degree to reduce its viscosity. 20 microliter of the solution is applied on the scleral tissue. AdminStamp 600 Microneedle Array Device with 187 five hundred micron tall stainless steel microneedles or 33MP array are applied pressed on the tissue (needles facing scleral tissue) where solution is applied. The device is pressed until complete penetration of needles in the tissue. The device is rotated 180 degree while inserted in the tissue to form circular holes. The process is repeated (solution, application of needles, rotation and removal of needles from the tissue) two times on the same area. The excess solution wiped off. A 100 microliter of PBS is applied 3 times to induce polymer precipitation in situ. The deposited solution precipitates in the scleral tissue and entrapped drug in the precipitated polymer is released in a sustained manner. In another example, another eye is used to deposit or inject dexamethasone loaded microspheres suspension in PBS (size less than 50 microns, drug loading 20 percent, PLGA 50:50 polymer, molecular weight 50000 g/mole suspended in PBS solution). The suspension is loaded in the syringe. A 3 by 3 microarray hollow needle hub from Micropoint Technologies (33MP) is attached to the syringe. The array is pressed on scleral tissue until complete penetration of needles in the tissue (needle length 300 microns by using 700 micron spacer on the needle hub). The array is pulled about 90 percent from the tissue and the suspension is pushed form the syringe to fill the space created by pulling the needle. The array is removed and excess suspension is wiped off. If needed, Resure™ ophthalmic sealant or fibrin sealant is applied on the injection area to temporary lock the suspension inside the tissue. Tissues from untreated eyes and treated eyes are cut and analyzed by histology. The drug elution from the cut section is monitored by HPLC or UV-VIS spectrophotometer and a drug elution profile is generated.

In another embodiment, an array of cavities (4 cylindrical cavities in 2 by 2 format, 200 micron dia, 200 microns height) are created using UV laser or mechanical or other means in the scleral tissue (under the eyelid). The cavities are then filled using injectable compositions such as PLGA solution with ophthalmic drugs like dexamethasone or moxifloxacin. After implant formation via precipitation or crosslinking and the like. If desired, the treatment area may be sealed using ReSure™ ophthalmic sealant or fibrin sealant. Drug can be released from the implanted array from few days to few months for many ophthalmic diseases.

In another embodiment, prefabricated microimplants may be loaded in "array in array" device (Example 22). The base array device may be inserted up to 20 to 500 microns depth on ophthalmic tissue, preferably in scleral or corneal tissue. The implants are pushed out using plunger array device is withdrawn from the tissue. If desired, an ophthalmic sealant such as Resure ocular sealant may be applied to prevent leaks and infection. It is preferred that the implanted device does not breach total thickness of cornea or scleral tissue. The preferred implant occupies/uses only 10-70 percent of corneal or scleral tissue thickness, preferably about 15 to 60 percent of thickness is used for implantation of ophthalmic implants. In one illustrative embodiment dexamethasone loaded microimplant array as described above (total dose 0.4 mg per array sustained released in 7-30 days) is used to treat postoperative pain and inflammation.

Example 13

In Situ Microarray Implants Made Using Dissolvable Arrays
Preparation of Degradable Polymer Implant Dissolvable microarray implant is made using method as described in Example 6c or obtain commercially. A dissolvable array made using hyaluronic acid is used to perforate sheep skin tissue. The array is inserted into skin tissue and allowed to dissolve. Some PBS solution may be added to assist dissolution. After complete dissolution, a suction cup and vacuum is used to aspirate biological fluids and dissolved array matter in the tissue. A polymer solution (PLGA solution (10 percent in NMP with rifampin (10 percent relative to polymer plus drug weight) is applied on the treated area and allowed to permeate in the cavity. Exposure time 1 to 10 minutes. The solution fills the cavity space created by dissolution of array. The excess solution is wiped off. The deposited solution in the cavities undergoes precipitation of polymer in the cavity forming PLGA polymer entrapping the drug rifampin. In another example, a fibrin glue components are dispensed from the duel syringe applicator (provided by the fibrin glue manufacturer). The dispense fluid is spread on the array treated area and allowed to permeate inside the artificial cavities. The excess solution is wiped of before crosslinking of fibrin components. The fibrin glue precursors deposited inside the cavity conform to the cavity shape and undergo gelation and form a fibrin clot in the cavity. If a protein such as bone growth factor is added in the fibrin glue, it gets encapsulated in the clot and released from the clot.

Example 14

Degradable Drug Delivery Microimplant Array Formed In Situ and its Drug Release Profiles
Biodegradable Polymer Microimplant Array Formed In Situ Using Microneedle Array.

Example 14A

Array Formed by Direct Injection of Injectable Composition Via Hollow Microneedle Array.

Ten pieces of 2 cm by 2 cm sheep skin tissue are incubated in 10 ml 0.25 percent glutaraldehyde solution in PBS (pH 7.2) for 24 h. The fixed tissue pieces are washed with PBS several times, wiped clean and stored in PBS in refrigerator until use. The glutaraldehyde treated tissue as above is used as a model substrate for creating porosity and forming implant in the artificial porosity. The glutaraldehyde treatment stabilizes the tissue and enables the tissue to be used in drug delivery experiments without contamination and degradation. 100 mg of Poly(dl-lactide-co-polyglycolide) (PLGA) (50:50), 0.2 inherent viscosity 0.2 dl/g from Purac Biomaterials, Lincolnshire, USA (catalog name PURASORB PDLG 5002) is dissolved in 900 mg dimethyl sulfoxide (DMSO). 0.8 ml of this PDLG 5002 solution is then mixed with 8.0 mg moxifloxacin base as an exemplary drug and 5 microliter of methylene blue solution (10 mg in 2 ml DMSO, is added as an exemplary colorant). The solution is transferred to 3 ml glass syringe. A 3 by 3 hollow microarray is (33MP) is attached to the syringe and the blue solution of PDLG in DMSO is injected in the tissue. The array needles are inserted completely and then withdrawn/pulled out to a predetermined length (80 percent of needle length) and then syringe is pressed to inject solution. The injection process is done at 15 different locations on the 2 cm by 2 cm glutaraldehyde fixed tissue. The excess solution is wiped off from each injection to remove any surface contamination. The water soluble DMSO is dissipated in the tissue, precipitating the water insoluble PLGA polymer in the artificial cavities. Total 135 micro PLGA implants with encapsulated moxifloxacin (9 times 15) are created in situ. The infused sample is placed in 3 mL of PBS (containing 0.02% Na-azide as preservative, pH 7.4). The PBS is collected at each time point and fresh PBS is added. The release is monitored several days. The collected PBS is analyzed using a UV spectrophotometer (wavelength 294 nm) to determine the moxifloxacin base concentration that is eluted from the tissue sample at the various time points.

In another variation of this method, a 3 ml suspension (60 mg of microspheres suspended in 3 ml glycerol) comprising PLGA microspheres (Rifampin encapsulated in PDLG 5002, 10 percent rifampin loading, average size 10-100 microns), is filled in the 5 ml syringe. The array needles are then pressed in tissue completely forming cavities. The syringe is then pushed to force the suspension via hollow needles into the tissue cavities. The array is pulled back and excess suspension is wiped off with the tissue paper. The glycerol is dissipated in the tissue leaving behind the microspheres inside the cavities. The rifampin inside the microparticles is released and is monitored over several time points.

Example 14B

Array Formed Using Two Step Method: Creating Artificial Cavities in the Tissue and then Infusing the Injectable Drug Delivery Composition in the Cavities The porosity in the skin tissue is first created by pressing 3 by 3 hollow microneedle (33MP) array at 15 different locations on the 2 cm by 2 cm tissue as above (135 total cavities). The PLGA and moxifloxacin, methylene blue solution in DMSO as above is poured on the treated porous area and incubated for 5-30 minutes. The excess surface solution is wiped off with tissue paper. After dissipation of DMSO by tissue, the infused solution is converted into precipitated polymer in the artificial pores created by the array microneedles. The release of profile of moxifloxacin from the formed PLGA microimplants in the cavity is monitored over several time points.

Example 14C

In Situ Drug Delivery Array Formed by Inserting the Porosity Creation Needle/Array Via Injectable Composition or Polymer Solution Layer on Tissue.

The PLGA, methylene blue and moxifloxacin solution in DMSO as above is poured on the tissue first to form a liquid solution layer on the tissue surface. A 3 by 3 hollow microneedle array (33MP) is pressed on the tissue via polymer solution layer. As the array needles penetrate the tissue and they form cavities inside the tissue, the solution that is adhered to the needles surface is carried away in the cavities during insertion process (9 injections, 135 total cavities). After complete insertion, the array is removed from the surface and excess surface solution is wiped off with a tissue paper. The infused solution in the cavity is converted into precipitated polymer in the artificial pores created by the microneedles. Care is taken that no surface polymer is present on the tissue surface. The release of profile of moxifloxacin from the formed PLGA implants in the cavity is monitored over several days.

In another variation of this method, a suspension comprising PLGA microspheres (Rifampin encapsulated in PDLG 5002, 10 percent rifampin loading, average size 10-100 microns, suspended in glycerol) is applied instead of PLGA polymer solution. The rifampin encapsulated microspheres are made per Example 3 or are obtained by spray drying method. The array is then pressed in tissue forming cavities and pushing the microspheres inside the cavity. The array is pulled back and excess suspension is wiped off with the tissue paper. The glycerol is dissipated in the tissue leaving behind the microspheres inside the cavity. The rifampin inside the microparticles is released and is monitored over several time points.

Example 15

Cell Encapsulated Microimplant Array Formed In Situ in the Tissue

Example 15A

Array Formed by Direct Injection of Injectable Composition Via Hollow Microneedle Array.

All the experiments in involving live cells and animal experiments are generally carried out in sterile environment unless mentioned otherwise (use of sterile hood and space; use of sterilized plastic and glass ware; sterile filtered liquid, tissue culture mediums and solutions; sterile handling techniques and the like). Ten pieces of 2 cm by 2 cm freshly procured sheep skin tissue are used in this experiment. The tissue is sterilized by incubating in 70 percent ethanol for 30 minutes followed by three 10 minutes incubations in sterile PBS. Chinese hamster ovary (CHO) cells (a cell line derived from the ovary of the Chinese hamster) is prepared for encapsulation in the array. Chinese hamster ovary (CHO) cells (supplied by ATCC, CHO-K1 (ATCC® CRL-9618) are thawed to 37 degree C. and transferred to a 75 centimeter square tissue culture flask containing 20 ml of ATCC formulated F-12K Medium with fetal bovine serum (final concentration of 10%). The cells are incubated at 37° C. in a suitable incubator that provides 5% CO2 in air atmosphere. The medium is changed daily. After 2-3 days and reaching full confluence, the cell culture medium is removed and cells are rinsed with 0.25% trypsin, 0.03% EDTA solution. Additional 1 to 2 mL of trypsin-EDTA solution is added and is incubated at 37 degree C. until the cells detach. The cells are centrifuged, supernatant is removed. Fibrin glue components from EVICEL® or TISSEEL (2 ml final volume) are mixed as per manufacturer instruction and transferred to sterile 5 ml centrifuge tube. The fibrin glue components are then mixed with CHO-K1 cell suspension (30 microliters, 100000 cells, exemplary live cell suspension). The mixture is vortexed and quickly transferred to 3 ml syringe. A steam sterilized 3 by 3 hollow microarray is (33MP) is attached to the sterile syringe containing cells and fibrin glue component. The microarray needles are inserted into the tissue completely, the needles are pulled back about 90 percent from the tissue and the created cavity is injected with fibrin glue and cell suspension. Care is taken that the fibrin glue is not prematurely crosslinked or gelled before injecting it into the tissue (fibrin glue gel time 1-2 minutes depending on formulation used). Those skilled in this art understand that Chinese hamster ovary (CHO) cells used in this example is for illustration only and other mammalian cells can also be used in place of CHO cells. The fibrin glue cross slinks along with the cells in the cavities in the tissue. Upon crosslinking, the array is withdrawn from the tissue leaving behind gelled fibrin glue sealant microimplant array with live cells. The cells used here are for illustration only to show that cells can be entrapped without losing viability. The cell viability in the deposited materials can be checked by cutting the treated area and using cell live-dead assay for cell viability. The viability of cells is checked in the fibrin gel using live-dead cell assay (Acridine orange and propidium iodide as dyes). The live cells appear green and dead cells appear red when entrapped cells are viewed under the microscope and using blue light for illumination. The cell viability also can be checked using tripan blue assay. The dead cells are stained blue and live cells appear transparent. Cell viability is generally found in the range of 60-90 percent in fibrin glue.

In another modification of above example, flask of fully-grown human foreskin fibroblasts cells (ATCC sourced) are passaged in Minimum Essential Medium (MEM)/10% fetal bovine serum (FBS) are resuspended in MEM/10% FBS and approximately 100000 cells suspended in 0.2 ml sterile PBS or MEM are carefully transferred in the 5 ml sterile tube containing 2 ml fibrin glue components (fibrinogen and thrombin the major components mixed together). The fibrin glue precursors and HFF cell suspension is injected via 33MP array in the tissue as above and upon crosslinking 2-10 minutes, the array is removed leaving behind the crosslinked fibrin glue in the cavities created by the array. The same experiment can be done on live mouse tissue. The back surface of the mouse is shaved, sterilized with iodine and then fibrin glue and mouse fibroblasts are then injected in the skin tissue as above. For humans, fibroblast cells from suitable donor or autologous HFF cells may be used.

In another experiment as above, fibrin glue is substituted with synthetic biodegradable crosslinker precursors based on PEG-lactate acrylate macromonomer is used. 2 g of PEG-LACTATE-5-acrylate prepared per Example 10D is dissolved in 8 g PBS and sterile filtered. To this solution, sterile filtered eosin y (final concentration 20 ppm), vinyl pyrrolidinone (10 microliter/ml final concentration) and triethanol amine (final concentration 90 mM) are added. 100000 HFF cells suspended in 0.2 ml sterile PBS or MEM are carefully transferred to the macromonomer solution and vortexed. The cell suspension is infused using 33MP array as above in dermal tissue or live tissue. The array needles are removed and the treated are skin is exposed to 512 nm laser (intensity 10-100 mW per centimeter square) light or high intensity white floodlight. The cell suspension undergoes polymerization and crosslinking without damaging the cells. In another embodiment, 36 microneedle array is used to make 36 cavities first and then fibrin glue components and cell mixture is infused in the cavities. The excess solution is wiped off and the solution in the cavities undergo crosslinking and form a fibrin clot inside the cavities forming a microimplant array with cells with fibrin sealant as encapsulation matrix.

In another variation, thermoreversible gelatin solution is used as a cell carrier. 1 g gelatin is dissolved in 9 ml PBS and the solution is warmed to 60-70 degree to dissolve the gelatin. The solution is cooled to 37 degree C. 2 ml of this solution is mixed with 0.2 ml sterile PBS containing 100000 HFF cells suspended. The warm mixture is loaded in syringe, attached to 33MP injector. The microarray needles are pushed in the sheep skin tissue and injected with gelatin solution with cells.

The injector is left in the skin for 30 minutes. A small portion of ice is applied to accelerate gelation of gelatin. After gelation of gelatin in the cavities, the array is withdrawn leaving behind the gelatin gel with encapsulated HFF. Other thermosensitive gel polymer such as Pluronic or PEG based polymer or n-isopropylacrylamide based polymers or copolymers may also be used in place of gelatin as long as they do not have components that are toxic to cells.

Example 15B

Array Formed Using Two Step Method: Creating Artificial Cavities in the Tissue and then Infusing the Cell Encapsulation Compositions.

The porosity in the skin tissue as used in is first created by pressing 3 by 3 hollow microneedle (33MP) array at 15 different locations on the 2 cm by 2 cm tissue as above (135 total cavities). The fibrin glue with cells suspension or PEG-LACTATE-5-acrylate solution with cells or gelatin solution with cells is applied on the tissue where cavities are created. The solution is incubated for 2-5 minutes. Air jet may be used to aid in filling the solution in the cavity. Excess solution is wiped off and the solution in the cavity allowed to gel (exposed to visible light for PEG-LACTATE-5-acrylate solution). The gelled solution in the cavity entrap cells for local or systemic therapeutic effect.

Example 15C

In Situ Drug Delivery Array Formed by Inserting the Porosity Creation Needle/Array Via Cell Encapsulation Compositions Comprising Cells.

A gelatin or fibrin glue or PEG-LACTATE-5-acrylate solution with cells is first applied on the tissue to form a layer and then 3 by 3 hollow microneedle array (33MP) is pressed on the tissue through the cell suspension. As the array needles penetrate the tissue and they form cavities inside the tissue, the solution that is adhered to the needles surface is carried away in the cavities during insertion process (135 total cavities). After complete insertion, the array is removed from the surface and excess surface solution is wiped off with a tissue paper. The infused solution is crosslinked inside the cavity and entrapping the cells.

Example 15D

Delivery of Cells Using Oscillating Needle

From a rat biopsy sample, rat cells (fibroblasts) are isolated, expanded in a culture dish and resuspended in a 1 ml PBS buffer (about 1 million cells in one ml PBS). The cell suspension is infused in the same rat skin using an oscillating needle as described before. The oscillating needle helps to infuse the cells in large surface are uniformly as opposed to single injection of cell suspension using a syringe and needle. This uniform distribution of cells using oscillating needle device can be beneficial in many stem cells based therapies.

Example 15E

Microimplant Arrays Containing Live Cells Made Using Blood Plasma Based Biodegradable Hydrogels.

Porcine pericardial tissue were cut in 1 inch×1 inch dimension and vacuum dried for 2 days. The dried tissue is cut in 1 cm×1 cm pieces and 9 holes (3×3 arrays) are made using 21G needle. The tissues with cavity are then placed on a thin glass slide. The 3T3 cells are cultured for 5 days in a standard cell culture medium and cell culture flask. The cells are trypsinized and centrifuged. The centrifuged cells are resuspended in 0.05 ml sterile porcine plasma and mixed with 10 microliters 20% triethanolamine solution. To this solution, 50 microliters of 30% PTE-050GS glutarate NHS ester crosslinker solution in PBS (20 mM pH 7.2). Crosslinker PTE-050GS is purchased from NOF Corporation, Tokyo, Japan; molecular weight 5000 g/mole, 4 arm star shaped, with terminal NHS groups and glutarate as degradable ester. The mixture is added to 9 cavities of array, excess solution is wiped from the tissue surface and the mixture is allowed to form a crosslinked gel. The crosslinker reacts with the plasma proteins and form a crosslinked gel in 10-30 seconds. The crosslinked gel with live cells are stained using Tripan blue stain solution. The live and dead cells are counted using microscope in the array at 10 random locations. The array gels had 25±10 live cells and 1±1 dead cells. The high number of live cells indicate tolerance of crosslinking reaction conditions by the cells entrapped in the gel array. It also indicates the successful formation of live cell arrays in the tissue Example 16

Preparation of Microneedle Array Comprising Cells.

Chinese hamster ovary (CHO) cells (supplied by ATCC, CHO-K1 (ATCC® CRL-9618) are thawed to 37 degree C. and transferred to a 75 centimeter square tissue culture flask. containing 20 ml of ATCC formulated F-12K Medium with fetal bovine serum (final concentration of 10%). CHO cells are used as an illustrative mammalian cell line. The cells are incubated at 37° C. in a suitable incubator that provides 5% $CO_2$ in air atmosphere. The medium is changed daily. After 2-3 days and reaching full confluence, the cell culture medium is removed and cells are rinsed with 0.25% trypsin, 0.03% EDTA solution. Additional 1 to 2 mL of trypsin-EDTA solution is added and is incubated at 37 degree C. until the cells detach. The cells are centrifuged, supernatant is removed and cells are resuspended 5 ml PBS containing 10 percent DMSO as cryopreservative agent. Silicone base MPatch™ Microneedle templates are procured from Micropoint Technologies Pte Ltd. (Singapore). The mold has following characteristics: 20 mm dia and 4 mm height. 10 by 10 microneedle 700 microns height pyramidal shaped cavities with 200 microns by 200 microns base and 500 microns pitch. The mold is washed with mild soap, sterilized using 70 percent isopropanol and used to prepare cell containing microarray. The PBS containing cell suspension is added on top to mold cavities until all mold cavities are filled with the PBS. The mold is centrifuged at 1000 rpm to drive occupy cell suspension all the space in mold cavity. The mold is rapidly cooled to −80 degree C. to freeze the PBS and cell suspension in mold cavity. Upon complete solidification of PBS solution, the array is stored at −192 or at liquid nitrogen temperature to preserve cell viability. Before use, a sticky tape is applied on the base of the needle with needles sticking out of surface. The array is removed immediately used to insert in the sheep skin tissue at room temperature or live skin tissue. The needles undergo melting at room temperature inside the tissue releasing the cells in cells which get nutrients and other essential environment inside the live tissue environment. The viability of cells inside the tissue is checked using live dead assay as mentioned before.

In another modification of above example, ATCC formulated F-12K Medium with fetal bovine serum is used in place of PBS.

In another modification of above example, human foreskin fibroblasts (HFF) cells in PBS are used in place of CHO cells.

In another modification of above example, human foreskin fibroblasts (HFF) cells in fibrin glue precursors (before crosslinking) are used in place of PBS. This produces frozen array with fibrin glue precursors. The cells stay entrapped in fibrin glue which get crosslinked upon insertion in the body under physiological conditions (pH 7.4, 37 degree).

In another modification of above example, PEG based precursors (Example 10D, 10E, 15), DMSO as a cryopreservative and cells are encapsulated in a hydrogel. The precursors are cast and crosslinked in array format with live cells. The array is stored with live cells at −192 degree C. in liquid nitrogen until use. Prior to use, the array is inserted in the tissue at around −20 degree C. in frozen state where the hydrogel provides mechanical integrity to the cells and DMSO provides protection from freezing during storage.

Example 17

Drug Release from Implanted Arrays

Example 17A

Bupivacaine Controlled Release from the In Situ Created Microimplant Array Prepared Using Oscillating Needle and PLGA Polymer Solution.

In another embodiment, bupivacaine releasing microimplants array is prepared using oscillating needle to create porosity and infuse polymer solution in the porosity. Briefly 172 mg PLGA polymer (PDLG 5002) is dissolved in 1.75 ml DMSO. 0.75 ml of polymer solution and 23 mg of bupivacaine base is mixed, the solution is applied on the glutaraldehyde fixed bovine pericardium tissue. A commercial tattoo machine needle (permanent make up machine needle) is used to create porosity and drive the solution inside the tissue. The needle is moved on one square centimeter area. The machine needle oscillated at 6000 minutes per minute. After about one minute, the machine is stopped and excess bupivacaine solution is wiped off from the tissue surface. Care is taken to ensure that no polymer sample is precipitated on the tissue surface. A control sample is prepared/tattooed using identical conditions where only polymer solution in DMSO without drug is used for infusion.

The treated areas (bupivacaine treated and polymer treated control) are cut from the tissue and are subjected to drug release in PBS at 37 degree C. for several days. The concentration of bupivacaine in the eluted samples is monitored using UV spectrophotometer (absorbance monitored at 262.5 nm). A bupivacaine base release profile elution curve is shown in FIG. 13 along with polymer. The microimplants created by oscillating needle successfully penetrated the tissue and infused the drug in the tissue. The DMSO is dissipated in the tissue leaving behind PLGA polymer along with hydrophobic bupivacaine base. The release from the precipitated polymer is shown in FIG. 13. It is clear from the FIG. 13 that the bupivacaine is released in a sustained manner for few days.

Example 17B

In Situ Created Micro Array Implant Containing Drug Encapsulated Microspheres.
Microarray Implants Filled with Rifampin Encapsulated Microspheres.

Rifampin containing red/yellow microspheres are prepared using spray drying method or prepared according to Example 3. Microspheres are prepared using PLGA polymer (PDLG 5002 from Purac) polymer with 20 percent rifampin loading relative to the polymer plus drug weight. Control PLGA microspheres without rifampin are prepared under identical spry drying conditions. 4.9 mg of rifampin encapsulated microspheres are suspended in 0.25 ml glycerol. One/two drops of the suspension are added on the 2 by 2 cm glutaraldehyde fixed sheep tissue. The 33MP microarray needles are pressed on the tissue via rifampin suspension to create 3 by 3 micro array cavities and infuse the cavities with the rifampin microspheres. The procedure is repeated 9 times on the same tissue at different locations to create 135 micro cavities loaded with rifampin microspheres. The excess suspension is wiped of using tissue paper. No loosely adherent microspheres in the tissue are noticed. The glycerol in the suspension is dissipated in the tissue leaving behind the microspheres in the cavities. Identical procedure is used to incorporate control microspheres without drug. The rifampin treated tissue and control tissue are incubated at 37 degree C. in 3 ml PBS and rifampin in treated and control samples is monitored at various time points. Rifampin concentration in the eluted samples is analyzed using UV-VIS spectrophotometer (wavelength 474 nm). Release of rifampin from the treated tissue and control sample is shown in FIG. 14. The treated samples show a sustained release of rifampin from the in situ formed micro array implants and as expected, control samples did not show any significant release of rifampin.

Example 18

Microencapsulated Islets in Sodium Alginate
Immunoisolation of Islets in Alginate Crosslinked Hydrogels 1.6 g sodium alginate (molecular weight 277000 g/mole, 67 percent gulnuronic acid) content is dissolved 100 ml HEPES buffer pH 7.4. Separately freshly obtained islets are centrifuged and the pellet is washed with HEPES buffer. The process is repeated until pellet is free from calcium ion from the culture media. 1 ml of the alginate solution is mixed with rat islet cell suspension (10000 islets) and mixed thoroughly. The cell suspension is fed via a syringe pump and atomized through an atomizing apparatus. The condition of the apparatus (air pressure, nozzle diameter and the like are adjusted to get 100-500 micron size droplets) and are collected in 1.1 percent calcium chloride solution to form calcium alginate microspheres containing live islet cells. The microspheres are filtered and washed with 0.5 and 0.25 percent calcium solution and incubated for 3 minutes in CHES-buffered 1.1 percent calcium chloride, and again washed with 1.1% calcium chloride solution. The microspheres are incubated in poly (L-lysine) (a 0.1% solution of molecular weight 20100 g/mole; in 10 mM HEPES-buffered saline, pH 7.4, Sigma) for 8 min and subsequently washed with HEPES-buffered saline (HBSS). The viability of the islets is checked using tripan blue assay. For additional information on microencapsulation of islets, please refer to E. C. Opara et al.; Methods Mol Biol., Volume 1001, page 261-266 (2013), cited herein for reference only.

The islets containing microspheres are inserted in 1000 micron dia and 600 micron height cavities (36 cavities) in the sheep skin tissue and the cavity is sealed using fibrin sealant or DuraSeal sealant. The diameter of encapsulated cells microparticles must be less than the cavity size diameter to ensure entry of cells in the cavities.

Example 19

Formation of Implanted Array in the Tissue Using "Array in Array" Device.

Example 19A

External Formation Cylindrical Microimplant Suitable for Implanting Using "Array in Array" Device and Implanting them to Form a Drug Delivery Array.

25.2 mg bupivacaine base, 49.9 mg PDLG 5004 polymer and 0.45 ml tetrahydrofuran (THF) are mixed to prepare a bupivacaine base coating solution (copolymer of DL-lactide and Glycolide in a 50/50 molar ratio and with an inherent viscosity midpoint of 0.4 dl/g). 10 mg bupivacaine base, 49.8 mg PDLG 5004 polymer (PLGA copolymer 50:50 lactide to glycolide ratio) and 0.45 ml tetrahydrofuran are mixed to prepare a bupivacaine base coating solution (20 percent drug solution). 49.9 mg PDLG 5004 polymer and 0.45 ml tetrahydrofuran are mixed to prepare control coating solution with no drug (control solution). Six 30 cm long, 100 micron diameter twisted submucosa tissue threads are washed 3 times using distilled water and then finally with acetone and dried at room temperature for 24 h. 2 pieces each are incubated for 5 minutes in 50 percent, 20 percent and control solutions, dried at room temperature for 15 minutes. The process is repeated three times and coated threads are dried under vacuum for 30 minutes. One piece of thread is incubated in 3 ml PBS (pH 7.4) and bupivacaine base release is monitored at 37 degree C. for 5 days. Fresh PBS is exchanged for at every time point and the bupivacaine concentration is monitored using UV spectrophotometer (absorbance measurement at 262.5). Release profile for other threads is obtained using same procedure. Bupivacaine base release from the control (triangles), 20 percent bupivacaine coating (solid circles) and 50 percent bupivacaine coating (rectangles) is shown in FIG. 17. As expected, the control sample did not show any release of bupivacaine. The threads coated with 20 and 50 percent solution provides sustained release of bupivacaine up to 72 hours. The coated threads as above are cut using microtome machine to produce coated microcylinders (approximate 100 mm diameter and 1000 micron length). The cut microspheres are placed in hollow cavities of microneedle array (similar to "base array" as described in FIG. 6A, 10×10 hollow stainless steel microneedle array with 1200 mm needle ID, 1200 mm needle length, 1 mm distance between each needle). The array needles are inserted in the porcine skin tissue. Using a wire/rod (1000 micron OD), each microcylinders is pushed out of the hollow cavity in to the tissue. After pushing all the 100 microcylinders, the array is pulled out from the tissue leaving behind 100 microimplants in an array format in the tissue. A total of 300 microimplants are inserted which provides a cumulative length of 30 cm thread which is used in drug release study. The porcine tissue is cut and bupivacaine release is monitored as above.

Example 19B

Casting of Implants in "Array in Array" Device and Implanting them in the Skin Tissue In another modification of above embodiment, the needles of the 10 by 10 array as used in Example 19A are inserted in 0.5 mm thick leather sheet. The drug/polymer coating solution as above is poured into the hollow cavities of the array. Since the other end of needles are blocked using a leather, the solutions pools into the cavity. Excess solution is wiped off and the solvent is evaporated under vacuum leaving behind PLGA implants with bupivacaine in the cavity. The array is removed from the leather and is then inserted in the porcine dermal tissue. The cast PLGA implants in the hollow cavity of the array are then pushed out in the skin tissue using a wire/rod as above to form PLGA based biodegradable polymer implant array. In another modification of above example, THF in the coating solution is replaced with dioxane and the solution is poured in cavities of the array and cooled to −5 degree C. and lyophilized to remove dioxane completely, leaving behind the lyophilized PLGA implant in the array cavity. The lyophilized implant is inserted in the skin tissue to form a microimplant array as discussed previously.

Example 20

Biodegradable Arrays Made from Crosslinked Synthetic Biodegradable Polymers.

Example 20A

Biodegradable Microneedle Made from Polyethylene Glycol Based Macromonomers
Use of UV Initiated Polymerization of Biodegradable Macromonomers to Produce Biodegradable Implantable Microarray with or without Drug 3 g of PEG-LACTATE-5-acrylate diacrylate prepared per Example 10D is dissolved in 9 g PBS. 300 mg Irgacure 2959 is dissolved in 700 mg n-methyl pyrrolidone. 50 microliter of Irgacure 2959 solution is added to the PEG-LACTATE-5-acrylate solution and 100 mg heparin as model water soluble drug is added to the solution. The solution is transferred to a 50 ml Schlenk tube and subjected to three freeze-thaw cycles under vacuum 3 times to remove dissolved gases from the solution. The solution is sterile filtered using 0.2 micron filter. The sterile solution (precursor solution) is filled inside sterile cavities of MPatch™ Microneedle array. The excess solution is wiped off from the mold surface and spun for 5 minutes at around 5400 rpm. The solution is exposed to long UV ultraviolet light (Black-Ray UV lamp, 360 nm light, 10000 mW/cm2 intensity) for 5 minutes to photopolymerize and crosslink the infused precursor in the array cavities. The crosslinked array is air dried. A polyester one side adhesive tape is attached to the base of dry crosslinked PEG gel and the array is removed from the mold cavity. The array has sharp needles which can be inserted in the skin or tissue. In one embodiment, array is made with no drug.

To further improve mechanical strength and hardness of tip, the precursor array solution is mixed with biocompatible and biodegradable inorganic or organic filler materials, especially at the tip of the array are used. In one embodiment calcium carbonate or magnesium carbonate powder (size less than 300 microns) is used. Two precursor solutions are prepared. One solution has 100 percent (relative to precursor macromonomer weight) magnesium carbonate is added and the other solution did not have any magnesium carbonate added. The magnesium carbonate precursor solution is added into mold, crosslinked via UV initiated polymerization, dried and the array is produced. This array has 20 percent magnesium carbonate fine particulate salt added as biocompatible biodegradable filler to increase stiffness of the array. In separate experiment, the precursor with magnesium carbonate is added first and added only up to 10 percent of the cavity volume is filled (tip of the array) and spun for 2 minuets. The second solution without magnesium carbonate is then added to the array cavity on top of the first solution and cavities are filled completely. The excess solution is wiped off and the mold is spun for 5 minutes and then exposed to light. The precursor undergoes polymerization. The crosslinked product is dried in the mold and removed with the polyester tape backing as above. The crosslinked array has magnesium carbonate reinforced tip at the bottom of the tip which helps to insert in the skin tissue.

In another embodiment, magnesium carbonate in the above is replaced with rifampin loaded microspheres. The biodegradable microparticles/microspheres serve as a reinforcement of the crosslinked hydrogel matrix as well as sustained release carrier for drugs. In another embodiment, sodium hyaluronate or other water soluble biocompatible polymers are added to reinforce the gel for improved mechanical properties.

Example 20B

Use of Visible Light Initiated Polymerization of Biodegradable Macromonomers to Produce Biodegradable Implantable Microarray with or without Drug In 100 ml beaker 3 g of PEG-LACTATE-5-acrylate diacrylate prepared as above is dissolved in 9 g PBS. In another 10 ml glass vial, 300 mg eosin Y is dissolved in 700 mg n-vinyl pyrrolidinone. 30 microliter of eosin y solution, 1 ml of 5 M triethanol amine in PBS are added to PEG-LACTATE-5-acrylate solution. The solution is degassed using three freeze thaw cycles. (the solution is cooled in liquid nitrogen and vacuum is applied and the frozen solution is warmed at room temperature under vacuum). The solution is sterile filtered and protected from light using aluminum foil. The precursor solution is added on top of MPatch™ Microneedle array mold and spun for 10 minutes (5400 rpm) to infuse the solution completely in the mold cavities. The infused solution is crosslinked by photopolymerization by exposing it to 512 nm laser (argon laser, intensity 100 mW per centimeter square) light or high intensity white floodlight. The light polymerizes and crosslinks the PEG-LACTATE-5-acrylate monomer and forms a gel in the mold. The gel in the mold is air dried. A polyester adhesive tape is attached to the base of the array needles and the array is removed gently from the mold. The array has sharp tip and is biodegradable if implanted in the skin tissue. Cells or drugs may be added to crosslinked gels for sustained release. Also, biodegradable microparticles/microspheres with or without drug encapsulation may be added (5 to 80 percent of gel volume) in the array.

Example 20C

Synthetic Biodegradable Crosslinked Hydrogel Based Arrays for Implantation.
Use of PEG Based Crosslinked Hydrogels.
PEG Based Crosslinked Hydrogel Arrays Made by Condensation Polymerization Reaction of Precursors Comprising Nucleophilic and Electrophilic Reactive Groups.

In a 50 ml beaker, 1 g of tetrafunctional star shaped amine terminated polymer, molecular weight 10000 g/mole with terminal amine groups (available from Laysan Bio, Inc. AL, PEG10K-4Amine) is dissolved in 4 g PBS (20 mM, pH 7.4). Separately, 1 g of PEG10KARM glutarate NHS ester is dissolved in 4 g PBS (20 mM pH 7.6). 20 microliter of above amine solution is mixed with 20 microliter solution of NHS ester and the gel time is checked. If the gel time is too fast (within 30 seconds, pH of the PBS used in PEG NHS ester is changed to mildly acidic to mildly basic region (pH 6.8 to 7.8). If too slow polymerization or crosslinking, the pH is adjusted to basic side (up to pH 7.8). The pH can be adjusted using 1 N HCl or 1 N NaOH. The gel time is adjusted to about 60-120 seconds. Both solutions are sterile filtered, degassed and then mixed and filled immediately in the mold and spun for 2 h and then air dried. The crosslinked gels array is attached to polyester tape with adhesive and is removed from the mold. The array has PEG based synthetic crosslinked hydrogel which can be inserted in the tissue.

The array can be reinforced at the tip using magnesium carbonate as a filler as described above. The PDLG 5002 based biodegradable microparticles/microspheres may be added with or without drug as a mechanical reinforcement agent and/or sustained drug release agent. The biodegradable microparticles may be added at 5 to 80 percent of gel volume in the array. In another embodiment, sodium hyaluronate or other water soluble biocompatible polymers are added to reinforce the gel for improved mechanical properties.

Example 20D

Array Produced Using Melted Polyethylene Glycol Polymer with or without Reinforcing Agent Polyethylene glycol, molecular weight 35000 (PEG35K) is used in this experiment. 5 g of PEG35K and 20 mg rifampin are mixed. The polymer is melted until drug is completely dissolved, degassed the melted polymer using three freeze-thaw cycles and poured into silicon rubber mold as used above. The mold is preheated to 60 degree to avoid premature cooling inside the cavity. The melted polymer is added in the mold cavities and excess polymer is wiped off. The mold is then spun at 5400 rpm 60 degree for 2 hours under heated chamber maintained at 60 degree for 1 hour and cooled. The base material is attached with the polyester tape and the PEG based array is removed from the mold. The melted material is also degassed under vacuum prior to use. The melted polymer has higher density and sharp tips. The array can be inserted in the skin where PEG is dissolved in the tissue producing a cavity.

In another variation of above embodiment, rifampin encapsulated PDLG based microspheres are added 20 percent of the weight of PEG (weight percent can be varied from 1 to 80 percent of the PEG, preferably 5 to 50 percent). The rest of the procedure is same as before. This produces melted PEG based microarray with drug encapsulated microspheres. In another variation, PEG is added with sodium chloride powder (pre sieved and used 300 microns or less fraction, weight percent may vary from 5 to 80 percent) as reinforcing agent for PEG polymer. Other water soluble biocompatible inorganic or organic solids (sugars, amino acids and the like) may also be used as filler. The use of inorganic filler increases stiffness and improves use of insertion. In another variation, an injection molding method is used to prepared PEG based arrays. In another variation, the same material is used as a base material instead of tape. The inserted material in contact with the tissue is dissolved leaving behind the base material.

In another variation of this embodiment, Pluronic F127, Pluronic F68, Tetronic 908, Pluronic F108 is used as water soluble low melting polymer.

In another embodiment, an exemplary polyethylene glycol-co-polylactone copolymer, PEG-polylactate polymer that is water soluble and low melting (melting point less than 70 degree C.) is used to prepare the array.

Example 21

Implanted Arrays Made Islets of Langerhans.

Example 21A

Preparation of Array Containing Islets of Langerhans in the Skin Tissue Using Two Step Methods
Preparation of Artificial Porosity Using Dissolvable Array or Removable Array Sodium hyaluronate based dissolvable array is a gift from Micropoint Technology. The array is applied using an applicator provided by the manufacturer. On a shaved sheep skin, the 20 microneedle array (FIG. 22A) is applied on the tissue to create multiple cavities. The needles of the array penetrate the skin and produce micro cavities replicating the shape of array needles. Rat islets are isolated from rat pancreas tissue are cultured in RPMI 1640 medium (GIBCO) (10 mM (4-(2-hydroxyethyl)-1-piperazineethanesulfonic acid, HEPES buffer with 10% fetal bovine serum and 1 percent antibiotic-antimycotic mixture). Separately, in a 100 ml beaker 3 g of PEG-LACTATE-5-acrylate diacrylate prepared per Example 10D is dissolved in 9 g PBS. In another vial, 10 ml glass vial, 300 mg eosin Y is dissolved in 700 mg n-vinyl pyrrolidinone. 30 microliter of eosin y solution, 1 ml of 5M triethanol amine in PBS are added to PEG-LACTATE-5-acrylate solution. The solution is sterile filtered and protected from light using aluminum foil. About 1000 islet cells maintained in culture media are centrifuged at 100 g for 1 minute to produce a pellet. The supernatant media is removed and the islets are resuspended in one ml sterile PEG macromonomer solution containing eosin and triethanol amine. The fluid from the porosity created in the skin tissue is aspirated and the islets suspended in macromonomer solution is applied on the area where porosity is created. The solution is incubated for 2-10 minutes and islets are allowed to infuse in the artificial cavities. The cavity size (average diameter) is substantially higher than the size of islet cells. The excess solution from the skin tissue is wiped off and the infused solution is crosslinked by photopolymerization by exposing it to 512 nm laser (argon laser, intensity 100 mW per centimeter square) light or high intensity white floodlight. The light polymerizes and crosslinks the PEG-LACTATE-5-acrylate monomer and forms a gel in the mold entrapping the islets of Langerhans in the gel. The polymerized gel is permeable to tissue fluids and nutrients as well as insulin. The treated area is further treated with macromonomer solution without islets to seal the treated area. Alternatively, fibrin sealant can be used to seal the treated area. The treated section is cut and viability of langerhans is checked using standard live-dead cell assay available from Molecular Probe or Thermo Fisher Scientific. The live cells appear green and dead cells appear red when viewed using microscope.

An identical experiment is conducted on live rat tissue. Briefly rats are made diabetic by injecting 50 mg/kg streptozotocin dissolved in a citric acid buffer solution (pH 4.5). Rat with blood glucose levels 300 mg/dL are used for the study. Diabetic rats are anesthetized and shaved on the back. The porosity is created on the shaved area as above and rat islets are infused in the porous cavities. Three groups treatment are created containing 5 animals each. One group received the porosity treatment using dissolvable microneedles but no islet infusion (control group). The second group (control B) are treated with dissolvable microneedles followed by islet solution incubation for 5 minutes. The excess solution is wiped of and the treated area is sealed using PEG macromonomer solution and polymerized as above. Control B has islets in the artificial cavity but no encapsulation matrix to protect against immune cells. In the third group (treatment group), the islets are infused in the cavity along with macromonomer solution as above and sealed using the same macromonomer solution. The treatment groups had islets encapsulated in immunoprotective gel made of PEG macromonomers. Control B and treatment group received approximately 2500 islets per rat. Glucose levels are monitored each rat in and all groups are monitored for one month. Other method of cavity creation methods described in this invention in place of dissolvable array to create cavities may also be used.

Example 21B

Preparation of Array Containing Islets of Langerhans in the Skin Tissue Using Two Step Methods
Preparation of Artificial Porosity Using Hollow Needle Microarray and Filling the Cavity Using Islets of Langerhans.

In a 100 ml beaker 3 g of PEG-LACTATE-5-acrylate diacrylate prepared per Example 10D is dissolved in 9 g PBS. In another 10 ml glass vial, 300 mg eosin Y is dissolved in 700 mg n-vinyl pyrrolidinone. 30 microliter of eosin y solution, 1 ml of 5 M triethanol amine in PBS are added to PEG-LACTATE-5-acrylate solution. The solution is sterile filtered and protected from light using aluminum foil. About 5000 islet cells maintained in culture media are centrifuged at 100 g for 1 minute to produce a pellet. The supernatant media is removed and the islets are resuspended in one ml sterile PEG macromonomer solution containing eosin and triethanol amine. The solution is loaded in sterile 3 by 3 hollow microneedle array (33MP). On a porcine skin tissue, the array needles are firmly pressed against the tissue and all needles are completely inserted in the tissue. The needles are pulled back about 800 microns (about 80 percent of the needle height) and the polymer-islet suspension is injected in the tissue to fill the cavity. This process is repeated 15 times at different tissue locations creating 135 microneedle cavities filled with macromonomer solution. The treated area is wiped off using tissue paper to remove surface solution. The treated area is exposed to argon laser light (513 nm) for 2 minutes to crosslink the macromonomer in the solution. The treated area is covered with 0.2 ml macromonomer solution without islet cells and exposed with light to seal the treated area.

In another embodiment, alginate encapsulated islets are used in place of islets alone. The alginate encapsulation matrix provides Immunoprotection to the islets.

Example 22

Microimplants Array Implanted Using "Array in Array" (AIA) Device

Example 22A

Fabrication of "Array in Array" Device.
Design 1

The 33MP hollow microneedle device from Micropoint is used. The female hub of the device is cut using a diamond cutting wheel at the base of the hub leaving behind 3 by 3 array needles attached to 1 mm thick disk. The needles are 1 mm in height attached to stainless steel 1 mm disk. This part serves as a base array as described in FIG. 6A. The hollow cavities of the needle are coated with silicone oil to help in casting process. 1 ml of EasyCast® Clear Casting Epoxy precursor resins are mixed (epoxy resin and amine hardener). The hollow metal part is transferred to a paper cylinder and the resin solution is poured over the needles and its base. The resin is added to create a 1 mm thick disk upon casting. Upon curing, the cured resin disk and its array needles are removed from the bottom hub. The solid needles of epoxy cast resin are polished to reduce its diameter so that it can easily be inserted in the needles of hollow needle array. The cast portion of array represents plunger array as Described in FIG. 6B. In another variation, instead of epoxy resin, a light curable dental cavity filling resin or ethylene glycol dimethacrylate with Irgacure 2950 as UV light photoinitiator is used in place of epoxy resin. The monomer solution along with UV photoinitiator is added on the mold as above and cured using 360 nm UV light for 5 minutes. The cast array made of photo cured methacrylate polymer or dental resin can be used to push the implant out as described below. In another example, two part silicone rubber precursor SYLGARD® 184 (Dow Corning) is cast inside the array to make a rubber based plunger array.

Design 2
AIA Array Made Using Rigid Stainless Steel Base Plate

In another embodiment, an "array in array" device described according to FIG. 6 is made. The base array design is shown in FIG. 6A. A stainless steel plate, 1 mm thick and 20 mm length and 20 mm width is used. At the center of the plate 25 holes with 0.55 mm dia are drilled in the 5 by 5 matrix format. 25 hollow needles 0.55 mm OD and 0.31 ID with sharp cutting edge are inserted in each hole. The needle length protruded perpendicular to plate surface and 1 mm height (needle height) from the surface. The needles are adhesively joined to the plate surface. 4 guide posts (2.5 mm dia cylinders) are also attached along the periphery and at the center of each side of the plate. The excess length from other end of plate surface is cut and polished exposing the cavity holes on plate surface. FIGS. 15A and 15B show illustrative images of the fabricated base array with 25 hollow microneedles with 1 mm length and 0.31 mm diameter.

The plunger array is prepared in a similar manner (Design 2 shown in FIG. 6B) as base array. A stainless steel rectangular plate, 3 mm thick and 20 mm length and 20 mm width is used. At the center of the plate 25 holes with 0.3 mm dia are drilled in the 5 by 5 matrix format. The matrix position and format is same as base array needle format. 25 hollow SS wires (OD 0.3) are inserted in the holes. The solid needle length protruded perpendicular to plate surface and 1 mm height (needle height) from the surface (total wire length including plate thickness is 2 mm). The end of the wire is flat and does not have sharp edge. The purpose array is to push the implant from base array cavity volume. The plunger needles are adhesively joined to the plate surface. 4 guide holes (2.6 mm dia) are also drilled along the periphery and at the center of each side of the plate (position identical to guide posts). The excess length from other end of plate surface is cut and polished. FIGS. 15C and 15D show the illustrative fabricated plunger array with 25 hollow microneedles with 1 mm length and 0.3 mm diameter.

When plunger array is kept on top of base array without insertion, the position of each array needle matches with each other and the plunger array needles can insert inside the base array cavity needles (FIG. 15E). A spacer plastic sheet, 2 mm thick, is kept on base array top surface. The presence of spacer sheet prevents insertion of plunger array needles into base array needle cavities. After removal of spacer sheet, the aligned needles of plunger array enter the cavity of corresponding base array microneedle (FIG. 15F).

Design 3
Flexible AIA Array

In another variation of AIA apparatus, the stainless steel base plate in the bottom and/or top array is replaced with flexible rubber/plastic like material. A 1 mm thick polyurethane foam or polystyrene foam is cut into 20 mm by 20 mm rectangular pieces. Twenty five 24 gauge syringe needles are inserted in the foam in a 5 by 5 format with needle to needle distance is kept at 2 mm. SYLGARD® 184 (Dow Corning), a two component clear curable silicone elastomer is used. The base material of SYLGARD® 184 is mixed with a curing agent in 10:1 (SYLGARD®-to-curing agent ratio). The mixture is then degas sed for 10 min and added on top of foam and needle until (final liquid thickness 1 mm). The silicone rubber is cured for 48 h until soft elastic transparent rubber is obtained. The cured rubber along with its needle is lifted from the foam. One side of the silicone rubber had 1 mm long 24 gauge needle in 5 by 5 array format and other side has excess needle material which is cut along the surface of the cut, thus creating 25 openings of cavities on rubber surface. Similarly, plunger array needles in the same pattern as hollow needle are cast using 0.3 mm stainless steel wire/rod with 1 mm needle length and excess rod is cut from the rubber surface. The plunger array needles fit inside the hollow cavity of base array. Silicone rubber being flexible, it can potentially help to use on curved surface of the skin in actual practice.

Both the base array and plunger arrays can be used in various configurations and some preferred embodiments are discussed below.

Design 4
Use of Microimplant Cassette/Cartridge

In this modification, the drug/cell loaded microimplant is loaded or cast inside a separate cartridge (separate from base and plunger array) which may be manufactured, sterilized and packaged separately than AIA device or it may be pre-inserted, pre-aligned and deployed along with AIA device. The cartridge has base plate with holes/cavities whose internal diameter shape is same or slightly less than the holes in the base array. The array arrangement (5 by 5 as an example is same as base array). Holes in the cartridge are partially or completely filled with prefabricated drug/cell based unibody microimplants. The cartridge is placed on top of base array plate with center of holes in cartridge are aligned the holes on base array plate. The plunger array needles are then aligned with cartridge implant center, pushed. The plunger array pushes the cartridge microimplants via base cavity needle cavity into tissue. Once in the skin/tissue, the base array, cartridge and plunger array are removed leaving behind the implants in the cartridge in the skin/tissue.

The cartridge has a base plate with holes to store drug/cell implants and optionally a protective covering on top and bottom plate to prevent movement of implant during storage and handling. The part of the protective covering may be made from water soluble or biodegradable biocompatible polymer. A stainless steel rectangular plate 500 microns thick and 20 mm length and 20 mm width is used. At the center of the plate 25 holes with 0.29 mm dia are drilled in the 5 by 5 matrix format.

The matrix position and format is same as base array needle format as shown in design 2 above. The plate is kept on Teflon sheet and the holes of the plate are filled with PEG based macromonomer solution with photoinitiator (Example 10) and bupivacaine loaded PLGA microspheres (20 percent loading). The monomer solution/suspension is exposed to long UV light (360 nm). The polymerization forms biodegradable hydrogels inside the holes with drug loaded microspheres. The water in the hydrogel is removed by lyophilization. A protective polyester sheet is placed at the bottom of cartridge plate. The plate with solid lyophilized microimplants with diameter 0.29 diameter is placed on top of base array plate with center of holes matching the center of base array cavity holes and the protective cover is removed. The base array needles are then inserted in the sheep skin tissue and the plunger array is kept on top of cartridge array where center of plunger needles aligns the center of cartridge implant/holes. The plunger array is pushed downward which pushes the hydrogel implant via base cavity array into tissue. The base array along with cartridge and plunger array are removed from the tissue leaving the hydrogel implant for local or systemic drug therapy. The stainless steel plate of cartridge can have holes for alignment which can be used with guiding posts on the base array surface.

In another variation prefabricated cylindrical implants such as shown in FIG. 15H are used. To hold the implant in place, the base plate bottom surface has been spray/dip coated with collagen or gelatin film foam. The implants are pushed and the coated film/foam is removed just prior to use. In another embodiment same as above, the protective foam cover is not removed but is cut/stamped out by the plunger array and is transported inside the tissue and implanted (in this case plunger array needles have a cutting edge to stamp out the foam). The gelatin/collagen is safely removed by the body by biodegradation process.

In another embodiment, biodegradable polymer implant (PLGA implant) is cast from a solution in situ, solvent is removed and the microimplant is inserted in the tissue as discussed before.

In another variation, stainless steel base plate in the cartridge is substituted with silicone rubber sheet with holes for guide posts for alignment.

Example 22B

In Situ Formation of Microimplant Array Using "Array in Array" (AIA) Apparatus.
Using the AIA Apparatus in a Closed Configuration Formation of microimplant array using biodegradable polymer and drug or hydrogels with live cells. In this embodiment, gelatin gel is used as a model for skin tissue. 10 percent gelatin solution is cast into 4 mm thick 1 inch diameter gel. The "array in array" device (AIA device) as discussed above is used. The base array device such as shown in FIG. 15 B and top array plunger device such as shown in FIG. 15D are used. The plunger array (PA array) needles (all 25 needles) are inserted in base array corresponding base array cavities (such as shown in FIG. 15D). In this arrangement, most of the hollow cavity space in the base array is occupied by the plunger array needles. The device such as shown in FIG. 15D is inserted in gelatin gel to create 5 by 5 array holes. The gelatin gel cannot be cored in the cavity space of base array needles because the space is occupied by the plunger array needles. Upon complete insertion, the plunger array is removed and the space/volume created by the removal of plunger array is filled by an injectable composition. 1 g of PLGA (50:50 lactide: glycolide, PDLG 5002) polymer and 10 mg of coumarin and 9 ml n-methyl pyrrolidone are mixed until complete solution. The green solution (exemplary injectable composition) is injected using a syringe in each cavity (25 total cavities). After filling the cavities, excess solution is wiped off. The cavity is exposed to 2 ml PBS solution to accelerate precipitation of the polymer in the cavities. Using a plastic rod, each precipitated microimplant is individually pushed into gelatin gel or plunger array is used to push all implants at once. The gelatin gel with PLGA microimplants is cut into rectangular shape and is photographed under blue light (FIG. 15G). The 5 by 5 array of PLGA based microimplants is clearly visible in gelatin gel and is fluorescent in nature (FIG. 15G). In another modification of above example, PLGA solution is replaced with fibrin glue precursor solution with human foreskin fibroblasts cells (HFF) (about 1 million live cells in one ml of fibrinogen and thrombin mixture). The solution is allowed to form a gel in the base array cavities and the fibrin glue gels with live HFF cells are left in the gelatin gel. A total of 25 microimplants in 5 by 5 arrangements with fibrin glue as encapsulation matrix with live HFF cells is formed in the gelatin. The gelatin gel can be substituted with live skin tissue. In another variation of above example, the empty space created in base array cavity is filled with PEG based macromonomer solution (Example 10D and 15A) are used to form soft hydrogel based arrays with live cells. Briefly, a precursor solution of macromonomer solution along with initiator, catalysts and cells (PEG based macromonomer, eosin as initiator and argon laser light; see Example 15 or 20 for additional details) is first loaded with cells, and filled in to hollow cavities of base array needles as described above and exposed to argon laser light for 120 seconds. The light polymerizes macromonomer solution into crosslinked gel which entraps the cells. The array is inserted in the skin tissue and the cell loaded implant is pushed out using the plunger array needle as described above.

In another embodiment, the base array cavities of AIA device are first filled with biocompatible dissolvable compounds such as frozen saline solution or PBS solution, sodium chloride powder, melted PEG polymer and the like. The base array is inserted in the gelatin gel and the dissolvable components is absorbed in the gel or tissue creating a space for cavity filling.

In another embodiment, base array is first directly inserted in the porcine skin tissue and the cavities later filled injectable compositions such as biodegradable polymer based solution (PLGA solution with coumarin as an example).

The precipitated polymer is left in the skin tissue after removal of base array needles.

In another embodiment, 1 ml of gelatin solution (5 percent in PBS, warmed to 60 degree C., exemplary thermosensitive precursor solution) and 100 mg of rifampin loaded microspheres are mixed and the warm solution is filled in the hollow array cavities as described above. The array is kept in refrigerator (4 degree C. for 12 h) to form gelatin gel inside the hollow cavities. The gelatin gel with entrapped rifampin loaded PLGA microspheres is pushed out in the skin tissue using the plunger array as above. The microspheres in the implanted gelatin hydrogel in the skin tissue release rifampin in a sustained manner.

Example 22C

Formation of Microimplant Array Using "Array in Array" (AIA) Apparatus.
Use of Prefabricated Implants Loaded in AIA Apparatus and then Implanted.

The base array cavities of AIA apparatus can be filled with prefabricated microimplants. In one embodiment, cut gut based fibers/threads are first coated with PLGA and coumarin based compositions as described before to obtain a coated fiber. The coated fiber is then cut into several microcylindrical rods. Average length of cut microcylinder is 496 microns and PLGA coating had a thickness of approximately 40 microns (FIG. 15H). The cut microcylindrical rods are placed inside the cavity of base array and plunger array is placed on top of base array with 2 mm polyethylene sheet as a spacer. The device is transported on top of sheep skin and bottom ray needles are inserted completely in the skin. The spacer sheet is removed and the plunger array is pushed in the base array cavities. The plunger array pushes the implant in the skin. Both base array and top array are removed from the skin tissue leaving 25 implanted rods in an array format. The implanted array can provide sustained drug delivery and fluorescent coating helps to visualize the implants in the skin. FIG. 15H shows coated microcylindrical rods in the skin tissue imaged under blue light. The image shows 5 by 5 matrix type implantation arrangement in the skin tissue with fluorescent green coating. In some cases, a pressurized saline is used to push the implant from the base array cavities in the tissue. The sterile saline solution is attached to 22 gauge needle and 0.5-10 psi pressurized saline is discharged from the 22 gauge needle in the base array cavity to dislodge the implant from the array into tissue.

In another variation, synthetic crosslinked biodegradable hydrogels (microcylindrical rods with drug encapsulated microspheres are cast as microcylindrical rods. The drug loaded hydrogels rods are placed inside the cavities of the AIA device and the injected in the skin tissue using plunger array as described above. 200 mg of PEG 35K-lactate-acrylate macromonomer (prepared per Example 10D) is dissolved in 800 mg PBS. After complete dissolution, 300 mg Irgacure 2959 is dissolved in 700 mg n-methyl pyrrolidone. 5 microliters of Irgacure 2959 solution is added to the macromonomer solution. The solution is sterile filtered using 0.2 micron filter. The sterile solution (precursor solution) mixed with 200 mg of PLGA microspheres (size 10-300 microns, 10 percent dexamethasone relative to PLGA plus drug weight) is added. The solution is filled with silicone rubber mold with cylindrical mold cavity (size 50 micron diameter, 30 micron height) or silicone base MPatch™ Microneedle templates from Micropoint Technologies Pte Ltd. (Singapore). The infused solution used then exposed to the long UV ultraviolet light (Black-Ray UV lamp, 360 nm light, 10000 mW/cm2 intensity) for 5 minutes to photopolymerize and crosslink the infused precursor solution. The polymerized hydrogel implants are lyophilized and are removed from the mold and added in microneedle cavities of base array of AIA device as above. The AIA base array device with implants in the cavity is infused in the skin tissue and the implants are pushed using plunger array or pressurized nitrogen gas or pressurized saline fluid. A 22 gauge needle connected to 0.2 micron filtered nitrogen or carbon dioxide gas cylinder and gas flow from needle is used to push each individual implant in the tissue. The base array is removed from the tissue leaving behind biodegradable hydrogel with encapsulated hydrogel implant array in the skin tissue.

In another variation, the gelatin or PLGA solution is cast first outside to form microimplants. The size of the implant is chosen in such a manner that they can fit inside in the cavities of hollow array. The externally made implants are added in the cavities of hollow array. The array is then inserted in the skin tissue and the implants are pushed out using epoxy based plunger array as above. In this embodiment, the array microimplant is made first externally and then used in the device to implant it inside the body. The implant does not need sharp edges to be inserted in body. The metal hollow array does the function of piercing the skin tissue and carrying the implant in tis cavity. The array plunger helps to push out the implant from the hollow array.

In another variation, 200 mg of rifampin loaded microspheres are filled in the cavities as a dry powder and then the powder is pushed/distributed in the tissue using the plunger array as described above. In some cases, the powder may be compacted using water soluble biocompatible and biodegradable binder like dextran or polyethylene glycol to make a unibody implant.

Example 23

Delivery of Lyophilized Protein Drug in Solid State Implanted Array Comprising Botulinum Toxin Botox® is a trade name for Botulinum toxin based drug formulation. Botox is neurotoxic protein produced by the bacterium *Clostridium* and is sold to treat variety of medical conditions. Botox is sold as a dry lyophilized protein powder with each vial containing 50 or 100 units of drug and each vial contains one nanograms of drug along with salt and other additives. One Botox vial containing 100 units is diluted with sterile 0.1 ml of 0.1 percent sodium hyaluronate (mechanical property enhancer and bulking agent) in PBS buffer and 0.1 mg sodium fluorscein (as a coloring/fluorescent agent). The 3.53 microliter of the Botox solution is loaded 100 cavities of base array of 10 by 10 AIA apparatus as discussed in Example 22. The apparatus has 100 cylindrical cavities with 500 microns height and 310 microns diameter. The solution is lyophilized in the cavities at −5-10 degree C. for 72 h. A 10 by 10 plunger array of the AIA apparatus is applied on top of the base array aligning its needle but not inserted. A polyethylene 2 mm spacer is kept between the bottom and top array to prevent accidental insertion of plunger array in the base array. Each 100 array needle contain approximately 3.53 units of Botulinum toxin. The device is terminally sterilized and used on the skin tissue. During usage, the base array needles are inserted in the tissue, spacer is removed and the plunger array is pushed to inject the fluorescent implant in the tissue. Once injected, both the arrays are taken out leaving behind the implant in the tissue. Under blue light, implantation of the injected microimplant array is visible as green array. Multiple arrays may be used to treat more areas on the skin if needed. The sodium hyaluronate and fluorscein dissolve away leaving behind Botulinum toxin for therapeutic effect. This method delivers Botulinum toxin in solid state without dilution in saline as used in current practice.

In another embodiment, the Botulinum toxin is mixed with precursors of crosslinkers such as fibrin sealant and PEG-lactate macromonomer solution and crosslinked to produce biodegradable hydrogel implant with encapsulated Botulinum toxin. The encapsulated implant is then delivered using AIA apparatus as before. The Botulinum toxin is released in a sustained manner for therapeutic action from the crosslinked biodegradable hydrogel.

Other protein drugs such as vaccines can be delivered in the solid state using similarly to Botox as described before. It is preferred that such microimplants are colored or fluorescent for easy visualization of implanted therapeutic array. Bulking agents such as collagen, gelatin, polyethylene glycol, polyvinyl alcohol, polyvinyl pyrrolidone, hydroxy propyl cellulose, hydroxy ethyl cellulose, dextran, maltose, chitosan, human or bovine albumin, may be added to improve mechanical handling and ease of delivery. The concentration of each additive must be determined such that it gives sufficient strength and bulkiness to the implant during implantation. Generally, the concentration of additive is about 0.5 to 99 percent, typically 1 to 95 percent of the total lyophilized mass of the drug. The additive should not deactivate (not reduce or eliminate its biological activity) the Botox or other protein drug. Human serum albumin is the most preferred bulking agent for Botox.

In another modification, one hundred (200 micron diameter and 500 mm length) lyophilized collagen sponge microcylindrical implants are obtained from commercial source (puntal implants used for dry eye treatment). Alternatively, the 200 micron diameter implants can be stamped out from 500 micron thick collagen foam sponge. Botox solution (100 units) is diluted with 0.1 ml saline solution and each collagen implant is treated with 1 microliter of solution of Botox solution and the implant is immediately frozen and lyophilized. The lyophilized implant containing one unit of Botox drug is implanted in the skin tissue using AIA array (5 by 5 stainless steel array FIGS. 15A-15H) apparatus, total dose 25 units per array per treatment. Each implant from the AIA apparatus cavity may be individually inserted manually in the skin giving a dose of 1 unit of Botox per implant. The hollow microneedle array with preloaded microimplants as above may be sterilized and packaged. The package also contains a sterile metal rod to push the implant during implantation or array of rods to push all implants at once. This device and its method of implantation does not require the drug delivery implant to have sharp needle at distal end which allows more choice of materials to be used for sustained drug delivery.

Example 24

Use of Live Cells for Cosmetic or Facelift Application.
Deposition of Live Cells Using Oscillating Needle for Facelift Application.

A skin sample from a human donor is used as a source material. The skin sample is carefully treated with collagenase enzyme to dissolve extracellular matrix and the live fibroblast cells are isolated from the sample. The cells are passaged 1-20 times to expand the number of cells. The expanded fibroblast cells are isolated in a sterile manner, combined from all culture flasks to make a cell suspension containing 1000 to 10 million live cells in 1-2 ml cell culture medium. Hyaluronic acid is added in the medium as non-toxic a thickening agent. The suspension is injected at in the facial tissue or other desired area using oscillating needle device as described before. The suspension is added a visualization agent such as fluorescent dye like sodium fluorscein or fluorescent microspheres to aid in deposition. The cells are injected preferably in the same donor's tissue (autologous cell therapy) at the rate of 1 to 10000, preferably 1 to 5000, even more preferably 1 to 1000 cells per injection. The injected live cells grow and produce extracellular matrix providing face lift effect. The distribution of cells in the desired area, ability to cover large area in a small period of treatment time and ability to visualize the treated area using fluorescence of the agent provides most effective face living/cosmetic treatment.

Example 25

Drug Delivery Array Prepared Using Biodegradable Metal Magnesium Alloy Based Drug Delivery Array A 100 mm length, 100 mm width and 500 microns thick magnesium alloy (AZ31) foil is procured from Goodfellow Corporation, Coraopolis, Pa., USA (product code 343-198-08). The sheet is stamped/cut to produce 5 mm long, 500 microns wide and 500 microns thick strips. One end of the strip is ground and sharpened to have a fine cutting edge via machining (sharp edge length 50 microns). The rest of the area is used to create holes in the body of the implant (creation of artificial porosity, laser drilling, holes diameter 150 microns, 500 microns height, 6 holes in 2 by 3 matrix format). The drilled area is polished to smoothen the edges. 9 such strips are prepared. The strips with holes are dip coated in PLGA solution containing rifampin as a model drug. 0.8 g of PLGA [(50:50 lactide:glycolide, PDLG 5002)] polymer, 200 mg of rifampin and 1 ml tetrahydrofuran are mixed until complete solution. The coated red solution is dried in air and then under the vacuum. The red polymer in the holes and on the surface of the magnesium strips is clearly visible to the necked eye. The length of the needle is then reduced from 5 mm to 1000 micron with sharp edge at distal end and middle area of the 1000 long implant is occupied with 150 microns size holes filled with PLGA polymer with rifampin. 9 such implants are manually attached in 3 by 3 array format and attached to the medical adhesive tape (base side of implant is attached to the adhesive layer of the tape and other end (distal end) has sharp edge. The needle is attached perpendicular to the tape surface. Each microneedle is separated by 2 mm on the adhesive tape, has a distal sharp end and is loaded with rifampin in PLGA as biodegradable polymer. The array thus prepared as above is similar (but not the same) in design as shown in FIG. 26E. The array is pressed on an excised porcine skin tissue (sharp edge touching perpendicular to the skin surface) and the needles are inserted in the tissue. A gentle pressure is applied on the backside of the tape. The tape is gently removed from the skin surface leaving behind the magnesium based microimplant array in the tissue. The magnesium alloy provides a biodegradable metal based skeletal material that assists in skin penetration. The biodegradable polymer (PLGA) provides sustained release function to the array. The artificial porosity provides higher surface area for increased drug loading. The entire device is degradable and need not be removed once implanted.

In another modification of above embodiment, a microneedle array with hollow metal microneedle is created and the hollow cavities of the needle are filled with drug delivery compositions (FIG. 26A). A 300 microns ID and 100 microns wall thickness magnesium AZ31 alloy tube is cut at 5 mm length. One end of the tube is cut at an angle 30 degree to produce a sharp cutting edge. The tube cavity is then filled with PLGA solution with rifampin in dioxane (20 percent PLGA concentration in dioxane, 20 percent rifampin weight relative to PLGA weight). The solvent dioxane is removed lyophilization at −5 to −10 degree C. for several days. The tube is then cut to 1 mm in length with sharp edge at distal end. The hollow cavity of the tube is filled with lyophilized PLGA polymer with rifampin as a model drug. 16 such needles are prepared and are then attached to the back of adhesive tape. The base of the microneedles is attached to the adhesive layer of the tape and distal sharp end is on the other end for skin penetration. The array is formed in 4 by 4 format with distance between the needle is at 1 mm. The array is implanted in the porcine skin tissue as discussed above and the adhesive tape is removed. The implanted array delivers the drug via PLGA in the needle cavity. The metal based sharp edge that enables easy penetration in the skin and the metal and PLGA based composition is removed from the tissue by biodegradation process. Rifampin is released from the PLGA in a sustained manner.

In another modification of the above embodiment, the AZ31 foil as above is stamped/cut to produce 500 microns diameter and 500 microns height (sheet thickness) microcylinders. The microcylinders are then dip coated with rifampin solution 3 times to produce about 50 micron thick coating layer. A coating layer without the drug as a controlled release layer is applied as outermost layer. The PLGA coated microcylinders are inserted in the cavity of the base array of AIA the apparatus described in FIG. 6. The coated microcylinders are then implanted using the plunger array apparatus as described before. This microimplant array has a magnesium based biodegradable metal as a reinforcing agent which enables smooth pushing of drug delivery composition in the tissue. In another modification, a microneedle array with hybrid needle such as shown in FIG. 26C is prepared. The needle has metal based tip (2606) and drug delivery body (cylindrical body, 2607, in this illustrative case). The needle only uses metal based tip (2606) for tissue penetration and drug delivery implant body (2607) is made using biodegradable polymer or hydrogel. The body 2607 may comprise drug or live cells. The body (2607) may also be a pre-fabricated microimplant with drug or cells as discussed in this invention. The implant body 2607 may be porous and the porosity may be filled with drugs or cells. This design enables implantation of soft materials like hydrogel material with live cells. In another modification, a cage with a cavity (cavity for 2607 implant storage in this cage) and solid tip such as shown in 2606 is made and the prefabricated implant body (2607) is kept inside the cage cavity. The metal cage provides more rigidity to the microneedle structure and thus enables to insert materials like hydrogels to be implanted with little force and the entire implantation process is tolerated by the cells maintaining their viability for therapeutic use.

Although the present invention has been particularly shown and described with reference to exemplary embodiments thereof, it will be understood by those of ordinary skill in the art that various changes in form and details may be made therein without departing from the spirit and scope of the present invention as defined by the appended claims. Therefore, the present embodiments are to be considered as illustrative and not restrictive and the invention is not to be limited to the written description.

Example 26

Preparation of Porous Microimplants.
Preparation Porous Synthetic Biodegradable Polymer Microimplant.
Preparation of Porous Structure by Salt Leaching.

Example 26A

Preparation of Porous Poly(L-Lactide-Co-Caprolactone Copolymer

In 250 ml beaker, 1 g of Poly(L-lactide-co-caprolactone) copolymer (70/30; PURASORB PLC 7015 from PURAC Biochem, Netherlands) is dissolved in 10 ml 1,4-dioxane. After complete dissolution, 3 g sodium chloride (finely grounded and sieved, 75 to 125 micron particle size fraction) is added to the mixture and the suspension is vigorously stirred. The stirred liquid suspension is quickly frozen using liquid nitrogen. The dioxane is removed by lyophilization. Using a 1 mm diameter cookie cutter, 1 mm cylindrical pieces are cut from the freeze-dried polymer. The cut pieces are incubated in distilled water to 24-72 h to remove sodium chloride. The leaching of sodium chloride produces porous microimplants. Suspension could also be first poured into glass or polyethylene tube (1 mm dia) or silicone rubber tube, frozen and lyophilized to produce a 1 mm dia freeze-dried solid. The freeze-dried solid is cut into 100-2000 micron size sections and the sections are exposed to water for sufficient time (1-7 days) to extract sodium chloride substantially or almost completely or completely. By changing the particle size of porogen (sodium chloride) and its volume in the above example, porous solids with different amount of porosity and as well pore size can be obtained. Alternatively, the polymer solution in dioxane is filled in cavities of MPatch™ silicone rubber mold cavities, centrifuged to remove air bubble and uniform filling of cavities and then cooled in liquid nitrogen and then lyophilized. The lyophilized porous biodegradable microneedles are separated from the mold and can be used as prefabricated porous microimplants which can be implanted using the AIA like device. The microneedles array needles can also be applied an adhesive tape to make a microneedle array and porous microneedles can then be implanted as PLGA based porous microneedle array.

Example 26B

Preparation of Porous Structure by Leaching Out Organic Solvent Soluble Polymer.

In a 250 ml conical flask, 4 g Poly (PLGA, lactide-co-glycolide) (lactide:glycolide (50:50), molecular weight 30000 to 60000 g/mole.) from Aldrich and 4 g polyethylene glycol (PEG, molecular weight 10000 g/mole.) is dissolved in 100 ml warm dry dioxane under nitrogen atmosphere (50 degree C.). About 10 ml of the solution in filled in a test tube and the tube is frozen using liquid nitrogen. The frozen solution is lyophilized (freeze-dried) at −5 degree C. for 4-5 days to freeze-dry all the solvent (dioxane). The freeze-dried polymer is removed from the tube and is then incubated in 1000 ml beaker containing 500 ml ethanol for 7-10 days. Ethanol is replaced twice a day. The PEG, which is used as an organic solvent soluble porogen is leached out in ethanol and a porous PLGA polymer is obtained. The PLGA is further dried in vacuum at 50 degree C. for 3 days to remove trace amount of dioxane and ethanol.

Example 26C

Preparation of Porous Structure by Leaching Out Organic Soluble Polymer.
Preparation of Porous Hydrophilic Biodegradable Polymer (Collagen).

In a 250 ml beaker, 100 mg Type I collagen is dissolved in 10 ml 0.5 M acetic acid. To this solution, 10 mg of poly(ethyl methacrylate) spherical beads are added (from Polysciences, Particle size 140-220 microns) are added. The suspension is stirred and quickly frozen using liquid nitrogen. The frozen solution is lyophilized to remove water and then transferred 100 ml methanol. The poly(ethyl methacrylate) is extracted out in methanol for 7 days with fresh methanol exchanged every day. The dissolution of poly (ethyl methacrylate) by methanol creates porosity in the collagen matrix. In a similar embodiment, 10 g Poly (L-lactide) PURASORB PL 18 is completely dissolved in 100 ml dioxane. 5 g poly(ethyl methacrylate) microspheres are added to the mixture and the mixture is quickly frozen before solvent corrodes the microspheres and then freeze dried at −5 degree C. The freeze-dried product is then subjected to extraction with methanol wherein only microspheres are soluble and Poly (L-lactide) is not soluble. The extracted microspheres leave behind spherical empty space or cavities or porosity which can be used to fill other degradable polymer with drugs.

Example 26D

Porosity Using Mechanical or Laser Drilling or Injection Molding.

A high molecular weight polycaprolactone or polylactic acid cylindrical rod (1 mm diameter) is extruded or injection molded from a laboratory based plastic processing extrusion machine or injection molding machine. Alternatively the rod can be solution casted in a cylindrical mold and solvent is removed. The extruded/injection rod is cut to 0.5 mm dia and 0.5 mm length and the pieces are subjected to laser drilling or mechanical drilling. Several 25-100 microns in diameter and 50-100 microns in depth cylindrical holes are drilled on the polymer rod surface. UV, infrared or visible light based laser systems are used to drill the holes.

Example 26E

Porous structures can be made by knitting and/or weaving biodegradable fibers. Fibers suitable for implantation may be knitted or weaved to create a fabric with certain amount of porosity. The weaving and knitting pattern may be changed to create small or large amount of empty space between fibers to obtain a desirable porous volume. Additionally, fabrics may be used as a starting material to create cavities in the fabric structure.

Example 27

Delivery of in situ forming crosslinkable compositions can be performed by using oscillating needle devices. This can include delivery of a composition that crosslinks via an enzymatic pathway. The formation of fibrin gel particles can be performed in situ.

A commercially available EVICEL® from Ethicon or TISSEEL® from Baxter may be used. The components of fibrin glue (fibrinogen, thrombin, factor 8, calcium ions and the like) are supplied as a two component mixture. The components of commercially available fibrin sealant are mixed in a sterile cup (total volume of mixed components 1-2 ml). To this solution 5 drops ophthalmic sodium fluorscein solution are added or 10 mg of indocyanine green dye added as a fluorescent/coloring agent or coloring agent. If no color is desired, the formulation can be used without the use of coloring agent or dye. The colored fibrin formulation is then loaded in the oscillating needle of the tattoo machine and injected (tattooed) into pericardial tissue or in live skin tissue. The excess solution on the tissue surface is wiped off. The injected solution droplets undergo enzymatic polymerization/crosslinking and form fibrin glue/gel particles in situ inside the tissue. Care is taken to inject the formulation before the fibrin glue forms gel (usually 1-2 minutes). If components prematurely gel, then a new mixture is prepared and used quickly. The fibrinogen solution may be diluted using PBS to slow the gelation process. Alternatively a modified tattoo machine like device is used wherein the components are mixed inside the device just prior to injection and injected by an oscillating needle. The colorant or fluorescence of particles or droplets provides visual clue on the amount of injected solution at each injection site. A drug may be added to the composition. Drugs that interfere with the fibrin glue formation such as TPA or heparin cannot be used for local delivery using this method. Many drugs can be used with fibrin glue system. Live cell suspensions may be added to the fibrin glue components to deliver live cell based compositions. A multilumen needle may be used to deliver fibrin glue precursors (one lumen for fibrinogen solution) and another lumen for thrombin solution. The components are injected simultaneously and crosslinked in situ.

REFERENCES

This application cross-references: U.S. patent application Ser. No. 14/736,007 filed Jun. 10, 2015, which is a divisional of U.S. patent application Ser. No. 14/209,827 filed Mar. 13, 2014 now U.S. Pat. No. 9,072,678, which claims priority to each of U.S. Provisional Patent Application No. 61/946,825 filed Mar. 2, 2014; U.S. Provisional Patent Application No. 61/934,795 filed Feb. 2, 2014; U.S. Provisional Patent Application No. 61/820,449 filed May 7, 2013; each of these applications being herein incorporated by specific reference in their entirety for all purposes. References incorporated by specific reference in their entirety:

J. Brandrup et al., "Polymer Handbook", John Wiley & Sons (2003). G. Orive et al., Advanced Drug Delivery Reviews, page 3, (2014). D.D. Perrin et al., "Purification of Laboratory Chemicals", Pergamon Press, Oxford, (1980). J. Seitzet al., Adv. Healthcare Mater., volume 4, page 1915-1936 (2015). A.B. Nair et al., International Journal of Pharmaceutics, volume 375, page 22- 27 (2013). E.H. Tudor et al., Lasers in Surgery and Medicine, volume 46, page 281 (2014). X. Gu et al., Colloids and Surfaces B: Biointerfaces, volume 144, page 170- 179 (2016). C Xianhua et al., Rare Metal Materials and Engineering, volume 45(9), page 2269-2274 (2016). B.M. Torrisi et al., J Control Release., volume 165(2), 146-152 (2013). B. Bediz et al., Pharm Res., volume 31(1), page 117-135 (2014). L.Y. Yeo et al., Small, Volume 7(1), Page 12-48 (2011). R. G. Willaert et al., Fermentation, volume 1, page 38-78 (2015). T.-M. Tuan-Mahmood et al., European Journal of Pharmaceutical Sciences, volume 50, page 623-637 (2013). M.R. Parasiteet et al., Advanced Drug Delivery Reviews, volume 56, page 581-587 (2004). E. Larraneta et al., Materials Science and Engineering R, volume 104, page 1-32 (2016). S.C. Byalekere et al., J Cutan. Aesthet Surg., volume 7(2), page 93-97 (2014) Y. Lu et al., Int. J Pharm., volume 461(0), page 258-269 (2014). E.C. Opara et al., Methods Mol Biol., volume 1001, page 261-266 (2013). M. Rizwan et al., Polymers, volume 9, page 137 (2017).

Cited US Patents and Patent Applications incorporated by specific reference in their entirety:

U.S. Pat. No. 5,410,016
U.S. Pat. No. 5,411,554
U.S. Pat. No. 5,529,914
U.S. Pat. No. 5,567,435
U.S. Pat. No. 5,626,863
U.S. Pat. No. 5,626,863
U.S. Pat. No. 5,631,015
U.S. Pat. No. 5,801,033
U.S. Pat. No. 6,004,573
U.S. Pat. No. 6,306,922
U.S. Pat. No. 6,323,278
U.S. Pat. No. 6,352,667
U.S. Pat. No. 6,534,591
U.S. Pat. No. 6,566,406
U.S. Pat. No. 6,599,627
U.S. Pat. No. 6,887,974
U.S. Pat. No. 7,009,034
U.S. Pat. No. 7,592,418
U.S. Pat. No. 7,740,877
U.S. Pat. No. 7,790,141
U.S. Pat. No. 7,919,112
U.S. Pat. No. 8,067,031
U.S. Pat. No. 8,557,535
U.S. Pat. No. 8,821,945
U.S. Pat. No. 9,072,678
U.S. Pat. No. 9,345,777
U.S. Pat. No. Application 20140256617
U.S. Pat. No. Application 20140147510

The invention claimed is:

1. A method of making a sustained biodegradable implant in a tissue, the method comprising:
    creating a plurality of artificial cavities of predetermined shape and volume in the tissue;
    filling the plurality of artificial cavities partially or completely with an injectable liquid polymeric implant-forming composition selected from a cross-linkable composition, thermoreversible composition, or neat liquid carrier composition; and
    forming the sustained biodegradable implant in the plurality of artificial cavities from the implant-forming composition.

2. The method of claim 1, wherein the cross-linkable composition includes one or more cross-linkable precursors, wherein the one or more cross-linkable precursors are cross-linked to form a crosslinked composition as the sustained biodegradable implant.

3. The method according to claim 2, further comprising forming a solid or a hydrogel from the crosslinking.

4. The method according to claim 3, wherein the conversion into a solid or hydrogel is initiated by a stimulus selected from the group consisting of light, chemical reaction, or enzymatic reaction.

5. The method according to claim 2, wherein the one or more precursors is selected from the group consisting of a macromonomer, component of condensation, polymerizable precursor, fibrin glue component, or combinations thereof.

6. The method according to claim 2, wherein the one or more precursors includes polyethylene glycol.

7. The method according to claim 1, further comprising forming the crosslinked composition into one or more microparticles or a film or a combination thereof.

8. The method according to claim 1, wherein the thermoreversible composition forms a gel after implantation at about 37° C.

9. The method according to claim 1, wherein the injectable liquid polymeric implant-forming composition comprises a polymer dissolved in an aqueous solution.

10. The method according to claim 9, wherein the polymer shows a thermoreversible property in the aqueous solution and is selected from a group consisting of polymers or copolymers of: pluronics; poly ethyleneoxides; polypropylene oxides; reverse pluronics; polyacrylamides; gelatins; cellulose derivatives; polylactones, polylactic acids; polyglycolic acids; polylactice-co-glycolides; polyhydroxy acids; and combinations thereof.

11. The method according to claim 10, wherein a concentration of the polymer in the aqueous solution ranges from about 2% to about 45%.

12. The method according to claim 1, wherein the neat liquid carrier composition is polymeric or non-polymeric and substantially liquid at room temperature and/or about body temperature.

13. The method according to claim 12, wherein the neat liquid carrier is selected from a group consisting of: polymers, dendrimers, copolymers or oligomers of glycolide, dl-lactide, d-lactide, l-lactide, caprolactone, dioxanone and trimethylene carbonate; degradable polyurethanes; polyamides; polyesters; polypeptides; polyhydroxyacids; polyorthocarbonates; polylactic acid; polyglycolic acid; polyanhydrides; and polylactones; a copolymer of polyethylene glycol and polylactone; and a copolymer of PEO-PPO-PEO and polylactone.

14. The method according to claim 12, wherein the non-polymeric neat liquid carrier is selected from a group consisting of: sucrose acetate isobutyrate; vitamin E and its derivatives; fatty acids; oleic acids and its derivatives; fatty alcohols; liquid non-ionic surfactants; polysorbate, Tween.40 or Tween 80.

15. The method according to claim 1, wherein the neat liquid carrier comprises a viscosity-modifying agent.

16. The method according to claim 15, wherein the viscosity-modifying agent is a biocompatible organic solvent.

17. The method according to claim 15, wherein the viscosity-modifying agent is selected from the group consisting of dimethyl sulfoxide, n-methyl pyrrolidinone, ethanol, glycerol, polyethylene glycol, and acetone.

18. The method according to claim 15, wherein the viscosity-modifying agent is added in 1 to 99 percent of the neat liquid carrier.

19. The method of claim 1, further comprising at least one of:
    forming at least 4 artificial cavities per square centimeter in the live tissue;
    forming from 4 artificial cavities to 6,000 artificial cavities per square centimeter in the live tissue;
    forming the cavities to have a spacing between adjacent cavities to range from 1 micron to 10 mm; or
    forming a volume of each artificial cavity to be in a range from about 1×10E-12 ml to about 0.05 ml.

20. The method of claim 1, wherein the creating the plurality of artificial cavities includes at least one of displacing tissue, destroying tissue, or combination thereof.

21. The method of claim 1, wherein the creating the plurality of artificial cavities includes at least one of laser ablation, microneedle array, oscillating needle, mechanical drilling, ultrasonic drilling, water drilling, or combination thereof.

* * * * *